United States Patent
Carstensen et al.

(10) Patent No.: US 10,947,520 B2
(45) Date of Patent: Mar. 16, 2021

(54) COMPOSITIONS COMPRISING POLYPEPTIDES HAVING GALACTANASE ACTIVITY AND POLYPEPTIDES HAVING BETA-GALACTOSIDASE ACTIVITY

(71) Applicant: Novozymes A/S, Bagsvaerd (DK)

(72) Inventors: Lone Carstensen, Allerod (DK); Nikolaj Spodsberg, Holte (DK); Morten Gjermansen, Greve (DK); Jesper Salomon, Holte (DK); Kristian B. R. M. Krogh, Bagsvaerd (DK); Eduardo Antonio Della Pia, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 21 days.

(21) Appl. No.: 16/096,507

(22) PCT Filed: May 24, 2017

(86) PCT No.: PCT/EP2017/062598
§ 371 (c)(1),
(2) Date: Oct. 25, 2018

(87) PCT Pub. No.: WO2017/202946
PCT Pub. Date: Nov. 30, 2017

(65) Prior Publication Data
US 2019/0127717 A1    May 2, 2019

(30) Foreign Application Priority Data
May 24, 2016 (EP) .................... 16170964

(51) Int. Cl.
| | | |
|---|---|---|
| C12N 9/12 | (2006.01) | |
| C12N 9/38 | (2006.01) | |
| C12N 9/24 | (2006.01) | |
| A23K 20/189 | (2016.01) | |
| C12N 15/75 | (2006.01) | |

(52) U.S. Cl.
CPC .......... *C12N 9/2471* (2013.01); *A23K 20/189* (2016.05); *C12N 9/2402* (2013.01); *C12N 15/75* (2013.01); *C12Y 302/01023* (2013.01)

(58) Field of Classification Search
CPC .............................. C12N 9/2471; C12N 15/76
See application file for complete search history.

(56) References Cited

U.S. PATENT DOCUMENTS

| 2019/0019635 A1 | 1/2019 | Huo | |
| 2019/0194635 A1* | 6/2019 | Nymand-Grarup | A23K 50/30 |

FOREIGN PATENT DOCUMENTS

| WO | 97/16982 A1 | 5/1997 |
| WO | 01/59083 A1 | 8/2001 |
| WO | 2008/102743 A1 | 8/2008 |
| WO | 2009/132008 A2 | 10/2009 |
| WO | 2017/202946 A1 | 11/2017 |
| WO | 2017/202997 A1 | 11/2017 |

OTHER PUBLICATIONS

Anonymous, NCBI Reference Sequence No. WP_019006306.1 (2013).
Anonymous, NCBI Reference Sequence No. WP_075154426.1 (2016).
Anonymous, UniParc Accession No. UPI000AE4DCAA (2017).
Vahjen et al., Animal Feed Science and Tech, vol. 120, Nos. 3-4, pp. 259-276 (2005).
Andrew, UniProt accession No. A0A0Q4QZW5 (2016).
Andrew, UniProt accession No. A0A0Q9KNZ9 (2016).
Andrew, UniProt accession No. A0A0Q9MEL5 (2016).
Condon et al., UniProt accession No. W7F3E0 (2014).
Dodson et al., UniProt accession No. B4AK09 (2008).
Dragosits et al., UniProt accession No. T1SCI0 (2013).
Ehrlich et al., UniProt accession No. A0A0F0IMF7 (2015).
Jeong et al., UniProt accession No. A0A0K2FAB3 (2015).
Kocher et al., British Poultry Science, vol. 43, No. 1, pp. 54-63 (2002).
Lian et al., EMBLCDS Accession No. AFK65333 (2014).
Meng et al., Poultry Science, vol. 84, No. 8, pp. 1242-1251 (2005).
Moreno et al., UniProt accession No. W4AK00 (2014).
Orly et al., FEBS Journal, vol. 280, No. 3, pp. 950-964 (2013).
Sakamoto et al., Appl. Microbiol. Biotechnol., vol. 97, No. 7, pp. 2895-2906 (2013).
Sakamoto et al., Appl. Microbiol. Biotechnol., vol. 97, No. 12, pp. 5201-5213 (2013).
Shipkowshi et al., Applied and Environmental Microbiology, vol. 72, No. 12, pp. 7730-7738 (2006).
Uroz et al., UniProt accession No. A0A0J1CW07 (2015).
Vries et al., Carbohydr Research, vol. 327, No. 4, pp. 401-410 (2000).
Ward et al., UniProt accession No. C6J3F7 (2009).

* cited by examiner

*Primary Examiner* — Tekchand Saidha
(74) *Attorney, Agent, or Firm* — Elias Lambiris

(57) ABSTRACT

The present invention relates to compositions comprising polypeptides having galactanase activity and polypeptides having beta-galactosidase activity for use in e.g. animal feed. The present invention further relates to polypeptides having beta-galactosidase activity, polypeptides having galactanase activity and polynucleotides encoding the polypeptides. The invention also relates to nucleic acid constructs, vectors, and host cells comprising the polynucleotides as well as methods of producing and using the polypeptides.

19 Claims, No Drawings
Specification includes a Sequence Listing.

COMPOSITIONS COMPRISING POLYPEPTIDES HAVING GALACTANASE ACTIVITY AND POLYPEPTIDES HAVING BETA-GALACTOSIDASE ACTIVITY

CROSS-REFERENCE TO RELATED APPLICATIONS

This application is a 35 U.S.C. 371 national application of international application no. PCT/EP2017/062598 filed May 24, 2017, which claims priority or the benefit under 35 U.S.C. 119 of European application no. 16170964.7 filed May 24, 2016. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to compositions comprising polypeptides having galactanase activity and polypeptides having beta-galactosidase activity for use in e.g. animal feed. The present invention further relates to polypeptides having beta-galactosidase activity, polypeptides having galactanase activity and polynucleotides encoding the polypeptides. The invention also relates to nucleic acid constructs, vectors, and host cells comprising the polynucleotides as well as methods of producing and using the polypeptides.

Description of the Related Art

Soybean is a species of legume native to East Asia and is the second biggest feed crop globally and the biggest protein source applied in animal feed. Soybean can be manufactured (defatted) to produce soybean meal (SBM), and SBM is a significant and cheap source of high quality protein for animal feeds. Other common types of legume are chickpea, lupin, lentil, peanut, beans or peas which can also be processed and used as animal feed. Legumes, such as soybean, contain significant amounts of galactan polysaccharides which need to be degraded by enzymes to release the sugars, and thus energy, therein.

However, there are few solutions which efficiently degrade galactan polysaccharides and thus energy which is in the legume cannot be properly utilised by an animal. Up to 70% of a farmers expenses is from the cost of animal feed.

Shipkowski et at in Applied and Environmental Microbiology, 2006, 72(12), 7730 discloses the beta-galactosidase LacA and the galactanase GalA and the use of these two enzymes in degrading galactan. Tabachnikov et al in Febs Journal, 2013, 280(3), 950 discloses the beta-galactosidase GanB and the galactanase GanA and the use of these two enzymes in degrading galactan. However, as disclosed herein these prior art solutions are not very effective at releasing galactose from legumes, such as soybean. Thus the object of this invention is to provide a solution which efficiently releases sugars from galactan polysaccharides and thereby improves the nutritional value of the legumes to reduce the feed costs by reformulation of the diet or to provide more energy to the animal resulting in improved animal growth.

SUMMARY OF THE INVENTION

The present invention relates to compositions comprising one or more GH53 polypeptides having galactanase activity and one or more GH42 polypeptides having beta-galactosidase activity.

The present application further relates to granules comprising the polypeptide(s) of the invention; animal feed additives comprising the polypeptide(s) of the invention; liquid formulations comprising the polypeptide(s) of the invention; animal feed and pelleted animal feed comprising the polypeptide(s) of the invention; methods of releasing galactose from plant based material; methods of improving one or more performance parameters of an animal and use of the composition of the invention in animal feed, in animal feed additives, in the preparation of a composition for use in animal feed, for improving the nutritional value of an animal feed, for increasing digestibility of the animal feed, for improving one or more performance parameters in an animal and/or for releasing galactose from plant based material.

The invention also relates to isolated polypeptide having beta-galactosidase or galactanase activity, polynucleotides encoding the polypeptides of the present invention; nucleic acid constructs; expression vectors; recombinant host cells comprising the polynucleotides and methods of producing the polypeptides.

OVERVIEW OF SEQUENCE LISTING

SEQ ID NO: 1 is the gene sequence of the GH53 galactanase as isolated from *Cohnella* sp-60555.

SEQ ID NO: 2 is the amino acid sequence as deduced from SEQ ID NO: 1.

SEQ ID NO: 3 is the amino acid sequence of the mature GH53 galactanase from *Cohnella* sp-60555.

SEQ ID NO: 4 is the amino acid sequence of SEQ ID NO: 3 with His-tag.

SEQ ID NO: 5 is the gene sequence of the GH53 galactanase as isolated from *Cohnella xylanilytica*.

SEQ ID NO: 6 is the amino acid sequence as deduced from SEQ ID NO: 5.

SEQ ID NO: 7 is the amino acid sequence of the mature GH53 galactanase from *Cohnella xylanilytica*.

SEQ ID NO: 8 is the amino acid sequence of SEQ ID NO: 7 with His-tag.

SEQ ID NO: 9 is the gene sequence of the GH53 galactanase as isolated from *Paenibacillus tundrae*.

SEQ ID NO: 10 is the amino acid sequence as deduced from SEQ ID NO: 9.

SEQ ID NO: 11 is the amino acid sequence of the mature GH53 galactanase from *Paenibacillus tundrae*.

SEQ ID NO: 12 is the amino acid sequence of SEQ ID NO: 11 with His-tag.

SEQ ID NO: 13 is the gene sequence of the GH53 galactanase as isolated from *Paenibacillus barcinonensis*.

SEQ ID NO: 14 is the amino acid sequence as deduced from SEQ ID NO: 13.

SEQ ID NO: 15 is the amino acid sequence of the mature GH53 galactanase from *Paenibacillus barcinonensis*.

SEQ ID NO: 16 is the amino acid sequence of SEQ ID NO: 15 with His-tag.

SEQ ID NO: 17 is the gene sequence of the GH53 galactanase as isolated from *Paenibacillus* sp-62603.

SEQ ID NO: 18 is the amino acid sequence as deduced from SEQ ID NO: 17.

SEQ ID NO: 19 is the amino acid sequence of the mature GH53 galactanase from *Paenibacillus* sp-62603.

SEQ ID NO: 20 is the amino acid sequence of SEQ ID NO: 19 with His-tag.

SEQ ID NO: 21 is the gene sequence of the GH53 galactanase as isolated from *Paenibacillus xylanilyticus*.

SEQ ID NO: 22 is the amino acid sequence as deduced from SEQ ID NO: 21.

SEQ ID NO: 23 is the amino acid sequence of the mature GH53 galactanase from *Paenibacillus xylanilyticus*.

SEQ ID NO: 24 is the amino acid sequence of SEQ ID NO: 23 with His-tag.

SEQ ID NO: 25 is the gene sequence of the GH53 galactanase as isolated from *Paenibacillus* sp-18179.

SEQ ID NO: 26 is the amino acid sequence as deduced from SEQ ID NO: 25.

SEQ ID NO: 27 is the amino acid sequence of the mature GH53 galactanase from *Paenibacillus* sp-18179.

SEQ ID NO: 28 is the amino acid sequence of SEQ ID NO: 27 with His-tag.

SEQ ID NO: 29 is the gene sequence of the GH53 galactanase as isolated from *Paenibacillus peoriae*. (D448RG) SEQ ID NO: 30 is the amino acid sequence as deduced from SEQ ID NO: 29.

SEQ ID NO: 31 is the amino acid sequence of the mature GH53 galactanase from *Paenibacillus peoriae*.

SEQ ID NO: 32 is the amino acid sequence of SEQ ID NO: 31 with His-tag.

SEQ ID NO: 33 is the gene sequence of the GH53 galactanase as isolated from *Paenibacillus xylanexedens*.

SEQ ID NO: 34 is the amino acid sequence as deduced from SEQ ID NO: 33.

SEQ ID NO: 35 is the amino acid sequence of the mature GH53 galactanase from *Paenibacillus xylanexedens*.

SEQ ID NO: 36 is the amino acid sequence of SEQ ID NO: 35 with His-tag.

SEQ ID NO: 37 is the gene sequence of the GH53 galactanase as isolated from *Cohnella laeviribosi*.

SEQ ID NO: 38 is the amino acid sequence as deduced from SEQ ID NO: 37.

SEQ ID NO: 39 is the amino acid sequence of the mature GH53 galactanase from *Cohnella laeviribosi*.

SEQ ID NO: 40 is the amino acid sequence of SEQ ID NO: 39 with His-tag.

SEQ ID NO: 41 is the gene sequence of the GH42 beta-galactosidase as isolated from *Paenibacillus* sp-18026.

SEQ ID NO: 42 is the amino acid sequence as deduced from SEQ ID NO: 41.

SEQ ID NO: 43 is the gene sequence of the GH42 beta-galactosidase as isolated from *Bacillus pumilus*.

SEQ ID NO: 44 is the amino acid sequence as deduced from SEQ ID NO: 43.

SEQ ID NO: 45 is the amino acid sequence as deduced from SEQ ID NO: 43 with MHHHHHH-tag.

SEQ ID NO: 46 is the gene sequence of the GH42 beta-galactosidase as isolated from *Bacillus nealsonii*.

SEQ ID NO: 47 is the amino acid sequence as deduced from SEQ ID NO: 46.

SEQ ID NO: 48 is the amino acid sequence as deduced from SEQ ID NO: 46 with MHHHHHH-tag.

SEQ ID NO: 49 is the gene sequence of the GH42 beta-galactosidase as isolated from *Burkholderia sediminicola*.

SEQ ID NO: 50 is the amino acid sequence as deduced from SEQ ID NO: 49.

SEQ ID NO: 51 is the amino acid sequence as deduced from SEQ ID NO: 49 with MHHHHHH-tag.

SEQ ID NO: 52 is the gene sequence of the GH42 beta-galactosidase as isolated from *Bacillus alcalophilus*.

SEQ ID NO: 53 is the amino acid sequence as deduced from SEQ ID NO: 52.

SEQ ID NO: 54 is the amino acid sequence as deduced from SEQ ID NO: 52 with MHHHHHH-tag.

SEQ ID NO: 55 is the gene sequence of the GH42 beta-galactosidase as isolated from *Bacillus* sp-11182.

SEQ ID NO: 56 is the amino acid sequence as deduced from SEQ ID NO: 55.

SEQ ID NO: 57 is the amino acid sequence as deduced from SEQ ID NO: 55 with MHHHHHHPR-tag.

SEQ ID NO: 58 is the gene sequence of the GH42 beta-galactosidase as isolated from *Bacillus* sp-62759.

SEQ ID NO: 59 is the amino acid sequence as deduced from SEQ ID NO: 58.

SEQ ID NO: 60 is the amino acid sequence as deduced from SEQ ID NO: 58 with MHHHHHHPR-tag.

SEQ ID NO: 61 is the gene sequence of the GH42 beta-galactosidase as isolated from *Paenibacillus* sp-18054.

SEQ ID NO: 62 is the amino acid sequence as deduced from SEQ ID NO: 61.

SEQ ID NO: 63 is the amino acid sequence as deduced from SEQ ID NO: 61 with MHHHHHHPR-tag.

SEQ ID NO: 64 is the gene sequence of the GH42 beta-galactosidase as isolated from *Paenibacillus* sp-62047.

SEQ ID NO: 65 is the amino acid sequence as deduced from SEQ ID NO: 64.

SEQ ID NO: 66 is the amino acid sequence as deduced from SEQ ID NO: 64 with MHHHHHHPR-tag.

SEQ ID NO: 67 is the gene sequence of the GH42 beta-galactosidase as isolated from *Paenibacillus* sp-62603.

SEQ ID NO: 68 is the amino acid sequence as deduced from SEQ ID NO: 67.

SEQ ID NO: 69 is the amino acid sequence as deduced from SEQ ID NO: 67 with MHHHHHHPR-tag.

SEQ ID NO: 70 is the gene sequence of the GH42 beta-galactosidase as isolated from *Paenibacillus woosongensis*.

SEQ ID NO: 71 is the amino acid sequence as deduced from SEQ ID NO: 70.

SEQ ID NO: 72 is the amino acid sequence as deduced from SEQ ID NO: 70 with MHHHHHHPR-tag.

SEQ ID NO: 73 is the gene sequence of the GH42 beta-galactosidase as isolated from *Paenibacillus* sp-62253.

SEQ ID NO: 74 is the amino acid sequence as deduced from SEQ ID NO: 73.

SEQ ID NO: 75 is the amino acid sequence as deduced from SEQ ID NO: 73 with MHHHHHHPR-tag.

SEQ ID NO: 76 is the gene sequence of the GH42 beta-galactosidase as isolated from *Paenibacillus* sp-62758.

SEQ ID NO: 77 is the amino acid sequence as deduced from SEQ ID NO: 76.

SEQ ID NO: 78 is the amino acid sequence as deduced from SEQ ID NO: 76 with MHHHHHHPR-tag.

SEQ ID NO: 79 is the amino acid sequence of the mature GH53 galactanase from *Humicola insolens* as disclosed in WO1997/032014 SEQ ID NO: 80 is the amino acid sequence of the mature GH53 galactanase from *Myceliophthora thermophile* as disclosed in WO1997/032014.

SEQ ID NO: 81 is the GH53 galactanase conserved motif GV[T/M]PD[W/M]VQ[I/V]GNE.

SEQ ID NO: 82 is the GH53 galactanase conserved motif WADP[A/G]xQxKPxAW.

SEQ ID NO: 83 is the GH42 beta-galactosidase conserved motif DW[K/R]RF[V/I]T[A/D]Q[T/M].

SEQ ID NO: 84 is the *Bacillus clausii* secretion signal.

SEQ ID NO: 85 is the amino acid sequence of the GH42 beta-galactosidase LacA from *Bacillus subtilis* (strain 168)

as disclosed by Shipkowski et at in *Applied and Environmental Microbiology,* 2006, 72(12), 7730 (Swissprot: 007012).

SEQ ID NO: 86 is the amino acid sequence of the GH53 galactanase GalA from *Bacillus subtilis* (strain 168) as disclosed by Shipkowski et at in *Applied and Environmental Microbiology,* 2006, 72(12), 7730 (Swissprot: 007013).

SEQ ID NO: 87 is the amino acid sequence of the GH42 beta-galactosidase ganB from *Geobacillus stearothermophilus* as disclosed by Tabachnikov et al in *Febs Journal,* 2013, 280(3), 950 7730 (Swissprot: F8TRX0).

SEQ ID NO: 88 is the amino acid sequence of the GH53 galactanase ganA from *Geobacillus stearothermophilus* as disclosed by Tabachnikov et al in *Febs Journal,* 2013, 280(3), 950 7730 (Swissprot: F8TRX1).

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Animal: The term "animal" refers to all animals except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Beta-galactosidase: The term "beta-galactosidase" means an β-D-galactoside galactohydrolase (EC 3.2.1.23) that catalyzes the hydrolysis of terminal non-reducing β-D-galactose residues in β-D-galactosides, such as lactose (1,4-O-β-D-galactopyranosyl-D-glucose), oligosaccharides, glycolipids, and glycoproteins. Beta-galactosidase activity can be determined using 4-nitrophenyl beta-D-galactopyranoside (available from Megazyme International, Bray, Co. Wicklow, Ireland) as substrate in 100 mM MES (Sigma) buffer pH 7.0±0.05 at room temperature. The enzyme is diluted in 2-fold dilutions and then the 4-nitrophenyl beta-D-galactopyranoside substrate is dissolved in the solution containing the enzyme. The beta-galactosidase activity is followed directly in the buffer by measuring the absorbance of released pNP at 405 nm as function of time. A detailed assay can be found in the beta-galactosidase assay as described herein. In one aspect, the polypeptides of the present invention have at least 60%, such as at least 70%, at least 75%, at least 80%, at least 85%, at least 90%, at least 95% or at least 100% of the beta-galactosidase activity of the polypeptide of SEQ ID NO: 42.

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Fragment: The term "fragment" means a polypeptide having one or more (e.g., several) amino acids absent from the amino and/or carboxyl terminus of a mature polypeptide or domain; wherein the fragment has beta-galactosidase activity or galactanase activity.

In one aspect, the fragment comprises at least 90% of the length of the mature polypeptide, such as at least 284 amino acids of SEQ ID NO: 3, at least 286 amino acids of SEQ ID NO: 7, at least 284 amino acids of SEQ ID NO: 11, at least 284 amino acids of SEQ ID NO: 15, at least 284 amino acids of SEQ ID NO: 19, at least 284 amino acids of SEQ ID NO: 23, at least 464 amino acids of SEQ ID NO: 27, at least 285 amino acids of SEQ ID NO: 31, at least 284 amino acids of SEQ ID NO: 35, at least 284 amino acids of SEQ ID NO: 39, at least 616 amino acids of SEQ ID NO: 42, at least 619 amino acids of SEQ ID NO: 44, at least 618 amino acids of SEQ ID NO: 47, at least 588 amino acids of SEQ ID NO: 50, at least 618 amino acids of SEQ ID NO: 53, at least 617 amino acids of SEQ ID NO: 56, at least 619 amino acids of SEQ ID NO: 59, at least 621 amino acids of SEQ ID NO: 62, at least 621 amino acids of SEQ ID NO: 65, at least 620 amino acids of SEQ ID NO: 68, at least 616 amino acids of SEQ ID NO: 71, at least 616 amino acids of SEQ ID NO: 74 or at least 617 amino acids of SEQ ID NO: 77.

In another aspect, the fragment comprises at least 92% of the length of the mature polypeptide, such as at least 290 amino acids of SEQ ID NO: 3, at least 292 amino acids of SEQ ID NO: 7, at least 290 amino acids of SEQ ID NO: 11, at least 290 amino acids of SEQ ID NO: 15, at least 290 amino acids of SEQ ID NO: 19, at least 290 amino acids of SEQ ID NO: 23, at least 474 amino acids of SEQ ID NO: 27, at least 291 amino acids of SEQ ID NO: 31, at least 290 amino acids of SEQ ID NO: 35, at least 290 amino acids of SEQ ID NO: 39, at least 630 amino acids of SEQ ID NO: 42, at least 632 amino acids of SEQ ID NO: 44, at least 632 amino acids of SEQ ID NO: 47, at least 601 amino acids of SEQ ID NO: 50, at least 632 amino acids of SEQ ID NO: 53, at least 631 amino acids of SEQ ID NO: 56, at least 632 amino acids of SEQ ID NO: 59, at least 635 amino acids of SEQ ID NO: 62, at least 634 amino acids of SEQ ID NO: 65, at least 633 amino acids of SEQ ID NO: 68, at least 630 amino acids of SEQ ID NO: 71, at least 630 amino acids of SEQ ID NO: 74 or at least 631 amino acids of SEQ ID NO: 77.

In another aspect, the fragment comprises at least 94% of the length of the mature polypeptide, such as at least 297 amino acids of SEQ ID NO: 3, at least 298 amino acids of SEQ ID NO: 7, at least 297 amino acids of SEQ ID NO: 11, at least 297 amino acids of SEQ ID NO: 15, at least 297 amino acids of SEQ ID NO: 19, at least 297 amino acids of SEQ ID NO: 23, at least 485 amino acids of SEQ ID NO: 27, at least 297 amino acids of SEQ ID NO: 31, at least 297 amino acids of SEQ ID NO: 35, at least 297 amino acids of SEQ ID NO: 39, at least 643 amino acids of SEQ ID NO: 42, at least 646 amino acids of SEQ ID NO: 44, at least 645 amino acids of SEQ ID NO: 47, at least 614 amino acids of SEQ ID NO: 50, at least 645 amino acids of SEQ ID NO: 53, at least 644 amino acids of SEQ ID NO: 56, at least 646 amino acids of SEQ ID NO: 59, at least 649 amino acids of SEQ ID NO: 62, at least 648 amino acids of SEQ ID NO: 65, at least 647 amino acids of SEQ ID NO: 68, at least 643 amino acids of SEQ ID NO: 71, at least 643 amino acids of SEQ ID NO: 74 or at least 644 amino acids of SEQ ID NO: 77.

In another aspect, the fragment comprises at least 96% of the length of the mature polypeptide, such as at least 303 amino acids of SEQ ID NO: 3, at least 305 amino acids of SEQ ID NO: 7, at least 303 amino acids of SEQ ID NO: 11, at least 303 amino acids of SEQ ID NO: 15, at least 303 amino acids of SEQ ID NO: 19, at least 303 amino acids of SEQ ID NO: 23, at least 495 amino acids of SEQ ID NO: 27, at least 304 amino acids of SEQ ID NO: 31, at least 303 amino acids of SEQ ID NO: 35, at least 303 amino acids of SEQ ID NO: 39, at least 657 amino acids of SEQ ID NO: 42, at least 660 amino acids of SEQ ID NO: 44, at least 659 amino acids of SEQ ID NO: 47, at least 627 amino acids of SEQ ID NO: 50, at least 659 amino acids of SEQ ID NO: 53, at least 658 amino acids of SEQ ID NO: 56, at least 660 amino acids of SEQ ID NO: 59, at least 663 amino acids of SEQ ID NO: 62, at least 662 amino acids of SEQ ID NO: 65, at least 661 amino acids of SEQ ID NO: 68, at least 657 amino acids of SEQ ID NO: 71, at least 657 amino acids of SEQ ID NO: 74 or at least 658 amino acids of SEQ ID NO: 77.

In another aspect, the fragment comprises at least 98% of the length of the mature polypeptide, such as at least 309 amino acids of SEQ ID NO: 3, at least 311 amino acids of SEQ ID NO: 7, at least 309 amino acids of SEQ ID NO: 11, at least 309 amino acids of SEQ ID NO: 15, at least 309 amino acids of SEQ ID NO: 19, at least 309 amino acids of SEQ ID NO: 23, at least 505 amino acids of SEQ ID NO: 27, at least 310 amino acids of SEQ ID NO: 31, at least 309 amino acids of SEQ ID NO: 35, at least 309 amino acids of SEQ ID NO: 39, at least 671 amino acids of SEQ ID NO: 42, at least 674 amino acids of SEQ ID NO: 44, at least 673 amino acids of SEQ ID NO: 47, at least 640 amino acids of SEQ ID NO: 50, at least 673 amino acids of SEQ ID NO: 53, at least 672 amino acids of SEQ ID NO: 56, at least 674 amino acids of SEQ ID NO: 59, at least 677 amino acids of SEQ ID NO: 62, at least 676 amino acids of SEQ ID NO: 65, at least 675 amino acids of SEQ ID NO: 68, at least 671 amino acids of SEQ ID NO: 71, at least 671 amino acids of SEQ ID NO: 74 or at least 672 amino acids of SEQ ID NO: 77.

In another aspect, the fragment comprises at least 99% of the length of the mature polypeptide, such as at least 312 amino acids of SEQ ID NO: 3, at least 314 amino acids of SEQ ID NO: 7, at least 312 amino acids of SEQ ID NO: 11, at least 312 amino acids of SEQ ID NO: 15, at least 312 amino acids of SEQ ID NO: 19, at least 312 amino acids of SEQ ID NO: 23, at least 510 amino acids of SEQ ID NO: 27, at least 313 amino acids of SEQ ID NO: 31, at least 312 amino acids of SEQ ID NO: 35, at least 312 amino acids of SEQ ID NO: 39, at least 678 amino acids of SEQ ID NO: 42, at least 681 amino acids of SEQ ID NO: 44, at least 680 amino acids of SEQ ID NO: 47, at least 647 amino acids of SEQ ID NO: 50, at least 680 amino acids of SEQ ID NO: 53, at least 679 amino acids of SEQ ID NO: 56, at least 681 amino acids of SEQ ID NO: 59, at least 684 amino acids of SEQ ID NO: 62, at least 683 amino acids of SEQ ID NO: 65, at least 682 amino acids of SEQ ID NO: 68, at least 678 amino acids of SEQ ID NO: 71, at least 678 amino acids of SEQ ID NO: 74 or at least 679 amino acids of SEQ ID NO: 77.

Galactanase: The term "galactanase", also called endo-1,4-β-galactanase, means an arabinogalactan endo-β-1,4-galactanase (E.C. 3.2.1.89) that catalyses the hydrolysis of (1→4)-β-D-galactosidic linkages in type I arabinogalactans. Galactanase activity can be determined by reducing ends using the colorimetric assay developed by Lever (Analytical Biochemistry 47, 273-279, 1972). The galactanase produces reducing end sugars which react with PAHBAH generating an increase of colour which is proportional to the enzyme activity under the conditions used in the assay. A detailed assay can be found in the galactanase assay as described herein.

The galactanases of the present invention have at least 60%, such as at least 70%, at least 75%, at least 80%, at least 85%, at least 90%, at least 95% or at least 100% of the galactanase activity of the polypeptide of SEQ ID NO: 3.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 316 of SEQ ID NO: 2 and amino acids −32 to −1 of SEQ ID NO: 2 are a signal peptide. In another aspect, the mature polypeptide is amino acids 1 to 316 of SEQ ID NO: 3. In an alternative aspect, the mature polypeptide is amino acids 1 to 324 of SEQ ID NO: 4.

In one aspect, the mature polypeptide is amino acids 1 to 318 of SEQ ID NO: 6 and amino acids −29 to −1 of SEQ ID NO: 6 are a signal peptide. In another aspect, the mature polypeptide is amino acids 1 to 318 of SEQ ID NO: 7. In an alternative aspect, the mature polypeptide is amino acids 1 to 326 of SEQ ID NO: 8.

In one aspect, the mature polypeptide is amino acids 1 to 316 of SEQ ID NO: 10 and amino acids −33 to −1 of SEQ ID NO: 10 are a signal peptide. In another aspect, the mature polypeptide is amino acids 1 to 316 of SEQ ID NO: 11. In an alternative aspect, the mature polypeptide is amino acids 1 to 324 of SEQ ID NO: 12.

In one aspect, the mature polypeptide is amino acids 1 to 316 of SEQ ID NO: 14 and amino acids −35 to −1 of SEQ ID NO: 14 are a signal peptide. In another aspect, the mature polypeptide is amino acids 1 to 316 of SEQ ID NO: 15. In an alternative aspect, the mature polypeptide is amino acids 1 to 324 of SEQ ID NO: 16.

In one aspect, the mature polypeptide is amino acids 1 to 316 of SEQ ID NO: 18 and amino acids −31 to −1 of SEQ ID NO: 18 are a signal peptide. In another aspect, the mature polypeptide is amino acids 1 to 316 of SEQ ID NO: 19. In an alternative aspect, the mature polypeptide is amino acids 1 to 324 of SEQ ID NO: 20.

In one aspect, the mature polypeptide is amino acids 1 to 316 of SEQ ID NO: 22 and amino acids −33 to −1 of SEQ ID NO: 22 are a signal peptide. In another aspect, the mature polypeptide is amino acids 1 to 316 of SEQ ID NO: 23. In an alternative aspect, the mature polypeptide is amino acids 1 to 324 of SEQ ID NO: 24.

In one aspect, the mature polypeptide is amino acids 1 to 516 of SEQ ID NO: 26 and amino acids −29 to −1 of SEQ ID NO: 26 are a signal peptide. In another aspect, the mature polypeptide is amino acids 1 to 516 of SEQ ID NO: 27. In an alternative aspect, the mature polypeptide is amino acids 1 to 524 of SEQ ID NO: 28.

In one aspect, the mature polypeptide is amino acids 1 to 317 of SEQ ID NO: 30 and amino acids −33 to −1 of SEQ ID NO: 30 are a signal peptide. In another aspect, the mature polypeptide is amino acids 1 to 317 of SEQ ID NO: 31. In an alternative aspect, the mature polypeptide is amino acids 1 to 325 of SEQ ID NO: 32.

In one aspect, the mature polypeptide is amino acids 1 to 316 of SEQ ID NO: 34 and amino acids −33 to −1 of SEQ ID NO: 34 are a signal peptide. In another aspect, the mature polypeptide is amino acids 1 to 316 of SEQ ID NO: 35. In an alternative aspect, the mature polypeptide is amino acids 1 to 324 of SEQ ID NO: 36.

In one aspect, the mature polypeptide is amino acids 1 to 316 of SEQ ID NO: 38 and amino acids −31 to −1 of SEQ ID NO: 38 are a signal peptide. In another aspect, the mature polypeptide is amino acids 1 to 316 of SEQ ID NO: 39. In an alternative aspect, the mature polypeptide is amino acids 1 to 324 of SEQ ID NO: 40.

In one aspect, the mature polypeptide is amino acids 1 to 685 of SEQ ID NO: 42.

In one aspect, the mature polypeptide is amino acids 1 to 688 of SEQ ID NO: 44. In another aspect, the mature polypeptide is amino acids 1 to 695 of SEQ ID NO: 45.

In one aspect, the mature polypeptide is amino acids 1 to 687 of SEQ ID NO: 47. In another aspect, the mature polypeptide is amino acids 1 to 694 of SEQ ID NO: 48.

In one aspect, the mature polypeptide is amino acids 1 to 654 of SEQ ID NO: 50. In another aspect, the mature polypeptide is amino acids 1 to 661 of SEQ ID NO: 51.

In one aspect, the mature polypeptide is amino acids 1 to 687 of SEQ ID NO: 53. In another aspect, the mature polypeptide is amino acids 1 to 694 of SEQ ID NO: 54.

In one aspect, the mature polypeptide is amino acids 1 to 686 of SEQ ID NO: 56. In another aspect, the mature polypeptide is amino acids 1 to 695 of SEQ ID NO: 57.

In one aspect, the mature polypeptide is amino acids 1 to 688 of SEQ ID NO: 59. In another aspect, the mature polypeptide is amino acids 1 to 697 of SEQ ID NO: 60.

In one aspect, the mature polypeptide is amino acids 1 to 691 of SEQ ID NO: 62. In another aspect, the mature polypeptide is amino acids 1 to 700 of SEQ ID NO: 63.

In one aspect, the mature polypeptide is amino acids 1 to 690 of SEQ ID NO: 65. In another aspect, the mature polypeptide is amino acids 1 to 699 of SEQ ID NO: 66.

In one aspect, the mature polypeptide is amino acids 1 to 689 of SEQ ID NO: 68. In another aspect, the mature polypeptide is amino acids 1 to 698 of SEQ ID NO: 69.

In one aspect, the mature polypeptide is amino acids 1 to 685 of SEQ ID NO: 71. In another aspect, the mature polypeptide is amino acids 1 to 694 of SEQ ID NO: 72.

In one aspect, the mature polypeptide is amino acids 1 to 685 of SEQ ID NO: 74. In another aspect, the mature polypeptide is amino acids 1 to 694 of SEQ ID NO: 75.

In one aspect, the mature polypeptide is amino acids 1 to 686 of SEQ ID NO: 77. In another aspect, the mature polypeptide is amino acids 1 to 695 of SEQ ID NO: 78.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having beta-galactosidase or galactanase activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nutrient Digestibility: The term "nutrient digestibility" means the fraction of a nutrient that disappears from the gastro-intestinal tract or a specified segment of the gastro-intestinal tract, e.g. the small intestine. Nutrient digestibility may be measured as the difference between what is administered to the subject and what. comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Operably linked: The term "operably linked" means a configuration in which a control sequence is placed at an appropriate position relative to the coding sequence of a polynucleotide such that the control sequence directs expression of the coding sequence.

Release×g galactose per kg soybean meal: The term "release×g galactose per kg soybean meal" means the amount of galactose in grams which is released into the supernatant after soybean meal has been incubation with an enzyme. For the purpose of the present invention, the release of galactose per kg soybean meal may be determined when performed under the reaction conditions 20 mg galactanase and 20 mg beta-galactosidase per kg soybean meal in 10% w/v 0.1M citric acid-phosphate buffer pH 6.5 incubating at 40° C. for 2 hours as described in the Galactose SBM Assay herein.

In a more detailed embodiment, a 10 w/v % slurry of soybean meal is prepared from soybean meal milled to a 0.5 mm particle size and 0.1 M citric acid-phosphate buffer, pH 6.5±0.05. The incubation vessels with the 10 w/v % slurry of soybean meal is heated to a stable temperature of 40±2° C. while stirring. When a stable temperature had been achieved, the six D-(+)-galactose standards are added to the incubation vessels to in-vessel concentrations of 5, 2.5, 1.25, 0.625, 0.313 and 0.157 mg galactose per mL incubation volume. Each standard is incubated in duplicates. The diluted enzymes are then added to their respective incubation vessels in the volumes required to reach their desired concentrations (in mg EP/kg soybean meal). Each enzyme treatment is incubated in triplicates. Additionally, two times three incubation vessels are included without standards or enzyme treatments as blank treatments to obtain the baseline galactose concentration in the soybean meal slurry. The incubation vessels are incubated at 40±2° C., while stirring for 2 hours. After incubation the vessels are centrifuged at 1500 g at 5° C. for 15 minutes. The supernatants are then analyzed in an assay based on the Raffinose/Galactose kit from Megazyme (product name K-RAFGA) and the concentration of galactose is then calculated as described in the Galactose SBM Assay herein.

Plant based material: The term "plant based material" means that the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labelled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having beta-galactosidase or galactanase activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having galactanase or beta-galactosidase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. In one aspect, the galactanase variants of the present invention have at least 60%, such as at least 70%, at least 75%, at least 80%, at least 85%, at least 90%, at least 95% or at least 100% of the galactanase activity of the polypeptide of SEQ ID NO: 3. In one aspect, the beta-galactosidase variants of the present invention have at least 60%, such as at least 70%, at least 75%, at least 80%, at least 85%, at least 90%, at least 95% or at least 100% of the beta-galactosidase activity of the polypeptide of SEQ ID NO: 42.

Nomenclature

For purposes of the present invention, the nomenclature [Y/F] means that the amino acid at this position may be a tyrosine (Try, Y) or a phenylalanine (Phe, F). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Beta-galactosidase is a glycoside hydrolase enzyme that hydrolyses the terminal non-reducing β-D-galactose residues in β-D-galactosides, such as lactose, oligosaccharides, glycolipids, and glycoproteins that is present in, e.g. legumes, vegetables, grains, cereals and the like. Galactanase is a glycoside hydrolase enzyme that hydrolyses the endo galactosidic linkages in type I arabinogalactans.

The inventors have found that beta-galactosidases from glycoside hydrolase family 42 (herein referred to as GH42) in combination with one or more GH53 galactanases are surprisingly good at releasing galactose by degrading galactan polymers found in the pectin of legumes, such as soybean. The use of a single enzyme class does not result in a significant release of galactose.

Whilst both Shipkowski et at and Tabachnikov et al disclose the combination of a beta-galactosidase and galactanase, neither the combination of LacA and GalA or the combination of GanB and GanA release the concentration of galactose as the combination of enzymes disclosed in the present invention (see example 14). Further, neither GalA or GanA comprise the motif GV[T/M]PD[W/M]VQ[I/V]GNE (SEQ ID NO: 81) or the motif WADP[A/G]xQxKPxAW (SEQ ID NO: 82).

The degradation of galactan can be measured as the amount of galactose released into the supernatant when e.g. soybean meal is treated with a GH42 beta-galactosidases and a GH53 galactanase. Increased amounts of solubilisation will result in more galactose being released which can be detected using e.g. the Galactose SBM Assay method as described herein.

Compositions Comprising GH42 Beta-Galactosidases and GH53 Galactanases

Thus in a first aspect, the invention relates to a composition comprising one or more GH53 polypeptides having galactanase activity and one or more GH42 polypeptides having beta-galactosidase activity.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82).

In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In one embodiment, the GH42 polypeptide comprises the motif DW[K/R]RF[V/I]T[A/D]Q[T/M] (SEQ ID NO: 83). In one preferred embodiment, the GH53 polypeptide comprises the motif GV[T/M]PD[W/M]VQ[I/V]GNE (SEQ ID NO: 81) and the GH42 polypeptide comprises the motif DW[K/R]RF[V/I]T[A/D]Q[T/M] (SEQ ID NO: 83). In one preferred embodiment, the GH53 polypeptide comprises the motif WADP[A/G]xQxKPxAW (SEQ ID NO: 82) and the GH42 polypeptide comprises the motif DW[K/R]RF[V/I]T[A/D]Q[T/M] (SEQ ID NO: 83). In a more preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82) and the GH42 polypeptide comprises the motif DW[K/R]RF[V/I]T[A/D]Q[T/M] (SEQ ID NO: 83).

In another embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment, the GH53 polypeptide having galactanase activity is obtained or obtainable from the taxonomic order Bacillales, preferably the taxonomic family Paenibacillaceae. In one embodiment, the GH42 polypeptide having beta-galactosidase activity is obtained or obtainable from the taxonomic order Bacillales. In one embodiment, the GH53 polypeptide having galactanase activity is obtained or obtainable from the taxonomic family Paenibacillaceae and the GH42 polypeptide having beta-galactosidase activity is obtained or obtainable from the taxonomic order Bacillales.

In an embodiment, the invention relates to a composition comprising one or more GH53 polypeptides having galactanase activity and one or more GH42 polypeptides having beta-galactosidase activity, wherein:
  (a) the GH53 polypeptide comprises the motif GV[T/M]PD[W/M]VQ[I/V]GNE (SEQ ID NO: 81) and/or the motif WADP[A/G]xQxKPxAW (SEQ ID NO: 82); and
  (b) the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide having galactanase activity is obtained or obtainable from the taxonomic order Bacillales, preferably the taxonomic family Paenibacillaceae. In one embodiment, the GH42 polypeptide having beta-galactosidase activity is obtained or obtainable from the taxonomic order Bacillales. In one embodiment, the GH53 polypeptide having galactanase activity is obtained or obtainable from the taxonomic family Paenibacillaceae and the GH42 polypeptide having beta-galactosidase activity is obtained or obtainable from the taxonomic order Bacillales.

In an embodiment, the invention relates to a composition comprising one or more GH53 polypeptides having galactanase activity and one or more GH42 polypeptides having beta-galactosidase activity, wherein:
  (a) the GH42 polypeptide comprises the motif DW[K/R]RF[V/I]T[A/D]Q[T/M] (SEQ ID NO: 83); and
  (b) the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide having galactanase activity is obtained or obtainable from the taxonomic order Bacillales, preferably the taxonomic family Paenibacillaceae. In one embodiment, the GH42 polypeptide having beta-galactosidase activity is obtained or obtainable from the taxonomic order Bacillales. In one embodiment, the GH53 polypeptide having galactanase activity is obtained or obtainable from the taxonomic family Paenibacillaceae and the GH42 polypeptide having beta-galactosidase activity is obtained or obtainable from the taxonomic order Bacillales.

In an embodiment, the invention relates to a composition comprising one or more GH53 polypeptides having galactanase activity and one or more GH42 polypeptides having beta-galactosidase activity, wherein:
  (a) the GH53 polypeptide comprises the motif GV[T/M]PD[W/M]VQ[I/V]GNE (SEQ ID NO: 81) and/or the motif WADP[A/G]xQxKPxAW (SEQ ID NO: 82);
  (b) the GH42 polypeptide comprises the motif DW[K/R]RF[V/I]T[A/D]Q[T/M] (SEQ ID NO: 83); and
  (c) the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein.

In one embodiment, the coating comprises a salt coating and a wax coating as described herein.

In one embodiment, the GH53 polypeptide having galactanase activity is obtained or obtainable from the taxonomic order Bacillales, preferably the taxonomic family Paenibacillaceae. In one embodiment, the GH42 polypeptide having beta-galactosidase activity is obtained or obtainable from the taxonomic order Bacillales. In one embodiment, the GH53 polypeptide having galactanase activity is obtained or obtainable from the taxonomic family Paenibacillaceae and the GH42 polypeptide having beta-galactosidase activity is obtained or obtainable from the taxonomic order Bacillales.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
 (a) a polypeptide having at least 80% sequence identity to the polypeptide of SEQ ID NO: 3;
 (b) a polypeptide having at least 80% sequence identity to the polypeptide of SEQ ID NO: 7;
 (c) a polypeptide having at least 80% sequence identity to the polypeptide of SEQ ID NO: 11;
 (d) a polypeptide having at least 80% sequence identity to the polypeptide of SEQ ID NO: 15;
 (e) a polypeptide having at least 80% sequence identity to the polypeptide of SEQ ID NO: 19;
 (f) a polypeptide having at least 80% sequence identity to the polypeptide of SEQ ID NO: 23;
 (g) a polypeptide having at least 80% sequence identity to the polypeptide of SEQ ID NO: 27;
 (h) a polypeptide having at least 80% sequence identity to the polypeptide of SEQ ID NO: 31;
 (i) a polypeptide having at least 80% sequence identity to the polypeptide of SEQ ID NO: 35;
 (j) a polypeptide having at least 80% sequence identity to the polypeptide of SEQ ID NO: 39;
 (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (l) a polypeptide comprising the polypeptide of (a), (b), (c), (d), (e), (f), (g), (h), (i), (j) or (k) and a N-terminal and/or C-terminal His-tag and/or HQ-tag;
 (m) a polypeptide comprising the polypeptide of (a), (b), (c), (d), (e), (f), (g), (h), (i), (j) or (k) and a N-terminal and/or C-terminal extension of between 1 and 10 amino acids; and
 (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81).

In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
 (a) a polypeptide having at least 85% sequence identity to the polypeptide of SEQ ID NO: 3;
 (b) a polypeptide having at least 85% sequence identity to the polypeptide of SEQ ID NO: 7;
 (c) a polypeptide having at least 85% sequence identity to the polypeptide of SEQ ID NO: 11;
 (d) a polypeptide having at least 85% sequence identity to the polypeptide of SEQ ID NO: 15;
 (e) a polypeptide having at least 85% sequence identity to the polypeptide of SEQ ID NO: 19;
 (f) a polypeptide having at least 85% sequence identity to the polypeptide of SEQ ID NO: 23;
 (g) a polypeptide having at least 85% sequence identity to the polypeptide of SEQ ID NO: 27;
 (h) a polypeptide having at least 85% sequence identity to the polypeptide of SEQ ID NO: 31;
 (i) a polypeptide having at least 85% sequence identity to the polypeptide of SEQ ID NO: 35;
 (j) a polypeptide having at least 85% sequence identity to the polypeptide of SEQ ID NO: 39;
 (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (l) a polypeptide comprising the polypeptide of (a), (b), (c), (d), (e), (f), (g), (h), (i), (j) or (k) and a N-terminal and/or C-terminal His-tag and/or HQ-tag;
 (m) a polypeptide comprising the polypeptide of (a), (b), (c), (d), (e), (f), (g), (h), (i), (j) or (k) and a N-terminal and/or C-terminal extension of between 1 and 10 amino acids; and
 (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
  (a) a polypeptide having at least 90% sequence identity to the polypeptide of SEQ ID NO: 3;
  (b) a polypeptide having at least 90% sequence identity to the polypeptide of SEQ ID NO: 7;
  (c) a polypeptide having at least 90% sequence identity to the polypeptide of SEQ ID NO: 11;
  (d) a polypeptide having at least 90% sequence identity to the polypeptide of SEQ ID NO: 15;
  (e) a polypeptide having at least 90% sequence identity to the polypeptide of SEQ ID NO: 19;
  (f) a polypeptide having at least 90% sequence identity to the polypeptide of SEQ ID NO: 23;
  (g) a polypeptide having at least 90% sequence identity to the polypeptide of SEQ ID NO: 27;
  (h) a polypeptide having at least 90% sequence identity to the polypeptide of SEQ ID NO: 31;
  (i) a polypeptide having at least 90% sequence identity to the polypeptide of SEQ ID NO: 35;
  (j) a polypeptide having at least 90% sequence identity to the polypeptide of SEQ ID NO: 39;
  (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (l) a polypeptide comprising the polypeptide of (a), (b), (c), (d), (e), (f), (g), (h), (i), (j) or (k) and a N-terminal and/or C-terminal His-tag and/or HQ-tag;
  (m) a polypeptide comprising the polypeptide of (a), (b), (c), (d), (e), (f), (g), (h), (i), (j) or (k) and a N-terminal and/or C-terminal extension of between 1 and 10 amino acids; and
  (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
  (a) a polypeptide having at least 95% sequence identity to the polypeptide of SEQ ID NO: 3;
  (b) a polypeptide having at least 95% sequence identity to the polypeptide of SEQ ID NO: 7;
  (c) a polypeptide having at least 95% sequence identity to the polypeptide of SEQ ID NO: 11;
  (d) a polypeptide having at least 95% sequence identity to the polypeptide of SEQ ID NO: 15;
  (e) a polypeptide having at least 95% sequence identity to the polypeptide of SEQ ID NO: 19;
  (f) a polypeptide having at least 95% sequence identity to the polypeptide of SEQ ID NO: 23;
  (g) a polypeptide having at least 95% sequence identity to the polypeptide of SEQ ID NO: 27;
  (h) a polypeptide having at least 95% sequence identity to the polypeptide of SEQ ID NO: 31;
  (i) a polypeptide having at least 95% sequence identity to the polypeptide of SEQ ID NO: 35;
  (j) a polypeptide having at least 95% sequence identity to the polypeptide of SEQ ID NO: 39;
  (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (l) a polypeptide comprising the polypeptide of (a), (b), (c), (d), (e), (f), (g), (h), (i), (j) or (k) and a N-terminal and/or C-terminal His-tag and/or HQ-tag;
  (m) a polypeptide comprising the polypeptide of (a), (b), (c), (d), (e), (f), (g), (h), (i), (j) or (k) and a N-terminal and/or C-terminal extension of between 1 and 10 amino acids; and (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH42 polypeptide is selected from the group consisting of:

(a) a polypeptide having at least 80% sequence identity to the polypeptide of SEQ ID NO: 42;
(b) a polypeptide having at least 80% sequence identity to the polypeptide of SEQ ID NO: 44;
(c) a polypeptide having at least 80% sequence identity to the polypeptide of SEQ ID NO: 47;
(d) a polypeptide having at least 80% sequence identity to the polypeptide of SEQ ID NO: 50;
(e) a polypeptide having at least 80% sequence identity to the polypeptide of SEQ ID NO: 53;
(f) a polypeptide having at least 80% sequence identity to the polypeptide of SEQ ID NO: 56;
(g) a polypeptide having at least 80% sequence identity to the polypeptide of SEQ ID NO: 59;
(h) a polypeptide having at least 80% sequence identity to the polypeptide of SEQ ID NO: 62;
(i) a polypeptide having at least 80% sequence identity to the polypeptide of SEQ ID NO: 65;
(j) a polypeptide having at least 80% sequence identity to the polypeptide of SEQ ID NO: 68;
(k) a polypeptide having at least 80% sequence identity to the polypeptide of SEQ ID NO: 71;
(l) a polypeptide having at least 80% sequence identity to the polypeptide of SEQ ID NO: 74;
(m) a polypeptide having at least 80% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH42 polypeptide is selected from the group consisting of:

(a) a polypeptide having at least 85% sequence identity to the polypeptide of SEQ ID NO: 42;
(b) a polypeptide having at least 85% sequence identity to the polypeptide of SEQ ID NO: 44;
(c) a polypeptide having at least 85% sequence identity to the polypeptide of SEQ ID NO: 47;
(d) a polypeptide having at least 85% sequence identity to the polypeptide of SEQ ID NO: 50;
(e) a polypeptide having at least 85% sequence identity to the polypeptide of SEQ ID NO: 53;
(f) a polypeptide having at least 85% sequence identity to the polypeptide of SEQ ID NO: 56;
(g) a polypeptide having at least 85% sequence identity to the polypeptide of SEQ ID NO: 59;
(h) a polypeptide having at least 85% sequence identity to the polypeptide of SEQ ID NO: 62;
(i) a polypeptide having at least 85% sequence identity to the polypeptide of SEQ ID NO: 65;
(j) a polypeptide having at least 85% sequence identity to the polypeptide of SEQ ID NO: 68;
(k) a polypeptide having at least 85% sequence identity to the polypeptide of SEQ ID NO: 71;

(l) a polypeptide having at least 85% sequence identity to the polypeptide of SEQ ID NO: 74;
(m) a polypeptide having at least 85% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH42 polypeptide is selected from the group consisting of:
(a) a polypeptide having at least 90% sequence identity to the polypeptide of SEQ ID NO: 42;
(b) a polypeptide having at least 90% sequence identity to the polypeptide of SEQ ID NO: 44;
(c) a polypeptide having at least 90% sequence identity to the polypeptide of SEQ ID NO: 47;
(d) a polypeptide having at least 90% sequence identity to the polypeptide of SEQ ID NO: 50;
(e) a polypeptide having at least 90% sequence identity to the polypeptide of SEQ ID NO: 53;
(f) a polypeptide having at least 90% sequence identity to the polypeptide of SEQ ID NO: 56;
(g) a polypeptide having at least 90% sequence identity to the polypeptide of SEQ ID NO: 59;
(h) a polypeptide having at least 90% sequence identity to the polypeptide of SEQ ID NO: 62;
(i) a polypeptide having at least 90% sequence identity to the polypeptide of SEQ ID NO: 65;
(j) a polypeptide having at least 90% sequence identity to the polypeptide of SEQ ID NO: 68;
(k) a polypeptide having at least 90% sequence identity to the polypeptide of SEQ ID NO: 71;
(l) a polypeptide having at least 90% sequence identity to the polypeptide of SEQ ID NO: 74;
(m) a polypeptide having at least 90% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH42 polypeptide is selected from the group consisting of:
  (a) a polypeptide having at least 95% sequence identity to the polypeptide of SEQ ID NO: 42;
  (b) a polypeptide having at least 95% sequence identity to the polypeptide of SEQ ID NO: 44;
  (c) a polypeptide having at least 95% sequence identity to the polypeptide of SEQ ID NO: 47;
  (d) a polypeptide having at least 95% sequence identity to the polypeptide of SEQ ID NO: 50;
  (e) a polypeptide having at least 95% sequence identity to the polypeptide of SEQ ID NO: 53;
  (f) a polypeptide having at least 95% sequence identity to the polypeptide of SEQ ID NO: 56;
  (g) a polypeptide having at least 95% sequence identity to the polypeptide of SEQ ID NO: 59;
  (h) a polypeptide having at least 95% sequence identity to the polypeptide of SEQ ID NO: 62;
  (i) a polypeptide having at least 95% sequence identity to the polypeptide of SEQ ID NO: 65;
  (j) a polypeptide having at least 95% sequence identity to the polypeptide of SEQ ID NO: 68;
  (k) a polypeptide having at least 95% sequence identity to the polypeptide of SEQ ID NO: 71;
  (l) a polypeptide having at least 95% sequence identity to the polypeptide of SEQ ID NO: 74;
  (m) a polypeptide having at least 95% sequence identity to the polypeptide of SEQ ID NO: 77;
  (n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
  (p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
  (q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
  (a) a polypeptide having at least 80% sequence identity to the polypeptide of SEQ ID NO: 3;
  (b) a polypeptide having at least 80% sequence identity to the polypeptide of SEQ ID NO: 7;
  (c) a polypeptide having at least 80% sequence identity to the polypeptide of SEQ ID NO: 11;
  (d) a polypeptide having at least 80% sequence identity to the polypeptide of SEQ ID NO: 15;
  (e) a polypeptide having at least 80% sequence identity to the polypeptide of SEQ ID NO: 19;
  (f) a polypeptide having at least 80% sequence identity to the polypeptide of SEQ ID NO: 23;
  (g) a polypeptide having at least 80% sequence identity to the polypeptide of SEQ ID NO: 27;
  (h) a polypeptide having at least 80% sequence identity to the polypeptide of SEQ ID NO: 31;
  (i) a polypeptide having at least 80% sequence identity to the polypeptide of SEQ ID NO: 35;
  (j) a polypeptide having at least 80% sequence identity to the polypeptide of SEQ ID NO: 39;
  (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (l) a polypeptide comprising the polypeptide of (a), (b), (c), (d), (e), (f), (g), (h), (i), (j) or (k) and a N-terminal and/or C-terminal His-tag and/or HQ-tag;
  (m) a polypeptide comprising the polypeptide of (a), (b), (c), (d), (e), (f), (g), (h), (i), (j) or (k) and a N-terminal and/or C-terminal extension of between 1 and 10 amino acids; and
  (n) a fragment of the polypeptide of (a), (b), (c), (d), (e), (f), (g), (h), (i), (j), (k) or (l) having galactanase activity and having at least 90% of the length of the mature polypeptide;
and wherein the GH42 polypeptide is selected from the group consisting of:
  (a) a polypeptide having at least 80% sequence identity to the polypeptide of SEQ ID NO: 42;
  (b) a polypeptide having at least 80% sequence identity to the polypeptide of SEQ ID NO: 44;
  (c) a polypeptide having at least 80% sequence identity to the polypeptide of SEQ ID NO: 47;
  (d) a polypeptide having at least 80% sequence identity to the polypeptide of SEQ ID NO: 50;
  (e) a polypeptide having at least 80% sequence identity to the polypeptide of SEQ ID NO: 53;

(f) a polypeptide having at least 80% sequence identity to the polypeptide of SEQ ID NO: 56;
(g) a polypeptide having at least 80% sequence identity to the polypeptide of SEQ ID NO: 59;
(h) a polypeptide having at least 80% sequence identity to the polypeptide of SEQ ID NO: 62;
(i) a polypeptide having at least 80% sequence identity to the polypeptide of SEQ ID NO: 65;
(j) a polypeptide having at least 80% sequence identity to the polypeptide of SEQ ID NO: 68;
(k) a polypeptide having at least 80% sequence identity to the polypeptide of SEQ ID NO: 71;
(l) a polypeptide having at least 80% sequence identity to the polypeptide of SEQ ID NO: 74;
(m) a polypeptide having at least 80% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
(a) a polypeptide having at least 85% sequence identity to the polypeptide of SEQ ID NO: 3;
(b) a polypeptide having at least 85% sequence identity to the polypeptide of SEQ ID NO: 7;
(c) a polypeptide having at least 85% sequence identity to the polypeptide of SEQ ID NO: 11;
(d) a polypeptide having at least 85% sequence identity to the polypeptide of SEQ ID NO: 15;
(e) a polypeptide having at least 85% sequence identity to the polypeptide of SEQ ID NO: 19;
(f) a polypeptide having at least 85% sequence identity to the polypeptide of SEQ ID NO: 23;
(g) a polypeptide having at least 85% sequence identity to the polypeptide of SEQ ID NO: 27;
(h) a polypeptide having at least 85% sequence identity to the polypeptide of SEQ ID NO: 31;
(i) a polypeptide having at least 85% sequence identity to the polypeptide of SEQ ID NO: 35;
(j) a polypeptide having at least 85% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide;

and wherein the GH42 polypeptide is selected from the group consisting of:
(a) a polypeptide having at least 85% sequence identity to the polypeptide of SEQ ID NO: 42;
(b) a polypeptide having at least 85% sequence identity to the polypeptide of SEQ ID NO: 44;
(c) a polypeptide having at least 85% sequence identity to the polypeptide of SEQ ID NO: 47;
(d) a polypeptide having at least 85% sequence identity to the polypeptide of SEQ ID NO: 50;
(e) a polypeptide having at least 85% sequence identity to the polypeptide of SEQ ID NO: 53;
(f) a polypeptide having at least 85% sequence identity to the polypeptide of SEQ ID NO: 56;
(g) a polypeptide having at least 85% sequence identity to the polypeptide of SEQ ID NO: 59;
(h) a polypeptide having at least 85% sequence identity to the polypeptide of SEQ ID NO: 62;
(i) a polypeptide having at least 85% sequence identity to the polypeptide of SEQ ID NO: 65;
(j) a polypeptide having at least 85% sequence identity to the polypeptide of SEQ ID NO: 68;

(k) a polypeptide having at least 85% sequence identity to the polypeptide of SEQ ID NO: 71;
(l) a polypeptide having at least 85% sequence identity to the polypeptide of SEQ ID NO: 74;
(m) a polypeptide having at least 85% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 7;
(c) a polypeptide having at least 90% sequence identity to the polypeptide of SEQ ID NO: 11;
(d) a polypeptide having at least 90% sequence identity to the polypeptide of SEQ ID NO: 15;
(e) a polypeptide having at least 90% sequence identity to the polypeptide of SEQ ID NO: 19;
(f) a polypeptide having at least 90% sequence identity to the polypeptide of SEQ ID NO: 23;
(g) a polypeptide having at least 90% sequence identity to the polypeptide of SEQ ID NO: 27;
(h) a polypeptide having at least 90% sequence identity to the polypeptide of SEQ ID NO: 31;
(i) a polypeptide having at least 90% sequence identity to the polypeptide of SEQ ID NO: 35;
(j) a polypeptide having at least 90% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide;
and wherein the GH42 polypeptide is selected from the group consisting of:
(a) a polypeptide having at least 90% sequence identity to the polypeptide of SEQ ID NO: 42;
(b) a polypeptide having at least 90% sequence identity to the polypeptide of SEQ ID NO: 44;
(c) a polypeptide having at least 90% sequence identity to the polypeptide of SEQ ID NO: 47;
(d) a polypeptide having at least 90% sequence identity to the polypeptide of SEQ ID NO: 50;
(e) a polypeptide having at least 90% sequence identity to the polypeptide of SEQ ID NO: 53;
(f) a polypeptide having at least 90% sequence identity to the polypeptide of SEQ ID NO: 56;
(g) a polypeptide having at least 90% sequence identity to the polypeptide of SEQ ID NO: 59;
(h) a polypeptide having at least 90% sequence identity to the polypeptide of SEQ ID NO: 62;
(i) a polypeptide having at least 90% sequence identity to the polypeptide of SEQ ID NO: 65;
(j) a polypeptide having at least 90% sequence identity to the polypeptide of SEQ ID NO: 68;
(k) a polypeptide having at least 90% sequence identity to the polypeptide of SEQ ID NO: 71;
(l) a polypeptide having at least 90% sequence identity to the polypeptide of SEQ ID NO: 74;
(m) a polypeptide having at least 90% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:
(a) a polypeptide having at least 95% sequence identity to the polypeptide of SEQ ID NO: 3;
(b) a polypeptide having at least 95% sequence identity to the polypeptide of SEQ ID NO: 7;
(c) a polypeptide having at least 95% sequence identity to the polypeptide of SEQ ID NO: 11;
(d) a polypeptide having at least 95% sequence identity to the polypeptide of SEQ ID NO: 15;
(e) a polypeptide having at least 95% sequence identity to the polypeptide of SEQ ID NO: 19;
(f) a polypeptide having at least 95% sequence identity to the polypeptide of SEQ ID NO: 23;
(g) a polypeptide having at least 95% sequence identity to the polypeptide of SEQ ID NO: 27;
(h) a polypeptide having at least 95% sequence identity to the polypeptide of SEQ ID NO: 31;
(i) a polypeptide having at least 95% sequence identity to the polypeptide of SEQ ID NO: 35;
(j) a polypeptide having at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide;
and wherein the GH42 polypeptide is selected from the group consisting of:
(a) a polypeptide having at least 95% sequence identity to the polypeptide of SEQ ID NO: 42;
(b) a polypeptide having at least 95% sequence identity to the polypeptide of SEQ ID NO: 44;
(c) a polypeptide having at least 95% sequence identity to the polypeptide of SEQ ID NO: 47;
(d) a polypeptide having at least 95% sequence identity to the polypeptide of SEQ ID NO: 50;
(e) a polypeptide having at least 95% sequence identity to the polypeptide of SEQ ID NO: 53;
(f) a polypeptide having at least 95% sequence identity to the polypeptide of SEQ ID NO: 56;
(g) a polypeptide having at least 95% sequence identity to the polypeptide of SEQ ID NO: 59;
(h) a polypeptide having at least 95% sequence identity to the polypeptide of SEQ ID NO: 62;
(i) a polypeptide having at least 95% sequence identity to the polypeptide of SEQ ID NO: 65;
(j) a polypeptide having at least 95% sequence identity to the polypeptide of SEQ ID NO: 68;
(k) a polypeptide having at least 95% sequence identity to the polypeptide of SEQ ID NO: 71;
(l) a polypeptide having at least 95% sequence identity to the polypeptide of SEQ ID NO: 74;
(m) a polypeptide having at least 95% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;

(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and (q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 81). In an alternative embodiment, the GH53 polypeptide comprises the motif WADP[A/G]xQxKPxAW (SEQ ID NO: 82). In a preferred embodiment, the GH53 polypeptide comprises the motifs GV[T/M]PD[W/M]VQ[I/V]GNE (SEQ ID NO: 81) and WADP[A/G]xQxKPxAW (SEQ ID NO: 82).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH42 polypeptides having beta-galactosidase activity, wherein the GH53 polypeptide is selected from the group consisting of:

(a) a polypeptide comprising or consisting of amino acids 1 to 316 of SEQ ID NO: 3;
(b) a polypeptide comprising or consisting of amino acids 1 to 318 of SEQ ID NO: 7;
(c) a polypeptide comprising or consisting of amino acids 1 to 316 of SEQ ID NO: 11;
(d) a polypeptide comprising or consisting of amino acids 1 to 316 of SEQ ID NO: 15;
(e) a polypeptide comprising or consisting of amino acids 1 to 316 of SEQ ID NO: 19;
(f) a polypeptide comprising or consisting of amino acids 1 to 316 of SEQ ID NO: 23;
(g) a polypeptide comprising or consisting of amino acids 1 to 516 of SEQ ID NO: 27;
(h) a polypeptide comprising or consisting of amino acids 1 to 317 of SEQ ID NO: 31;
(i) a polypeptide comprising or consisting of amino acids 1 to 316 of SEQ ID NO: 35;
(j) a polypeptide comprising or consisting of amino acids 1 to 316 of SEQ ID NO: 39; and
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises 1, 2, 3, 4, 5, 6, 7, 8, 9 or 10 amino acid substitutions, preferably conservative substitutions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide;

and wherein the GH42 polypeptide is selected from the group consisting of:

(a) a polypeptide comprising or consisting of amino acids 1 to 685 of SEQ ID NO: 42;
(b) a polypeptide comprising or consisting of amino acids 1 to 688 of SEQ ID NO: 44;
(c) a polypeptide comprising or consisting of amino acids 1 to 687 of SEQ ID NO: 47;
(d) a polypeptide comprising or consisting of amino acids 1 to 654 of SEQ ID NO: 50;
(e) a polypeptide comprising or consisting of amino acids 1 to 687 of SEQ ID NO: 53;
(f) a polypeptide comprising or consisting of amino acids 1 to 686 of SEQ ID NO: 56;
(g) a polypeptide comprising or consisting of amino acids 1 to 688 of SEQ ID NO: 59;
(h) a polypeptide comprising or consisting of amino acids 1 to 691 of SEQ ID NO: 62;
(i) a polypeptide comprising or consisting of amino acids 1 to 690 of SEQ ID NO: 65;
(j) a polypeptide comprising or consisting of amino acids 1 to 689 of SEQ ID NO: 68;
(k) a polypeptide comprising or consisting of amino acids 1 to 685 of SEQ ID NO: 71;
(l) a polypeptide comprising or consisting of amino acids 1 to 685 of SEQ ID NO: 74;
(m) a polypeptide comprising or consisting of amino acids 1 to 686 of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises 1, 2, 3, 4, 5, 6, 7, 8, 9 or 10 amino acid substitutions, preferably conservative substitutions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag;
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m), (n) or (o) having galactanase activity and having at least 90% of the length of the mature polypeptide.

In one embodiment to any part of the first aspect, the composition (e.g. granule) comprises at least 0.01 mg of polypeptide (enzyme protein) per kilogram of composition, such as at least 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition. In one embodiment, the composition comprises at most 250 g of polypeptide per kilogram of composition, such as at most 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 250 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition and 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof. In one embodiment to any part of the first aspect, the ratio of galactanase to beta-galactosidase is in the range of 100:1 to 1:100 galactanase: beta-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: beta-galactosidase.

In one embodiment to any part of the first aspect, the composition (e.g. granule) comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the first aspect, the composition (e.g. granule) comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment to any part of the first aspect, the composition (e.g. granule) comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

Combinations

Specific combinations of GH53 polypeptides having galactanase activity and GH42 polypeptides having beta-galactosidase activity of the first aspect of the invention are as follows.

In an embodiment, the composition of the invention comprises the GH53 polypeptide of SEQ ID NO: 3 and the GH42 polypeptide of SEQ ID NO: 42. In an embodiment, the composition of the invention comprises the GH53 polypeptide of SEQ ID NO: 3 and the GH42 polypeptide of SEQ ID NO: 44. In an embodiment, the composition of the invention comprises the GH53 polypeptide of SEQ ID NO: 3 and the GH42 polypeptide of SEQ ID NO: 47. In an embodiment, the composition of the invention comprises the GH53 polypeptide of SEQ ID NO: 3 and the GH42 polypeptide of SEQ ID NO: 50. In an embodiment, the composition of the invention comprises the GH53 polypeptide of SEQ ID NO: 3 and the GH42 polypeptide of SEQ ID NO: 53. In an embodiment, the composition of the invention comprises the GH53 polypeptide of SEQ ID NO: 3 and the GH42 polypeptide of SEQ ID NO: 56. In an embodiment, the composition of the invention comprises the GH53 polypeptide of SEQ ID NO: 3 and the GH42 polypeptide of SEQ ID NO: 59. In an embodiment, the composition of the invention comprises the GH53 polypeptide of SEQ ID NO: 3 and the GH42 polypeptide of SEQ ID NO: 62. In an embodiment, the composition of the invention comprises the GH53 polypeptide of SEQ ID NO: 3 and the GH42 polypeptide of SEQ ID NO: 65. In an embodiment, the composition of the invention comprises the GH53 polypeptide of SEQ ID NO: 3 and the GH42 polypeptide of SEQ ID NO: 68. In an embodiment, the composition of the invention comprises the GH53 polypeptide of SEQ ID NO: 3 and the GH42 polypeptide of SEQ ID NO: 71. In an embodiment, the composition of the invention comprises the GH53 polypeptide of SEQ ID NO: 3 and the GH42 polypeptide of SEQ ID NO: 74. In an embodiment, the composition of the invention comprises the GH53 polypeptide of SEQ ID NO: 3 and the GH42 polypeptide of SEQ ID NO: 77.

In an embodiment, the composition of the invention comprises the GH53 polypeptide of SEQ ID NO: 7 and the GH42 polypeptide of SEQ ID NO: 42. In an embodiment, the composition of the invention comprises the GH53 polypeptide of SEQ ID NO: 7 and the GH42 polypeptide of SEQ ID NO: 44. In an embodiment, the composition of the invention comprises the GH53 polypeptide of SEQ ID NO: 7 and the GH42 polypeptide of SEQ ID NO: 47. In an embodiment, the composition of the invention comprises the GH53 polypeptide of SEQ ID NO: 7 and the GH42 polypeptide of SEQ ID NO: 50. In an embodiment, the composition of the invention comprises the GH53 polypeptide of SEQ ID NO: 7 and the GH42 polypeptide of SEQ ID NO: 53. In an embodiment, the composition of the invention comprises the GH53 polypeptide of SEQ ID NO: 7 and the GH42 polypeptide of SEQ ID NO: 56. In an embodiment, the composition of the invention comprises the GH53 polypeptide of SEQ ID NO: 7 and the GH42 polypeptide of SEQ ID NO: 59. In an embodiment, the composition of the invention comprises the GH53 polypeptide of SEQ ID NO: 7 and the GH42 polypeptide of SEQ ID NO: 62. In an embodiment, the composition of the invention comprises the GH53 polypeptide of SEQ ID NO: 7 and the GH42 polypeptide of SEQ ID NO: 65. In an embodiment, the composition of the invention comprises the GH53 polypeptide of SEQ ID NO: 7 and the GH42 polypeptide of SEQ ID NO: 68. In an embodiment, the composition of the invention comprises the GH53 polypeptide of SEQ ID NO: 7 and the GH42 polypeptide of SEQ ID NO: 71. In an embodiment, the composition of the invention comprises the GH53 polypeptide of SEQ ID NO: 7 and the GH42 polypeptide of SEQ ID NO: 74. In an embodiment, the composition of the invention comprises the GH53 polypeptide of SEQ ID NO: 7 and the GH42 polypeptide of SEQ ID NO: 77.

In an embodiment, the composition of the invention comprises the GH53 polypeptide of SEQ ID NO: 11 and the GH42 polypeptide of SEQ ID NO: 42. In an embodiment, the composition of the invention comprises the GH53 polypeptide of SEQ ID NO: 11 and the GH42 polypeptide of SEQ ID NO: 44. In an embodiment, the composition of the invention comprises the GH53 polypeptide of SEQ ID NO: 11 and the GH42 polypeptide of SEQ ID NO: 47. In an embodiment, the composition of the invention comprises the GH53 polypeptide of SEQ ID NO: 11 and the GH42 polypeptide of SEQ ID NO: 50. In an embodiment, the composition of the invention comprises the GH53 polypeptide of SEQ ID NO: 11 and the GH42 polypeptide of SEQ ID NO: 53. In an embodiment, the composition of the invention comprises the GH53 polypeptide of SEQ ID NO: 11 and the GH42 polypeptide of SEQ ID NO: 56. In an embodiment, the composition of the invention comprises the GH53 polypeptide of SEQ ID NO: 11 and the GH42 polypeptide of SEQ ID NO: 59. In an embodiment, the composition of the invention comprises the GH53 polypeptide of SEQ ID NO: 11 and the GH42 polypeptide of SEQ ID NO: 62. In an embodiment, the composition of the invention comprises the GH53 polypeptide of SEQ ID NO: 11 and the GH42 polypeptide of SEQ ID NO: 65. In an embodiment, the composition of the invention comprises the GH53 polypeptide of SEQ ID NO: 11 and the GH42 polypeptide of SEQ ID NO: 68. In an embodiment, the composition of the invention comprises the GH53 polypeptide of SEQ ID NO: 11 and the GH42 polypeptide of SEQ ID NO: 71. In an embodiment, the composition of the invention comprises the GH53 polypeptide of SEQ ID NO: 11 and the GH42 polypeptide of SEQ ID NO: 74. In an embodiment, the composition of the invention comprises the GH53 polypeptide of SEQ ID NO: 11 and the GH42 polypeptide of SEQ ID NO: 77.

In an embodiment, the composition of the invention comprises the GH53 polypeptide of SEQ ID NO: 15 and the GH42 polypeptide of SEQ ID NO: 42. In an embodiment, the composition of the invention comprises the GH53 polypeptide of SEQ ID NO: 15 and the GH42 polypeptide of SEQ ID NO: 44. In an embodiment, the composition of the invention comprises the GH53 polypeptide of SEQ ID NO: 15 and the GH42 polypeptide of SEQ ID NO: 47. In an embodiment, the composition of the invention comprises the GH53 polypeptide of SEQ ID NO: 15 and the GH42 polypeptide of SEQ ID NO: 50. In an embodiment, the composition of the invention comprises the GH53 polypeptide of SEQ ID NO: 15 and the GH42 polypeptide of SEQ ID NO: 53. In an embodiment, the composition of the invention comprises the GH53 polypeptide of SEQ ID NO: 15 and the GH42 polypeptide of SEQ ID NO: 56. In an embodiment, the composition of the invention comprises the GH53 polypeptide of SEQ ID NO: 15 and the GH42 polypeptide of SEQ ID NO: 59. In an embodiment, the composition of the invention comprises the GH53 polypeptide of SEQ ID NO: 15 and the GH42 polypeptide of SEQ ID NO: 62. In an embodiment, the composition of the invention comprises the GH53 polypeptide of SEQ ID NO: 15 and the GH42 polypeptide of SEQ ID NO: 65. In an embodiment, the composition of the invention comprises the GH53 polypeptide of SEQ ID NO: 15 and the GH42 polypeptide of SEQ ID NO: 68. In an embodiment, the composition of the invention comprises the GH53 polypeptide of SEQ ID NO: 15 and the GH42 polypeptide of SEQ ID NO: 71. In an embodiment, the composition of the invention comprises the GH53 polypeptide of SEQ ID NO: 15 and the GH42 polypeptide of SEQ ID NO: 74. In an embodiment, the composition of the invention comprises the GH53 polypeptide of SEQ ID NO: 15 and the GH42 polypeptide of SEQ ID NO: 77.

In an embodiment, the composition of the invention comprises the GH53 polypeptide of SEQ ID NO: 19 and the GH42 polypeptide of SEQ ID NO: 42. In an embodiment, the composition of the invention comprises the GH53 polypeptide of SEQ ID NO: 19 and the GH42 polypeptide of SEQ ID NO: 44. In an embodiment, the composition of the invention comprises the GH53 polypeptide of SEQ ID NO: 19 and the GH42 polypeptide of SEQ ID NO: 47. In an embodiment, the composition of the invention comprises the GH53 polypeptide of SEQ ID NO: 19 and the GH42 polypeptide of SEQ ID NO: 50. In an embodiment, the composition of the invention comprises the GH53 polypeptide of SEQ ID NO: 19 and the GH42 polypeptide of SEQ ID NO: 53. In an embodiment, the composition of the invention comprises the GH53 polypeptide of SEQ ID NO: 19 and the GH42 polypeptide of SEQ ID NO: 56. In an embodiment, the composition of the invention comprises the GH53 polypeptide of SEQ ID NO: 19 and the GH42 polypeptide of SEQ ID NO: 59. In an embodiment, the composition of the invention comprises the GH53 polypeptide of SEQ ID NO: 19 and the GH42 polypeptide of SEQ ID NO: 62. In an embodiment, the composition of the invention comprises the GH53 polypeptide of SEQ ID NO: 19 and the GH42 polypeptide of SEQ ID NO: 65. In an embodiment, the composition of the invention comprises the GH53 polypeptide of SEQ ID NO: 19 and the GH42 polypeptide of SEQ ID NO: 68. In an embodiment, the composition of the invention comprises the GH53 polypeptide of SEQ ID NO: 19 and the GH42 polypeptide of SEQ ID NO: 71. In an embodiment, the composition of the invention comprises the GH53 polypeptide of SEQ ID NO: 19 and the GH42 polypeptide of SEQ ID NO: 74. In an embodiment, the composition of the invention comprises the GH53 polypeptide of SEQ ID NO: 19 and the GH42 polypeptide of SEQ ID NO: 77.

In an embodiment, the composition of the invention comprises the GH53 polypeptide of SEQ ID NO: 23 and the GH42 polypeptide of SEQ ID NO: 42. In an embodiment, the composition of the invention comprises the GH53 polypeptide of SEQ ID NO: 23 and the GH42 polypeptide of SEQ ID NO: 44. In an embodiment, the composition of the invention comprises the GH53 polypeptide of SEQ ID NO: 23 and the GH42 polypeptide of SEQ ID NO: 47. In an embodiment, the composition of the invention comprises the GH53 polypeptide of SEQ ID NO: 23 and the GH42 polypeptide of SEQ ID NO: 50. In an embodiment, the composition of the invention comprises the GH53 polypeptide of SEQ ID NO: 23 and the GH42 polypeptide of SEQ ID NO: 53. In an embodiment, the composition of the invention comprises the GH53 polypeptide of SEQ ID NO: 23 and the GH42 polypeptide of SEQ ID NO: 56. In an embodiment, the composition of the invention comprises the GH53 polypeptide of SEQ ID NO: 23 and the GH42 polypeptide of SEQ ID NO: 59. In an embodiment, the composition of the invention comprises the GH53 polypeptide of SEQ ID NO: 23 and the GH42 polypeptide of SEQ ID NO: 62. In an embodiment, the composition of the invention comprises the GH53 polypeptide of SEQ ID NO: 23 and the GH42 polypeptide of SEQ ID NO: 65. In an embodiment, the composition of the invention comprises the GH53 polypeptide of SEQ ID NO: 23 and the GH42 polypeptide of SEQ ID NO: 68. In an embodiment, the composition of the invention comprises the GH53 polypeptide of SEQ ID NO: 23 and the GH42 polypeptide of SEQ ID NO: 71. In an embodiment, the composition of the invention comprises the GH53 polypeptide of SEQ ID NO: 23 and the GH42 polypeptide of SEQ ID NO: 74. In an embodiment, the composition of the invention comprises the GH53 polypeptide of SEQ ID NO: 23 and the GH42 polypeptide of SEQ ID NO: 77.

In an embodiment, the composition of the invention comprises the GH53 polypeptide of SEQ ID NO: 27 and the GH42 polypeptide of SEQ ID NO: 42. In an embodiment, the composition of the invention comprises the GH53 polypeptide of SEQ ID NO: 27 and the GH42 polypeptide of SEQ ID NO: 44. In an embodiment, the composition of the invention comprises the GH53 polypeptide of SEQ ID NO: 27 and the GH42 polypeptide of SEQ ID NO: 47. In an embodiment, the composition of the invention comprises the GH53 polypeptide of SEQ ID NO: 27 and the GH42 polypeptide of SEQ ID NO: 50. In an embodiment, the composition of the invention comprises the GH53 polypeptide of SEQ ID NO: 27 and the GH42 polypeptide of SEQ ID NO: 53. In an embodiment, the composition of the invention comprises the GH53 polypeptide of SEQ ID NO: 27 and the GH42 polypeptide of SEQ ID NO: 56. In an embodiment, the composition of the invention comprises the GH53 polypeptide of SEQ ID NO: 27 and the GH42 polypeptide of SEQ ID NO: 59. In an embodiment, the composition of the invention comprises the GH53 polypeptide of SEQ ID NO: 27 and the GH42 polypeptide of SEQ ID NO: 62. In an embodiment, the composition of the invention comprises the GH53 polypeptide of SEQ ID NO: 27 and the GH42 polypeptide of SEQ ID NO: 65. In an embodiment, the composition of the invention comprises the GH53 polypeptide of SEQ ID NO: 27 and the GH42 polypeptide of SEQ ID NO: 68. In an embodiment, the composition of the invention comprises the GH53 polypeptide of SEQ ID NO: 27 and the GH42 polypeptide of SEQ ID NO: 71. In an embodiment, the composition of the invention comprises the GH53 polypeptide of SEQ ID NO: 27 and the GH42 polypeptide of SEQ ID NO: 74. In an embodiment, the composition of the invention comprises the GH53 polypeptide of SEQ ID NO: 27 and the GH42 polypeptide of SEQ ID NO: 77.

In an embodiment, the composition of the invention comprises the GH53 polypeptide of SEQ ID NO: 31 and the GH42 polypeptide of SEQ ID NO: 42. In an embodiment, the composition of the invention comprises the GH53 polypeptide of SEQ ID NO: 31 and the GH42 polypeptide of SEQ ID NO: 44. In an embodiment, the composition of the invention comprises the GH53 polypeptide of SEQ ID NO: 31 and the GH42 polypeptide of SEQ ID NO: 47. In an embodiment, the composition of the invention comprises the GH53 polypeptide of SEQ ID NO: 31 and the GH42 polypeptide of SEQ ID NO: 50. In an embodiment, the composition of the invention comprises the GH53 polypeptide of SEQ ID NO: 31 and the GH42 polypeptide of SEQ ID NO: 53. In an embodiment, the composition of the invention comprises the GH53 polypeptide of SEQ ID NO: 31 and the GH42 polypeptide of SEQ ID NO: 56. In an embodiment, the composition of the invention comprises the GH53 polypeptide of SEQ ID NO: 31 and the GH42 polypeptide of SEQ ID NO: 59. In an embodiment, the composition of the invention comprises the GH53 polypeptide of SEQ ID NO: 31 and the GH42 polypeptide of SEQ ID NO: 62. In an embodiment, the composition of the invention comprises the GH53 polypeptide of SEQ ID NO: 31 and the GH42 polypeptide of SEQ ID NO: 65. In an embodiment, the composition of the invention comprises the GH53 polypeptide of SEQ ID NO: 31 and the GH42 polypeptide of SEQ ID NO: 68. In an embodiment, the composition of the invention comprises the GH53 polypeptide of SEQ ID NO: 31 and the GH42 polypeptide of SEQ ID NO: 71. In an embodiment, the composition of the invention comprises the GH53 polypeptide of SEQ ID NO: 31 and the GH42 polypeptide of SEQ ID NO: 74. In an embodiment, the composition of the invention comprises the GH53 polypeptide of SEQ ID NO: 31 and the GH42 polypeptide of SEQ ID NO: 77.

In an embodiment, the composition of the invention comprises the GH53 polypeptide of SEQ ID NO: 35 and the GH42 polypeptide of SEQ ID NO: 42. In an embodiment, the composition of the invention comprises the GH53 polypeptide of SEQ ID NO: 35 and the GH42 polypeptide of SEQ ID NO: 44. In an embodiment, the composition of the invention comprises the GH53 polypeptide of SEQ ID NO: 35 and the GH42 polypeptide of SEQ ID NO: 47. In an embodiment, the composition of the invention comprises the GH53 polypeptide of SEQ ID NO: 35 and the GH42 polypeptide of SEQ ID NO: 50. In an embodiment, the composition of the invention comprises the GH53 polypeptide of SEQ ID NO: 35 and the GH42 polypeptide of SEQ ID NO: 53. In an embodiment, the composition of the invention comprises the GH53 polypeptide of SEQ ID NO: 35 and the GH42 polypeptide of SEQ ID NO: 56. In an embodiment, the composition of the invention comprises the GH53 polypeptide of SEQ ID NO: 35 and the GH42 polypeptide of SEQ ID NO: 59. In an embodiment, the composition of the invention comprises the GH53 polypeptide of SEQ ID NO: 35 and the GH42 polypeptide of SEQ ID NO: 62. In an embodiment, the composition of the invention comprises the GH53 polypeptide of SEQ ID NO: 35 and the GH42 polypeptide of SEQ ID NO: 65. In an embodiment, the composition of the invention comprises the GH53 polypeptide of SEQ ID NO: 35 and the GH42 polypeptide of SEQ ID NO: 68. In an embodiment, the composition of the invention comprises the GH53 polypeptide of SEQ ID NO: 35 and the GH42 polypeptide of SEQ ID NO: 71. In an embodiment, the composition of the invention comprises the GH53 polypeptide of SEQ ID NO: 35 and the GH42 polypeptide of SEQ ID NO: 74. In an embodiment, the composition of the invention comprises the GH53 polypeptide of SEQ ID NO: 35 and the GH42 polypeptide of SEQ ID NO: 77.

In an embodiment, the composition of the invention comprises the GH53 polypeptide of SEQ ID NO: 39 and the GH42 polypeptide of SEQ ID NO: 42. In an embodiment, the composition of the invention comprises the GH53 polypeptide of SEQ ID NO: 39 and the GH42 polypeptide of SEQ ID NO: 44. In an embodiment, the composition of the invention comprises the GH53 polypeptide of SEQ ID NO: 39 and the GH42 polypeptide of SEQ ID NO: 47. In an embodiment, the composition of the invention comprises the GH53 polypeptide of SEQ ID NO: 39 and the GH42 polypeptide of SEQ ID NO: 50. In an embodiment, the composition of the invention comprises the GH53 polypeptide of SEQ ID NO: 39 and the GH42 polypeptide of SEQ ID NO: 53. In an embodiment, the composition of the invention comprises the GH53 polypeptide of SEQ ID NO: 39 and the GH42 polypeptide of SEQ ID NO: 56. In an embodiment, the composition of the invention comprises the GH53 polypeptide of SEQ ID NO: 39 and the GH42 polypeptide of SEQ ID NO: 59. In an embodiment, the composition of the invention comprises the GH53 polypeptide of SEQ ID NO: 39 and the GH42 polypeptide of SEQ ID NO: 62. In an embodiment, the composition of the invention comprises the GH53 polypeptide of SEQ ID NO: 39 and the GH42 polypeptide of SEQ ID NO: 65. In an embodiment, the composition of the invention comprises the GH53 polypeptide of SEQ ID NO: 39 and the GH42 polypeptide of SEQ ID NO: 68. In an embodiment, the composition of the invention comprises the GH53 polypeptide of SEQ ID NO: 39 and the GH42 polypeptide of SEQ ID NO: 71. In an embodiment, the composition of the invention comprises the GH53 polypeptide of SEQ ID NO: 39 and the GH42 polypeptide of SEQ ID NO: 74. In an embodiment, the composition of the invention comprises the GH53 polypeptide of SEQ ID NO: 39 and the GH42 polypeptide of SEQ ID NO: 77.

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

Polypeptides Having Galactanase Activity

In a second aspect, the invention relates to polypeptides having galactanase activity and having a sequence identity to the mature polypeptide of SEQ ID NO: 2 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 2.

In one embodiment, the polypeptide preferably comprises or consists of the amino acid sequence of SEQ ID NO: 2 or an allelic variant thereof; comprises the amino acid sequence of SEQ ID NO: 2 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 2. In another embodiment, the polypeptide comprises or consists of amino acids 1 to 316 of SEQ ID NO: 2. In an embodiment, the polypeptide has been isolated.

In a continuation of the second aspect, the invention further relates to polypeptides having galactanase activity having a sequence identity to SEQ ID NO: 3 of at least 82%. In an embodiment, the polypeptide has a sequence identity to SEQ ID NO: 3 of at least 85%. In an embodiment, the polypeptide has a sequence identity to SEQ ID NO: 3 of at least 86%. In an embodiment, the polypeptide has a sequence identity to SEQ ID NO: 3 of at least 87%. In an embodiment, the polypeptide has a sequence identity to SEQ ID NO: 3 of at least 88%. In an embodiment, the polypeptide has a sequence identity to SEQ ID NO: 3 of at least 89%. In an embodiment, the polypeptide has a sequence identity to SEQ ID NO: 3 of at least 90%. In an embodiment, the polypeptide has a sequence identity to SEQ ID NO: 3 of at least 91%. In an embodiment, the polypeptide has a sequence identity to SEQ ID NO: 3 of at least 92%. In an embodiment, the polypeptide has a sequence identity to SEQ ID NO: 3 of at least 93%. In an embodiment, the polypeptide has a sequence identity to SEQ ID NO: 3 of at least 94%. In an embodiment, the polypeptide has a sequence identity to SEQ ID NO: 3 of at least 95%. In an embodiment, the polypeptide has a sequence identity to SEQ ID NO: 3 of at least 96%. In an embodiment, the polypeptide has a sequence identity to SEQ ID NO: 3 of at least 97%. In an embodiment, the polypeptide has a sequence identity to SEQ ID NO: 3 of at least 98%. In an embodiment, the polypeptide has a sequence identity to SEQ ID NO: 3 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 4.

In one embodiment, the polypeptide preferably comprises or consists of the amino acid sequence of SEQ ID NO: 3 or an allelic variant thereof; comprises the amino acid sequence of SEQ ID NO: 3 and a N-terminal and/or C-terminal His-tag and/or HQ-tag such as SEQ ID NO: 4; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 3. In another embodiment, the polypeptide comprises or consists of amino acids 1 to 324 of SEQ ID NO: 4. In an embodiment, the polypeptide has been isolated.

In a continuation of the second aspect, the invention relates to a polypeptide having galactanase activity encoded by a polynucleotide having a sequence identity to the mature polypeptide coding sequence of SEQ ID NO: 1 or the cDNA sequence thereof of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the second aspect, the invention relates to variants of SEQ ID NO: 3 having galactanase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In another embodiment, the number of substitutions, deletions, and/or insertions in SEQ ID NO: 3 is not more than 10, e.g., 1, 2, 3, 4, 5, 6, 7, 8, 9 or 10. In a further embodiment, the number of substitutions, preferably conservative substitutions, in SEQ ID NO: 3 is not more than 10, e.g., 1, 2, 3, 4, 5, 6, 7, 8, 9 or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for beta-galactosidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Carbohydrate molecules are often attached to a polypeptide from a fungal source during post-translational modification. In order to aid mass spectrometry analysis, the polypeptide can be incubated with an endoglycosidase to deglycosylate each N-linked position. For every deglycosylated N-linked site, one N-acetyl hexosamine remains on the protein backbone.

In an embodiment, the polypeptide of the second aspect comprises the motif GV[T/M]PD[W/M]VQ[I/V]GNE (SEQ ID NO: 81) and/or the motif WADP[A/G]xQxKPxAW (SEQ ID NO: 82).

In a third aspect, the invention relates to polypeptides having galactanase activity and having a sequence identity to the mature polypeptide of SEQ ID NO: 6 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 6.

In one embodiment, the polypeptide preferably comprises or consists of the amino acid sequence of SEQ ID NO: 6 or an allelic variant thereof; comprises the amino acid sequence of SEQ ID NO: 6 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 6. In another embodiment, the polypeptide comprises or consists of amino acids 1 to 318 of SEQ ID NO: 6. In an embodiment, the polypeptide has been isolated.

In a continuation of the third aspect, the invention further relates to polypeptides having galactanase activity having a sequence identity to SEQ ID NO: 7 of at least 83%. In an embodiment, the polypeptide has a sequence identity to SEQ ID NO: 7 of at least 85%. In an embodiment, the polypeptide has a sequence identity to SEQ ID NO: 7 of at least 86%. In an embodiment, the polypeptide has a sequence identity to SEQ ID NO: 7 of at least 87%. In an embodiment, the polypeptide has a sequence identity to SEQ ID NO: 7 of at least 88%. In an embodiment, the polypeptide has a sequence identity to SEQ ID NO: 7 of at least 89%. In an embodiment, the polypeptide has a sequence identity to SEQ ID NO: 7 of at least 90%. In an embodiment, the polypeptide has a sequence identity to SEQ ID NO: 7 of at least 91%. In an embodiment, the polypeptide has a sequence identity to SEQ ID NO: 7 of at least 92%. In an embodiment, the polypeptide has a sequence identity to SEQ ID NO: 7 of at least 93%. In an embodiment, the polypeptide has a sequence identity to SEQ ID NO: 7 of at least 94%. In an embodiment, the polypeptide has a sequence identity to SEQ ID NO: 7 of at least 95%. In an embodiment, the polypeptide has a sequence identity to SEQ ID NO: 7 of at least 96%. In an embodiment, the polypeptide has a sequence identity to SEQ ID NO: 7 of at least 97%. In an embodiment, the polypeptide has a sequence identity to SEQ ID NO: 7 of at least 98%. In an embodiment, the polypeptide has a sequence identity to SEQ ID NO: 7 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 7. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 8.

In one embodiment, the polypeptide preferably comprises or consists of the amino acid sequence of SEQ ID NO: 7 or an allelic variant thereof; comprises the amino acid sequence of SEQ ID NO: 7 and a N-terminal and/or C-terminal His-tag and/or HQ-tag such as SEQ ID NO: 8; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 318 of SEQ ID NO: 7. In another embodiment, the polypeptide comprises or consists of amino acids 1 to 326 of SEQ ID NO: 8. In an embodiment, the polypeptide has been isolated.

In a continuation of the third aspect, the invention relates to a polypeptide having galactanase activity encoded by a polynucleotide having a sequence identity to the mature polypeptide coding sequence of SEQ ID NO: 5 or the cDNA sequence thereof of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the third aspect, the invention relates to variants of SEQ ID NO: 7 having galactanase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 7 is not more than 10, e.g., 1, 2, 3, 4, 5, 6, 7, 8, 9 or 10. In another embodiment, the number of substitutions, deletions, and/or insertions in SEQ ID NO: 7 is not more than 10, e.g., 1, 2, 3, 4, 5, 6, 7, 8, 9 or 10. In a further embodiment, the number of substitutions, preferably conservative substitutions, in SEQ ID NO: 7 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the third aspect comprises the motif GV[T/M]PD[W/M]VQ[I/V]GNE (SEQ ID NO: 81) and/or the motif WADP[A/G]xQxKPxAW (SEQ ID NO: 82).

In a fourth aspect, the invention relates to polypeptides having galactanase activity and having a sequence identity to the mature polypeptide of SEQ ID NO: 10 of at least 99.0%, e.g., at least 99.3%, at least 99.6% which have galactanase activity. In one embodiment, the polypeptides differ by up to 3 amino acids, e.g., 1, 2 or 3 amino acids from the mature polypeptide of SEQ ID NO: 10.

In one embodiment, the polypeptide preferably comprises or consists of the amino acid sequence of SEQ ID NO: 10 or an allelic variant thereof; comprises the amino acid sequence of SEQ ID NO: 10 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 10. In another embodiment, the polypeptide comprises or consists of amino acids 1 to 316 of SEQ ID NO: 10. In an embodiment, the polypeptide has been isolated.

In a continuation of the fourth aspect, the invention further relates to polypeptides having galactanase activity having a sequence identity to SEQ ID NO: 11 of at least 99.0%. In an embodiment, the polypeptide has a sequence identity to SEQ ID NO: 11 of at least 99.3%. In an embodiment, the polypeptide has a sequence identity to SEQ ID NO: 11 of at least 99.6%.

In one embodiment, the polypeptides differ by up to 3 amino acids, e.g., 1, 2 or 3 amino acids from SEQ ID NO: 11. In one embodiment, the polypeptides differ by up to 3 amino acids, e.g., 1, 2 or 3 amino acids from SEQ ID NO: 12.

In one embodiment, the polypeptide preferably comprises or consists of the amino acid sequence of SEQ ID NO: 11 or an allelic variant thereof; comprises the amino acid sequence of SEQ ID NO: 11 and a N-terminal and/or C-terminal His-tag and/or HQ-tag such as SEQ ID NO: 12; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 11. In another embodiment, the polypeptide comprises or consists of amino acids 1 to 324 of SEQ ID NO: 12. In an embodiment, the polypeptide has been isolated.

In a continuation of the fourth aspect, the invention relates to a polypeptide having galactanase activity encoded by a polynucleotide having a sequence identity to the mature polypeptide coding sequence of SEQ ID NO: 9 or the cDNA sequence thereof of at least 99.0%, e.g., at least 99.3%, at least 99.6%, or 100%. In a further embodiment, the polypeptide has been isolated.

In a continuation of the fourth aspect, the invention relates to variants of SEQ ID NO: 11 having galactanase activity comprising one or more amino acid alterations (i.e. substitutions, deletions, and/or insertions or any combination thereof) in 1 to 3 positions, such as as 1, 2 or 3 positions. In another embodiment, the number of substitutions, deletions, and/or insertions in SEQ ID NO: 11 is not more than 3, e.g., 1, 2 or 3. In a further embodiment, the number of substitutions, preferably conservative substitutions, in SEQ ID NO: 11 is not more than 3, e.g., 1, 2 or 3.

Examples of amino acid changes and conservative substitutions are described in the second aspect of the invention.

In an embodiment, the polypeptide of the fourth aspect comprises the motif GV[T/M]PD[W/M]VQ[I/V]GNE (SEQ ID NO: 81) and/or the motif WADP[A/G]xQxKPxAW (SEQ ID NO: 82).

In a fifth aspect, the invention relates to polypeptides having galactanase activity and having a sequence identity to the mature polypeptide of SEQ ID NO: 14 of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, which have galactanase activity. In one embodiment, the polypeptides differ by up to 11 amino acids, e.g., 1, 2, 3, 4, 5, 6, 7, 8, 9, 10 or 11 amino acids from the mature polypeptide of SEQ ID NO: 14.

In one embodiment, the polypeptide preferably comprises or consists of the amino acid sequence of SEQ ID NO: 14 or an allelic variant thereof; comprises the amino acid sequence of SEQ ID NO: 14 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 14. In another embodiment, the polypeptide comprises or consists of amino acids 1 to 316 of SEQ ID NO: 14. In an embodiment, the polypeptide has been isolated.

In a continuation of the fifth aspect, the invention further relates to polypeptides having galactanase activity having a sequence identity to SEQ ID NO: 15 of at least 96.4%. In an embodiment, the polypeptide has a sequence identity to SEQ ID NO: 15 of at least 96.7%. In an embodiment, the polypeptide has a sequence identity to SEQ ID NO: 15 of at least 97.0%. In an embodiment, the polypeptide has a sequence identity to SEQ ID NO: 15 of at least 97.3%. In an embodiment, the polypeptide has a sequence identity to SEQ ID NO: 15 of at least 97.6%. In an embodiment, the polypeptide has a sequence identity to SEQ ID NO: 15 of at least 98.0%. In an embodiment, the polypeptide has a sequence identity to SEQ ID NO: 15 of at least 98.3%. In an embodiment, the polypeptide has a sequence identity to SEQ ID NO: 15 of at least 98.6%. In an embodiment, the polypeptide has a sequence identity to SEQ ID NO: 15 of at least 99.0%. In an embodiment, the polypeptide has a sequence identity to SEQ ID NO: 15 of at least 99.3%. In an embodiment, the polypeptide has a sequence identity to SEQ ID NO: 15 of at least 99.6%.

In one embodiment, the polypeptides differ by up to 11 amino acids, e.g., 1, 2, 3, 4, 5, 6, 7, 8, 9, 10 or 11 amino acids from SEQ ID NO: 15. In one embodiment, the polypeptides differ by up to 11 amino acids, e.g., 1, 2, 3, 4, 5, 6, 7, 8, 9, 10 or 11 amino acids from SEQ ID NO: 16.

In one embodiment, the polypeptide preferably comprises or consists of the amino acid sequence of SEQ ID NO: 15 or an allelic variant thereof; comprises the amino acid sequence of SEQ ID NO: 15 and a N-terminal and/or C-terminal His-tag and/or HQ-tag such as SEQ ID NO: 16; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 15. In another embodiment, the polypeptide comprises or consists of amino acids 1 to 324 of SEQ ID NO: 16. In an embodiment, the polypeptide has been isolated.

In a continuation of the fifth aspect, the invention relates to a polypeptide having galactanase activity encoded by a polynucleotide having a sequence identity to the mature polypeptide coding sequence of SEQ ID NO: 13 or the cDNA sequence thereof of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, or 100%. In a further embodiment, the polypeptide has been isolated.

In a continuation of the fifth aspect, the invention relates to variants of SEQ ID NO: 15 having galactanase activity comprising one or more amino acid alterations (i.e. substitutions, deletions, and/or insertions or any combination thereof) in 1 to 11 positions, such as as 1, 2, 3, 4, 5, 6, 7, 8, 9, 10 or 11 positions. In another embodiment, the number of substitutions, deletions, and/or insertions in SEQ ID NO: 15 is not more than 10, e.g., 1, 2, 3, 4, 5, 6, 7, 8, 9 or 10. In a further embodiment, the number of substitutions, preferably conservative substitutions, in SEQ ID NO: 15 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the fifth aspect comprises the motif GV[T/M]PD[W/M]VQ[I/V]GNE (SEQ ID NO: 81) and/or the motif WADP[A/G]xQxKPxAW (SEQ ID NO: 82).

In a sixth aspect, the invention relates to polypeptides having galactanase activity and having a sequence identity to the mature polypeptide of SEQ ID NO: 18 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 18.

In one embodiment, the polypeptide preferably comprises or consists of the amino acid sequence of SEQ ID NO: 18 or an allelic variant thereof; comprises the amino acid sequence of SEQ ID NO: 18 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 18. In another embodiment, the polypeptide comprises or consists of amino acids 1 to 316 of SEQ ID NO: 18. In an embodiment, the polypeptide has been isolated.

In a continuation of the sixth aspect, the invention further relates to polypeptides having galactanase activity having a sequence identity to SEQ ID NO: 19 of at least 84%. In an embodiment, the polypeptide has a sequence identity to SEQ ID NO: 19 of at least 85%. In an embodiment, the polypeptide has a sequence identity to SEQ ID NO: 19 of at least 86%. In an embodiment, the polypeptide has a sequence identity to SEQ ID NO: 19 of at least 87%. In an embodiment, the polypeptide has a sequence identity to SEQ ID NO: 19 of at least 88%. In an embodiment, the polypeptide has a sequence identity to SEQ ID NO: 19 of at least 89%. In an embodiment, the polypeptide has a sequence identity to SEQ ID NO: 19 of at least 90%. In an embodiment, the polypeptide has a sequence identity to SEQ ID NO: 19 of at least 91%. In an embodiment, the polypeptide has a sequence identity to SEQ ID NO: 19 of at least 92%. In an embodiment, the polypeptide has a sequence identity to SEQ ID NO: 19 of at least 93%. In an embodiment, the polypeptide has a sequence identity to SEQ ID NO: 19 of at least 94%. In an embodiment, the polypeptide has a sequence identity to SEQ ID NO: 19 of at least 95%. In an embodiment, the polypeptide has a sequence identity to SEQ ID NO: 19 of at least 96%. In an embodiment, the polypeptide has a sequence identity to SEQ ID NO: 19 of at least 97%. In an embodiment, the polypeptide has a sequence identity to SEQ ID NO: 19 of at least 98%. In an embodiment, the polypeptide has a sequence identity to SEQ ID NO: 19 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 19. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 20.

In one embodiment, the polypeptide preferably comprises or consists of the amino acid sequence of SEQ ID NO: 19 or an allelic variant thereof; comprises the amino acid sequence of SEQ ID NO: 19 and a N-terminal and/or C-terminal His-tag and/or HQ-tag such as SEQ ID NO: 20; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 19. In another embodiment, the polypeptide comprises or consists of amino acids 1 to 324 of SEQ ID NO: 20. In an embodiment, the polypeptide has been isolated.

In a continuation of the sixth aspect, the invention relates to a polypeptide having galactanase activity encoded by a polynucleotide having a sequence identity to the mature polypeptide coding sequence of SEQ ID NO: 17 or the cDNA sequence thereof of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixth aspect, the invention relates to variants of SEQ ID NO: 19 having galactanase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 19 is not more than 10, e.g., 1, 2, 3, 4, 5, 6, 7, 8, 9 or 10. In another embodiment, the number of substitutions, deletions, and/or insertions in SEQ ID NO: 19 is not more than 10, e.g., 1, 2, 3, 4, 5, 6, 7, 8, 9 or 10. In a further embodiment, the number of substitutions, preferably conservative substitutions, in SEQ ID NO: 19 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the sixth aspect comprises the motif GV[T/M]PD[W/M]VQ[I/V]GNE (SEQ ID NO: 81) and/or the motif WADP[A/G]xQxKPxAW (SEQ ID NO: 82).

In a seventh aspect, the invention relates to polypeptides having galactanase activity and having a sequence identity to the mature polypeptide of SEQ ID NO: 22 of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, which have galactanase activity. In one embodiment, the polypeptides differ by up to 11 amino acids, e.g., 1, 2, 3, 4, 5, 6, 7, 8, 9, 10 or 11 amino acids from the mature polypeptide of SEQ ID NO: 22.

In one embodiment, the polypeptide preferably comprises or consists of the amino acid sequence of SEQ ID NO: 22 or an allelic variant thereof; comprises the amino acid sequence of SEQ ID NO: 22 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 22. In another embodiment, the polypeptide comprises or consists of amino acids 1 to 316 of SEQ ID NO: 22. In an embodiment, the polypeptide has been isolated.

In a continuation of the seventh aspect, the invention further relates to polypeptides having galactanase activity having a sequence identity to SEQ ID NO: 23 of at least 96.4%. In an embodiment, the polypeptide has a sequence identity to SEQ ID NO: 23 of at least 96.7%. In an embodiment, the polypeptide has a sequence identity to SEQ ID NO: 23 of at least 97.0%. In an embodiment, the polypeptide has a sequence identity to SEQ ID NO: 23 of at least 97.3%. In an embodiment, the polypeptide has a sequence identity to SEQ ID NO: 23 of at least 97.6%. In an embodiment, the polypeptide has a sequence identity to SEQ ID NO: 23 of at least 98.0%. In an embodiment, the polypeptide has a sequence identity to SEQ ID NO: 23 of at least 98.3%. In an embodiment, the polypeptide has a sequence identity to SEQ ID NO: 23 of at least 98.6%. In an embodiment, the polypeptide has a sequence identity to SEQ ID NO: 23 of at least 99.0%. In an embodiment, the polypeptide has a sequence identity to SEQ ID NO: 23 of at least 99.3%. In an embodiment, the polypeptide has a sequence identity to SEQ ID NO: 23 of at least 99.6%.

In one embodiment, the polypeptides differ by up to 11 amino acids, e.g., 1, 2, 3, 4, 5, 6, 7, 8, 9, 10 or 11 amino acids from SEQ ID NO: 23. In one embodiment, the polypeptides differ by up to 11 amino acids, e.g., 1, 2, 3, 4, 5, 6, 7, 8, 9, 10 or 11 amino acids from SEQ ID NO: 24.

In one embodiment, the polypeptide preferably comprises or consists of the amino acid sequence of SEQ ID NO: 23 or an allelic variant thereof; comprises the amino acid sequence of SEQ ID NO: 23 and a N-terminal and/or C-terminal His-tag and/or HQ-tag such as SEQ ID NO: 24; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 23. In another embodiment, the polypeptide comprises or consists of amino acids 1 to 324 of SEQ ID NO: 24. In an embodiment, the polypeptide has been isolated.

In a continuation of the seventh aspect, the invention relates to a polypeptide having galactanase activity encoded by a polynucleotide having a sequence identity to the mature polypeptide coding sequence of SEQ ID NO: 21 or the cDNA sequence thereof of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, or 100%. In a further embodiment, the polypeptide has been isolated.

In a continuation of the seventh aspect, the invention relates to variants of SEQ ID NO: 23 having galactanase activity comprising one or more amino acid alterations (i.e. substitutions, deletions, and/or insertions or any combination thereof) in 1 to 1 positions, such as as 1, 2, 3, 4, 5, 6, 7, 8, 9, 10 or 11 positions. In another embodiment, the number of substitutions, deletions, and/or insertions in SEQ ID NO: 23 is not more than 10, e.g., 1, 2, 3, 4, 5, 6, 7, 8, 9 or 10. In a further embodiment, the number of substitutions, preferably conservative substitutions, in SEQ ID NO: 23 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the seventh aspect comprises the motif GV[T/M]PD[W/M]VQ[I/V]GNE (SEQ ID NO: 81) and/or the motif WADP[A/G]xQxKPxAW (SEQ ID NO: 82).

In an eighth aspect, the invention relates to polypeptides having galactanase activity and having a sequence identity to the mature polypeptide of SEQ ID NO: 26 of at least 86%, e.g., at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 26.

In one embodiment, the polypeptide preferably comprises or consists of the amino acid sequence of SEQ ID NO: 26 or an allelic variant thereof; comprises the amino acid sequence of SEQ ID NO: 26 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 26. In another embodiment, the polypeptide comprises or consists of amino acids 1 to 516 of SEQ ID NO: 26. In an embodiment, the polypeptide has been isolated.

In a continuation of the eighth aspect, the invention further relates to polypeptides having galactanase activity having a sequence identity to SEQ ID NO: 27 of at least 86%. In an embodiment, the polypeptide has a sequence identity to SEQ ID NO: 27 of at least 87%. In an embodiment, the polypeptide has a sequence identity to SEQ ID NO: 27 of at least 88%. In an embodiment, the polypeptide has a sequence identity to SEQ ID NO: 27 of at least 89%. In an embodiment, the polypeptide has a sequence identity to SEQ ID NO: 27 of at least 90%. In an embodiment, the polypeptide has a sequence identity to SEQ ID NO: 27 of at least 91%. In an embodiment, the polypeptide has a sequence identity to SEQ ID NO: 27 of at least 92%. In an embodiment, the polypeptide has a sequence identity to SEQ ID NO: 27 of at least 93%. In an embodiment, the polypeptide has a sequence identity to SEQ ID NO: 27 of at least 94%. In an embodiment, the polypeptide has a sequence identity to SEQ ID NO: 27 of at least 95%. In an embodiment, the polypeptide has a sequence identity to SEQ ID NO: 27 of at least 96%. In an embodiment, the polypeptide has a sequence identity to SEQ ID NO: 27 of at least 97%. In an embodiment, the polypeptide has a sequence identity to SEQ ID NO: 27 of at least 98%. In an embodiment, the polypeptide has a sequence identity to SEQ ID NO: 27 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 27. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 28.

In one embodiment, the polypeptide preferably comprises or consists of the amino acid sequence of SEQ ID NO: 27 or an allelic variant thereof; comprises the amino acid sequence of SEQ ID NO: 27 and a N-terminal and/or C-terminal His-tag and/or HQ-tag such as SEQ ID NO: 28; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 516 of SEQ ID NO: 27. In another embodiment, the polypeptide comprises or consists of amino acids 1 to 524 of SEQ ID NO: 28. In an embodiment, the polypeptide has been isolated.

In a continuation of the eighth aspect, the invention relates to a polypeptide having galactanase activity encoded by a polynucleotide having a sequence identity to the mature polypeptide coding sequence of SEQ ID NO: 25 or the cDNA sequence thereof of at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eighth aspect, the invention relates to variants of SEQ ID NO: 27 having galactanase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In another embodiment, the number of substitutions, deletions, and/or insertions in SEQ ID NO: 27 is not more than 10, e.g., 1, 2, 3, 4, 5, 6, 7, 8, 9 or 10. In a further embodiment, the number of substitutions, preferably conservative substitutions, in SEQ ID NO: 27 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the eighth aspect comprises the motif GV[T/M]PD[W/M]VQ[I/V]GNE (SEQ ID NO: 81) and/or the motif WADP[A/G]xQxKPxAW (SEQ ID NO: 82).

In a ninth aspect, the invention relates to polypeptides having galactanase activity and having a sequence identity to the mature polypeptide of SEQ ID NO: 30 of at least 99.3%, e.g., at least 99.6% which have galactanase activity. In one embodiment, the polypeptides differ by up to 2 amino acids, e.g., 1 or 2 amino acids from the mature polypeptide of SEQ ID NO: 30.

In one embodiment, the polypeptide preferably comprises or consists of the amino acid sequence of SEQ ID NO: 30 or an allelic variant thereof; comprises the amino acid sequence of SEQ ID NO: 30 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 30. In another embodiment, the polypeptide comprises or consists of amino acids 1 to 317 of SEQ ID NO: 30. In an embodiment, the polypeptide has been isolated.

In a continuation of the ninth aspect, the invention further relates to polypeptides having galactanase activity having a sequence identity to SEQ ID NO: 31 of at least 99.3%. In an embodiment, the polypeptide has a sequence identity to SEQ ID NO: 31 of at least 99.6%.

In one embodiment, the polypeptides differ by up to 2 amino acids, e.g., 1 or 2 amino acids from SEQ ID NO: 31. In one embodiment, the polypeptides differ by up to 2 amino acids, e.g., 1 or 2 amino acids from SEQ ID NO: 32.

In one embodiment, the polypeptide preferably comprises or consists of the amino acid sequence of SEQ ID NO: 31 or an allelic variant thereof; comprises the amino acid sequence of SEQ ID NO: 31 and a N-terminal and/or C-terminal His-tag and/or HQ-tag such as SEQ ID NO: 32; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 317 of SEQ ID NO: 31. In another embodiment, the polypeptide comprises or consists of amino acids 1 to 325 of SEQ ID NO: 32. In an embodiment, the polypeptide has been isolated.

In a continuation of the ninth aspect, the invention relates to a polypeptide having galactanase activity encoded by a polynucleotide having a sequence identity to the mature polypeptide coding sequence of SEQ ID NO: 29 or the cDNA sequence thereof of at least 99.3%, e.g., at least 99.6%, or 100%. In a further embodiment, the polypeptide has been isolated.

In a continuation of the ninth aspect, the invention relates to variants of SEQ ID NO: 31 having galactanase activity comprising one or more amino acid alterations (i.e. substitutions, deletions, and/or insertions or any combination thereof) in 1 to 2 positions, such as as 1 or 2 positions. In another embodiment, the number of substitutions, deletions, and/or insertions in SEQ ID NO: 31 is not more than 2, e.g., 1 or 2. In a further embodiment, the number of substitutions, preferably conservative substitutions, in SEQ ID NO: 31 is not more than 2, e.g., 1 or 2.

Examples of amino acid changes and conservative substitutions are described in the second aspect of the invention.

In an embodiment, the polypeptide of the ninth aspect comprises the motif GV[T/M]PD[W/M]VQ[I/V]GNE (SEQ ID NO: 81) and/or the motif WADP[A/G]xQxKPxAW (SEQ ID NO: 82).

In a tenth aspect, the invention relates to polypeptides having galactanase activity and having a sequence identity to the mature polypeptide of SEQ ID NO: 34 of at least 99.3%, e.g., at least 99.6% which have galactanase activity. In one embodiment, the polypeptides differ by up to 2 amino acids, e.g., 1 or 2 amino acids from the mature polypeptide of SEQ ID NO: 34.

In one embodiment, the polypeptide preferably comprises or consists of the amino acid sequence of SEQ ID NO: 34 or an allelic variant thereof; comprises the amino acid sequence of SEQ ID NO: 34 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 34. In another embodiment, the polypeptide comprises or consists of amino acids 1 to 316 of SEQ ID NO: 34. In an embodiment, the polypeptide has been isolated.

In a continuation of the tenth aspect, the invention further relates to polypeptides having galactanase activity having a sequence identity to SEQ ID NO: 35 of at least 99.3%. In an embodiment, the polypeptide has a sequence identity to SEQ ID NO: 35 of at least 99.6%.

In one embodiment, the polypeptides differ by up to 2 amino acids, e.g., 1 or 2 amino acids from SEQ ID NO: 35. In one embodiment, the polypeptides differ by up to 2 amino acids, e.g., 1 or 2 amino acids from SEQ ID NO: 36.

In one embodiment, the polypeptide preferably comprises or consists of the amino acid sequence of SEQ ID NO: 35 or an allelic variant thereof; comprises the amino acid sequence of SEQ ID NO: 35 and a N-terminal and/or C-terminal His-tag and/or HQ-tag such as SEQ ID NO: 36; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 35. In another embodiment, the polypeptide comprises or consists of amino acids 1 to 324 of SEQ ID NO: 36. In an embodiment, the polypeptide has been isolated.

In a continuation of the tenth aspect, the invention relates to a polypeptide having galactanase activity encoded by a polynucleotide having a sequence identity to the mature polypeptide coding sequence of SEQ ID NO: 33 or the cDNA sequence thereof of at least 99.3%, e.g., at least 99.6%, or 100%. In a further embodiment, the polypeptide has been isolated.

In a continuation of the tenth aspect, the invention relates to variants of SEQ ID NO: 7 having galactanase activity comprising one or more amino acid alterations (i.e. substitutions, deletions, and/or insertions or any combination thereof) in 1 to 2 positions, such as as 1 or 2 positions. In another embodiment, the number of substitutions, deletions, and/or insertions in SEQ ID NO: 7 is not more than 2, e.g., 1 or 2. In a further embodiment, the number of substitutions, preferably conservative substitutions, in SEQ ID NO: 7 is not more than 2, e.g., 1 or 2.

Examples of amino acid changes and conservative substitutions are described in the second aspect of the invention.

In an embodiment, the polypeptide of the tenth aspect comprises the motif GV[T/M]PD[W/M]VQ[I/V]GNE (SEQ ID NO: 81) and/or the motif WADP[A/G]xQxKPxAW (SEQ ID NO: 82).

In a eleventh aspect, the invention relates to polypeptides having galactanase activity and having a sequence identity to the mature polypeptide of SEQ ID NO: 38 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 38.

In one embodiment, the polypeptide preferably comprises or consists of the amino acid sequence of SEQ ID NO: 38 or an allelic variant thereof; comprises the amino acid sequence of SEQ ID NO: 38 and a N-terminal and/or C-terminal His-tag and/or HQ-tag; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 38. In another embodiment, the polypeptide comprises or consists of amino acids 1 to 316 of SEQ ID NO: 38. In an embodiment, the polypeptide has been isolated.

In a continuation of the eleventh aspect, the invention further relates to polypeptides having galactanase activity having a sequence identity to SEQ ID NO: 39 of at least 83%. In an embodiment, the polypeptide has a sequence identity to SEQ ID NO: 39 of at least 85%. In an embodiment, the polypeptide has a sequence identity to SEQ ID NO: 39 of at least 86%. In an embodiment, the polypeptide has a sequence identity to SEQ ID NO: 39 of at least 87%. In an embodiment, the polypeptide has a sequence identity to SEQ ID NO: 39 of at least 88%. In an embodiment, the polypeptide has a sequence identity to SEQ ID NO: 39 of at least 89%. In an embodiment, the polypeptide has a sequence identity to SEQ ID NO: 39 of at least 90%. In an embodiment, the polypeptide has a sequence identity to SEQ ID NO: 39 of at least 91%. In an embodiment, the polypeptide has a sequence identity to SEQ ID NO: 39 of at least 92%. In an embodiment, the polypeptide has a sequence identity to SEQ ID NO: 39 of at least 93%. In an embodiment, the polypeptide has a sequence identity to SEQ ID NO: 39 of at least 94%. In an embodiment, the polypeptide has a sequence identity to SEQ ID NO: 39 of at least 95%. In an embodiment, the polypeptide has a sequence identity to SEQ ID NO: 39 of at least 96%. In an embodiment, the polypeptide has a sequence identity to SEQ ID NO: 39 of at least 97%. In an embodiment, the polypeptide has a sequence identity to SEQ ID NO: 39 of at least 98%. In an embodiment, the polypeptide has a sequence identity to SEQ ID NO: 39 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 39. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 40.

In one embodiment, the polypeptide preferably comprises or consists of the amino acid sequence of SEQ ID NO: 39 or an allelic variant thereof; comprises the amino acid sequence of SEQ ID NO: 39 and a N-terminal and/or C-terminal His-tag and/or HQ-tag such as SEQ ID NO: 40; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 39. In another embodiment, the polypeptide comprises or consists of amino acids 1 to 324 of SEQ ID NO: 40. In an embodiment, the polypeptide has been isolated.

In a continuation of the eleventh aspect, the invention relates to a polypeptide having galactanase activity encoded by a polynucleotide having a sequence identity to the mature polypeptide coding sequence of SEQ ID NO: 37 or the cDNA sequence thereof of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eleventh aspect, the invention relates to variants of SEQ ID NO: 35 having galactanase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 35 is not more than 10, e.g., 1, 2, 3, 4, 5, 6, 7, 8, 9 or 10. In another embodiment, the number of substitutions, deletions, and/or insertions in SEQ ID NO: 35 is not more than 10, e.g., 1, 2, 3, 4, 5, 6, 7, 8, 9 or 10. In a further embodiment, the number of substitutions, preferably conservative substitutions, in SEQ ID NO: 35 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the eleventh aspect comprises the motif GV[T/M]PD[W/M]VQ[I/V]GNE (SEQ ID NO: 81) and/or the motif WADP[A/G]xQxKPxAW (SEQ ID NO: 82).

Polypeptides Having Beta-Galactosidase Activity

In a twelfth aspect, the invention relates to polypeptides having beta-galactosidase activity and having a sequence identity to the mature polypeptide of SEQ ID NO: 42 of at least 82% which have beta-galactosidase activity. In an embodiment, the polypeptide has a sequence identity to SEQ ID NO: 42 of at least 85%. In an embodiment, the polypeptide has a sequence identity to SEQ ID NO: 42 of at least 86%. In an embodiment, the polypeptide has a sequence identity to SEQ ID NO: 42 of at least 87%. In an embodiment, the polypeptide has a sequence identity to SEQ ID NO: 42 of at least 88%. In an embodiment, the polypeptide has a sequence identity to SEQ ID NO: 42 of at least 89%. In an embodiment, the polypeptide has a sequence identity to SEQ ID NO: 42 of at least 90%. In an embodiment, the polypeptide has a sequence identity to SEQ ID NO: 42 of at least 91%. In an embodiment, the polypeptide has a sequence identity to SEQ ID NO: 42 of at least 92%. In an embodiment, the polypeptide has a sequence identity to SEQ ID NO: 42 of at least 93%. In an embodiment, the polypeptide has a sequence identity to SEQ ID NO: 42 of at least 94%. In an embodiment, the polypeptide has a sequence identity to SEQ ID NO: 42 of at least 95%. In an embodiment, the polypeptide has a sequence identity to SEQ ID NO: 42 of at least 96%. In an embodiment, the polypeptide has a sequence identity to SEQ ID NO: 42 of at least 97%. In an embodiment, the polypeptide has a sequence identity to SEQ ID NO: 42 of at least 98%. In an embodiment, the polypeptide has a sequence identity to SEQ ID NO: 42 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 42.

In one embodiment, the polypeptide preferably comprises or consists of the amino acid sequence of SEQ ID NO: 42 or an allelic variant thereof; comprises the amino acid sequence of SEQ ID NO: 42 and a N-terminal and/or C-terminal His-tag and/or HQ-tag; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 42. In another embodiment, the polypeptide comprises or consists of amino acids 1 to 685 of SEQ ID NO: 42. In an embodiment, the polypeptide has been isolated.

In a continuation of the twelfth aspect, the invention relates to a polypeptide having beta-galactosidase activity encoded by a polynucleotide having a sequence identity to the mature polypeptide coding sequence of SEQ ID NO: 41 or the cDNA sequence thereof of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twelfth aspect, the invention relates to variants of SEQ ID NO: 42 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 42 is not more than 10, e.g., 1, 2, 3, 4, 5, 6, 7, 8, 9 or 10. In another embodiment, the number of substitutions, deletions, and/or insertions in SEQ ID NO: 42 is not more than 10, e.g., 1, 2, 3, 4, 5, 6, 7, 8, 9 or 10. In a further embodiment, the number of substitutions, preferably conservative substitutions, in SEQ ID NO: 42 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twelfth aspect comprises the motif DW[K/R]RF[V/I]T[A/D]Q[T/M] (SEQ ID NO: 83).

In a thirteenth aspect, the invention relates to polypeptides having beta-galactosidase activity and having a sequence identity to the mature polypeptide of SEQ ID NO: 44 of at least 99.8% which have beta-galactosidase activity. In an embodiment, the polypeptide has a sequence identity to SEQ ID NO: 44 of at least 99.9%.

In one embodiment, the polypeptides differ by 1 or 2 amino acids from the mature polypeptide of SEQ ID NO: 44.

In one embodiment, the polypeptide preferably comprises or consists of the amino acid sequence of SEQ ID NO: 44 or an allelic variant thereof; comprises the amino acid sequence of SEQ ID NO: 44 and a N-terminal and/or C-terminal His-tag and/or HQ-tag such as SEQ ID NO: 45; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 688 of SEQ ID NO: 44. In an embodiment, the polypeptide has been isolated.

In a continuation of the thirteenth aspect, the invention further relates to polypeptides having beta-galactosidase activity having a sequence identity to SEQ ID NO: 45 of at least 99.8%, e.g., at least 99.9% which have beta-galactosidase activity. In one embodiment, the polypeptides differ by 1 or 2 amino acids from the mature polypeptide of SEQ ID NO: 45.

In one embodiment, the polypeptide preferably comprises or consists of the amino acid sequence of SEQ ID NO: 45 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 695 of SEQ ID NO: 45. In an embodiment, the polypeptide has been isolated.

In a continuation of the thirteenth aspect, the invention relates to a polypeptide having beta-galactosidase activity encoded by a polynucleotide having a sequence identity to the mature polypeptide coding sequence of SEQ ID NO: 43 or the cDNA sequence thereof of at least 99.8%, e.g., at least 99.9%, or 100%. In a further embodiment, the polypeptide has been isolated.

In a continuation of the thirteenth aspect, the invention relates to variants of SEQ ID NO: 44 having beta-galactosidase activity comprising one or more amino acid alterations (i.e. substitutions, deletions, and/or insertions or any combination thereof) in 1 to 2 positions, such as as 1 or 2 positions. In another embodiment, the number of substitutions, deletions, and/or insertions in SEQ ID NO: 44 is not more than 2, e.g., 1 or 2. In a further embodiment, the number of substitutions, preferably conservative substitutions, in SEQ ID NO: 44 is not more than 2, e.g., 1 or 2.

Examples of amino acid changes and conservative substitutions are described in the second aspect of the invention.

In an embodiment, the polypeptide of the thirteenth aspect comprises the motif DW[K/R]RF[V/I]T[A/D]Q[T/M] (SEQ ID NO: 83).

In a fourteenth aspect, the invention relates to polypeptides having beta-galactosidase activity and having a sequence identity to the mature polypeptide of SEQ ID NO: 47 of at least 80% which have beta-galactosidase activity. In an embodiment, the polypeptide has a sequence identity to SEQ ID NO: 47 of at least 85%. In an embodiment, the polypeptide has a sequence identity to SEQ ID NO: 47 of at least 86%. In an embodiment, the polypeptide has a sequence identity to SEQ ID NO: 47 of at least 87%. In an embodiment, the polypeptide has a sequence identity to SEQ ID NO: 47 of at least 88%. In an embodiment, the polypeptide has a sequence identity to SEQ ID NO: 47 of at least 89%. In an embodiment, the polypeptide has a sequence identity to SEQ ID NO: 47 of at least 90%. In an embodiment, the polypeptide has a sequence identity to SEQ ID NO: 47 of at least 91%. In an embodiment, the polypeptide has a sequence identity to SEQ ID NO: 47 of at least 92%. In an embodiment, the polypeptide has a sequence identity to SEQ ID NO: 47 of at least 93%. In an embodiment, the polypeptide has a sequence identity to SEQ ID NO: 47 of at least 94%. In an embodiment, the polypeptide has a sequence identity to SEQ ID NO: 47 of at least 95%. In an embodiment, the polypeptide has a sequence identity to SEQ ID NO: 47 of at least 96%. In an embodiment, the polypeptide has a sequence identity to SEQ ID NO: 47 of at least 97%. In an embodiment, the polypeptide has a sequence identity to SEQ ID NO: 47 of at least 98%. In an embodiment, the polypeptide has a sequence identity to SEQ ID NO: 47 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 47.

In one embodiment, the polypeptide preferably comprises or consists of the amino acid sequence of SEQ ID NO: 47 or an allelic variant thereof; comprises the amino acid sequence of SEQ ID NO: 47 and a N-terminal and/or C-terminal His-tag and/or HQ-tag such as SEQ ID NO: 48; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 687 of SEQ ID NO: 47. In an embodiment, the polypeptide has been isolated.

In a continuation of the fourteenth aspect, the invention further relates to polypeptides having beta-galactosidase activity having a sequence identity to SEQ ID NO: 48 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 48.

In one embodiment, the polypeptide preferably comprises or consists of the amino acid sequence of SEQ ID NO: 48 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 694 of SEQ ID NO: 48. In an embodiment, the polypeptide has been isolated.

In a continuation of the fourteenth aspect, the invention relates to a polypeptide having beta-galactosidase activity encoded by a polynucleotide having a sequence identity to the mature polypeptide coding sequence of SEQ ID NO: 46 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the fourteenth aspect, the invention relates to variants of SEQ ID NO: 47 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 47 is not more than 10, e.g., 1, 2, 3, 4, 5, 6, 7, 8, 9 or 10. In another embodiment, the number of substitutions, deletions, and/or insertions in SEQ ID NO: 47 is not more than 10, e.g., 1, 2, 3, 4, 5, 6, 7, 8, 9 or 10. In a further embodiment, the number of substitutions, preferably conservative substitutions, in SEQ ID NO: 47 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the fourteenth aspect comprises the motif DW[K/R]RF[V/I]T[A/D]Q[T/M] (SEQ ID NO: 83).

In a fifteenth aspect, the invention relates to polypeptides having beta-galactosidase activity and having a sequence identity to the mature polypeptide of SEQ ID NO: 50 of at least 90% which have beta-galactosidase activity. In an embodiment, the polypeptide has a sequence identity to SEQ ID NO: 50 of at least 91%. In an embodiment, the polypeptide has a sequence identity to SEQ ID NO: 50 of at least 92%. In an embodiment, the polypeptide has a sequence identity to SEQ ID NO: 50 of at least 93%. In an embodiment, the polypeptide has a sequence identity to SEQ ID NO: 50 of at least 94%. In an embodiment, the polypeptide has a sequence identity to SEQ ID NO: 50 of at least 95%. In an embodiment, the polypeptide has a sequence identity to SEQ ID NO: 50 of at least 96%. In an embodiment, the polypeptide has a sequence identity to SEQ ID NO: 50 of at least 97%. In an embodiment, the polypeptide has a sequence identity to SEQ ID NO: 50 of at least 98%. In an embodiment, the polypeptide has a sequence identity to SEQ ID NO: 50 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 50.

In one embodiment, the polypeptide preferably comprises or consists of the amino acid sequence of SEQ ID NO: 50 or an allelic variant thereof; comprises the amino acid sequence of SEQ ID NO: 50 and a N-terminal and/or C-terminal His-tag and/or HQ-tag such as SEQ ID NO: 51; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 654 of SEQ ID NO: 50. In an embodiment, the polypeptide has been isolated.

In a continuation of the fifteenth aspect, the invention further relates to polypeptides having beta-galactosidase activity having a sequence identity to SEQ ID NO: 51 of at least 90%, e.g., at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 51.

In one embodiment, the polypeptide preferably comprises or consists of the amino acid sequence of SEQ ID NO: 51 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 661 of SEQ ID NO: 51. In an embodiment, the polypeptide has been isolated.

In a continuation of the fifteenth aspect, the invention relates to a polypeptide having beta-galactosidase activity encoded by a polynucleotide having a sequence identity to the mature polypeptide coding sequence of SEQ ID NO: 49 or the cDNA sequence thereof of at least 90%, e.g., at least 91%, at least 92%, at least 93%, at least 94%, at least 95%, at least 96%, at least 97%, at least 98%, at least 99%, or 100%. In a further embodiment, the polypeptide has been isolated.

In a continuation of the fifteenth aspect, the invention relates to variants of SEQ ID NO: 50 having beta-galactosidase activity comprising one or more amino acid alterations (i.e. substitutions, deletions, and/or insertions or any combination thereof) in 1 to 50 positions, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 50 is not more than 10, e.g., 1, 2, 3, 4, 5, 6, 7, 8, 9 or 10. In another embodiment, the number of substitutions, deletions, and/or insertions in SEQ ID NO: 50 is not more than 10, e.g., 1, 2, 3, 4, 5, 6, 7, 8, 9 or 10. In a further embodiment, the number of substitutions, preferably conservative substitutions, in SEQ ID NO: 50 is not more than 10, e.g., 1, 2, 3, 4, 5, 6, 7, 8, 9 or 10.

Examples of amino acid changes and conservative substitutions are described in the second aspect of the invention.

In a sixteenth aspect, the invention relates to polypeptides having beta-galactosidase activity and having a sequence identity to the mature polypeptide of SEQ ID NO: 53 of at least 80% which have beta-galactosidase activity. In an embodiment, the polypeptide has a sequence identity to SEQ ID NO: 53 of at least 85%. In an embodiment, the polypeptide has a sequence identity to SEQ ID NO: 53 of at least 86%. In an embodiment, the polypeptide has a sequence identity to SEQ ID NO: 53 of at least 87%. In an embodiment, the polypeptide has a sequence identity to SEQ ID NO: 53 of at least 88%. In an embodiment, the polypeptide has a sequence identity to SEQ ID NO: 53 of at least 89%. In an embodiment, the polypeptide has a sequence identity to SEQ ID NO: 53 of at least 90%. In an embodiment, the polypeptide has a sequence identity to SEQ ID NO: 53 of at least 91%. In an embodiment, the polypeptide has a sequence identity to SEQ ID NO: 53 of at least 92%. In an embodiment, the polypeptide has a sequence identity to SEQ ID NO: 53 of at least 93%. In an embodiment, the polypeptide has a sequence identity to SEQ ID NO: 53 of at least 94%. In an embodiment, the polypeptide has a sequence identity to SEQ ID NO: 53 of at least 95%. In an embodiment, the polypeptide has a sequence identity to SEQ ID NO: 53 of at least 96%. In an embodiment, the polypeptide has a sequence identity to SEQ ID NO: 53 of at least 97%. In an embodiment, the polypeptide has a sequence identity to SEQ ID NO: 53 of at least 98%. In an embodiment, the polypeptide has a sequence identity to SEQ ID NO: 53 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 53.

In one embodiment, the polypeptide preferably comprises or consists of the amino acid sequence of SEQ ID NO: 53 or an allelic variant thereof; comprises the amino acid sequence of SEQ ID NO: 53 and a N-terminal and/or C-terminal His-tag and/or HQ-tag such as SEQ ID NO: 54; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 687 of SEQ ID NO: 53. In an embodiment, the polypeptide has been isolated.

In a continuation of the sixteenth aspect, the invention further relates to polypeptides having beta-galactosidase activity having a sequence identity to SEQ ID NO: 54 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 54.

In one embodiment, the polypeptide preferably comprises or consists of the amino acid sequence of SEQ ID NO: 54 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 694 of SEQ ID NO: 54. In an embodiment, the polypeptide has been isolated.

In a continuation of the sixteenth aspect, the invention relates to a polypeptide having beta-galactosidase activity encoded by a polynucleotide having a sequence identity to the mature polypeptide coding sequence of SEQ ID NO: 52 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixteenth aspect, the invention relates to variants of SEQ ID NO: 53 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 53 is not more than 10, e.g., 1, 2, 3, 4, 5, 6, 7, 8, 9 or 10. In another embodiment, the number of substitutions, deletions, and/or insertions in SEQ ID NO: 53 is not more than 10, e.g., 1, 2, 3, 4, 5, 6, 7, 8, 9 or 10. In a further embodiment, the number of substitutions, preferably conservative substitutions, in SEQ ID NO: 53 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the sixteenth aspect comprises the motif DW[K/R]RF[V/I]T[A/D]Q[T/M] (SEQ ID NO: 83).

In a seventeenth aspect, the invention relates to polypeptides having beta-galactosidase activity and having a sequence identity to the mature polypeptide of SEQ ID NO: 56 of at least 80% which have beta-galactosidase activity. In an embodiment, the polypeptide has a sequence identity to SEQ ID NO: 56 of at least 85%. In an embodiment, the polypeptide has a sequence identity to SEQ ID NO: 56 of at least 86%. In an embodiment, the polypeptide has a sequence identity to SEQ ID NO: 56 of at least 87%. In an embodiment, the polypeptide has a sequence identity to SEQ ID NO: 56 of at least 88%. In an embodiment, the polypeptide has a sequence identity to SEQ ID NO: 56 of at least 89%. In an embodiment, the polypeptide has a sequence identity to SEQ ID NO: 56 of at least 90%. In an embodiment, the polypeptide has a sequence identity to SEQ ID NO: 56 of at least 91%. In an embodiment, the polypeptide has a sequence identity to SEQ ID NO: 56 of at least 92%. In an embodiment, the polypeptide has a sequence identity to SEQ ID NO: 56 of at least 93%. In an embodiment, the polypeptide has a sequence identity to SEQ ID NO: 56 of at least 94%. In an embodiment, the polypeptide has a sequence identity to SEQ ID NO: 56 of at least 95%. In an embodiment, the polypeptide has a sequence identity to SEQ ID NO: 56 of at least 96%. In an embodiment, the polypeptide has a sequence identity to SEQ ID NO: 56 of at least 97%. In an embodiment, the polypeptide has a sequence identity to SEQ ID NO: 56 of at least 98%. In an embodiment, the polypeptide has a sequence identity to SEQ ID NO: 56 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 56.

In one embodiment, the polypeptide preferably comprises or consists of the amino acid sequence of SEQ ID NO: 56 or an allelic variant thereof; comprises the amino acid sequence of SEQ ID NO: 56 and a N-terminal and/or C-terminal His-tag and/or HQ-tag such as SEQ ID NO: 57; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 686 of SEQ ID NO: 56. In an embodiment, the polypeptide has been isolated.

In a continuation of the seventeenth aspect, the invention further relates to polypeptides having beta-galactosidase activity having a sequence identity to SEQ ID NO: 57 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 57.

In one embodiment, the polypeptide preferably comprises or consists of the amino acid sequence of SEQ ID NO: 57 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 695 of SEQ ID NO: 57. In an embodiment, the polypeptide has been isolated.

In a continuation of the seventeenth aspect, the invention relates to a polypeptide having beta-galactosidase activity encoded by a polynucleotide having a sequence identity to the mature polypeptide coding sequence of SEQ ID NO: 55 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the seventeenth aspect, the invention relates to variants of SEQ ID NO: 56 having beta-galactosidase activity comprising one or more amino acid alterations (i.e. substitutions, deletions, and/or insertions or any combination thereof) in 1 to 50 positions, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 56 is not more than 10, e.g., 1, 2, 3, 4, 5, 6, 7, 8, 9 or 10. In another embodiment, the number of substitutions, deletions, and/or insertions in SEQ ID NO: 56 is not more than 10, e.g., 1, 2, 3, 4, 5, 6, 7, 8, 9 or 10. In a further embodiment, the number of substitutions, preferably conservative substitutions, in SEQ ID NO: 56 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the seventeenth aspect comprises the motif DW[K/R]RF[V/I]T[A/D]Q[T/M] (SEQ ID NO: 83).

In an eighteenth aspect, the invention relates to polypeptides having beta-galactosidase activity and having a sequence identity to the mature polypeptide of SEQ ID NO: 59 of at least 80% which have beta-galactosidase activity. In an embodiment, the polypeptide has a sequence identity to SEQ ID NO: 59 of at least 85%. In an embodiment, the polypeptide has a sequence identity to SEQ ID NO: 59 of at least 86%. In an embodiment, the polypeptide has a sequence identity to SEQ ID NO: 59 of at least 87%. In an embodiment, the polypeptide has a sequence identity to SEQ ID NO: 59 of at least 88%. In an embodiment, the polypeptide has a sequence identity to SEQ ID NO: 59 of at least 89%. In an embodiment, the polypeptide has a sequence identity to SEQ ID NO: 59 of at least 90%. In an embodiment, the polypeptide has a sequence identity to SEQ ID NO: 59 of at least 91%. In an embodiment, the polypeptide has a sequence identity to SEQ ID NO: 59 of at least 92%. In an embodiment, the polypeptide has a sequence identity to SEQ ID NO: 59 of at least 93%. In an embodiment, the polypeptide has a sequence identity to SEQ ID NO: 59 of at least 94%. In an embodiment, the polypeptide has a sequence identity to SEQ ID NO: 59 of at least 95%. In an embodiment, the polypeptide has a sequence identity to SEQ ID NO: 59 of at least 96%. In an embodiment, the polypeptide has a sequence identity to SEQ ID NO: 59 of at least 97%. In an embodiment, the polypeptide has a sequence identity to SEQ ID NO: 59 of at least 98%. In an embodiment, the polypeptide has a sequence identity to SEQ ID NO: 59 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 59.

In one embodiment, the polypeptide preferably comprises or consists of the amino acid sequence of SEQ ID NO: 59 or an allelic variant thereof; comprises the amino acid sequence of SEQ ID NO: 59 and a N-terminal and/or C-terminal His-tag and/or HQ-tag such as SEQ ID NO: 60; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 688 of SEQ ID NO: 59. In an embodiment, the polypeptide has been isolated.

In a continuation of the eighteenth aspect, the invention further relates to polypeptides having beta-galactosidase activity having a sequence identity to SEQ ID NO: 60 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 60.

In one embodiment, the polypeptide preferably comprises or consists of the amino acid sequence of SEQ ID NO: 60 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 697 of SEQ ID NO: 60. In an embodiment, the polypeptide has been isolated.

In a continuation of the eighteenth aspect, the invention relates to a polypeptide having beta-galactosidase activity encoded by a polynucleotide having a sequence identity to the mature polypeptide coding sequence of SEQ ID NO: 58 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eighteenth aspect, the invention relates to variants of SEQ ID NO: 59 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 59 is not more than 10, e.g., 1, 2, 3, 4, 5, 6, 7, 8, 9 or 10. In another embodiment, the number of substitutions, deletions, and/or insertions in SEQ ID NO: 59 is not more than 10, e.g., 1, 2, 3, 4, 5, 6, 7, 8, 9 or 10. In a further embodiment, the number of substitutions, preferably conservative substitutions, in SEQ ID NO: 59 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the eighteenth aspect comprises the motif DW[K/R]RF[V/I]T[A/D]Q[T/M] (SEQ ID NO: 83).

In a nineteenth aspect, the invention relates to polypeptides having beta-galactosidase activity and having a sequence identity to the mature polypeptide of SEQ ID NO: 62 of at least 80% which have beta-galactosidase activity. In an embodiment, the polypeptide has a sequence identity to SEQ ID NO: 62 of at least 85%. In an embodiment, the polypeptide has a sequence identity to SEQ ID NO: 62 of at least 86%. In an embodiment, the polypeptide has a sequence identity to SEQ ID NO: 62 of at least 87%. In an embodiment, the polypeptide has a sequence identity to SEQ ID NO: 62 of at least 88%. In an embodiment, the polypeptide has a sequence identity to SEQ ID NO: 62 of at least 89%. In an embodiment, the polypeptide has a sequence identity to SEQ ID NO: 62 of at least 90%. In an embodiment, the polypeptide has a sequence identity to SEQ ID NO: 62 of at least 91%. In an embodiment, the polypeptide has a sequence identity to SEQ ID NO: 62 of at least 92%. In an embodiment, the polypeptide has a sequence identity to SEQ ID NO: 62 of at least 93%. In an embodiment, the polypeptide has a sequence identity to SEQ ID NO: 62 of at least 94%. In an embodiment, the polypeptide has a sequence identity to SEQ ID NO: 62 of at least 95%. In an embodiment, the polypeptide has a sequence identity to SEQ ID NO: 62 of at least 96%. In an embodiment, the polypeptide has a sequence identity to SEQ ID NO: 62 of at least 97%. In an embodiment, the polypeptide has a sequence identity to SEQ ID NO: 62 of at least 98%. In an embodiment, the polypeptide has a sequence identity to SEQ ID NO: 62 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 62.

In one embodiment, the polypeptide preferably comprises or consists of the amino acid sequence of SEQ ID NO: 62 or an allelic variant thereof; comprises the amino acid sequence of SEQ ID NO: 62 and a N-terminal and/or C-terminal His-tag and/or HQ-tag such as SEQ ID NO: 63; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 691 of SEQ ID NO: 62. In an embodiment, the polypeptide has been isolated.

In a continuation of the nineteenth aspect, the invention further relates to polypeptides having beta-galactosidase activity having a sequence identity to SEQ ID NO: 63 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 63.

In one embodiment, the polypeptide preferably comprises or consists of the amino acid sequence of SEQ ID NO: 63 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 700 of SEQ ID NO: 63. In an embodiment, the polypeptide has been isolated.

In a continuation of the nineteenth aspect, the invention relates to a polypeptide having beta-galactosidase activity encoded by a polynucleotide having a sequence identity to the mature polypeptide coding sequence of SEQ ID NO: 61 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the nineteenth aspect, the invention relates to variants of SEQ ID NO: 62 having beta-galactosidase activity comprising one or more amino acid alterations (i.e. substitutions, deletions, and/or insertions or any combination thereof) in 1 to 50 positions, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In an embodiment, the number of positions comprising one or more amino acid substitutions, and/or one or more amino acid deletions, and/or one or more amino acid insertions or any combination thereof in SEQ ID NO: 62 is not more than 10, e.g., 1, 2, 3, 4, 5, 6, 7, 8, 9 or 10. In another embodiment, the number of substitutions, deletions, and/or insertions in SEQ ID NO: 62 is not more than 10, e.g., 1, 2, 3, 4, 5, 6, 7, 8, 9 or 10. In a further embodiment, the number of substitutions, preferably conservative substitutions, in SEQ ID NO: 62 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the nineteenth aspect comprises the motif DW[K/R]RF[V/I]T[A/D]Q[T/M] (SEQ ID NO: 83).

In a twentieth aspect, the invention relates to polypeptides having beta-galactosidase activity and having a sequence identity to the mature polypeptide of SEQ ID NO: 65 of at least 88% which have beta-galactosidase activity. In an embodiment, the polypeptide has a sequence identity to SEQ ID NO: 65 of at least 89%. In an embodiment, the polypeptide has a sequence identity to SEQ ID NO: 65 of at least 90%. In an embodiment, the polypeptide has a sequence identity to SEQ ID NO: 65 of at least 91%. In an embodiment, the polypeptide has a sequence identity to SEQ ID NO: 65 of at least 92%. In an embodiment, the polypeptide has a sequence identity to SEQ ID NO: 65 of at least 93%. In an embodiment, the polypeptide has a sequence identity to SEQ ID NO: 65 of at least 94%. In an embodiment, the polypeptide has a sequence identity to SEQ ID NO: 65 of at least 95%. In an embodiment, the polypeptide has a sequence identity to SEQ ID NO: 65 of at least 96%. In an embodiment, the polypeptide has a sequence identity to SEQ ID NO: 65 of at least 97%. In an embodiment, the polypeptide has a sequence identity to SEQ ID NO: 65 of at least 98%. In an embodiment, the polypeptide has a sequence identity to SEQ ID NO: 65 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 65.

In one embodiment, the polypeptide preferably comprises or consists of the amino acid sequence of SEQ ID NO: 65 or an allelic variant thereof; comprises the amino acid sequence of SEQ ID NO: 65 and a N-terminal and/or C-terminal His-tag and/or HQ-tag such as SEQ ID NO: 66; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 690 of SEQ ID NO: 65. In an embodiment, the polypeptide has been isolated.

In a continuation of the twentieth aspect, the invention further relates to polypeptides having beta-galactosidase activity having a sequence identity to SEQ ID NO: 66 of at least 88%, e.g., at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 66.

In one embodiment, the polypeptide preferably comprises or consists of the amino acid sequence of SEQ ID NO: 66 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 699 of SEQ ID NO: 66. In an embodiment, the polypeptide has been isolated.

In a continuation of the twentieth aspect, the invention relates to a polypeptide having beta-galactosidase activity encoded by a polynucleotide having a sequence identity to the mature polypeptide coding sequence of SEQ ID NO: 64 or the cDNA sequence thereof of at least 88%, e.g., at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twentieth aspect, the invention relates to variants of SEQ ID NO: 65 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 65 is not more than 10, e.g., 1, 2, 3, 4, 5, 6, 7, 8, 9 or 10. In another embodiment, the number of substitutions, deletions, and/or insertions in SEQ ID NO: 65 is not more than 10, e.g., 1, 2, 3, 4, 5, 6, 7, 8, 9 or 10. In a further embodiment, the number of substitutions, preferably conservative substitutions, in SEQ ID NO: 65 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twentieth aspect comprises the motif DW[K/R]RF[V/I]T[A/D]Q[T/M] (SEQ ID NO: 83).

In a twenty-first aspect, the invention relates to polypeptides having beta-galactosidase activity and having a sequence identity to the mature polypeptide of SEQ ID NO: 68 of at least 80% which have beta-galactosidase activity. In an embodiment, the polypeptide has a sequence identity to SEQ ID NO: 68 of at least 85%. In an embodiment, the polypeptide has a sequence identity to SEQ ID NO: 68 of at least 86%. In an embodiment, the polypeptide has a sequence identity to SEQ ID NO: 68 of at least 87%. In an embodiment, the polypeptide has a sequence identity to SEQ ID NO: 68 of at least 88%. In an embodiment, the polypeptide has a sequence identity to SEQ ID NO: 68 of at least 89%. In an embodiment, the polypeptide has a sequence identity to SEQ ID NO: 68 of at least 90%. In an embodiment, the polypeptide has a sequence identity to SEQ ID NO: 68 of at least 91%. In an embodiment, the polypeptide has a sequence identity to SEQ ID NO: 68 of at least 92%. In an embodiment, the polypeptide has a sequence identity to SEQ ID NO: 68 of at least 93%. In an embodiment, the polypeptide has a sequence identity to SEQ ID NO: 68 of at least 94%. In an embodiment, the polypeptide has a sequence identity to SEQ ID NO: 68 of at least 95%. In an embodiment, the polypeptide has a sequence identity to SEQ ID NO: 68 of at least 96%. In an embodiment, the polypeptide has a sequence identity to SEQ ID NO: 68 of at least 97%. In an embodiment, the polypeptide has a sequence identity to SEQ ID NO: 68 of at least 98%. In an embodiment, the polypeptide has a sequence identity to SEQ ID NO: 68 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 68.

In one embodiment, the polypeptide preferably comprises or consists of the amino acid sequence of SEQ ID NO: 68 or an allelic variant thereof; comprises the amino acid sequence of SEQ ID NO: 68 and a N-terminal and/or C-terminal His-tag and/or HQ-tag such as SEQ ID NO: 69; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 689 of SEQ ID NO: 68. In an embodiment, the polypeptide has been isolated.

In a continuation of the twenty-first aspect, the invention further relates to polypeptides having beta-galactosidase activity having a sequence identity to SEQ ID NO: 69 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 69.

In one embodiment, the polypeptide preferably comprises or consists of the amino acid sequence of SEQ ID NO: 69 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 698 of SEQ ID NO: 69. In an embodiment, the polypeptide has been isolated.

In a continuation of the twenty-first aspect, the invention relates to a polypeptide having beta-galactosidase activity encoded by a polynucleotide having a sequence identity to the mature polypeptide coding sequence of SEQ ID NO: 67 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twenty-first aspect, the invention relates to variants of SEQ ID NO: 68 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 68 is not more than 10, e.g., 1, 2, 3, 4, 5, 6, 7, 8, 9 or 10. In another embodiment, the number of substitutions, deletions, and/or insertions in SEQ ID NO: 68 is not more than 10, e.g., 1, 2, 3, 4, 5, 6, 7, 8, 9 or 10. In a further embodiment, the number of substitutions, preferably conservative substitutions, in SEQ ID NO: 68 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twenty-first aspect comprises the motif DW[K/R]RF[V/I]T[A/D]Q[T/M] (SEQ ID NO: 83).

In a twenty-second aspect, the invention relates to polypeptides having beta-galactosidase activity and having a sequence identity to the mature polypeptide of SEQ ID NO: 71 of at least 80% which have beta-galactosidase activity. In an embodiment, the polypeptide has a sequence identity to SEQ ID NO: 71 of at least 85%. In an embodiment, the polypeptide has a sequence identity to SEQ ID NO: 71 of at least 86%. In an embodiment, the polypeptide has a sequence identity to SEQ ID NO: 71 of at least 87%. In an embodiment, the polypeptide has a sequence identity to SEQ ID NO: 71 of at least 88%. In an embodiment, the polypeptide has a sequence identity to SEQ ID NO: 71 of at least 89%. In an embodiment, the polypeptide has a sequence identity to SEQ ID NO: 71 of at least 90%. In an embodiment, the polypeptide has a sequence identity to SEQ ID NO: 71 of at least 91%. In an embodiment, the polypeptide has a sequence identity to SEQ ID NO: 71 of at least 92%. In an embodiment, the polypeptide has a sequence identity to SEQ ID NO: 71 of at least 93%. In an embodiment, the polypeptide has a sequence identity to SEQ ID NO: 71 of at least 94%. In an embodiment, the polypeptide has a sequence identity to SEQ ID NO: 71 of at least 95%. In an embodiment, the polypeptide has a sequence identity to SEQ ID NO: 71 of at least 96%. In an embodiment, the polypeptide has a sequence identity to SEQ ID NO: 71 of at least 97%. In an embodiment, the polypeptide has a sequence identity to SEQ ID NO: 71 of at least 98%. In an embodiment, the polypeptide has a sequence identity to SEQ ID NO: 71 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 71.

In one embodiment, the polypeptide preferably comprises or consists of the amino acid sequence of SEQ ID NO: 71 or an allelic variant thereof; comprises the amino acid sequence of SEQ ID NO: 71 and a N-terminal and/or C-terminal His-tag and/or HQ-tag such as SEQ ID NO: 72; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 685 of SEQ ID NO: 71. In an embodiment, the polypeptide has been isolated.

In a continuation of the twenty-second aspect, the invention further relates to polypeptides having beta-galactosidase activity having a sequence identity to SEQ ID NO: 72 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 72.

In one embodiment, the polypeptide preferably comprises or consists of the amino acid sequence of SEQ ID NO: 72 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 694 of SEQ ID NO: 72. In an embodiment, the polypeptide has been isolated.

In a continuation of the twenty-second aspect, the invention relates to a polypeptide having beta-galactosidase activity encoded by a polynucleotide having a sequence identity to the mature polypeptide coding sequence of SEQ ID NO: 70 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twenty-second aspect, the invention relates to variants of SEQ ID NO: 71 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 71 is not more than 10, e.g., 1, 2, 3, 4, 5, 6, 7, 8, 9 or 10. In another embodiment, the number of substitutions, deletions, and/or insertions in SEQ ID NO: 71 is not more than 10, e.g., 1, 2, 3, 4, 5, 6, 7, 8, 9 or 10. In a further embodiment, the number of substitutions, preferably conservative substitutions, in SEQ ID NO: 71 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twenty-second aspect comprises the motif DW[K/R]RF[V/I]T[A/D]Q[T/M] (SEQ ID NO: 83).

In a twenty-third aspect, the invention relates to polypeptides having beta-galactosidase activity and having a sequence identity to the mature polypeptide of SEQ ID NO: 74 of at least 80% which have beta-galactosidase activity. In an embodiment, the polypeptide has a sequence identity to SEQ ID NO: 74 of at least 85%. In an embodiment, the polypeptide has a sequence identity to SEQ ID NO: 74 of at least 86%. In an embodiment, the polypeptide has a sequence identity to SEQ ID NO: 74 of at least 87%. In an embodiment, the polypeptide has a sequence identity to SEQ ID NO: 74 of at least 88%. In an embodiment, the polypeptide has a sequence identity to SEQ ID NO: 74 of at least 89%. In an embodiment, the polypeptide has a sequence identity to SEQ ID NO: 74 of at least 90%. In an embodiment, the polypeptide has a sequence identity to SEQ ID NO: 74 of at least 91%. In an embodiment, the polypeptide has a sequence identity to SEQ ID NO: 74 of at least 92%. In an embodiment, the polypeptide has a sequence identity to SEQ ID NO: 74 of at least 93%. In an embodiment, the polypeptide has a sequence identity to SEQ ID NO: 74 of at least 94%. In an embodiment, the polypeptide has a sequence identity to SEQ ID NO: 74 of at least 95%. In an embodiment, the polypeptide has a sequence identity to SEQ ID NO: 74 of at least 96%. In an embodiment, the polypeptide has a sequence identity to SEQ ID NO: 74 of at least 97%. In an embodiment, the polypeptide has a sequence identity to SEQ ID NO: 74 of at least 98%. In an embodiment, the polypeptide has a sequence identity to SEQ ID NO: 74 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 74.

In one embodiment, the polypeptide preferably comprises or consists of the amino acid sequence of SEQ ID NO: 74 or an allelic variant thereof; comprises the amino acid sequence of SEQ ID NO: 74 and a N-terminal and/or C-terminal His-tag and/or HQ-tag such as SEQ ID NO: 75; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 685 of SEQ ID NO: 74. In an embodiment, the polypeptide has been isolated.

In a continuation of the twenty-third aspect, the invention further relates to polypeptides having beta-galactosidase activity having a sequence identity to SEQ ID NO: 75 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 75.

In one embodiment, the polypeptide preferably comprises or consists of the amino acid sequence of SEQ ID NO: 75 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 694 of SEQ ID NO: 75. In an embodiment, the polypeptide has been isolated.

In a continuation of the twenty-third aspect, the invention relates to a polypeptide having beta-galactosidase activity encoded by a polynucleotide having a sequence identity to the mature polypeptide coding sequence of SEQ ID NO: 73 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twenty-third aspect, the invention relates to variants of SEQ ID NO: 74 having beta-galactosidase activity comprising one or more amino acid alterations (i.e. substitutions, deletions, and/or insertions or any combination thereof) in 1 to 50 positions, such as as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 74 is not more than 10, e.g., 1, 2, 3, 4, 5, 6, 7, 8, 9 or 10. In another embodiment, the number of substitutions, deletions, and/or insertions in SEQ ID NO: 74 is not more than 10, e.g., 1, 2, 3, 4, 5, 6, 7, 8, 9 or 10. In a further embodiment, the number of substitutions, preferably conservative substitutions, in SEQ ID NO: 74 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twenty-third aspect comprises the motif DW[K/R]RF[V/I]T[A/D]Q[T/M] (SEQ ID NO: 83).

In a twenty-fourth aspect, the invention relates to polypeptides having beta-galactosidase activity and having a sequence identity to the mature polypeptide of SEQ ID NO: 77 of at least 80% which have beta-galactosidase activity. In an embodiment, the polypeptide has a sequence identity to SEQ ID NO: 77 of at least 85%. In an embodiment, the polypeptide has a sequence identity to SEQ ID NO: 77 of at least 86%. In an embodiment, the polypeptide has a sequence identity to SEQ ID NO: 77 of at least 87%. In an embodiment, the polypeptide has a sequence identity to SEQ ID NO: 77 of at least 88%. In an embodiment, the polypeptide has a sequence identity to SEQ ID NO: 77 of at least 89%. In an embodiment, the polypeptide has a sequence identity to SEQ ID NO: 77 of at least 90%. In an embodiment, the polypeptide has a sequence identity to SEQ ID NO: 77 of at least 91%. In an embodiment, the polypeptide has a sequence identity to SEQ ID NO: 77 of at least 92%. In an embodiment, the polypeptide has a sequence identity to SEQ ID NO: 77 of at least 93%. In an embodiment, the polypeptide has a sequence identity to SEQ ID NO: 77 of at least 94%. In an embodiment, the polypeptide has a sequence identity to SEQ ID NO: 77 of at least 95%. In an embodiment, the polypeptide has a sequence identity to SEQ ID NO: 77 of at least 96%. In an embodiment, the polypeptide has a sequence identity to SEQ ID NO: 77 of at least 97%. In an embodiment, the polypeptide has a sequence identity to SEQ ID NO: 77 of at least 98%. In an embodiment, the polypeptide has a sequence identity to SEQ ID NO: 77 of at least 99%.

In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 77.

In one embodiment, the polypeptide preferably comprises or consists of the amino acid sequence of SEQ ID NO: 77 or an allelic variant thereof; comprises the amino acid sequence of SEQ ID NO: 77 and a N-terminal and/or C-terminal His-tag and/or HQ-tag such as SEQ ID NO: 78; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 686 of SEQ ID NO: 77. In an embodiment, the polypeptide has been isolated.

In a continuation of the twenty-fourth aspect, the invention further relates to polypeptides having beta-galactosidase activity having a sequence identity to SEQ ID NO: 78 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 78.

In one embodiment, the polypeptide preferably comprises or consists of the amino acid sequence of SEQ ID NO: 78 or an allelic variant thereof; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 695 of SEQ ID NO: 78. In an embodiment, the polypeptide has been isolated.

In a continuation of the twenty-fourth aspect, the invention relates to a polypeptide having beta-galactosidase activity encoded by a polynucleotide having a sequence identity to the mature polypeptide coding sequence of SEQ ID NO: 76 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twenty-fourth aspect, the invention relates to variants of SEQ ID NO: 77 having beta-galactosidase activity comprising one or more amino acid alterations (i.e. substitutions, deletions, and/or insertions or any combination thereof) in 1 to 50 positions, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions.

In an embodiment, the number of positions comprising one or more amino acid substitutions, and/or one or more amino acid deletions, and/or one or more amino acid insertions or any combination thereof in SEQ ID NO: 77 is not more than 10, e.g., 1, 2, 3, 4, 5, 6, 7, 8, 9 or 10. In another embodiment, the number of substitutions, deletions, and/or insertions in SEQ ID NO: 77 is not more than 10, e.g., 1, 2, 3, 4, 5, 6, 7, 8, 9 or 10. In a further embodiment, the number of substitutions, preferably conservative substitutions, in SEQ ID NO: 77 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twenty-fourth aspect comprises the motif DW[K/R]RF[V/I]T[A/D]Q[T/M] (SEQ ID NO: 83).

Sources of Polypeptides Having Beta-Galactosidase or Galactanase Activity

A polypeptide having beta-galactosidase or galactanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide having galactanase activity is a bacterial polypeptide, preferably from the phylum Firmicutes or more preferably from the class Bacilli. In one embodiment, the polypeptide having galactanase activity is from a bacterium of the order Bacillales, or from the family Paenibacillaceae, or from the genus *Cohnella* or from the species *Cohnella* sp-60555, *Cohnella xylanilytica* or *Cohnella laeviribosi*. In another embodiment, the polypeptide having galactanase activity is from a bacterium of the order Bacillales, or from the family Paenibacillaceae, or from the genus *Paenibacillus* or from the species *Paenibacillus tundra*, *Paenibacillus barcinonensis*, *Paenibacillus* sp-62603, *Paenibacillus xylanilyticus*, *Paenibacillus* sp-18179, *Paenibacillus peoriae* or *Paenibacillus xylanexedens*.

The polypeptide having beta-galactosidase activity is a bacterial polypeptide, preferably from the phylum Firmicutes or more preferably from the order Bacillales. In one embodiment, the polypeptide having galactanase activity is from a bacterium of the order Bacillales, or from the family Bacillaceae, or from the genus *Bacillus* or from the species *Bacillus pumilus, Bacillus nealsonii, Bacillus alcalophilus, Bacillus* sp-11182 or *Bacillus* sp-62759. In another embodiment, the polypeptide having galactanase activity is from a bacterium of the order Bacillales, or from the family Paenibacillaceae, or from the genus *Paenibacillus* or from the species *Paenibacillus* sp-18026, *Paenibacillus* sp-18054, *Paenibacillus* sp-62047, *Paenibacillus* sp-62603, *Paenibacillus woosongensis, Paenibacillus* sp-62253 or *Paenibacillus* sp-62758.

In one embodiment, the polypeptide having beta-galactosidase activity is a bacterial polypeptide, preferably from the phylum Proteobacteria, more preferably from the order Burkholderiales, from the family Burkholderiaceae, or from the genus *Burkholderia* or from the species *Burkholderia sediminicola*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Liquid Formulations Comprising GH42 Beta-Galactosidases and GH53 Galactanases

In a twenty-fifth aspect, the invention relates to a liquid formulation comprising one or more GH53 polypeptides having galactanase activity and one or more GH42 polypeptides having beta-galactosidase activity, wherein the liquid formulation comprises:

(A) 0.001% to 25% w/w of polypeptide having galactanase activity;
(B) 0.001% to 25% w/w of polypeptide having beta-galactosidase activity; and
(C) water.

In one embodiment of the twenty-fifth aspect, the invention relates to a liquid formulation comprising one or more GH53 polypeptides having galactanase activity and one or more GH42 polypeptides having beta-galactosidase activity, wherein the liquid formulation comprises:

(A) 0.001% to 25% w/w of polypeptide having galactanase activity;
(B) 0.001% to 25% w/w of polypeptide having beta-galactosidase activity;
(C) 20% to 80% w/w of polyol; and
(D) water.

In one embodiment of the twenty-fifth aspect, the invention relates to a liquid formulation comprising one or more GH53 polypeptides having galactanase activity and one or more GH42 polypeptides having beta-galactosidase activity, wherein the liquid formulation comprises:

(A) 0.001% to 25% w/w of polypeptide having galactanase activity;
(B) 0.001% to 25% w/w of polypeptide having beta-galactosidase activity;
(C) 0.001% to 2.0% w/w preservative; and
(D) water.

In one embodiment of the twenty-fifth aspect, the invention relates to a liquid formulation comprising one or more GH53 polypeptides having galactanase activity and one or more GH42 polypeptides having beta-galactosidase activity, wherein the liquid formulation comprises:

(A) 0.001% to 25% w/w of polypeptide having galactanase activity;
(B) 0.001% to 25% w/w of polypeptide having beta-galactosidase activity;
(C) 20% to 80% w/w of polyol;
(D) 0.001% to 2.0% w/w preservative; and
(E) water.

In one embodiment to any part of the twenty-fifth aspect, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment to any part of the twenty-fifth aspect, the GH53 polypeptide is selected from the group consisting of:

(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;
(g) a polypeptide having at least 80%, e.g., at least 85%, at least 90% or at least 95% sequence identity to the polypeptide of SEQ ID NO: 27;
(h) a polypeptide having at least 80%, e.g., at least 85%, at least 90% or at least 95% sequence identity to the polypeptide of SEQ ID NO: 31;
(i) a polypeptide having at least 80%, e.g., at least 85%, at least 90% or at least 95% sequence identity to the polypeptide of SEQ ID NO: 35;
(j) a polypeptide having at least 80%, e.g., at least 85%, at least 90% or at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.

In one embodiment to any part of the twenty-fifth aspect, the GH42 polypeptide comprises the motif DW[K/R]RF[V/I]T[A/D]Q[T/M] (SEQ ID NO: 83). In one embodiment to any part of the twenty-fifth aspect, the GH42 polypeptide is selected from the group consisting of:

(a) a polypeptide having at least 80%, e.g., at least 85%, at least 90% or at least 95% sequence identity to the polypeptide of SEQ ID NO: 42;
(b) a polypeptide having at least 80%, e.g., at least 85%, at least 90% or at least 95% sequence identity to the polypeptide of SEQ ID NO: 44;
(c) a polypeptide having at least 80%, e.g., at least 85%, at least 90% or at least 95% sequence identity to the polypeptide of SEQ ID NO: 47;
(d) a polypeptide having at least 80%, e.g., at least 85%, at least 90% or at least 95% sequence identity to the polypeptide of SEQ ID NO: 50;
(e) a polypeptide having at least 80%, e.g., at least 85%, at least 90% or at least 95% sequence identity to the polypeptide of SEQ ID NO: 53;
(f) a polypeptide having at least 80%, e.g., at least 85%, at least 90% or at least 95% sequence identity to the polypeptide of SEQ ID NO: 56;
(g) a polypeptide having at least 80%, e.g., at least 85%, at least 90% or at least 95% sequence identity to the polypeptide of SEQ ID NO: 59;
(h) a polypeptide having at least 80%, e.g., at least 85%, at least 90% or at least 95% sequence identity to the polypeptide of SEQ ID NO: 62;
(i) a polypeptide having at least 80%, e.g., at least 85%, at least 90% or at least 95% sequence identity to the polypeptide of SEQ ID NO: 65;
(j) a polypeptide having at least 80%, e.g., at least 85%, at least 90% or at least 95% sequence identity to the polypeptide of SEQ ID NO: 68;
(k) a polypeptide having at least 80%, e.g., at least 85%, at least 90% or at least 95% sequence identity to the polypeptide of SEQ ID NO: 71;
(l) a polypeptide having at least 80%, e.g., at least 85%, at least 90% or at least 95% sequence identity to the polypeptide of SEQ ID NO: 74;
(m) a polypeptide having at least 80%, e.g., at least 85%, at least 90% or at least 95% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag; and
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m) or (n) having galactanase activity and having at least 90% of the length of the mature polypeptide.

In one embodiment to any part of the twenty-fifth aspect, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH42 polypeptide comprises the motif DW[K/R]RF[V/I]T[A/D]Q[T/M](SEQ ID NO: 83). In one embodiment to any part of the twenty-fifth aspect, the GH53 polypeptide is selected from the group consisting of:
(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;
(g) a polypeptide having at least 80%, e.g., at least 85%, at least 90% or at least 95% sequence identity to the polypeptide of SEQ ID NO: 27;
(h) a polypeptide having at least 80%, e.g., at least 85%, at least 90% or at least 95% sequence identity to the polypeptide of SEQ ID NO: 31;
(i) a polypeptide having at least 80%, e.g., at least 85%, at least 90% or at least 95% sequence identity to the polypeptide of SEQ ID NO: 35;
(j) a polypeptide having at least 80%, e.g., at least 85%, at least 90% or at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide;

and the GH42 polypeptide is selected from the group consisting of:
(a) a polypeptide having at least 80%, e.g., at least 85%, at least 90% or at least 95% sequence identity to the polypeptide of SEQ ID NO: 42;
(b) a polypeptide having at least 80%, e.g., at least 85%, at least 90% or at least 95% sequence identity to the polypeptide of SEQ ID NO: 44;
(c) a polypeptide having at least 80%, e.g., at least 85%, at least 90% or at least 95% sequence identity to the polypeptide of SEQ ID NO: 47;

(d) a polypeptide having at least 80%, e.g., at least 85%, at least 90% or at least 95% sequence identity to the polypeptide of SEQ ID NO: 50;
(e) a polypeptide having at least 80%, e.g., at least 85%, at least 90% or at least 95% sequence identity to the polypeptide of SEQ ID NO: 53;
(f) a polypeptide having at least 80%, e.g., at least 85%, at least 90% or at least 95% sequence identity to the polypeptide of SEQ ID NO: 56;
(g) a polypeptide having at least 80%, e.g., at least 85%, at least 90% or at least 95% sequence identity to the polypeptide of SEQ ID NO: 59;
(h) a polypeptide having at least 80%, e.g., at least 85%, at least 90% or at least 95% sequence identity to the polypeptide of SEQ ID NO: 62;
(i) a polypeptide having at least 80%, e.g., at least 85%, at least 90% or at least 95% sequence identity to the polypeptide of SEQ ID NO: 65;
(j) a polypeptide having at least 80%, e.g., at least 85%, at least 90% or at least 95% sequence identity to the polypeptide of SEQ ID NO: 68;
(k) a polypeptide having at least 80%, e.g., at least 85%, at least 90% or at least 95% sequence identity to the polypeptide of SEQ ID NO: 71;
(l) a polypeptide having at least 80%, e.g., at least 85%, at least 90% or at least 95% sequence identity to the polypeptide of SEQ ID NO: 74;
(m) a polypeptide having at least 80%, e.g., at least 85%, at least 90% or at least 95% sequence identity to the polypeptide of SEQ ID NO: 77;
(n) a variant of SEQ ID NO: 42, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74 or SEQ ID NO: 77 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(o) a polypeptide comprising the polypeptide of (a), (b), (c), (d), (e), (f), (g), (h), (i), (j), (k), (l), (m) or (n) and a N-terminal and/or C-terminal His-tag and/or HQ-tag; and
(p) a polypeptide comprising the polypeptide of (a), (b), (c), (d), (e), (f), (g), (h), (i), (j), (k), (l), (m) or (n) and a N-terminal and/or C-terminal extension of between 1 and 10 amino acids; and
(q) a fragment of the polypeptide of (a), (b), (c), (d), (e), (f), (g), (h), (i), (j), (k), (l), (m) or (n) having galactanase activity and having at least 90% of the length of the mature polypeptide.

In one embodiment to any part of the twenty-fifth aspect, the GH53 polypeptide having galactanase activity is obtained or obtainable from the taxonomic family Paenibacillaceae.

In one embodiment to any part of the twenty-fifth aspect, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment to any part of the twenty-fifth aspect, the liquid formulation comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the twenty-fifth aspect, the liquid formulation comprises one or more polyols, preferably a polyol selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment to any part of the twenty-fifth aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol. In one embodiment to any part of the twenty-fifth aspect, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600. In one embodiment to any part of the twenty-fifth aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment to any part of the twenty-fifth aspect, the preservative is selected from the group consisting of sodium sorbate, potassium sorbate, sodium benzoate and potassion benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.01% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassion benzoate or any combination thereof.

In one embodiment to any part of the ninth aspect, the liquid formulation comprises 0.01% to 25% w/w polypeptide having beta-galactosidase activity, preferably 0.05% to 20% w/w polypeptide having beta-galactosidase activity, more preferably 0.2% to 15% w/w polypeptide having beta-galactosidase activity, more preferably 0.5% to 15% w/w polypeptide having beta-galactosidase activity or most preferably 1.0% to 10% w/w polypeptide having beta-galactosidase activity.

In one embodiment to any part of the ninth aspect, the liquid formulation comprises 0.01% to 25% w/w polypeptide having galactanase activity, preferably 0.05% to 20% w/w polypeptide having galactanase activity, more preferably 0.2% to 15% w/w polypeptide having galactanase activity, more preferably 0.5% to 15% w/w polypeptide having galactanase activity or most preferably 1.0% to 10% w/w polypeptide having galactanase activity.

In one embodiment to any part of the twenty-fifth aspect, the liquid formulation comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment to any part of the twenty-fifth aspect, the liquid formulation comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp.*, Carnobacterium sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

Methods of Improving Animal Performance

In a twenty-sixth aspect, the invention relates to a method of improving one or more performance parameters of an animal comprising administering to one or more animals the composition of the first aspect of the invention or any embodiment of the first aspect of the invention herein defined, such as in the section related to 'Compositions comprising GH42 beta-galactosidases and GH53 galactanases' or the section on 'Combinations'. In one preferred embodiment, the composition is a granule that optionally comprises a salt and/or wax and/or a flour coating. In one preferred embodiment, the composition is a liquid formulation as described in the twenty-fifth aspect.

The twenty-sixth aspect of the invention also relates to a method of improving one or more performance parameters of an animal comprising administering to one or more animals an animal feed additive comprising the composition of the first aspect of the invention or any embodiment of the first aspect of the invention herein defined, such as in the section related to 'Compositions comprising GH42 beta-galactosidases and GH53 galactanases' or the section on 'Combinations'. In one embodiment, animal feed additive comprises of one or more additional enzymes, one or more microbes, one or more vitamins, one or more minerals, one or more amino acids or any combination thereof. In a preferred embodiment, the animal feed additive is a granule that optionally comprises a salt and/or wax and/or a flour coating.

The twenty-sixth aspect of the invention also relates to a method of improving one or more performance parameters of an animal comprising administering to one or more animals an animal feed comprising the composition of the first aspect of the invention or any embodiment of the first aspect of the invention herein defined, such as in the section related to 'Compositions comprising GH42 beta-galactosidases and GH53 galactanases' or the section on 'Combinations' and plant based material. In one embodiment, the plant based material is from the taxonomic subclass rosids. In one embodiment, the animal feed comprises one or more formulating agents as defined herein. In one embodiment, the animal feed comprises one or more additional enzymes as defined herein. In one embodiment, the animal feed comprises one or more microbes as defined herein. In a preferred embodiment, the animal feed has been pelleted.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In an embodiment, the performance parameter is selected from the list consisting of body weight gain (BWG), European Production Efficiency Factor (EPEF) and feed conversion ratio (FCR).

Methods of Releasing Galactose

In a twenty-seventh aspect, the invention relates to method of releasing galactose from plant based material, comprising treating plant based material with the composition of the first aspect of the invention or any embodiment of the first aspect of the invention herein defined, such as in the section related to 'Compositions comprising GH42 beta-galactosidases and GH53 galactanases' or the section on 'Combinations'. In an embodiment, the plant based material is from the taxonomic subclass rosids. In one preferred embodiment, the composition is a granule that optionally comprises a salt and/or wax and/or a flour coating. In one preferred embodiment, the composition is a liquid formulation as described in the twenty-fifth aspect.

The twenty-seventh aspect of the invention also relates to a method of releasing galactose from plant based material, comprising treating plant based material with and animal feed additive comprising the composition of the first aspect of the invention or any embodiment of the first aspect of the invention herein defined, such as in the section related to 'Compositions comprising GH42 beta-galactosidases and GH53 galactanases' or the section on 'Combinations'. In one embodiment, the animal feed additive comprises one or more additional enzymes, one or more microbes, one or more vitamins, one or more minerals, one or more amino acids or any combination thereof. In an embodiment, the plant based material is from the taxonomic subclass rosids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Methods for Improving the Nutritional Value of an Animal Feed

The term improving the nutritional value of an animal feed means improving the availability of nutrients in the feed. The nutritional values refers in particular to improving the solubilisation and degradation of the non starch polysaccharide (NSP) fraction, such as the galactan polysaccharide in the cell wall pectic network, thereby increasing the amount of galactose released which can be utilised by the animal. Consequently, an improved galactose release will result in an improvement of the nutritional value of the feed, thus resulting in increased growth rate and/or weight gain and/or feed conversion (i.e. the weight of ingested feed relative to weight gain).

In a twenty-eighth aspect, the invention relates to a method for improving the nutritional value of an animal feed comprising treating the animal feed with the composition of the first aspect of the invention or any embodiment of the first aspect of the invention herein defined, such as in the section related to 'Compositions comprising GH42 beta-galactosidases and GH53 galactanases' or the section on 'Combinations'. In an embodiment, the animal feed comprises plant based material from the taxonomic subclass rosids. In one preferred embodiment, the composition is a granule that optionally comprises a salt and/or wax and/or a flour coating. In one preferred embodiment, the composition is a liquid formulation as described in the twenty-fifth aspect. In an embodiment, the animal feed will have improved nutrient digestibility.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

The twenty-eighth aspect of the invention also relates to a method for improving the nutritional value of an animal feed comprising treating the animal feed with an animal feed additive comprising the composition of the first aspect of the invention or any embodiment of the first aspect of the invention herein defined, such as in the section related to 'Compositions comprising GH42 beta-galactosidases and GH53 galactanases' or the section on 'Combinations'. In an embodiment, the animal feed comprises plant based material from the taxonomic subclass rosids.

In a preferred embodiment, the animal feed additive is a granule that optionally comprises a salt and/or wax and/or a flour coating. In an embodiment, the animal feed will have improved nutrient digestibility.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Method for Reducing the Anitnutritional Effects of an Animal Feed

An excessive amount of oligosaccharides in the hindgut can result in antinutritional effects due to flatulence production. By reducing the amount of oligosaccharide fermentation, the antinutritional effects of some animal feeds can be reduced resulting in improved gut and animal health.

In a twenty-ninth aspect, the invention relates to a method for improving the nutritional value of an animal feed comprising treating the animal feed with the composition of the first aspect of the invention or any embodiment of the first aspect of the invention herein defined, such as in the section related to 'Compositions comprising GH42 beta-galactosidases and GH53 galactanases' or the section on 'Combinations'. In an embodiment, the animal feed comprises plant based material from the taxonomic subclass rosids. In one preferred embodiment, the composition is a granule that optionally comprises a salt and/or wax and/or a flour coating. In one preferred embodiment, the composition is a liquid formulation as described in the twenty-fifth aspect. In an embodiment, the animal feed will have improved nutrient digestibility.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

The twenty-ninth aspect of the invention also relates to a method for improving the nutritional value of an animal feed comprising treating the animal feed with an animal feed additive comprising the composition of the first aspect of the invention or any embodiment of the first aspect of the invention herein defined, such as in the section related to 'Compositions comprising GH42 beta-galactosidases and GH53 galactanases' or the section on 'Combinations'. In an embodiment, the animal feed comprises plant based material from the taxonomic subclass rosids In a preferred embodiment, the animal feed additive is a granule that optionally comprises a salt and/or wax and/or a flour coating. In an embodiment, the animal feed will have improved nutrient digestibility.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Methods of Preparing an Animal Feed

In a thirtieth aspect, the invention relates to a method of preparing an animal feed, comprising mixing the composition of the first aspect of the invention or any embodiment of the first aspect of the invention herein defined, such as in the section related to 'Compositions comprising GH42 beta-galactosidases and GH53 galactanases' or the section on 'Combinations' with plant based material.

In one embodiment, the composition comprises one or more formulating agents as defined herein. In one embodiment, the composition comprises one or more additional enzymes as defined herein. In one embodiment, the composition comprises one or more microbes as defined herein. In one preferred embodiment, the composition is a granule that optionally comprises a salt and/or wax and/or a flour coating. In one preferred embodiment, the composition is a liquid formulation as described in the twenty-fifth aspect.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

The thirtieth aspect of the invention also relates to a method of preparing an animal feed, comprising mixing the composition of the first aspect of the invention or any embodiment of the first aspect of the invention herein defined, such as in the section related to 'Compositions comprising GH42 beta-galactosidases and GH53 galactanases' or the section on 'Combinations' with plant based material. In an embodiment, the animal feed comprises plant based material from the taxonomic subclass rosids. In a preferred embodiment, the animal feed additive is a granule that optionally comprises a salt and/or wax and/or a flour coating. In an embodiment, the animal feed will have improved nutrient digestibility.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Polynucleotides

The present invention also relates to isolated polynucleotides encoding a polypeptide of the present invention.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* galactanase I, *Trichoderma reesei* galactanase II, *Trichoderma reesei* galactanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* galactanase I, *Trichoderma reesei* galactanase II, *Trichoderma reesei* galactanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier.

The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Cohnella* cell. In one aspect, the cell is a *Cohnella* sp-60555 cell. In one aspect, the cell is a *Cohnella xylanilytica* cell. In one aspect, the cell is a *Cohnella laeviribosi* cell. In one aspect, the cell is a *Paenibacillus* cell. In one aspect, the cell is a *Paenibacillus tundra* cell. In one aspect, the cell is a *Paenibacillus barcinonensis* cell. In one aspect, the cell is a *Paenibacillus* sp-62603 cell. In one aspect, the cell is a *Paenibacillus xylanilyticus* cell. In one aspect, the cell is a *Paenibacillus* sp-18179 cell. In one aspect, the cell is a *Paenibacillus peoriae* cell. In one aspect, the cell is a *Paenibacillus xylanexedens* cell.

In one aspect, the cell is a *Bacillus pumilus* cell. In one aspect, the cell is a *Bacillus nealsonii* cell. In one aspect, the cell is a *Bacillus alcalophilus* cell. In one aspect, the cell is a *Bacillus* sp-11182 cell. In one aspect, the cell is a *Bacillus* sp-62759 cell. In one aspect, the cell is a *Paenibacillus* sp-18026 cell. In one aspect, the cell is a *Paenibacillus* sp-18054 cell. In one aspect, the cell is a *Paenibacillus* sp-62047 cell. In one aspect, the cell is a *Paenibacillus* sp-62603 cell. In one aspect, the cell is a *Paenibacillus woosongensis* cell. In one aspect, the cell is a *Paenibacillus* sp-62253 cell. In one aspect, the cell is a *Paenibacillus* sp-62758 cell. In one aspect, the cell is a *Burkholderia sediminicola* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

Preferably, the compositions are enriched in the polypeptides of the first aspect of the invention. The term "enriched" indicates that the beta-galactosidase activity and the galactanase activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10. In an embodiment, the composition comprises the polypeptides of the first aspect of the invention and one or more formulating agents, as described in the 'formulating agent' section below.

The present invention also relates to compositions comprising the polypeptide of the second aspect of the invention (SEQ ID NO: 3) having galactanase activity. In an embodiment, the composition further comprises one or more formulating agents.

The present invention also relates to compositions comprising the polypeptide of the third aspect of the invention (SEQ ID NO: 7) having galactanase activity. In an embodiment, the composition further comprises one or more formulating agents.

The present invention also relates to compositions comprising the polypeptide of the fourth aspect of the invention (SEQ ID NO: 11) having galactanase activity. In an embodiment, the composition further comprises one or more formulating agents.

The present invention also relates to compositions comprising the polypeptide of the fifth aspect of the invention (SEQ ID NO: 15) having galactanase activity. In an embodiment, the composition further comprises one or more formulating agents.

The present invention also relates to compositions comprising the polypeptide of the sixth aspect of the invention (SEQ ID NO: 19) having galactanase activity. In an embodiment, the composition further comprises one or more formulating agents.

The present invention also relates to compositions comprising the polypeptide of the seventh aspect of the invention (SEQ ID NO: 23) having galactanase activity. In an embodiment, the composition further comprises one or more formulating agents.

The present invention also relates to compositions comprising the polypeptide of the eighth aspect of the invention (SEQ ID NO: 27) having galactanase activity. In an embodiment, the composition further comprises one or more formulating agents.

The present invention also relates to compositions comprising the polypeptide of the ninth aspect of the invention (SEQ ID NO: 31) having galactanase activity. In an embodiment, the composition further comprises one or more formulating agents.

The present invention also relates to compositions comprising the polypeptide of the tenth aspect of the invention (SEQ ID NO: 35) having galactanase activity. In an embodiment, the composition further comprises one or more formulating agents.

The present invention also relates to compositions comprising the polypeptide of the eleventh aspect of the invention (SEQ ID NO: 39) having galactanase activity. In an embodiment, the composition further comprises one or more formulating agents.

The present invention also relates to compositions comprising the polypeptide of the twelfth aspect of the invention (SEQ ID NO: 42) having beta-galactosidase activity. In an embodiment, the composition further comprises one or more formulating agents.

The present invention also relates to compositions comprising the polypeptide of the thirteenth aspect of the invention (SEQ ID NO: 44) having beta-galactosidase activity. In an embodiment, the composition further comprises one or more formulating agents.

The present invention also relates to compositions comprising the polypeptide of the fourteenth aspect of the invention (SEQ ID NO: 47) having beta-galactosidase activity. In an embodiment, the composition further comprises one or more formulating agents.

The present invention also relates to compositions comprising the polypeptide of the fifteenth aspect of the invention (SEQ ID NO: 50) having beta-galactosidase activity. In an embodiment, the composition further comprises one or more formulating agents.

The present invention also relates to compositions comprising the polypeptide of the sixteenth aspect of the invention (SEQ ID NO: 53) having beta-galactosidase activity. In an embodiment, the composition further comprises one or more formulating agents.

The present invention also relates to compositions comprising the polypeptide of the seventeenth aspect of the invention (SEQ ID NO: 56) having beta-galactosidase activity. In an embodiment, the composition further comprises one or more formulating agents.

The present invention also relates to compositions comprising the polypeptide of the eighteenth aspect of the invention (SEQ ID NO: 59) having beta-galactosidase activity. In an embodiment, the composition further comprises one or more formulating agents.

The present invention also relates to compositions comprising the polypeptide of the nineteenth aspect of the invention (SEQ ID NO: 62) having beta-galactosidase activity. In an embodiment, the composition further comprises one or more formulating agents.

The present invention also relates to compositions comprising the polypeptide of the twentieth aspect of the invention (SEQ ID NO: 65) having beta-galactosidase activity. In an embodiment, the composition further comprises one or more formulating agents.

The present invention also relates to compositions comprising the polypeptide of the twenty-first aspect of the invention (SEQ ID NO: 68) having beta-galactosidase activity. In an embodiment, the composition further comprises one or more formulating agents.

The present invention also relates to compositions comprising the polypeptide of the twenty-second aspect of the invention (SEQ ID NO: 71) having beta-galactosidase activity. In an embodiment, the composition further comprises one or more formulating agents.

The present invention also relates to compositions comprising the polypeptide of the twenty-thrid aspect of the invention (SEQ ID NO: 74) having beta-galactosidase activity. In an embodiment, the composition further comprises one or more formulating agents.

The present invention also relates to compositions comprising the polypeptide of the twenty-fourth aspect of the invention (SEQ ID NO: 77) having beta-galactosidase activity. In an embodiment, the composition further comprises one or more formulating agents.

The compositions may comprise a polypeptide of the present invention as the major enzymatic component, e.g., a mono-component composition. Such a composition may further comprise a formulating agent, as described in the 'formulating agent' section below. Alternatively, the compositions may comprise multiple enzymatic activities, such as one or more (e.g., several) enzymes selected from the group consisting of phytase, galactanase, galactanase, protease, phospholipase, glucoronidase, lysophospholipase, amylase, beta-glucanase, beta-galactosidase, beta-xylosidase, endo-1,4-beta-galactanase acetyl xylan esterase, feruloyl esterase, cellulase, cellobiohydrolase, beta-glycosidase, pullulanase, or any mixture thereof.

It is at present contemplated that the galactanase is used (e.g. in feed) in one or more of the following amounts (dosage ranges): 0.01-200; 0.05-100; 0.1-50; 0.2-20; 0.1-1; 0.2-2; 0.5-5; or 1-10 wherein all these ranges are mg galactanase protein per kg substrate (ppm). It is at present contemplated that the beta-galactosidase is administered (e.g. in feed) in one or more of the following amounts (dosage ranges): 0.01-200; 0.05-100; 0.1-50; 0.2-20; 0.1-1; 0.2-2; 0.5-5; or 1-10 wherein all these ranges are mg beta-galactosidase protein per kg substrate (ppm). It is further contemplated that the ratio of galactanase to beta-galactosidase is in the range of 100:1 to 1:100 galactanase:beta-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: beta-galactosidase.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the beta-galactosidase and/or galactanase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the beta-galactosidase and/or galactanase of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product.

Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 μm, such as less than 10 μm or less than 5 μm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H2O), sodium phosphate dibasic heptahydrate (Na2HPO4.7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the beta-galactosidase and/or galactanase of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:
(a) a core comprising a beta-galactosidase according to the invention, and
(b) a coating consisting of one or more layer(s) surrounding the core.

In one embodiment, the coating comprises a salt coating as described herein. In one embodiment, the coating comprises a wax coating as described herein. In one embodiment, the coating comprises a salt coating and a wax coating as described herein.

Thus, in a further aspect, the present invention provides a granule, which comprises:

(a) a core comprising a galactanase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating and a wax coating as described herein.

Thus, in a further aspect, the present invention provides a granule, which comprises:

(a) a core comprising a beta-galactosidase and galactanase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating and a wax coating as described herein.

Plant Based Material

In an embodiment, the plant based material is from the taxonomic subclass rosids such as the taxonomic order Fabales or the the taxonomic order Brassicales.

In one embodiment, the plant based material from is from the family Fabaceae, such as the subfamilies Caesalpinioideae or Mimosoideae or Papilionoideae. In an embodiment, the plant based material from is from the sub-family Papilionoideae, such as the tribe Abreae or Amorpheae or Bossiaeeae or Brongniartieae or Cicereae or Crotalarieae or Dalbergieae or Desmodieae or Dipterygeae or Euchresteae or Fabeae or Galegeae or Genisteae or Hedysareae or Hypocalypteae or Indigofereae or Loteae or Millettieae or Mirbelieae or Phaseoleae or Podalyrieae or Psoraleeae or Robinieae or Sesbanieae or Sophoreae or Swartzieae or Thermopsideae or Trifolieae.

In one embodiment, the plant based material from the sub-family Papilionoideae is from the tribe Phaseoleae, such as the genus *Adenodolichos* or *Alistilus* or *Amphicarpaea* or *Ancistrotropis* or *Apios* or *Atylosia* or *Bionia* or *Bolusafra* or *Butea* or *Cajanus* or *Calopogonium* or *Camptosema* or *Canavalia* or *Centrosema* or *Cleobulia* or *Clitoria* or *Cochlianthus* or *Cochliasanthus* or *Collaea* or *Cologania* or *Condylostylis* or *Cratylia* or *Cymbosema* or *Decorsea* or *Dioclea* or *Dipogon* or *Dolichopsis* or *Dolichos* or *Dumasia* or *Dunbaria* or *Eriosema* or *Erythrina* or *Flemingia* or *Galactia* or *Glycine* or *Hardenbergia* or *Helicotropis* or *Kennedia* or *Lablab* or *Leptospron* or *Macroptilium* or *Macrotyloma* or *Mastersia* or *Mucuna* or *Mysanthus* or *Neonotonia* or *Neorautanenia* or *Nesphostylis* or *Nogra* or *Ophrestia* or *Otoptera* or *Oxyrhynchus* or *Pachyrhizus* or *Paracalyx* or *Phaseolus* or *Phylacium* or *Physostigma* or *Pseudeminia* or *Pseudovigna* or *Psophocarpus* or *Pueraria* or *Ramirezella* or *Rhodopis* or *Rhynchosia* or *Shuteria* or *Sigmoidotropis* or *Sinodolichos* or *Spathionema* or *Spatholobus* or *Sphenostylis* or *Strongylodon* or *Strophostyles* or *Teramnus* or *Teyleria* or *Vandasina* or *Vatovaea* or *Vigna* or *Wajira*.

In one embodiment, the plant based material from the sub-family Papilionoideae is from the genus *Glycine*, such as the species *Glycine* aff. *tabacina* or *Glycine albicans* or *Glycine aphyonota* or *Glycine arenaria* or *Glycine argyrea* or *Glycine canescens* or *Glycine clandestina* or *Glycine curvata* or *Glycine cyrtoloba* or *Glycine* dolichocarpa or *Glycine falcata* or *Glycine gracei* or *Glycine hirticaulis* or *Glycine lactovirens* or *Glycine latifolia* or *Glycine latrobeana* or *Glycine microphylla* or *Glycine peratosa* or *Glycine pindanica* or *Glycine pullenii* or *Glycine rubiginosa* or *Glycine stenophita* or *Glycine syndetika* or *Glycine tabacina* or *Glycine tomentella* or *Glycine* sp. T1 or *Glycine* sp. T5 or *Glycine gracilis* or *Glycine max* (soy bean) or *Glycine max×Glycine soja* or *Glycine soja* (wild soybean).

In one embodiment, the plant based material from the sub-family Papilionoideae is from the genus *Cajanus* such as the species *Cajanus cajan* (pigeon pea), *Cajanus cajanifolius* and *Cajanus scarabaeoide*.

In one embodiment, the plant based material from the sub-family Papilionoideae is from the genus *Phaseolus*, such as the species *Phaseolus acutifolius* (tepary bean) or *Phaseolus acutifolius* var. *latifolius* or *Phaseolus albescens* or *Phaseolus albiflorus* or *Phaseolus albinervus* or *Phaseolus altimontanus* or *Phaseolus amblyosepalus* or *Phaseolus angustissimus* or *Phaseolus augusti* or *Phaseolus bolivianus* or *Phaseolus campanulatus* or *Phaseolus carteri* or *Phaseolus chiapasanus* or *Phaseolus coccineus* (scarlet runner bean) or *Phaseolus coccineus* subsp. *coccineus* or *Phaseolus coccineus* subsp. *polyanthus* or *Phaseolus costaricensis* or *Phaseolus dasycarpus* or *Phaseolus dumosus* or *Phaseolus esperanzae* or *Phaseolus esquincensis* or *Phaseolus filiformis* (slimjim bean) or *Phaseolus glabellus* or *Phaseolus gladiolatus* or *Phaseolus grayanus* or *Phaseolus hintonii* or *Phaseolus jaliscanus* or *Phaseolus juquilensis* or *Phaseolus laxiflorus* or *Phaseolus leptostachyus* or *Phaseolus lignosus* or *Phaseolus lunatus* (lima bean) or *Phaseolus macrolepis* or *Phaseolus maculatifolius* or *Phaseolus maculatus* (co-colmeca bean) or *Phaseolus maculatus* subsp. *ritensis* or *Phaseolus macvaughii* or *Phaseolus magnilobatus* or *Phaseolus marechalii* or *Phaseolus micranthus* or *Phaseolus microcarpus* or *Phaseolus mollis* or *Phaseolus neglectus* or *Phaseolus nelsonii* or *Phaseolus nodosus* or *Phaseolus novoleonensis* or *Phaseolus oaxacanus* or *Phaseolus oligospermus* or *Phaseolus pachyrrhizoides* or *Phaseolus parvifolius* or *Phaseolus parvulus* or *Phaseolus pauciflorus* or *Phaseolus pedicellatus* or *Phaseolus perplexus* or *Phaseolus persistentus* or *Phaseolus plagiocylix* or *Phaseolus pluriflorus* or *Phaseolus polymorphus* or *Phaseolus polystachios* or *Phaseolus polystachios* subsp. *sinuatus* or *Phaseolus polystachios* subsp. *smilacifolius* or *Phaseolus reticulatus* or *Phaseolus rotundatus* or *Phaseolus salicifolius* or *Phaseolus sonorensis* or *Phaseolus talamancensis* or *Phaseolus tenellus* or *Phaseolus texensis* or *Phaseolus tuerckheimii* or *Phaseolus vulgaris* (French bean) or *Phaseolus vulgaris* var. *aborigineus* or *Phaseolus vulgaris* var. *nanus* or *Phaseolus xanthotrichus* or *Phaseolus xolocotzii* or *Phaseolus zimapanensis*.

In one embodiment, the plant based material from the sub-family Papilionoideae is from the tribe Cicereae, such as the genus *Cicer*, such as the species *Cicer anatolicum* or *Cicer arietinum* (chickpea) or *Cicer bijugum* or *Cicer canariense* or *Cicer chorassanicum* or *Cicer cuneatum* or *Cicer echinospermum* or *Cicer flexuosum* or *Cicer floribundum* or *Cicer graecum* or *Cicer incisum* or *Cicer isauricum* or *Cicerjudaicum* or *Cicer kermanense* or *Cicer macracanthum* or *Cicer microphyllum* or *Cicer montbretii* or *Cicer multijugum* or *Cicer nuristanicum* or *Cicer oxyodon* or *Cicer pinnatifidum* or *Cicer pungens* or *Cicer rechingeri* or *Cicer* reticulatum or *Cicer songaricum* or *Cicer spiroceras* or *Cicer stapfianum* or *Cicer subaphyllum* or *Cicer tragacanthoides* or *Cicer yamashitae*

In one embodiment, the plant based material from the sub-family Papilionoideae is from the tribe Genisteae, such as the genus *Adenocarpus* or *Anarthrophyllum* or *Argyrocytisus* or *Argyrolobium* or *Calicotome* or *Chamaecytisus* or *Cytisophyllum* or *Cytisus* or *Dichilus* or *Echinospartum* or *Erinacea* or *Genista* or *Gonocytisus* or *Hesperolaburnum* or *Laburnum* or *Lembotropis* or *Lupinus* or *Melolobium* or *Petteria* or *Podocytisus* or *Polhillia* or *Retama* or *Sellocharis* or *Spartium* or *Stauracanthus* or *Teline* or *Ulex*

In one embodiment, the plant based material from the sub-family Papilionoideae is from the tribe Fabeae, such as the genus *Lathyrus* or *Lens* or *Pisum* or *Vavilovia* or *Vicia*. In one embodiment, the plant based material from the sub-family Papilionoideae is from the genus *Lens*, such as the species *Lens culinaris* (lentil) or *Lens culinaris* subsp. *culinaris* or *Lens culinaris* subsp. *odemensis* or *Lens culinaris* subsp. *tomentosus* or *Lens cyanea* or *Lens ervoides* or *Lens lamottei* or *Lens nigricans* or *Lens orientalis* (ye bing dou).

In one embodiment, the plant based material from the sub-family Papilionoideae is from the genus *Vicia*, such as the species *Vicia garinensis* or *Vicia sojakii* or *Vicia rechingeri* or *Vicia kurdica* or *Vicia multijuga* or *Vicia akhmaganica* or *Vicia variabilis* or *Vicia variegata* or *Vicia persica* or *Vicia kotschyana* or *Vicia hirta* or *Vicia gregaria* or *Vicia ciceroidea* or *Vicia cappadocica* or *Vicia balansae* or *Vicia aucheri* or *Vicia* sp. 'telaponensis' or *Vicia venulosa* or *Vicia subvillosa* or *Vicia stenophylla* or *Vicia sicula* or *Vicia sibthorpii* or *Vicia semiglabra* or *Vicia scandens* or *Vicia pinetorum* or *Vicia picta* or *Vicia pectinata* or *Vicia paucifolia* or *Vicia palaestina* or *Vicia onobrychioides* or *Vicia ochroleuca* or *Vicia nataliae* or *Vicia montevidensis* or *Vicia monardii* or *Vicia minutiflora* or *Vicia menziesii* or *Vicia megalotropis* or *Vicia malosana* or *Vicia lunata* or *Vicia leucantha* or *Vicia leavenworthii* or *Vicia larissae* or *Vicia iranica* or *Vicia incana* or *Vicia hololasia* or *Vicia glauca* or *Vicia freyniana* or *Vicia floridana* or *Vicia filicaulis* or *Vicia ferreirensis* or *Vicia exigua* or *Vicia dennesiana* or *Vicia cypria* or *Vicia cretica* or *Vicia costata* or *Vicia claessensii* or *Vicia chaetocalyx* or *Vicia cassia* or *Vicia capreolata* or *Vicia caesarea* or *Vicia biennis* or *Vicia baicalensis* or *Vicia altissima* or *Vicia alpestris* or *Vicia acutifolia* or *Vicia pubescens* or *Vicia cirrhosa* or *Vicia koeieana* or *Vicia ramuliflora* or *Vicia multicaulis* or *Vicia parviflora* or *Vicia vicioides* or *Vicia tenuifolia* or *Vicia orobus* or *Vicia nigra* or *Vicia incisa* or *Vicia epetiolaris* or *Vicia crocea* or *Vicia sparsiflora* or *Vicia nummularia* or *Vicia dichroantha* or *Vicia cassubica* or *Vicia monantha* (bard vetch) or *Vicia cinerea* or *Vicia oroboides* or *Vicia tibetica* or *Vicia caroliniana* (Carolina or wood vetch) or *Vicia disperma* or *Vicia esdraelonensis* or *Vicia pulchella* or *Vicia mexicana* or *Vicia leucophaea* or *Vicia humilis* or *Vicia barbazitae* or *Vicia pyrenaica* or *Vicia qatmensis* or *Vicia lathyroides* or *Vicia cuspidata* or *Vicia dionysiensis* or *Vicia abbreviata* or *Vicia sepium* or *Vicia sericocarpa* or *Vicia noeana* or *Vicia hyrcanica* or *Vicia hybrida* or *Vicia galeata* or *Vicia ciliatula* or *Vicia assyriaca* or *Vicia tigridis* or *Vicia anatolica* or *Vicia sylvatica* or *Vicia dumetorum* or *Vicia mollis* or *Vicia aintabensis* or *Vicia peregrina* or *Vicia lutea* (yellow vetch) or *Vicia grandiflora* or *Vicia articulata* or *Vicia americana* or *Vicia michauxii* or *Vicia vicina* or *Vicia venosa* or *Vicia tetrasperma* or *Vicia ervilia* or *Vicia benghalensis* (purple or winter vetch) or *Vicia angustipinnata* or *Vicia amurensis* or *Vicia unijuga* or *Vicia pseudo-orobus* or *Vicia pisiformis* or *Vicia nipponica* or *Vicia nigricans* or *Vicia linearifolia* or *Vicia japonica* or *Vicia hirticalycina* or *Vicia fauriae* or *Vicia chosenensis* or *Vicia bungei* or *Vicia bifolia* or *Vicia amoena* or *Vicia montbretii* or *Vicia serratifolia* or *Vicia paucijuga* or *Vicia kalakhensis* or *Vicia johannis* or *Vicia hyaeniscyamus* or *Vicia galilaea* or *Vicia eristalioides* or *Vicia bithynica* or *Vicia melanops* or *Vicia ludoviciana* or *Vicia pannonica* or *Vicia narbonensis* or *Vicia villosa* or *Vicia hirsuta* or *Vicia sativa* (spring vetch) or *Vicia faba* (broad bean or fava bean) or *Vicia cracca* (bird vetch).

In one embodiment, the plant based material from the sub-family Papilionoideae is from the genus *Pisum*, such as the species *Pisum abyssinicum* (Abyssinian pea) or *Pisum fulvum* or *Pisum sativum* (pea) or *Pisum sativum* subsp. *asiaticum* or *Pisum sativum* subsp. *elatius* (wild pea) or *Pisum sativum* var. *pumilio* (Syrian fodder pea) or *Pisum sativum* subsp. *jomardii* or *Pisum sativum* subsp. *Sativum* or *Pisum sativum* var. *arvense* or *Pisum sativum* var. *choresmicum* or *Pisum sativum* var. *macrocarpon* (snow pea) or *Pisum sativum* var. *ponderosum* or *Pisum sativum* var. *tibetanicum* or *Pisum sativum* subsp. *transcaucasicum*

In one embodiment, the plant based material from the sub-family Papilionoideae is from the tribe Dalbergieae, such as the genus *Adesmia* or *Aeschynomene* or *Amicia* or *Andira* or *Arachis* or *Brya* or *Bryaspis* or *Cascaronia* or *Centrolobium* or *Chaetocalyx* or *Chapmannia* or *Cranocarpus* or *Cyclocarpa* or *Dalbergia* or *Diphysa* or *Discolobium* or *Etaballia* or *Fiebrigiella* or *Fissicalyx* or *Geissaspis* or *Geoffroea* or *Grazielodendron* or *Humularia* or *Hymenolobium* or *Inocarpus* or *Kotschya* or *Machaerium* or *Maraniona* or *Nissolia* or *Ormocarpopsis* or *Ormocarpum* or *Paramachaerium* or *Peltiera* or *Pictetia* or *Platymiscium* or *Platypodium* or *Poiretia* or *Pterocarpus* or *Ramorinoa* or *Riedeliella* or *Smithia* or *Soemmeringia* or *Steinbachiella* or *Stylosanthes* or *Tipuana* or *Weberbauerella* or *Zornia*.

In one embodiment, the plant based material from the sub-family Papilionoideae is from the genus *Arachis*, such as the species *Appressipila* (amendoim bravo) or *Arachis batizocoi* or *Arachis brevipetiolata* or *Arachis burchellii* or *Arachis burkartii* or *Arachis cardenasii* or *Arachis chiquitana* or *Arachis correntina* or *Arachis cruziana* or *Arachis decora* or *Arachis diogoi* or *Arachis duranensis* or *Arachis duranensis×Arachis stenosperma* or *Arachis glabrata* (amendoim-bravo) or *Arachis glabrata* var. *glabrata* or *Arachis glabrata* var. *hagenbeckii* or *Arachis glabrata*× *Arachis hypogaea* or *Arachis glandulifera* or *Arachis guaranitica* or *Arachis helodes* or *Arachis hermannii* or *Arachis hoehnei* or *Arachis hypogaea* (peanut) or *Arachis hypogaea* subsp. *Fastigiata* or *Arachis hypogaea* var. *vulgaris* (Spanish peanut) or *Arachis hypogaea* subsp. *Hypogaea* or *Arachis hypogaea* var. *hirsuta* or *Arachis ipaensis* or *Arachis ipaensis×Arachis magna* or *Arachis kempff-mercadoi* or *Arachis kretschmeri* or *Arachis kuhlmannii* or *Arachis linearifolia* or *Arachis lutescens* or *Arachis magna* or *Arachis major* or *Arachis matiensis* or *Arachis microsperma* or *Arachis monticola* or *Arachis palustris* or *Arachis paraguariensis* or *Arachis paraguariensis* subsp. *capibarensis* or *Arachis paraguariensis* subsp. *paraguariensis* or *Arachis pflugeae* or *Arachis pintoi* or *Arachis praecox* or *Arachis pusilla* (amendoim de caracar) or *Arachis repens* or *Arachis rigonii* or *Arachis schinini* or *Arachis simpsonii* or *Arachis stenophylla* or *Arachis stenosperma* or *Arachis stenosperma×Arachis cardenasii* or *Arachis sylvestris* (amendoim do porco) or *Arachis trinitensis* or *Arachis triseminata* or *Arachis tuberosa* or *Arachis valida* or *Arachis villosa* or *Arachis villosulicarpa* or *Arachis williamsii*.

In one aspect, the plant based material is from the taxonomic order Brassicales, such as the family Brassicaceae, preferably the tribe Brassiceae, more preferably the family *Brassica*.

In one embodiment, the plant based material from the tribe Brassiceae is from the family *Brassica*, such as *Brassica aucheri, Brassica balearica, Brassica barrelieri, Brassica carinata* (Abyssinian mustard), *Brassica carinata×Brassica napus, Brassica carinata×Brassica rapa, Brassica cretica, Brassica deflexa, Brassica desnottesii, Brassica drepanensis, Brassica elongata, Brassica fruticulosa, Brassica fruticulosa* subsp. *cossoniana, Brassica fruticulosa* subsp. *mauritanica, Brassica fruticulosa* subsp. *rifana, Brassica gravinae, Brassica hilarionis, Brassica* hybrid cultivar, *Brassica incana, Brassica insularis, Brassica insularis* subsp. *insularis, Brassica juncea* (Indian mustard), *Brassica juncea* var. *crassicaulis, Brassica juncea* var. *gemmifera, Brassica juncea* var. *gracilis, Brassica juncea* var. *juncea, Brassica juncea* var. *multiceps, Brassica juncea* var. *multisecta, Brassica juncea* var. *napiformis* (jie cai ge da), *Brassica juncea* var. *rugosa, Brassica juncea* var. *strumata, Brassica juncea* var. *subintegrifolia, Brassica juncea* var. *tumida* (zha cai), *Brassica juncea* var. *utilis, Brassica macrocarpa, Brassica maurorum, Brassica montana, Brassica napus* (rape), *Brassica napus* subsp. *rapifera* (Swedish turnip), *Brassica napus* var. *napus* (annual rape), *Brassica napus×Brassica rapa, Brassica nigra* (black mustard), *Brassica nigra* var. *abyssinica, Brassica oleracea, Brassica oleracea* var. *albiflora, Brassica oleracea* var. *alboglabra* (Chinese kale), *Brassica oleracea* var. *botrytis* (cauliflower), *Brassica oleracea* var. *capitata* (cabbage), *Brassica oleracea* var. *costata* (Bedford cabbage), *Brassica oleracea* var. *gemmifera* (Brussels sprouts), *Brassica oleracea* var. *gongylodes* (kohlrabi), *Brassica oleracea* var. *italica* (asparagus broccoli), *Brassica oleracea* var. *medullosa* (marrow-stem kale), *Brassica oleracea* var. *oleracea, Brassica oleracea* var. *ramosa* (branching bush kale), *Brassica oleracea* var. *sabauda, Brassica oleracea* var. *viridis* (kale), *Brassica oleracea×Brassica rapa* subsp. *pekinensis, Brassica oxyrrhina, Brassica procumbens, Brassica rapa* (field mustard), *Brassica rapa* subsp. *chinensis* (bok-choy), *Brassica rapa* var. *parachinensis* (cai xin), *Brassica rapa* var. *purpuraria* (purple stem mustard), *Brassica rapa* subsp. *narinosa, Brassica rapa* subsp. *nipposinica* (mizuna), *Brassica rapa* var. *perviridis* (kabuna), *Brassica rapa* subsp. *oleifera* (biennial turnip rape), *Brassica rapa* (Nippo-*oleifera* Group), *Brassica rapa* subsp. *pekinensis* (Chinese cabbage), *Brassica rapa* subsp. *rapa* (turnip), *Brassica rapa* var. *oleifera, Brassica rapa×Brassica nigra, Brassica repanda, Brassica repanda* subsp. *baldensis, Brassica repanda* subsp. *blancoana, Brassica repanda* subsp. *cadevallii, Brassica repanda* subsp. *confusa, Brassica repanda* subsp. *glabrescens, Brassica repanda* subsp. *gypsicola, Brassica repanda* subsp. *latisiliqua, Brassica repanda* subsp. *maritima, Brassica repanda* subsp. *repanda, Brassica repanda* subsp. *saxatilis, Brassica rupestris, Brassica ruvo* (broccoletto), *Brassica souliei, Brassica souliei* subsp. *amplexicaulis, Brassica spinescens, Brassica tournefortii, Brassica villosa* or *Brassica villosa* subsp. *Bivoniana*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Animal Feed and Animal Feed Additives

The present invention also relates to animal feed compositions and animal feed additives comprising one or more beta-galactosidases of the invention and one or more galactanases of the invention. In an embodiment, the animal feed or animal feed additive comprises a formulating agent, one or more beta-galactosidases of the invention and one or more galactanases of the invention. In a further embodiment, the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one beta-galactosidase of the invention and at least one galactanase of the invention as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

The animal feed composition of the invention may also contain insect protein, such as protein from mealworm, housefly or black soldier fly larvae, typically in meal form. Insect meal may replace fishmeal entirely or in part, and thus may constitute 0-10% of the total feed.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Brassicaceae, Amaranthaceae, and Poaceae, such as soybean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Amaranthaceae, e.g. beet, sugar beet, spinach or quinoa. Other examples of vegetable protein sources are rapeseed, crambe and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) beta-galactosidase/galactanase enzyme preparation may also be added before or during the feed ingredient step. Typically a liquid beta-galactosidase/galactanase enzyme preparation comprises a beta-galactosidase of the invention and a galactanase of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the beta-galactosidase/galactanase can be prepared by freezing a mixture of liquid enzyme solution with a bulking agent such as ground soybean meal, and then lyophilizing the mixture.

In an embodiment, the animal feed or animal feed additive comprises one or more additional enzymes. In an embodiment, the animal feed comprises one or more microbes. In an embodiment, the animal feed comprises one or more vitamins. In an embodiment, the animal feed comprises one or more minerals. In an embodiment, the animal feed comprises one or more amino acids. In an embodiment, the animal feed comprises one or more other feed ingredients.

In another embodiment, the animal feed or animal feed additive comprises the polypeptide of the invention, one or more formulating agents and one or more additional enzymes. In an embodiment, the animal feed or animal feed additive comprises the polypeptide of the invention, one or more formulating agents and one or more microbes. In an embodiment, the animal feed comprises the polypeptide of the invention, one or more formulating agents and one or more vitamins. In an embodiment, the animal feed or animal feed additive comprises one or more minerals. In an embodiment, the animal feed or animal feed additive comprises the polypeptide of the invention, one or more formulating agents and one or more amino acids. In an embodiment, the animal feed or animal feed additive comprises the polypeptide of the invention, one or more formulating agents and one or more other feed ingredients.

In a further embodiment, the animal feed or animal feed additive comprises the polypeptide of the invention, one or more formulating agents and one or more components selected from the list consisting of: one or more additional enzymes; one or more microbes; one or more vitamins; one or more minerals; one or more amino acids; and one or more other feed ingredients.

In an embodiment, the animal feed additive comprises one or more formulating agents, preferably as described herein below.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet, for each enzyme.

It is at present contemplated that the galactanase is administered in one or more of the following amounts (dosage ranges): 0.01-200; 0.05-100; 0.1-50; 0.2-20; 0.1-1; 0.2-2; 0.5-5; or 1-10 wherein all these ranges are mg galactanase protein per kg feed (ppm). It is at present contemplated that the beta-galactosidase is administered in one or more of the following amounts (dosage ranges): 0.01-200; 0.05-100; 0.1-50; 0.2-20; 0.1-1; 0.2-2; 0.5-5; or 1-10 wherein all these ranges are mg beta-galactosidase protein per kg feed (ppm). It is further contemplated that the ratio of the galactanase to beta-galactosidase is in the range of 100:1 to 1:100 galactanase: beta-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: beta-galactosidase.

For determining mg galactanase and/or mg beta-galactosidase protein per kg feed, the galactanase and/or beta-galactosidase is purified from the feed composition, and the specific activity of the purified galactanase and/or beta-galactosidase is determined using a relevant assay (see under galactanase or beta-galactosidase activity). The galactanase and/or beta-galactosidase activity of the feed composition as such is also determined using the same assay, and on the basis of these two determinations, the dosage in mg galactanase and/or mg beta-galactosidase protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg galactanase or mg beta-galactosidase protein in feed additives. Of course, if a sample is available of the galactanase or beta-galactosidase used for preparing the feed additive or the feed, the specific activity is determined from this sample (no need to purify the galactanase or beta-galactosidase from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, lysozyme and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the composition of the invention may also comprise at least one other enzyme selected from the group comprising of acetylxylan esterase (EC 3.1.1.23), acylglycerol lipase (EC 3.1.1.72), alpha-amylase (EC 3.2.1.1), beta-amylase (EC 3.2.1.2), arabinofuranosidase (EC 3.2.1.55), cellobiohydrolases (EC 3.2.1.91), cellulase (EC 3.2.1.4), feruloyl esterase (EC 3.1.1.73), galactanase (EC 3.2.1.89), alpha-galactosidase (EC 3.2.1.22), beta-galactosidase (EC 3.2.1.23), beta-glucanase (EC 3.2.1.6), beta-glucosidase (EC 3.2.1.21), triacylglycerol lipase (EC 3.1.1.3), lysophospholipase (EC 3.1.1.5), lysozyme (EC 3.2.1.17), alpha-mannosidase (EC 3.2.1.24), beta-mannosidase (mannanase) (EC 3.2.1.25), phytase (EC 3.1.3.8, EC 3.1.3.26, EC 3.1.3.72), phospholipase A1 (EC 3.1.1.32), phospholipase A2 (EC 3.1.1.4), phospholipase D (EC 3.1.4.4), protease (EC 3.4), pullulanase (EC 3.2.1.41), pectinesterase (EC 3.1.1.11), xylanase (EC 3.2.1.8, EC 3.2.1.136), beta-xylosidase (EC 3.2.1.37), or any combination thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), Ave-Mix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus licheniformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1 \times 10^{11}$ CFU/kg of dry matter. In a more preferred embodiment the bacterial count of each of the bacterial strains in the animal feed composition is between $1 \times 10^8$ and $1 \times 10^{10}$ CFU/kg of dry matter.

The bacterial count of each of the bacterial strains in the animal feed composition is between $1 \times 10^5$ and $1 \times 10^{15}$ CFU/animal/day, preferably between $1 \times 10^7$ and $1 \times 10^{13}$ CFU/animal/day, and more preferably between $1 \times 10^8$ and $1 \times 10^{12}$ CFU/animal/day. In a more preferred embodiment the bacterial count of each of the bacterial strains in the animal feed composition is between $1 \times 10^9$ and $1 \times 10^{11}$ CFU/animal/day.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Gallipro®, Gallipro® Max, Probios® Guard, Lactiferm® and Bioplus® (Chr Hansen), PoultryStar®, PoultryStar® sol, PoultryStar® me, AquaStar® (Biomin), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

Examples of commercial products are Crina® (DSM Nutritional Products); Cinergy™, Cinergy™ FIT, Biacid™, (Cargill), Digestarom® and Digestarom® DC (Biomin) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate).

Examples of commercial products are VevoVitall® (DSM Nutritional Products), Amasil®, Luprisil®, Lupro-Grain®, Lupro-Cid®, Lupro-Mix®, Lupro-Mix® NA (BASF), n-Butyric Acid AF (OXEA), Biacid™, Prohacid™ Classic and Prohacid™ Advance™ (Cargill), Biotronic® (Biomin) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

Uses

The present invention is also directed to methods for using the polypeptides having galactanase and/or beta-galactosidase activity, or compositions thereof, for e.g. animal feed. The present invention is also directed to processes for using the polypeptides having galactanase and/or beta-galactosidase activity, or compositions thereof, such as e.g. those described below.

Use in Animal Feed

The present invention is also directed to methods for using the galactanases and beta-galactosidase of the invention in animal feed.

The term animal includes all animals. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

In the use according to the invention the galactanases and beta-galactosidases can be fed to the animal before, after, or simultaneously with the diet. The latter is preferred.

In a particular embodiment, the form in which the galactanase and beta-galactosidase is added to the feed, or animal feed additive, is well-defined. Well-defined means that the galactanase and beta-galactosidase preparation is at least 50% pure as determined by Size-exclusion chromatography (see Example 12 of WO 01/58275). In other particular embodiments the galactanase and beta-galactosidase preparation is at least 60, 70, 80, 85, 88, 90, 92, 94, or at least 95% pure as determined by this method.

A well-defined galactanase and beta-galactosidase preparation is advantageous. For instance, it is much easier to dose correctly to the feed a galactanase and beta-galactosidase that is essentially free from interfering or contaminating other galactanases and beta-galactosidases. The term dose correctly refers in particular to the objective of obtaining consistent and constant results, and the capability of optimizing dosage based upon the desired effect.

For the use in animal feed, however, the galactanase and beta-galactosidase need not be that pure; it may e.g. include other enzymes, in which case it could be termed a galactanase and beta-galactosidase preparation.

The galactanase and beta-galactosidase preparation can be (a) added directly to the feed, or (b) it can be used in the production of one or more intermediate compositions such as feed additives or premixes that is subsequently added to the feed (or used in a treatment process). The degree of purity described above refers to the purity of the original galactanase and beta-galactosidase preparation, whether used according to (a) or (b) above.

PREFERRED EMBODIMENTS OF THE INVENTION

Preferred embodiments of the invention are described in the set of items below.

1. A composition comprising one or more GH53 polypeptides having galactanase activity and one or more GH42 polypeptides having beta-galactosidase activity.
2. The composition of item 1, wherein the GH53 polypeptide comprises the motif GV[T/M]PD[W/M]VQ[I/V]GNE (SEQ ID NO: 81) and/or the motif WADP[A/G]xQxKPxAW (SEQ ID NO: 82).
3. The composition of any of items 1 to 2, wherein the GH53 polypeptide and the GH42 polypeptide are obtained or obtainable from the taxonomic order Bacillales.
4. The composition of any of items 1 to 3 wherein the GH53 polypeptide is selected from the group consisting of:
   (a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;
   (b) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 7;
   (c) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 11;
   (d) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 15;
   (e) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19;
   (f) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 23;
   (g) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 27;
   (h) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 31;
   (i) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 35;
   (j) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 39;
   (k) a variant of SEQ ID NO: 3 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (l) a variant of SEQ ID NO: 7 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (m) a variant of SEQ ID NO: 11 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (n) a variant of SEQ ID NO: 15 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (o) a variant of SEQ ID NO: 19 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(p) a variant of SEQ ID NO: 23 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(q) a variant of SEQ ID NO: 27 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(r) a variant of SEQ ID NO: 31 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(s) a variant of SEQ ID NO: 35 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(t) a variant of SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(u) a polypeptide comprising the polypeptide of (a), (b), (c), (d), (e), (f), (g), (h), (i), (j), (k), (l), (m), (n), (o), (p), (q), (r), (s) or (t) and a N-terminal and/or C-terminal His-tag and/or HQ-tag;

(v) a polypeptide comprising the polypeptide of (a), (b), (c), (d), (e), (f), (g), (h), (i), (j), (k), (l), (m), (n), (o), (p), (q), (r), (s) or (t) and a N-terminal and/or C-terminal extension of between 1 and 10 amino acids; and (w) a fragment of the polypeptide of (a), (b), (c), (d), (e), (f), (g), (h), (i), (j), (k), (l), (m), (n), (o), (p), (q), (r), (s), (t) or (u) having galactanase activity and having at least 90% of the length of the mature polypeptide.

5. The composition of item 4, wherein the GH53 polypeptide comprises or consists of amino acids 1 to 316 of SEQ ID NO: 2, amino acids 1 to 316 of SEQ ID NO: 3, amino acids 1 to 324 of SEQ ID NO: 4, amino acids 1 to 318 of SEQ ID NO: 6, amino acids 1 to 318 of SEQ ID NO: 7, amino acids 1 to 326 of SEQ ID NO: 8, amino acids 1 to 316 of SEQ ID NO: 10, amino acids 1 to 316 of SEQ ID NO: 11, amino acids 1 to 324 of SEQ ID NO: 12, amino acids 1 to 316 of SEQ ID NO: 14, amino acids 1 to 316 of SEQ ID NO: 15, amino acids 1 to 324 of SEQ ID NO: 16, amino acids 1 to 316 of SEQ ID NO: 18, amino acids 1 to 316 of SEQ ID NO: 19, amino acids 1 to 324 of SEQ ID NO: 20, amino acids 1 to 316 of SEQ ID NO: 22, amino acids 1 to 316 of SEQ ID NO: 23, amino acids 1 to 324 of SEQ ID NO: 24, amino acids 1 to 516 of SEQ ID NO: 26, amino acids 1 to 516 of SEQ ID NO: 27, amino acids 1 to 524 of SEQ ID NO: 28, amino acids 1 to 317 of SEQ ID NO: 30, amino acids 1 to 317 of SEQ ID NO: 31, amino acids 1 to 325 of SEQ ID NO: 32, amino acids 1 to 316 of SEQ ID NO: 34, amino acids 1 to 316 of SEQ ID NO: 35, amino acids 1 to 324 of SEQ ID NO: 36, amino acids 1 to 316 of SEQ ID NO: 38, amino acids 1 to 316 of SEQ ID NO: 39 or amino acids 1 to 324 of SEQ ID NO: 40.

6. The composition of any of items 1 to 5, wherein the GH42 polypeptide is selected from the group consisting of:

(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 42;

(b) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 44;

(c) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 47;

(d) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 50;

(e) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 53;

(f) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 56;

(g) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 59;

(h) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 62;

(i) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 65;

(j) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 68;

(k) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 71;

(l) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 74;

(m) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 77;

(n) a variant of SEQ ID NO: 42 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(o) a variant of SEQ ID NO: 44 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(p) a variant of SEQ ID NO: 47 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(q) a variant of SEQ ID NO: 50 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(r) a variant of SEQ ID NO: 53 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(s) a variant of SEQ ID NO: 56 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(t) a variant of SEQ ID NO: 59 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(u) a variant of SEQ ID NO: 62 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(v) a variant of SEQ ID NO: 65 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(w) a variant of SEQ ID NO: 68 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(x) a variant of SEQ ID NO: 71 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(y) a variant of SEQ ID NO: 74 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(z) a variant of SEQ ID NO: 77 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(aa) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y) or (z) and a N-terminal and/or C-terminal His-tag and/or HQ-tag;

(ab) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y) or (z) and a N-terminal and/or C-terminal extension of up to 10 amino acids, e.g. 1, 2, 3, 4, 5, 6, 7, 8, 9 or 10 amino acids; and (ac) a fragment of the polypeptide of (a), (b), (c), (d), (e), (f), (g), (h), (i), (j), (k), (l), (m), (n), (o), (p), (q), (r), (s), (t), (u), (v), (w), (x), (y) or (z) having beta-galactosidase activity and having at least 90% of the length of the mature polypeptide.

7. The composition of item 6, wherein the GH42 polypeptide comprises or consists of amino acids 1 to 685 of SEQ ID NO: 42, amino acids 1 to 688 of SEQ ID NO: 44, amino acids 1 to 695 of SEQ ID NO: 45, amino acids 1 to 687 of SEQ ID NO: 47, amino acids 1 to 694 of SEQ ID NO: 48, amino acids 1 to 654 of SEQ ID NO: 50, amino acids 1 to 661 of SEQ ID NO: 51, amino acids 1 to 687 of SEQ ID NO: 53, amino acids 1 to 694 of SEQ ID NO: 54, amino acids 1 to 686 of SEQ ID NO: 56, amino acids 1 to 695 of SEQ ID NO: 57, amino acids 1 to 688 of SEQ ID NO: 59, amino acids 1 to 697 of SEQ ID NO: 60, amino acids 1 to 691 of SEQ ID NO: 62, amino acids 1 to 700 of SEQ ID NO: 63, amino acids 1 to 690 of SEQ ID NO: 65, amino acids 1 to 699 of SEQ ID NO: 66, amino acids 1 to 689 of SEQ ID NO: 68, amino acids 1 to 698 of SEQ ID NO: 69, amino acids 1 to 685 of SEQ ID NO: 71, amino acids 1 to 694 of SEQ ID NO: 72, amino acids 1 to 685 of SEQ ID NO: 74, amino acids 1 to 694 of SEQ ID NO: 75, amino acids 1 to 686 of SEQ ID NO: 77 or amino acids 1 to 695 of SEQ ID NO: 78.

8. The composition of any of items 1 to 7 further comprising one or more formulating agents.

9. The composition of item 8, wherein the one or more formulating agent is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

10. The composition of any of items 1 to 9 further comprising one or more additional enzymes.

11. The composition of item 10 wherein the one or more additional enzymes is selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

12. The composition of any of items 1 to 11 further comprising one or more microbes.

13. The composition of item 12, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediocosus acidilactici, Pediococcus* sp., *Propionibacterium thoenii, Propionibacterium* sp. and *Streptococcus* sp. or any combination thereof.

14. The composition of any of items 1 to 13, wherein the composition releases at least 12 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

15. The composition of item 14, wherein the composition releases at least 13 g, such as at least 14 g, at least 15 g, at least 16 g, at least 17 g, at least 18 g, at least 19 g, at least 20 g or at least 22 g galactose per kg soybean meal.

16. The composition of any of items 1 to 15 further comprising plant based material.

17. The composition of item 16, wherein the plant based material is from the taxonomic subclass rosids.

18. The composition of item 16, wherein the plant based material is from the family Fabaceae, preferably the sub-family Papilionoideae.

19. The composition of item 16, wherein the plant based material is from the tribe Phaseoleae, Cicereae, Genisteae, Fabeae, Dalbergieae or Phaseoleae or any combination thereof.

20. The composition of item 16, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

21. A granule comprising the composition of any of items 1 to 15.

22. The granule of item 21 wherein the granule is coated.

23. The granule of item 22 wherein the coating comprises a salt and/or wax and/or a flour.

24. An animal feed additive comprising the composition of any of items 1 to 15 or the granule of any of items 21 to 23.

25. The animal feed additive of item 24 further comprising one or more components selected from the list consisting of:
one or more vitamins;
one or more minerals;
one or more amino acids;
one or more phytogenics;
one or more prebiotics;
one or more organic acids; and
one or more other feed ingredients.

26. An animal feed comprising the composition of any of items 1 to 15, the granule of any of items 21 to 23 or the animal feed additive of any of items 24 to 25 and plant based material.

27. The animal feed of item 26, wherein the plant based material is from the taxonomic subclass rosids, preferably from the family Fabaceae, more preferably the sub-family Papilionoideae or even more preferably is from the tribe Phaseoleae, Cicereae, Genisteae, Fabeae, Dalbergieae or Phaseoleae or any combination thereof.

28. The animal feed of item 26, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

29. A pelleted animal feed comprising plant based material and the composition of any of items 1 to 15, the granule of any of items 21 to 23 or the animal feed additive of any of items 24 to 25.

30. The pelleted animal feed of item 29, wherein the plant based material is from the taxonomic subclass rosids, preferably from the family Fabaceae, more preferably the sub-family Papilionoideae or even more preferably is from the tribe Phaseoleae, Cicereae, Genisteae, Fabeae, Dalbergieae or Phaseoleae or any combination thereof.

31. The pelleted animal feed of item 29, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

32. The pelleted animal feed of any of items 29 to 31, wherein the composition of any of items 1 to 15, the granule of any of items 21 to 23 or the animal feed additive of any of items 24 to 25 is sprayed onto the pellet.

33. A liquid formulation comprising the composition of any of items 1 to 15.

34. The liquid formulation of item 34, wherein the polypeptide having beta-galactosidase activity is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

35. The liquid formulation of any of items 33 to 34, wherein the polypeptide having galactanase activity is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

36. The liquid formulation of any of items 33 to 35, wherein the formulation further comprises 20% to 80% w/w of polyol.

37. The liquid formulation of item 36, wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600 or any combination thereof.

38. The liquid formulation of any of items 33 to 37, wherein the formulation further comprises 0.01% to 2.0% w/w preservative.

39. The liquid formulation of item 38, wherein the preservative is selected from the group consisting of sodium sorbate, potassium sorbate, sodium benzoate and potassion benzoate or any combination thereof.

40. The liquid formulation of any of items 33 to 39 further comprising one or more components selected from the list consisting of:
    one or more enzymes;
    one or more microbes;
    one or more vitamins;
    one or more minerals;
    one or more amino acids;
    one or more phytogenics;
    one or more prebiotics;
    one or more organic acids; and
    one or more other feed ingredients.

41. A method of preparing an animal feed comprising applying the liquid formulation of any of items 33 to 40 onto plant based material.

42. The method of item 41, wherein the liquid formulation is applied via a spray.

43. The method of any of items 41 to 42, wherein the plant based material is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

44. The method of any of items 41 to 43, wherein the plant based material is in pelleted form.

45. A pelleted animal feed prepared using the method of any of items 41 to 44.

46. A method of releasing galactose from plant based material, comprising treating the plant based material with the composition of any of items 1 to 15, the granule of any of items 21 to 23, the animal feed additive of any of items 24 to 25 or the liquid formulation of any of items 33 to 40.

47. A method of improving one or more performance parameters of an animal comprising administering to one or more animals the composition of any of items 1 to 15, the granule of any of items 21 to 23, the animal feed additive of any of items 24 to 25, the animal feed of any of items 26 to 28, the pelleted animal feed of any of items 29 to 32 or 45 or the liquid formulation of any of items 33 to 40.

48. The method of item 47, wherein the performance parameter is selected from the list consisting of body weight gain (BWG), European Production Efficiency Factor (EPEF) and Feed Conversion Ratio (FCR) or any combination thereof.

49. A method for improving the nutritional value of an animal feed, comprising adding to the feed the composition of any of items 1 to 15, the granule of any of items 21 to 23, the animal feed additive of any of items 24 to 25 or the liquid formulation of any of items 33 to 40.

50. A method of preparing an animal feed, comprising mixing the composition of any of items 1 to 15, the granule of any of items 21 to 23, the animal feed additive of any of items 24 to 25 or the liquid formulation of any of items 33 to 40.

51. A method for reducing the anitnutritional effects of an animal feed, comprising adding to the feed the composition of any of items 1 to 15, the granule of any of items 21 to 23, the animal feed additive of any of items 24 to 25 or the liquid formulation of any of items 33 to 40.

52. The method of any of items 46 to 51, wherein the plant based material is from the taxonomic subclass rosids.

53. The method of any of items 46 to 51, wherein the plant based material is from the family Fabaceae, preferably the sub-family Papilionoideae.

54. The method of any of items 46 to 51, wherein the plant based material is from the tribe Phaseoleae, Cicereae, Genisteae, Fabeae, Dalbergieae or Phaseoleae or any combination thereof.

55. The method of any of items 46 to 51, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

56. Use of the composition of any of items 1 to 15, the granule of any of items 21 to 23, the animal feed additive of any of items 24 to 25, the animal feed of any of items 26 to 28, the pelleted animal feed of any of items 29 to 32 or 45 or the liquid formulation of any of items 33 to 40:
    in animal feed;
    in animal feed additives;
    in the preparation of a composition for use in animal feed;
    for improving the nutritional value of an animal feed;
    for increasing digestibility of the animal feed;
    for improving one or more performance parameters in an animal; and/or
    for releasing galactose from plant based material of the taxonomic subclass rosids.

57. An isolated polypeptide having galactanase activity, selected from the group consisting of:
    (a) a polypeptide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;
    (b) a polypeptide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 7;
    (c) a polypeptide having at least 99.0%, e.g., at least 99.3%, at least 99.6% or 100% sequence identity to the polypeptide of SEQ ID NO: 11;
    (d) a polypeptide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the polypeptide of SEQ ID NO: 15;
    (e) a polypeptide having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19;
    (f) a polypeptide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the polypeptide of SEQ ID NO: 23;
    (g) a polypeptide having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 27;
    (h) a polypeptide having at least 99.3%, e.g., at least 99.6% or 100% sequence identity to the polypeptide of SEQ ID NO: 31;
    (i) a polypeptide having at least 99.3%, e.g., at least 99.6% or 100% sequence identity to the polypeptide of SEQ ID NO: 35;
    (j) a polypeptide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 39;
    (k) a polypeptide encoded by a polynucleotide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
    (l) a polypeptide encoded by a polynucleotide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5;
    (m) a polypeptide encoded by a polynucleotide having at least 99.0%, e.g., at least 99.3%, at least 99.6% or 100% sequence identity to the mature polypeptide coding sequence of SEQ ID NO: 9;
    (n) a polypeptide encoded by a polynucleotide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the mature polypeptide coding sequence of SEQ ID NO: 13;
    (o) a polypeptide encoded by a polynucleotide having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17;
    (p) a polypeptide encoded by a polynucleotide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the mature polypeptide coding sequence of SEQ ID NO: 21;
    (q) a polypeptide encoded by a polynucleotide having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 25;
    (r) a polypeptide encoded by a polynucleotide having at least 99.3%, e.g., at least 99.6% or 100% sequence identity to the mature polypeptide coding sequence of SEQ ID NO: 29;

(s) a polypeptide encoded by a polynucleotide having at least 99.3%, e.g., at least 99.6% or 100% sequence identity to the mature polypeptide coding sequence of SEQ ID NO: 33;

(t) a polypeptide encoded by a polynucleotide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 37;

(u) a variant of SEQ ID NO: 3 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(v) a variant of SEQ ID NO: 7 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(w) a variant of SEQ ID NO: 11 wherein the variant has galactanase activity and comprises one or more amino acid substitutions, and/or one or more amino acid deletions, and/or one or more amino acid insertions or any combination thereof in 1, 2 or 3 positions;

(x) a variant of SEQ ID NO: 15 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;

(y) a variant of SEQ ID NO: 19 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(z) a variant of SEQ ID NO: 23 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;

(aa) a variant of SEQ ID NO: 27 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(ab) a variant of SEQ ID NO: 31 wherein the variant has galactanase activity and comprises one or more amino acid substitutions, and/or one or more amino acid deletions, and/or one or more amino acid insertions or any combination thereof in 1 or 2 positions;

(ac) a variant of SEQ ID NO: 35 wherein the variant has galactanase activity and comprises one or more amino acid substitutions, and/or one or more amino acid deletions, and/or one or more amino acid insertions or any combination thereof in 1 or 2 positions;

(ad) a variant of SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(ae) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) and a N-terminal and/or C-terminal His-tag and/or HQ-tag;

(af) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) and a N-terminal and/or C-terminal extension of up to 10 amino acids, e.g. 1, 2, 3, 4, 5, 6, 7, 8, 9 or 10 amino acids; and (ag) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) having galactanase activity and having at least 90% of the length of the mature polypeptide.

58. The polypeptide according to item 57, wherein the polypeptide comprises or consists of amino acids 1 to 316 of SEQ ID NO: 2, amino acids 1 to 316 of SEQ ID NO: 3, amino acids 1 to 324 of SEQ ID NO: 4, amino acids 1 to 318 of SEQ ID NO: 6, amino acids 1 to 318 of SEQ ID NO: 7, amino acids 1 to 326 of SEQ ID NO: 8, amino acids 1 to 316 of SEQ ID NO: 10, amino acids 1 to 316 of SEQ ID NO: 11, amino acids 1 to 324 of SEQ ID NO: 12, amino acids 1 to 316 of SEQ ID NO: 14, amino acids 1 to 316 of SEQ ID NO: 15, amino acids 1 to 324 of SEQ ID NO: 16, amino acids 1 to 316 of SEQ ID NO: 18, amino acids 1 to 316 of SEQ ID NO: 19, amino acids 1 to 324 of SEQ ID NO: 20, amino acids 1 to 316 of SEQ ID NO: 22, amino acids 1 to 316 of SEQ ID NO: 23, amino acids 1 to 324 of SEQ ID NO: 24, amino acids 1 to 516 of SEQ ID NO: 26, amino acids 1 to 516 of SEQ ID NO: 27, amino acids 1 to 524 of SEQ ID NO: 28, amino acids 1 to 317 of SEQ ID NO: 30, amino acids 1 to 317 of SEQ ID NO: 31, amino acids 1 to 325 of SEQ ID NO: 32, amino acids 1 to 316 of SEQ ID NO: 34, amino acids 1 to 316 of SEQ ID NO: 35, amino acids 1 to 324 of SEQ ID NO: 36, amino acids 1 to 316 of SEQ ID NO: 38, amino acids 1 to 316 of SEQ ID NO: 39 or amino acids 1 to 324 of SEQ ID NO: 40.

59. An isolated polypeptide having beta-galactosidase activity, selected from the group consisting of:
(a) a polypeptide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 42;
(b) a polypeptide having at least 99.8%, e.g., at least 99.9%, or 100% sequence identity to the polypeptide of SEQ ID NO: 44;
(c) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 47;

(d) a polypeptide having at least 90%, e.g., at least 91%, at least 92%, at least 93%, at least 94%, at least 95%, at least 96%, at least 97%, at least 98%, at least 99%, or 100% sequence identity to the polypeptide of SEQ ID NO: 50;

(e) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 53;

(f) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 56;

(g) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 59;

(h) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 62;

(i) a polypeptide having at least 88%, e.g., at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 65;

(j) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 68;

(k) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 71;

(l) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 74;

(m) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 77;

(n) a polypeptide encoded by a polynucleotide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 41;

(o) a polypeptide encoded by a polynucleotide having at least 99.8%, e.g., at least 99.9%, or 100% sequence identity to the mature polypeptide coding sequence of SEQ ID NO: 43;

(p) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 46;

(q) a polypeptide encoded by a polynucleotide having at least 90%, e.g., at least 91%, at least 92%, at least 93%, at least 94%, at least 95%, at least 96%, at least 97%, at least 98%, at least 99%, or 100% sequence identity to the mature polypeptide coding sequence of SEQ ID NO: 49;

(r) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 52;

(s) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 55;

(t) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 58;

(u) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 61;

(v) a polypeptide encoded by a polynucleotide having at least 88%, e.g., at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 64;

(w) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 67;

(x) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 70;

(y) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 73;
(z) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 76;
(aa) a variant of SEQ ID NO: 42 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(ab) a variant of SEQ ID NO: 44 wherein the variant has beta-galactosidase activity and comprises one or more amino acid substitutions, and/or one or more amino acid deletions, and/or one or more amino acid insertions or any combination thereof in 1 or 2 positions;
(ac) a variant of SEQ ID NO: 47 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(ad) a variant of SEQ ID NO: 50 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(ae) a variant of SEQ ID NO: 53 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(af) a variant of SEQ ID NO: 56 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(ag) a variant of SEQ ID NO: 59 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(ah) a variant of SEQ ID NO: 62 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(ai) a variant of SEQ ID NO: 65 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(aj) a variant of SEQ ID NO: 68 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(ak) a variant of SEQ ID NO: 71 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(al) a variant of SEQ ID NO: 74 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(am) a variant of SEQ ID NO: 77 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(an) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al) or (am) and a N-terminal and/or C-terminal His-tag and/or HQ-tag;
(ao) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al) or (am) and a N-terminal and/or C-terminal extension of up to 10 amino acids, e.g. 1, 2, 3, 4, 5, 6, 7, 8, 9 or 10 amino acids; and (ap) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al) or (am) having beta-galactosidase activity and having at least 90% of the length of the mature polypeptide.

60. The polypeptide according to item 59, wherein the polypeptide comprises or consists of amino acids 1 to 685 of SEQ ID NO: 42, amino acids 1 to 688 of SEQ ID NO: 44, amino acids 1 to 695 of SEQ ID NO: 45, amino acids 1 to 687 of SEQ ID NO: 47, amino acids 1 to 694 of SEQ ID NO: 48, amino acids 1 to 654 of SEQ ID NO: 50, amino acids 1 to 661 of SEQ ID NO: 51, amino acids 1 to 687 of SEQ ID NO: 53, amino acids 1 to 694 of SEQ ID NO: 54, amino acids 1 to 686 of SEQ ID NO: 56, amino acids 1 to 695 of SEQ ID NO: 57, amino acids 1 to 688 of SEQ ID NO: 59, amino acids 1 to 697 of SEQ ID NO: 60, amino acids 1 to 691 of SEQ ID NO: 62, amino acids 1 to 700 of SEQ ID NO: 63, amino acids 1 to 690 of SEQ ID NO: 65, amino acids 1 to 699 of SEQ ID NO: 66, amino acids 1 to 689 of SEQ ID NO: 68, amino acids 1 to 698 of SEQ ID NO: 69, amino acids 1 to 685 of SEQ ID NO: 71, amino acids 1 to 694 of SEQ ID NO: 72, amino acids 1 to 685 of SEQ ID NO: 74, amino acids 1 to 694 of SEQ ID NO: 75, amino acids 1 to 686 of SEQ ID NO: 77 or amino acids 1 to 695 of SEQ ID NO: 78.

61. A polynucleotide encoding the polypeptide of any of items 57 to 60.

62. A nucleic acid construct or expression vector comprising the polynucleotide of item 48 operably linked to one or more control sequences that direct the production of the polypeptide in an expression host.

63. A recombinant host cell comprising the polynucleotide of item 61 operably linked to one or more control sequences that direct the production of the polypeptide.

64. A method of producing the polypeptide of any of items 57 to 60, comprising:
  (a) cultivating a cell, which in its wild-type form produces the polypeptide, under conditions conductive for production of the polypeptide; and
  (b) recovering the polypeptide.

65. A method of producing the polypeptide of any of items 57 to 60, comprising:
  (a) cultivating the recombinant host cell of item 63 under conditions conducive for production of the polypeptide; and
  (b) recovering the polypeptide.

66. A transgenic plant, plant part or plant cell transformed with a polynucleotide encoding the polypeptide of any of items 57 to 60.

67. A whole broth formulation or cell culture composition comprising a polypeptide of any of items 57 to 60.

68. A composition comprising the polypeptide of any of items 57 to 60.

69. The composition of item 68 further comprising one or more formulating agents.

70. The composition of item 69, wherein the one or more formulating agent is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

71. The composition of any of items 68 to 70 which is in granulate form.

72. The composition of item 71 wherein the granule is coated.

73. The composition of item 72 wherein the coating comprises a salt and/or wax and/or a flour coating.

74. The composition of any of items 68 to 73 further comprising one or more additional enzymes.

75. The composition of item 74 wherein the one or more additional enzymes is selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

The present invention is further described by the following examples that should not be construed as limiting the scope of the invention.

EXAMPLES

Strains

The galactanases were derived from bacterial strains isolated from environmental samples by standard microbiological isolation techniques. Strains were identified and taxonomy was assigned based on DNA sequencing of the 16S ribosomal genes (Table 2).

TABLE 2

Isolation of bacterial strains

| Strain | Source | Country | Year | SEQ ID NO of gene | SEQ ID NO of polypeptide |
|---|---|---|---|---|---|
| Cohnella sp-60555 | Humus | Denmark | 2007 | 1 | 2 |
| Cohnella xylanilytica | Humus | Denmark | 2002 | 5 | 6 |
| Paenibacillus tundrae | Humus | Denmark | 2004 | 9 | 10 |
| Paenibacillus barcinonensis[1] | Soil from a rice field in Ebro River Delta | Tarragona, Spain | 1993 | 13 | 14 |
| Paenibacillus sp-62603 isolate 1 | Soil | China | 2009 | 17 | 18 |
| Paenibacillus xylanilyticus | Sand | United States | 1999 | 21 | 22 |
| Paenibacillus sp-18179 | Soil | Sweden | 2000 | 25 | 26 |
| Paenibacillus peoriae | Soil | Denmark | 2011 | 29 | 30 |
| Paenibacillus xylanexedens | Soil | Egypt | 1991 | 33 | 34 |
| Cohnella laeviribosi | Sand | Thailand | 1990 | 37 | 38 |
| Paenibacillus sp-18026[2] | Soil | Spain | 1989 | 41 | 42 |
| Bacillus pumilus[3] | Soil | United States | 2006 | 43 | 44 |
| Bacillus nealsonii | Marine | Australia | 1993 | 46 | 47 |
| Burkholderia sediminicola | Soil | Sweden | 2013 | 49 | 50 |
| Bacillus alcalophilus[4] | Soil | Finland | 1994 | 52 | 53 |
| Bacillus sp-11182 | Marine | Australia | 1993 | 55 | 56 |
| Bacillus sp-62759 | Soil | Egypt | 1991 | 58 | 59 |

TABLE 2-continued

Isolation of bacterial strains

| Strain | Source | Country | Year | SEQ ID NO of gene | SEQ ID NO of poly-peptide |
|---|---|---|---|---|---|
| *Paenibacillus* sp-18054 | Thermal sample | New Zealand | 1991 | 61 | 62 |
| *Paenibacillus* sp-62047 | Forest soil | China | 2011 | 64 | 65 |
| *Paenibacillus* sp-62603 isolate 2 | Rootzone | Sweden | 2013 | 67 | 68 |
| *Paenibacillus woosongensis* | Soil | Denmark | 1996 | 70 | 71 |
| *Paenibacillus* sp-62253 | Soil | United States | 2012 | 73 | 74 |
| *Paenibacillus* sp-62758 | Sand | Egypt | 1991 | 76 | 77 |

[1]Deposited as DSMZ15478/CECT 7022
[2]Deposited as DSMZ14046
[3]Deposited as NRRL B-50016
[4]Deposited as NCIMB 40263

Chromosomal DNA isolated from pure cultures of the individual strains with the DNeasy Blood & Tissue Kit from Qiagen (Hilden, Germany) was subjected to full genome sequencing using Illumina technology. Genome sequencing, the subsequent assembly of reads and the gene discovery (i.e. annotation of gene functions) is known to the person skilled in the art and the service can be purchased commercially.

The genome sequences were analyzed for galactanases from the CAZY database family GH53 (Lombard et al. The Carbohydrate-active enzymes database CAZy. Nucleic Acids Res 2013, 42:D490-D495.) This analysis identified ten genes encoding putative galactanases with the nucleotide sequences given in SEQ ID NO: 1, 5, 9, 13, 17, 21, 25, 29, 33 and 37.

The genome sequences were also analyzed for beta-galactosidases from the CAZY database family GH42 (Lombard et al. The Carbohydrate-active enzymes database CAZy. Nucleic Acids Res 2013, 42:D490-D495.) This analysis identified thirteen genes encoding putative beta-galactosidases with the nucleotide sequences given in SEQ ID NO: 41, 43, 46, 49, 52, 55, 58, 61, 64, 67, 70, 73 and 76.

Beta-Galactosidase Assay

Beta-galactosidase activity can be determined using 4-nitrophenyl β-D-galactopyranoside (available from Megazyme International, Bray, Co. Wicklow, Ireland) as follows.

The enzyme was diluted using 100 mM MES (Sigma) buffer pH 7.0±0.05 in 2-fold dilutions and then the 4-nitrophenyl β-D-galactopyranoside (1 mg/ml in 100 mM MES buffer pH 7.0±0.05) was added in the solution containing the enzyme. The respective galactosidase activity was followed directly in the buffer by measuring the absorbance of released pNP (para-nitro-phenol) at 405 nm for 5 minutes as function of time at room temperature (typically 23° C.). A concentration of 1 mg/mL of enzyme is a good starting point; it will however depend from enzyme to enzyme and their specific activity.

The activity is calculated as the slope of a plot of absorbance versus time (units: mOD/min) using the 1-5 minute time window and the 0-2 absorbance window. The activity can then be converted to specific activity by dividing the activity for the concentration of the enzyme (units: (mOD/min)/(mg/ml)).

Galactanase Assay

Galactanase activity can be determined using the reducing ends colorimetric assay. 10% soybean meal substrate (prepared from soybean meal milled to a 0.5 mm particle size) was filled with a solid dispenser into 96 well format plates. The weight was measured before and after addition of soybean meal and the substrate amount per well was estimated assuming equal distribution along the plate.

The enzymes were diluted to 0.6 ppm (final enzyme concentration in solution) in 100 mM activity buffer (100 mM acetate, 100 mM MES, 100 mM *Glycine* in 0.01% Triton X100, 1 mM $CaCl_2$, pH 6.5) and the samples were shaken for 2 hours at 40° C. The samples were centrifuged at 3000×g for 5 minutes and 75 µl of each sample (supernatant) was transferred to a new PCR-plate. 75 µl activity buffer was added to each sample, the samples were mixed then 75 µl of stop solution (15 mg/ml PAHBAH (Sigma H-9882) in Ka-Na-tartrate/NaOH solution, pH>10) was added. The solution was mixed for 10 min at 95° C., then 1 min. 10° C. and the samples were transferred to a new 96 MTP and absorbance was measured at 405 nm.

Galactose SBM Assay

Introduction

The concentration of galactose monosaccharides in a solution was measured spectrophotometrically after enzymatic hydrolysis of a galactose-rich substrate; soybean meal.

Summarizing, the enzyme(s) were incubated in a 10 w/v % slurry of soybean meal at pH 6.5±0.05 for 2 hours at 40±2° C. The supernatant was then analyzed in an assay based on the Raffinose/Galactose kit from Megazyme (product name K-RAFGA). First α-D-galactose in the supernatant was converted to β-D-galactose with the enzyme galactose mutarotase. Then β-D-galactose was oxidised by NAD+ to D-galactonic acid in the presence of β-galactose dehydrogenase. The amount of NADH formed in this reaction was stoichiometric with the amount of D-Galactose in the supernatant. NADH concentration was then measured by the increase in absorbance at 340 nm.

Soybean Meal Slurry

A 10 w/v % slurry of soybean meal was prepared from soybean meal milled to a 0.5 mm particle size and 0.1 M citric acid-phosphate buffer, pH 6.5±0.05.

0.1 M citric acid-phosphate buffer, pH 6.5±0.05 was heated to a temperature of approximately 40° C. while stirring. The preheated buffer was then transferred to the soybean meal. The resulting slurry was stirred while being heated (temperature was not monitored at this point—heating was only applied to ensure that temperature would not decrease too much while the slurry stirred). The slurry was then transferred with a pre-wetted wide-bore pipette to the vessel in which it should be incubated. The slurry was pipetted from an approximately central point in the mix. The time elapsed from the mixing of the slurry until transfer to the last incubation vessel was, at most, 15 minutes. Stirring speed was adjusted in such a way that particles were evenly distributed in the slurry.

Dilution of Enzymes

The enzymes were diluted to their desired concentrations in ultrapure water. The concentration to which the enzymes were diluted to was based on the prior concentration of the enzyme in mg enzyme protein per mL (mg EP/mL) and the mass (kg) of dry matter (soybean meal) in each incubation vessel.

$$V_{enzyme}(mL) = \frac{c_{enzyme}\left(mg\frac{EP}{mL}\right)}{m_{SBM}(kg)}$$

D-(+)-Galactose Standards

A standard curve was prepared from D-(+)-galactose and ultrapure water. A D-(+)-galactose stock was prepared by dissolving D-(+)-galactose in ultrapure water to a final concentration of 250 mg galactose per mL. The stock solution was diluted in a two-fold dilution row to obtain six standards with concentrations of 250, 125, 62.5, 31.25, 15.625 and 7.813 mg galactose per mL.

Incubation of α-Galactosidases on Soybean Meal

The incubation vessels with the 10 w/v % slurry of soybean meal were heated to a stable temperature of 40±2° C. while stirring. When a stable temperature had been achieved, the six D-(+)-galactose standards were added to the incubation vessels to in-vessel concentrations of 5, 2.5, 1.25, 0.625, 0.313 and 0.157 mg galactose per mL incubation volume. Each standard was incubated in duplicates.

The diluted enzymes were then added to their respective incubation vessels in the volumes required to reach their desired concentrations (in mg EP/kg soybean meal). Each enzyme treatment was incubated in triplicates.

Additionally, two times three incubation vessels were included without standards or enzyme treatments as blank treatments to obtain the baseline galactose concentration in the soybean meal slurry.

The incubation vessels were incubated at 40±2° C., while stirring for 2 hours. After incubation the vessels were centrifuged at 1500 g at 5° C. for 15 minutes.

Determination of Galactose Concentration

The supernatants in the now centrifuged incubation vessels were then analyzed in an assay based on the Raffinose/Galactose kit from Megazyme (product name K-RAFGA). Three reagents from the K-RAFGA kit was used in the assay: Assay Buffer (supplied and ready in Bottle 1 in the kit), β-NAD reagent (supplied in Bottle 2 in the kit, prepared as described in the kit prior to use) and GalDH+GalM solution (supplied in Bottle 3 in the kit, diluted 1:1 in ultrapure water prior to use). All steps described in the following were carried out using an Eppendorf 5075 automated pipetting system.

First the supernatants from the centrifuged incubation vessels were diluted 10 times in 0.1 M citric acid-phosphate buffer, pH 6.5±0.05 (1 part supernatant plus 9 parts 0.1 M citric acid-phosphate buffer, pH 6.5±0.05).

69 µL of each diluted supernatant was then transferred to a new vessel and 34 µL of ultrapure water was added to the diluted supernatants (which will be referred to as assay samples from here on out). Then 69 µL Assay Buffer was added to the assay samples followed by dilution in 687 µL ultrapure water. 34 µL β-NAD reagent was added to the assay samples, followed by addition of 14 µL GalDH+GalM solution and vigorous mixing.

262 µL of each assay sample was then transferred to a 96 well micro titer plate. Absorbance in each well of the 96 well micro titer plate was measured at 340 nm at 40±2° C. for a duration of 20 minutes or until absorbance in each well had reached a stable level. When a stable absorbance had been reached this stable absorbance was used in later calculations.

Calculation of Galactose Concentration

Absorbance of the assay samples from the galactose standards in the incubation vessels were used as a standard curve (6 standards, 5, 2.5, 1.25, 0.625, 0.313 and 0.157 mg galactose per mL incubation volume, n=2 per standard). An equation for the galactose standard curve was calculated in excel, where y is OD340 and x is galactose concentration in mg galactose per mL incubation volume:

$$OD_{340} = a * c_{gal}\left(\frac{mg}{mL}\right) + b$$

Galactose concentration in mg galactose per mL incubation volume for each sample was then given by:

$$c_{gal}\left(\frac{mg}{mL}\right) = \frac{OD_{340} - b}{a}$$

Galactose concentrations were then calculated on a dry-matter basis (g galactose per kg soybean meal) and are reported in the examples below:

$$c_{gal}\left(\frac{g}{kg}SBM\right) = \frac{c_{gal}\left(\frac{mg}{mL}\right) * V_{sample}(mL)}{m_{SBM}(g)}$$

Example 1: Cloning of GH53 Galactanases from *Cohnella* sp-60555, *Cohnella xylanilytica*, *Paenibacillus tundra*, *Paenibacillus barcinonensis*, *Paenibacillus* sp-62603, *Paenibacillus xylanilyticus*, *Paenibacillus* sp-18179, *Paenibacillus peoriae*, *Paenibacillus Xylanexedens* and *Cohnella laeviribosi* (SEQ ID NO: 4, 8, 12, 16, 20, 24, 28, 32, 36 and 40)

The genes encoding the galactanases were amplified by PCR and fused with regulatory elements, affinity purification tag and homology regions for recombination into the *B. subtilis* genome. The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension Gene* 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal (encoding the following amino acid sequence: MKKPLGKIVASTALLISVAFSSSIASA, SEQ ID NO: 84) replacing the native secretion signal. Furthermore the expression construct results in the addition of an amino terminal poly histidine purification tag on the natural mature protein allowing for enzyme purification through immobilized metal ion affinity chromatography.

The SOE-PCR product was transformed into *Bacillus subtilis* and integrated in the chromosome by homologous recombination into the pectate lyase locus. Subsequently one recombinant *Bacillus subtilis* clone containing the respective galactanase expression construct was selected and was cultivated on a rotary shaking table in 500 ml baffled Erlenmeyer flasks each containing 100 ml rich starch based media. After 3-5 days cultivation time at 30° C. to 37° C., enzyme containing supernatants were harvested by centrifugation and the enzymes were purified by immobilized metal affinity chromatography.

Example 2: Purification of GH53 Galactanases from *Cohnella* sp-60555, *Cohnella xylanilytica*, *Paenibacillus tundra*, *Paenibacillus barcinonensis*, *Paenibacillus* sp-62603, *Paenibacillus xylanilyticus*, *Paenibacillus* sp-18179, *Paenibacillus peoriae*, *Paenibacillus xylanexedens* and *Cohnella laeviribosi* (SEQ ID NO: 4, 8, 12, 16, 20, 24, 28, 32, 36 and 40)

The pH of the supernatant from example 1 was adjusted to pH 8, filtrated through a 0.2 μM filter, and then applied to a 5 ml HisTrap™ excel column (GE Healthcare Life Sciences, Pittsburgh, USA). Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column (GE Healthcare Life Sciences, Pittsburgh, USA)., equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3: Cloning of a GH42 Beta-Galactosidase from *Paenibacillus* sp-18026 (SEQ ID NO: 42)

The genes encoding the beta-galactosidases were amplified by PCR and fused with regulatory elements, affinity purification tag and homology regions for recombination into the *B. subtilis* genome. The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension* Gene 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The SOE-PCR product was transformed into *Bacillus subtilis* and integrated in the chromosome by homologous recombination into the pectate lyase locus. Subsequently one recombinant *Bacillus subtilis* clone containing the beta-galactosidase expression construct was selected and was cultivated on a rotary shaking table in 500 ml baffled Erlenmeyer flasks each containing 100 ml rich starch based media. After 3-5 days cultivation time at 30° C. to 37° C., enzyme containing supernatants were harvested by centrifugation and the enzymes were purified by immobilized metal affinity chromatography.

Example 4: Purification of the GH42 Beta-Galactosidases from *Paenibacillus* sp-18026 (SEQ ID NO: 42)

To the filtrated broth was added 1.2M ammonium sulphate. After filtration on 0.2 μm PES filter (Nalge Nunc International, Nalgene labware cat #595-4520), the filtrate was loaded onto a Phenyl Sepharose™ 6 Fast Flow column (high sub) (GE Healthcare, Piscataway, N.J., USA) pre-equilibrated in 25 mM HEPES pH 7.5 with 1.2M ammonium sulphate, and bound proteins were eluted with 25 mM HEPES pH 7.5 with no ammonium sulphate. The fractions were pooled and applied to a Sephadex™ G-25 (medium) (GE Healthcare, Piscataway, N.J., USA) column pre-equilibrated in 12.5 mM HEPES pH 7.8 and eluted with the same buffer (isocratic). The fractions were applied to a SOURCE™ 15Q (GE Healthcare, Piscataway, N.J., USA) column pre-equilibrated in 12.5 mM HEPES pH 7.8, and bound proteins were eluted with a linear gradient from 0-1000 mM sodium chloride.

Example 5: Cloning of GH42 Beta-Galactosidases from *Bacillus pumilus*, *Bacillus nealsonii*, *Burkholderia sediminicola*, *Bacillus alcalophilus*, *Bacillus* sp-11182, *Bacillus* sp-62759, *Paenibacillus* sp-18054, *Paenibacillus* sp-62047, *Paenibacillus* sp-62603, *Paenibacillus woosongensis*, *Paenibacillus* sp-62253, *Paenibacillus* sp-62758 (SEQ ID NO: 45, 48, 51, 54, 57, 60, 63, 66, 69, 72, 75 and 78)

The genes encoding the beta-galactosidases were amplified by PCR and fused with regulatory elements, affinity purification tag and homology regions for recombination into the *B. subtilis* genome. The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension* Gene 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

Furthermore the expression construct results in the addition of an amino terminal poly histidine purification tag on the natural mature protein allowing for enzyme purification through immobilized metal ion affinity chromatography.

The SOE-PCR product was transformed into *Bacillus subtilis* and integrated in the chromosome by homologous recombination into the pectate lyase locus. Subsequently one recombinant *Bacillus subtilis* clone containing the respective beta-galactosidase expression construct was selected and was cultivated on a rotary shaking table in 500 ml baffled Erlenmeyer flasks each containing 100 ml rich starch based media. After 3-5 days cultivation time at 30° C. to 37° C., enzyme containing supernatants were harvested by centrifugation and the enzymes were purified by immobilized metal affinity chromatography.

Example 6: Purification of GH42 beta-galactosidases from *Bacillus pumilus, Bacillus nealsonii, Burkholderia sediminicola, Bacillus alcalophilus, Bacillus* sp-11182, *Bacillus* sp-62759, *Paenibacillus* sp-18054, *Paenibacillus* sp-62047, *Paenibacillus* sp-62603, *Paenibacillus woosongensis, Paenibacillus* sp-62253, *Paenibacillus* sp-62758 (SEQ ID NO: 45, 48, 51, 54, 57, 60, 63, 66, 69, 72, 75 and 78)

The GH42 beta-galactosidases were purified as described in example 2.

Example 7: Hydrolysis of Soybean Meal (SBM) Using GH53 Galactanases

The release of galactose from soybean meal using galactanases (SEQ ID NO: 79 and 80) were determined using the Galactose SBM Assay. The results are presented in table 3 below.

TABLE 3

Release of galactose from soybean meal using known galactanases

| GH53 galactanase | Conc. GH53 [mg EP/kg] | Mean Galactose Release (g gal/kg SBM) |
| --- | --- | --- |
| SEQ ID NO: 79 | 20 | 2.8 |
| SEQ ID NO: 79 | 20 | 3.4 |
| SEQ ID NO: 80 | 20 | 1.9 |
| SEQ ID NO: 80 | 20 | 2.6 |
| Blank | — | 0.1 |

The results show that the GH53 galactanases do not release significant amounts of galactose on their own from soybean meal.

Example 8: Hydrolysis of Soybean Meal (SBM) Using a Known GH53 Galactanase in Combination with a GH42 Beta-Galactosidase The release of galactose from soybean meal using a galactanase (SEQ ID NO: 79 or 80) and a beta-galactosidases (SEQ ID NO: 42, 45, 48 or 51) were determined using the Galactose SBM Assay. The results are presented in tables 4, 5 and 6 below.

TABLE 4

Release of galactose from soybean meal using a GH53 galactanase (SEQ ID NO: 80) in combination with a GH42 beta-galactosidase (SEQ ID NO: 42)

| GH42 beta-galactosidase | GH53 galactanase | Conc. GH42 [mg EP/kg] | Conc. GH53 [mg EP/kg] | Mean Galactose Release (g gal/kg SBM) | Significance |
| --- | --- | --- | --- | --- | --- |
| SEQ ID NO: 42 | SEQ ID NO: 80 | 100 | 20 | 11.5 | A |
| Blank | Blank | — | — | −0.1 | B |

AB: Values within a column not sharing a capital letter are significantly different ($p < 0.05$).
Means were compared by Tukey HSD procedure in SAS JMP 11

TABLE 5

Release of galactose from soybean meal using a GH53 galactanase (SEQ ID NO: 79) in combination with a GH42 beta-galactosidase (SEQ ID NO: 42)

| GH42 beta-galactosidase | GH53 galactanase | Conc. GH42 [mg EP/kg] | Conc. GH53 [mg EP/kg] | Mean Galactose Release (g gal/kg SBM) | Significance |
| --- | --- | --- | --- | --- | --- |
| SEQ ID NO: 42 | SEQ ID NO: 79 | 100 | 20 | 12.4 | A |
| Blank | Blank | — | — | −0.8 | B |

AB: Values within a column not sharing a capital letter are significantly different ($p < 0.05$).
Means were compared by Tukey HSD procedure in SAS JMP 11

TABLE 6

Release of galactose from soybean meal using a GH53 galactanase (SEQ ID NO: 79) in combination with a GH42 beta-galactosidase (SEQ ID NO: 45, 48 or 51)

| GH42 beta-galactosidase | GH53 galactanase | Conc. GH42 [mg EP/kg] | Conc. GH53 [mg EP/kg] | Mean Galactose Release (g gal/kg SBM) | Signifcance |
| --- | --- | --- | --- | --- | --- |
| SEQ ID NO: 48 | SEQ ID NO: 79 | 100 | 20 | 13.2 | A |
| SEQ ID NO: 45 | SEQ ID NO: 79 | 100 | 20 | 12.1 | AB |
| SEQ ID NO: 51 | SEQ ID NO: 79 | 100 | 20 | 10.8 | B |
| Blank | Blank | — | — | 0.0 | C |

ABC: Values within a column not sharing a capital letter are significantly different ($p < 0.05$).
Means were compared by Tukey HSD procedure in SAS JMP 11

The results demonstrate that the two GH53 galactanases together with the GH42 beta-galactosidase released significantly higher amounts of galactose from soybean meal than using the galactanase on its own (from table 3).

Example 9: Hydrolysis of Soybean Meal (SBM) Using a GH53 Galactanase in Combination with Eight GH42 Beta-Galactosidases The release of galactose from soybean meal using a galactanase (SEQ ID NO: 4) and eight beta-galactosidases (SEQ ID NO: 42, 57, 60, 63, 66, 69, 72 and 75) were determined using the Galactose SBM Assay. The results are presented in table 7 below.

TABLE 7

Release of galactose from soybean meal using a GH53 galactanase (SEQ ID NO: 4) in combination with eight GH42 beta-galactosidases (SEQ ID NO: 42, 57, 60, 63, 66, 69, 72 and 75)

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 75 | SEQ ID NO: 4 | 20 | 20 | 28.7 | A |
| SEQ ID NO: 66 | SEQ ID NO: 4 | 20 | 20 | 28.6 | A |
| SEQ ID NO: 69 | SEQ ID NO: 4 | 20 | 20 | 28.2 | A |
| SEQ ID NO: 63 | SEQ ID NO: 4 | 20 | 20 | 28.2 | A |
| SEQ ID NO: 72 | SEQ ID NO: 4 | 20 | 20 | 27.9 | A |
| SEQ ID NO: 60 | SEQ ID NO: 4 | 20 | 20 | 27.6 | A |
| SEQ ID NO: 42 | SEQ ID NO: 4 | 20 | 20 | 27.3 | A |
| SEQ ID NO: 57 | SEQ ID NO: 4 | 20 | 20 | 27.2 | A |
| Blank | Blank | — | — | −0.2 | B |

AB: Values within a column not sharing a capital letter are significantly different ($p < 0.05$).
Means were compared by Tukey HSD procedure in SAS JMP 11

The results demonstrate that all of the GH42 beta-galactosidases tested in combination with the GH53 galactanase released significantly higher amounts of galactose from soybean meal than using a galactanase on its own (from table 3).

Example 10: Hydrolysis of Soybean Meal (SBM) Using a GH53 Galactanase in Combination with Six GH42 Beta-Galactosidases The release of galactose from soybean meal using a galactanase (SEQ ID NO: 4) and six beta-galactosidases (SEQ ID NO: 42, 45, 48, 51, 54 and 78) were determined using the Galactose SBM Assay. The results are presented in tables 8, 9 and 10 below.

TABLE 8

Release of galactose from soybean meal using a GH53 galactanase (SEQ ID NO: 4) in combination with three GH42 beta-galactosidase (SEQ ID NO: 42, 48 and 54)

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 42 | SEQ ID NO: 4 | 20 | 20 | 28.7 | A |
| SEQ ID NO: 54 | SEQ ID NO: 4 | 20 | 20 | 27.9 | A |
| SEQ ID NO: 48 | SEQ ID NO: 4 | 20 | 20 | 26.9 | A |
| Blank | Blank | — | — | 0.0 | B |

AB: Values within a column not sharing a capital letter are significantly different ($p < 0.05$).
Means were compared by Tukey HSD procedure in SAS JMP 11

TABLE 9

Release of galactose from soybean meal using a
GH53 galactanase (SEQ ID NO: 4) in combination
with three GH42 beta-galactosidase (SEQ ID NO: 42, 45 and 51)

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 45 | SEQ ID NO: 4 | 20 | 20 | 28.6 | A |
| SEQ ID NO: 42 | SEQ ID NO: 4 | 20 | 20 | 27.5 | A |
| SEQ ID NO: 51 | SEQ ID NO: 4 | 20 | 20 | 27.0 | A |
| Blank | Blank | — | — | −0.2 | B |

AB: Values within a column not sharing a capital letter are significantly different ($p < 0.05$).
Means were compared by Tukey HSD procedure in SAS JMP 11

TABLE 10

Release of galactose from soybean meal using a GH53 galactanase (SEQ ID NO: 4)
in combination with three GH42 beta-galactosidases (SEQ ID NO: 42 and 78)

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 78 | SEQ ID NO: 4 | 20 | 20 | 29.1 | A |
| SEQ ID NO: 42 | SEQ ID NO: 4 | 20 | 20 | 28.3 | A |
| Blank | Blank | — | — | −0.1 | B |

AB: Values within a column not sharing a capital letter are significantly different ($p < 0.05$).
Means were compared by Tukey HSD procedure in SAS JMP 11

The results demonstrate that all of the GH42 beta-galactosidases tested in combination with the GH53 galactanase released significantly higher amounts of galactose from soybean meal than using a galactanase on its own (from table 3).

Example 11: Hydrolysis of Soybean Meal (SBM) Using a GH42 Beta-Galactosidase in Combination with Ten GH53 Galactanases The release of galactose from soybean meal using a beta-galactosidase (SEQ ID NO: 42) and ten galactanases (SEQ ID NO: 4, 8, 12, 16, 20, 24, 28, 32, 36 and 40) were determined using the Galactose SBM Assay. The results are presented in tables 11, 12 and 13 below.

TABLE 11

Release of galactose from soybean meal using a beta-galactosidase (SEQ ID NO: 42)
and ten galactanases (SEQ ID NO: 4, 8, 12 and 16)

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 42 | SEQ ID NO: 4 | 20 | 20 | 28.0 | A |
| SEQ ID NO: 42 | SEQ ID NO: 8 | 20 | 20 | 26.8 | A |
| SEQ ID NO: 42 | SEQ ID NO: 16 | 20 | 20 | 20.4 | B |
| SEQ ID NO: 42 | SEQ ID NO: 12 | 20 | 20 | 19.8 | B |
| Blank | Blank | — | — | −0.1 | C |

ABC: Values within a column not sharing a capital letter are significantly different ($p < 0.05$).
Means were compared by Tukey HSD procedure in SAS JMP 11

TABLE 12

Release of galactose from soybean meal using a beta-galactosidase (SEQ ID NO: 42) and ten galactanases (SEQ ID NO: 4, 20, 24 and 28)

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 42 | SEQ ID NO: 4  | 20 | 20 | 28.6 | A |
| SEQ ID NO: 42 | SEQ ID NO: 28 | 20 | 20 | 25.8 | AB |
| SEQ ID NO: 42 | SEQ ID NO: 24 | 20 | 20 | 21.5 | BC |
| SEQ ID NO: 42 | SEQ ID NO: 20 | 20 | 20 | 14.9 | C |
| Blank | Blank | — | — | −0.1 | D |

ABCD: Values within a column not sharing a capital letter are significantly different ($p < 0.05$).
Means were compared by Tukey HSD procedure in SAS JMP 11

TABLE 13

Release of galactose from soybean meal using a beta-galactosidase (SEQ ID NO: 42) and ten galactanases (SEQ ID NO: 4, 32, 36 and 40)

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 42 | SEQ ID NO: 32 | 20 | 20 | 30.6 | A |
| SEQ ID NO: 42 | SEQ ID NO: 4  | 20 | 20 | 29.7 | A |
| SEQ ID NO: 42 | SEQ ID NO: 40 | 20 | 20 | 24.5 | B |
| SEQ ID NO: 42 | SEQ ID NO: 36 | 20 | 20 | 22.1 | B |
| Blank | Blank | — | — | −0.1 | C |

ABCD: Values within a column not sharing a capital letter are significantly different ($p < 0.05$).
Means were compared by Tukey HSD procedure in SAS JMP 11

The results demonstrate that all of the GH53 galactanases tested in combination with the GH42 beta-galactosidase released significantly higher amounts of galactose from soybean meal than using a galactanase on its own (from table 3).

Example 12: Hydrolysis of Soybean Meal (SBM) Using Using a GH53 Galactanase Alone, a GH42 Beta-Galactosidase Alone or a Combination of a GH53 Galactanase with a GH42 Beta-Galactosidase The release of galactose from soybean meal using three different GH42 beta-galactosidases (SEQ ID NO: 42, 51 and 78) alone or using three different GH53 galactanases (SEQ ID NO: 4, 28 and 40) alone was determined using the Galactose SBM Assay. Three different combinations using one of the GH42 beta-galactosidases together with one of the GH53 galactanases was also tested to demonstrate the synergistic effect of the combination of enzymes. The results are presented in table 14 below.

TABLE 14

Release of galactose from soybean meal using a GH53 galactanase alone, a GH42 beta-galactosidase alone or a combination of a GH53 galactanase with a GH42 beta-galactosidase

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 42 | SEQ ID NO: 28 | 20 | 20 | 22.0 | A |
| SEQ ID NO: 78 | SEQ ID NO: 4  | 20 | 20 | 21.0 | A |
| SEQ ID NO: 51 | SEQ ID NO: 40 | 20 | 20 | 19.7 | A |

TABLE 14-continued

Release of galactose from soybean meal using a GH53 galactanase alone, a GH42 beta-galactosidase alone or a combination of a GH53 galactanase with a GH42 beta-galactosidase

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| — | SEQ ID NO: 28 | — | 20 | 0.5 | B |
| — | SEQ ID NO: 40 | — | 20 | 0.2 | B |
| Blank | — | — | — | −0.2 | B |
| — | SEQ ID NO: 4 | — | 20 | −0.2 | B |
| SEQ ID NO: 78 | — | 20 | — | −0.3 | B |
| SEQ ID NO: 42 | — | 20 | — | −0.4 | B |
| SEQ ID NO: 51 | — | 20 | — | −0.4 | B |

AB: Values within a column not sharing a capital letter are significantly different (p < 0.05).
Means were compared by Tukey HSD procedure in SAS JMP 11

The results demonstrate that neither the GH53 galactanase alone nor the GH42 beta-galactosidase alone released a significant amount of galactose under the conditions tested. However, the three tested combinations of a GH53 galactanase together with a GH42 beta-galactosidase all released a significant amount of galactose from soybean meal, demonstrating the synergistic effects of the combination of enzymes.

Example 13: Animal Feed and Animal Feed Additives Comprising Galactanases and Beta-Galactosidases Animal Feed Additive A formulation of a galactanase and a beta-galactosidase (e.g. one or more of SEQ ID NO: 3, 4, 7, 8, 11, 12, 15, 16, 19, 20, 23, 24, 27, 28, 31, 32, 35, 36, 39 or 40 and one or more of SEQ ID NO: 42, 44, 47, 50, 53, 56, 59, 62, 65, 68, 71, 74 or 77) containing 0.01 g to 10 g galactanase and 0.01 g to 10 g beta-galactosidase is added to the following premix (per kilo of premix):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:
62.55% Maize
33.8% Soybean meal (50% crude protein)
1.0% Soybean oil
0.2% DL-Methionine
0.22% DCP (dicalcium phosphate)
0.76% CaCO$_3$ (calcium carbonate)
0.32% Sand
0.15% NaCl (sodium chloride)
1% of the above Premix The ingredients are mixed, and the feed is pelleted at the desired temperature, e.g. 60, 65, 75, 80, 85, 90 or even 95° C.

Liquid Formulation

A liquid formulation of a galactanase and a beta-galactosidase (e.g. one or more of SEQ ID NO: 3, 4, 7, 8, 11, 12, 15, 16, 19, 20, 23, 24, 27, 28, 31, 32, 35, 36, 39 or 40 and one or more of SEQ ID NO: 42, 44, 47, 50, 53, 56, 59, 62, 65, 68, 71, 74 or 77) comprises 0.1% to 10 w/w enzyme protein (combined), 40-60% glycerol, 0.1 to 0.5% sodium benzoate and water. The liquid formulation is sprayed onto the pelleted animal feed described above (in this case the animal feed additive would not include the beta-galactosidase or galactanase of the invention present).

Example 14: Hydrolysis of Soybean Meal (SBM) Using the Prior Art Combination of LacA and GalA or ganB and ganA Shipkowski et at, in *Applied and Environmental Microbiology*, 2006, 72(12), 7730, describe the GH53 galactanase GalA (Swissprot: 007013, SEQ ID NO: 86) and the GH42 beta-galactosidase LacA from *Bacillus subtilis* (strain 168) (Swissprot: 007012, SEQ ID NO: 85).

Tabachnikov et al, in *Febs Journal*, 2013, 280(3), 950 7730, describe the GH53 galactanase ganA (Swissprot: F8TRX1, SEQ ID NO: 88) and a GH42 beta-galactosidase ganB (Swissprot: F8TRX0, SEQ ID NO: 87) from *Geobacillus stearothermophilus*.

The release of galactose from soybean meal using the prior art combination GalA+LacA and the prior art combination ganA+ganB were determined using the Galactose SBM. As negative control, a blank sample was run. As positive control, the GH42 beta-galactosidase having SEQ ID NO: 42 and the GH53 galactanase having SEQ ID NO: 4 were used. The results are presented in table 15 below.

TABLE 15

Release of galactose from soybean meal using a prior art beta-galactosidase and galactanase

| GH42 beta-galactosidase | GH53 galactanase | Conc. GH42 [mg EP/kg] | Conc. GH53 [mg EP/kg] | Mean Galactose Release (g gal/kg SBM) | Signifcance |
|---|---|---|---|---|---|
| SEQ ID NO: 42 | SEQ ID NO: 4 | 20 | 20 | 21.4 | A |
| LacA (O07012) SEQ ID NO: 85 | GalA (O07013) SEQ ID NO: 86 | 20 | 20 | 6.1 | C |
| GanB (F8TRX0) SEQ ID NO: 87 | GanA (F8TRX1) SEQ ID NO: 88 | 20 | 20 | 7.1 | B |
| Blank | Blank | — | — | 3.7 | D |

ABC: Values within a column not sharing a capital letter are significantly different ($p < 0.05$).
Means were compared by Tukey HSD procedure in SAS JMP 11

The results demonstrate that the prior art combinations release significantly less galactose from soybean meal compared to a GH53 galactanase of the invention (SEQ ID NO: 4) together with a GH35 beta-galactosidases of the invention (SEQ ID NO: 42).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method of improving one or more performance parameters of an animal, comprising feeding the animal with plant-based material and a composition comprising one or more GH53 polypeptides having galactanase activity and one or more GH42 polypeptides having beta-galactosidase activity, wherein the plant-based material comprises soybean or soybean meal and the one or more performance parameters are selected from the group consisting of body weight gain (BWG), European Production Efficiency Factor (EPEF) and feed conversion ratio (FCR).

2. The method of claim 1, wherein the composition is a granule.

3. The method of claim 1, wherein the plant-based material and the composition are a pelleted animal feed.

4. The method of claim 1, wherein the composition further comprises one or more components selected from the list consisting of:
one or more vitamins;
one or more minerals;
one or more amino acids;
one or more prebiotics;
one or more phytogenics;
one or more organic acids; and
one or more other feed ingredients.

5. The method of claim 1, wherein the composition is a liquid composition.

6. The method of claim 1, wherein the GH53 polypeptide comprises the motif GV[T/M]PD[W/M]VQ[I/V]GNE (SEQ ID NO: 81) and/or the motif WADP[A/G]xQxKPxAW (SEQ ID NO: 82).

7. The method of claim 1, wherein the GH53 polypeptide is selected from the group consisting of:
(a) a polypeptide having at least 80% sequence identity to the polypeptide of SEQ ID NO: 3;
(b) a polypeptide having at least 80% sequence identity to the polypeptide of SEQ ID NO: 7;
(c) a polypeptide having at least 80% sequence identity to the polypeptide of SEQ ID NO: 11;
(d) a polypeptide having at least 80% sequence identity to the polypeptide of SEQ ID NO: 15;
(e) a polypeptide having at least 80% sequence identity to the polypeptide of SEQ ID NO: 19;
(f) a polypeptide having at least 80% sequence identity to the polypeptide of SEQ ID NO: 23;
(g) a polypeptide having at least 80% sequence identity to the polypeptide of SEQ ID NO: 27;
(h) a polypeptide having at least 80% sequence identity to the polypeptide of SEQ ID NO: 31;
(i) a polypeptide having at least 80% sequence identity to the polypeptide of SEQ ID NO: 35; and
(j) a polypeptide having at least 80% sequence identity to the polypeptide of SEQ ID NO: 39.

8. The method of claim 7, wherein the GH53 polypeptide:
comprises an N-terminal and/or C-terminal His-tag and/or HQ-tag;
comprises an N-terminal and/or C-terminal extension of up to 10 amino acids; or
is a fragment having galactanase activity and having at least 90% of the length of the mature polypeptide.

9. The method of claim 1, wherein the GH42 polypeptide is selected from the group consisting of:
(a) a polypeptide having at least 80% sequence identity to the polypeptide of SEQ ID NO: 42;
(b) a polypeptide having at least 80% sequence identity to the polypeptide of SEQ ID NO: 44;
(c) a polypeptide having at least 80% sequence identity to the polypeptide of SEQ ID NO: 47;
(d) a polypeptide having at least 80% sequence identity to the polypeptide of SEQ ID NO: 50;
(e) a polypeptide having at least 80% sequence identity to the polypeptide of SEQ ID NO: 53;
(f) a polypeptide having at least 80% sequence identity to the polypeptide of SEQ ID NO: 56;
(g) a polypeptide having at least 80% sequence identity to the polypeptide of SEQ ID NO: 59;
(h) a polypeptide having at least 80% sequence identity to the polypeptide of SEQ ID NO: 62;
(i) a polypeptide having at least 80% sequence identity to the polypeptide of SEQ ID NO: 65;
(j) a polypeptide having at least 80% sequence identity to the polypeptide of SEQ ID NO: 68;
(k) a polypeptide having at least 80% sequence identity to the polypeptide of SEQ ID NO: 71;
(l) a polypeptide having at least 80% sequence identity to the polypeptide of SEQ ID NO: 74; and
(m) a polypeptide having at least 80% sequence identity to the polypeptide of SEQ ID NO: 77.

10. The method of claim 9, wherein the GH42 polypeptide:
comprises an N-terminal and/or C-terminal His-tag and/or HQ-tag;
comprises an N-terminal and/or C-terminal extension of up to 10 amino acids; or
is a fragment having beta-galactosidase activity and having at least 90% of the length of the mature polypeptide.

11. The method of claim 1, wherein the GH53 polypeptide has at least 80% sequence identity to the polypeptide of SEQ ID NO: 3 and the GH42 polypeptide has at least 80% sequence identity to the polypeptide of SEQ ID NO: 42.

12. The method of claim 1, wherein the GH53 polypeptide has at least 85% sequence identity to the polypeptide of SEQ ID NO: 3 and the GH42 polypeptide has at least 85% sequence identity to the polypeptide of SEQ ID NO: 42.

13. The method of claim 1, wherein the GH53 polypeptide has at least 90% sequence identity to the polypeptide of SEQ ID NO: 3 and the GH42 polypeptide has at least 90% sequence identity to the polypeptide of SEQ ID NO: 42.

14. The method of claim 1, wherein the GH53 polypeptide has at least 95% sequence identity to the polypeptide of SEQ ID NO: 3 and the GH42 polypeptide has at least 95% sequence identity to the polypeptide of SEQ ID NO: 42.

15. The method of claim 1, wherein the GH53 is the polypeptide of SEQ ID NO: 3 or 4 and the GH42 polypeptide is the polypeptide of SEQ ID NO: 42.

16. The method of claim 11, wherein the GH53 polypeptide:
comprises an N-terminal and/or C-terminal His-tag and/or HQ-tag;
comprises an N-terminal and/or C-terminal extension of up to 10 amino acids; or
is a fragment having galactanase activity and having at least 90% of the length of the mature polypeptide.

17. The method of claim 11, wherein the GH42 polypeptide:
comprises an N-terminal and/or C-terminal His-tag and/or HQ-tag;
comprises an N-terminal and/or C-terminal extension of up to 10 amino acids; or
is a fragment having beta-galactosidase activity and having at least 90% of the length of the mature polypeptide.

18. The method of claim 11, wherein the GH53 polypeptide is a variant of SEQ ID NO: 3, wherein the variant has galactanase activity and comprises one or more amino acid substitutions, one or more amino acid deletions, and/or one or more amino acid insertions.

19. The method of claim 11, wherein the GH42 polypeptide is a variant of SEQ ID NO: 42, wherein the variant has beta-galactosidase activity and comprises one or more amino acid substitutions, one or more amino acid deletions, and/or one or more amino acid insertions.

* * * * *

SEQUENCE LISTING

```
<160> NUMBER OF SEQ ID NOS: 88

<210> SEQ ID NO 1
<211> LENGTH: 1047
<212> TYPE: DNA
<213> ORGANISM: Cohnella sp-60555
<220> FEATURE:
<221> NAME/KEY: CDS
<222> LOCATION: (1)..(1044)
<220> FEATURE:
<221> NAME/KEY: sig_peptide
<222> LOCATION: (1)..(96)
<220> FEATURE:
<221> NAME/KEY: mat_peptide
<222> LOCATION: (97)..(1044)

<400> SEQUENCE: 1 atg atg ttc aag aga acg gta acg ggc atg atg gcc ttg ctg ctg gtg      48
Met Met Phe Lys Arg Thr Val Thr Gly Met Met Ala Leu Leu Leu Val
        -30                 -25                 -20 ctg gct ctg ttc gtc gcg caa ggt tcg cag ccg cac caa gcc gcc gcg      96
Leu Ala Leu Phe Val Ala Gln Gly Ser Gln Pro His Gln Ala Ala Ala
    -15                 -10                  -5                  -1 gcg ccg tcg ttc gcc aaa ggg gcg gac atc agc tgg gtg ccg gga atg     144
Ala Pro Ser Phe Ala Lys Gly Ala Asp Ile Ser Trp Val Pro Gly Met
1               5                  10                  15 gaa gcc cag ggg tac aag tgg aag gac aag aac ggc gtg cag cgg gac     192
Glu Ala Gln Gly Tyr Lys Trp Lys Asp Lys Asn Gly Val Gln Arg Asp
                20                  25                  30 att ttg gac att ttg aaa aac gat tat cag atc aac tcc gtg cgc atc     240
Ile Leu Asp Ile Leu Lys Asn Asp Tyr Gln Ile Asn Ser Val Arg Ile
            35                  40                  45 cgc gtg tgg gtc aac cct tcg agc agc tac acg aac ggg tac ctg aac     288
Arg Val Trp Val Asn Pro Ser Ser Ser Tyr Thr Asn Gly Tyr Leu Asn
        50                  55                  60 aag gac cgt gcg gcc gcg ctg gcg aag cgg gcc aag gcg gcg ggg atg     336
Lys Asp Arg Ala Ala Ala Leu Ala Lys Arg Ala Lys Ala Ala Gly Met
65                  70                  75                  80
```

```
agc gtc atg ctg acg ctc cat tac agc gac agc tgg gcg gac ccc ggc      384
Ser Val Met Leu Thr Leu His Tyr Ser Asp Ser Trp Ala Asp Pro Gly
             85                  90                  95 caa cag acg aag ccg gcg gca tgg aag agc tac acg ttc cag caa ctg      432
Gln Gln Thr Lys Pro Ala Ala Trp Lys Ser Tyr Thr Phe Gln Gln Leu
    100                 105                 110 atg gac gcc gtg tgg aac tgg aca cgc gac gtc atg acg acg atg cag      480
Met Asp Ala Val Trp Asn Trp Thr Arg Asp Val Met Thr Thr Met Gln
            115                 120                 125 gcg aac ggc gtg acg ccg gac tgg gtg cag atc ggc aac gag acg aac      528
Ala Asn Gly Val Thr Pro Asp Trp Val Gln Ile Gly Asn Glu Thr Asn
130                 135                 140 aac ggc atg ctg tgg gac gac ggc aag gct tcg ctc agc atg aag aat      576
Asn Gly Met Leu Trp Asp Asp Gly Lys Ala Ser Leu Ser Met Lys Asn
145                 150                 155                 160 tat gcg tgg ctc gtg aac acg ggc aac aac gcg gtg aag tcg atc agc      624
Tyr Ala Trp Leu Val Asn Thr Gly Asn Asn Ala Val Lys Ser Ile Ser
                165                 170                 175 agc tcg acc aag acg atc gtg cac ctg gcc aac ggc tac gac aat tcg      672
Ser Ser Thr Lys Thr Ile Val His Leu Ala Asn Gly Tyr Asp Asn Ser
            180                 185                 190 ctg ttc gtc tgg aac atc gga ggc ttg atc gcc aac gga gcg acg ttc      720
Leu Phe Val Trp Asn Ile Gly Gly Leu Ile Ala Asn Gly Ala Thr Phe
        195                 200                 205 gac atc atc ggc atg tcg ctc tat ccg agc gcg tcg gat tgg tcg gcc      768
Asp Ile Ile Gly Met Ser Leu Tyr Pro Ser Ala Ser Asp Trp Ser Ala
    210                 215                 220 aag gtg acg cag acg atc gcg aac gcg aac gac atg atc tcg cgt tac      816
Lys Val Thr Gln Thr Ile Ala Asn Ala Asn Asp Met Ile Ser Arg Tyr
225                 230                 235                 240 ggc aag ccg atc atg gtg acg gag atc ggc atg gac tac agc cag ccg      864
Gly Lys Pro Ile Met Val Thr Glu Ile Gly Met Asp Tyr Ser Gln Pro
                245                 250                 255 agc gcg gcc aag agc ttc gtg tcg gac atc aag acg aag atc cgc aac      912
Ser Ala Ala Lys Ser Phe Val Ser Asp Ile Lys Thr Lys Ile Arg Asn
            260                 265                 270 ctg tcc ggc ggc aag ggg caa ggc gtg ttc tac tgg gag ccc gaa gcg      960
Leu Ser Gly Gly Lys Gly Gln Gly Val Phe Tyr Trp Glu Pro Glu Ala
        275                 280                 285 acg ccc ggc tac aac ggc ggc tac agc atg ggc gcc tgg caa gcg gac     1008
Thr Pro Gly Tyr Asn Gly Gly Tyr Ser Met Gly Ala Trp Gln Ala Asp
    290                 295                 300 atg aag ccg acg atc gcg ctc gag ggc ttc tgg aac taa                 1047
Met Lys Pro Thr Ile Ala Leu Glu Gly Phe Trp Asn
305                 310                 315

<210> SEQ ID NO 2
<211> LENGTH: 348
<212> TYPE: PRT
<213> ORGANISM: Cohnella sp-60555

<400> SEQUENCE: 2

Met Met Phe Lys Arg Thr Val Thr Gly Met Met Ala Leu Leu Leu Val
        -30                 -25                 -20

Leu Ala Leu Phe Val Ala Gln Gly Ser Gln Pro His Gln Ala Ala Ala
    -15                 -10                  -5                  -1

Ala Pro Ser Phe Ala Lys Gly Ala Asp Ile Ser Trp Val Pro Gly Met
1                   5                  10                  15

Glu Ala Gln Gly Tyr Lys Trp Lys Asp Lys Asn Gly Val Gln Arg Asp
            20                  25                  30
```

```
Ile Leu Asp Ile Leu Lys Asn Asp Tyr Gln Ile Asn Ser Val Arg Ile
            35                  40                  45

Arg Val Trp Val Asn Pro Ser Ser Tyr Thr Asn Gly Tyr Leu Asn
 50                  55                  60

Lys Asp Arg Ala Ala Ala Leu Ala Lys Arg Ala Lys Ala Ala Gly Met
 65                  70                  75                  80

Ser Val Met Leu Thr Leu His Tyr Ser Asp Ser Trp Ala Asp Pro Gly
                 85                  90                  95

Gln Gln Thr Lys Pro Ala Ala Trp Lys Ser Tyr Thr Phe Gln Gln Leu
                100                 105                 110

Met Asp Ala Val Trp Asn Trp Thr Arg Asp Val Met Thr Thr Met Gln
                115                 120                 125

Ala Asn Gly Val Thr Pro Asp Trp Val Gln Ile Gly Asn Glu Thr Asn
            130                 135                 140

Asn Gly Met Leu Trp Asp Asp Gly Lys Ala Ser Leu Ser Met Lys Asn
145                 150                 155                 160

Tyr Ala Trp Leu Val Asn Thr Gly Asn Asn Ala Val Lys Ser Ile Ser
                165                 170                 175

Ser Ser Thr Lys Thr Ile Val His Leu Ala Asn Gly Tyr Asp Asn Ser
            180                 185                 190

Leu Phe Val Trp Asn Ile Gly Gly Leu Ile Ala Asn Gly Ala Thr Phe
                195                 200                 205

Asp Ile Ile Gly Met Ser Leu Tyr Pro Ser Ala Ser Asp Trp Ser Ala
            210                 215                 220

Lys Val Thr Gln Thr Ile Ala Asn Ala Asn Asp Met Ile Ser Arg Tyr
225                 230                 235                 240

Gly Lys Pro Ile Met Val Thr Glu Ile Gly Met Asp Tyr Ser Gln Pro
                245                 250                 255

Ser Ala Ala Lys Ser Phe Val Ser Asp Ile Lys Thr Lys Ile Arg Asn
            260                 265                 270

Leu Ser Gly Gly Lys Gly Gln Gly Val Phe Tyr Trp Glu Pro Glu Ala
            275                 280                 285

Thr Pro Gly Tyr Asn Gly Gly Tyr Ser Met Gly Ala Trp Gln Ala Asp
            290                 295                 300

Met Lys Pro Thr Ile Ala Leu Glu Gly Phe Trp Asn
305                 310                 315

<210> SEQ ID NO 3
<211> LENGTH: 316
<212> TYPE: PRT
<213> ORGANISM: Cohnella sp-60555
<220> FEATURE:
<221> NAME/KEY: mat_peptide
<222> LOCATION: (1)..(316)

<400> SEQUENCE: 3

Ala Pro Ser Phe Ala Lys Gly Asp Ile Ser Trp Val Pro Gly Met
 1               5                  10                  15

Glu Ala Gln Gly Tyr Lys Trp Lys Asp Lys Asn Gly Val Gln Arg Asp
                 20                  25                  30

Ile Leu Asp Ile Leu Lys Asn Asp Tyr Gln Ile Asn Ser Val Arg Ile
            35                  40                  45

Arg Val Trp Val Asn Pro Ser Ser Tyr Thr Asn Gly Tyr Leu Asn
 50                  55                  60

Lys Asp Arg Ala Ala Ala Leu Ala Lys Arg Ala Lys Ala Ala Gly Met
```

```
                65                  70                  75                  80
        Ser Val Met Leu Thr Leu His Tyr Ser Asp Ser Trp Ala Asp Pro Gly
                            85                  90                  95

Gln Gln Thr Lys Pro Ala Ala Trp Lys Ser Tyr Thr Phe Gln Gln Leu
                        100                 105                 110

Met Asp Ala Val Trp Asn Trp Thr Arg Asp Val Met Thr Met Gln
                    115                 120                 125

Ala Asn Gly Val Thr Pro Asp Trp Val Gln Ile Gly Asn Glu Thr Asn
                    130                 135                 140

Asn Gly Met Leu Trp Asp Asp Gly Lys Ala Ser Leu Ser Met Lys Asn
        145                 150                 155                 160

Tyr Ala Trp Leu Val Asn Thr Gly Asn Asn Ala Val Lys Ser Ile Ser
                            165                 170                 175

Ser Ser Thr Lys Thr Ile Val His Leu Ala Asn Gly Tyr Asp Asn Ser
                        180                 185                 190

Leu Phe Val Trp Asn Ile Gly Gly Leu Ile Ala Asn Gly Ala Thr Phe
                    195                 200                 205

Asp Ile Ile Gly Met Ser Leu Tyr Pro Ser Ala Ser Asp Trp Ser Ala
                    210                 215                 220

Lys Val Thr Gln Thr Ile Ala Asn Ala Asn Asp Met Ile Ser Arg Tyr
        225                 230                 235                 240

Gly Lys Pro Ile Met Val Thr Glu Ile Gly Met Asp Tyr Ser Gln Pro
                            245                 250                 255

Ser Ala Ala Lys Ser Phe Val Ser Asp Ile Lys Thr Lys Ile Arg Asn
                        260                 265                 270

Leu Ser Gly Gly Lys Gly Gln Gly Val Phe Tyr Trp Glu Pro Glu Ala
                    275                 280                 285

Thr Pro Gly Tyr Asn Gly Gly Tyr Ser Met Gly Ala Trp Gln Ala Asp
                    290                 295                 300

Met Lys Pro Thr Ile Ala Leu Glu Gly Phe Trp Asn
        305                 310                 315

<210> SEQ ID NO 4
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 4

His His His His His His Pro Arg Ala Pro Ser Phe Ala Lys Gly Ala
        1               5                   10                  15

Asp Ile Ser Trp Val Pro Gly Met Glu Ala Gln Gly Tyr Lys Trp Lys
                    20                  25                  30

Asp Lys Asn Gly Val Gln Arg Asp Ile Leu Asp Ile Leu Lys Asn Asp
                        35                  40                  45

Tyr Gln Ile Asn Ser Val Arg Ile Arg Val Trp Val Asn Pro Ser Ser
                    50                  55                  60

Ser Tyr Thr Asn Gly Tyr Leu Asn Lys Asp Arg Ala Ala Ala Leu Ala
        65                  70                  75                  80

Lys Arg Ala Lys Ala Ala Gly Met Ser Val Met Leu Thr Leu His Tyr
                            85                  90                  95

Ser Asp Ser Trp Ala Asp Pro Gly Gln Gln Thr Lys Pro Ala Ala Trp
```

```
                100                 105                 110
Lys Ser Tyr Thr Phe Gln Gln Leu Met Asp Ala Val Trp Asn Trp Thr
            115                 120                 125

Arg Asp Val Met Thr Thr Met Gln Ala Asn Gly Val Thr Pro Asp Trp
130                 135                 140

Val Gln Ile Gly Asn Glu Thr Asn Asn Gly Met Leu Trp Asp Asp Gly
145                 150                 155                 160

Lys Ala Ser Leu Ser Met Lys Asn Tyr Ala Trp Leu Val Asn Thr Gly
                165                 170                 175

Asn Asn Ala Val Lys Ser Ile Ser Ser Thr Lys Thr Ile Val His
            180                 185                 190

Leu Ala Asn Gly Tyr Asp Asn Ser Leu Phe Val Trp Asn Ile Gly Gly
            195                 200                 205

Leu Ile Ala Asn Gly Ala Thr Phe Asp Ile Ile Gly Met Ser Leu Tyr
        210                 215                 220

Pro Ser Ala Ser Asp Trp Ser Ala Lys Val Thr Gln Thr Ile Ala Asn
225                 230                 235                 240

Ala Asn Asp Met Ile Ser Arg Tyr Gly Lys Pro Ile Met Val Thr Glu
                245                 250                 255

Ile Gly Met Asp Tyr Ser Gln Pro Ser Ala Ala Lys Ser Phe Val Ser
            260                 265                 270

Asp Ile Lys Thr Lys Ile Arg Asn Leu Ser Gly Gly Lys Gly Gln Gly
            275                 280                 285

Val Phe Tyr Trp Glu Pro Glu Ala Thr Pro Gly Tyr Asn Gly Gly Tyr
        290                 295                 300

Ser Met Gly Ala Trp Gln Ala Asp Met Lys Pro Thr Ile Ala Leu Glu
305                 310                 315                 320

Gly Phe Trp Asn

<210> SEQ ID NO 5
<211> LENGTH: 1044
<212> TYPE: DNA
<213> ORGANISM: Cohnella xylanilytica
<220> FEATURE:
<221> NAME/KEY: CDS
<222> LOCATION: (1)..(1041)
<220> FEATURE:
<221> NAME/KEY: sig_peptide
<222> LOCATION: (1)..(87)
<220> FEATURE:
<221> NAME/KEY: mat_peptide
<222> LOCATION: (88)..(1041)

<400> SEQUENCE: 5 atg ttg cgc aaa gcg gtt gcg gtg ttc atc acc ttg gtg ttg gga ctg      48
Met Leu Arg Lys Ala Val Ala Val Phe Ile Thr Leu Val Leu Gly Leu
            -25                 -20                 -15 act cta cta tcg gcg cag gga gga cga ccg cag gaa gcg gcg gcg gct      96
Thr Leu Leu Ser Ala Gln Gly Gly Arg Pro Gln Glu Ala Ala Ala Ala
        -10                 -5                  -1  1 ccg tcg ttc gct aag gga gcg gac atc agc tgg gtg ccg gga atg gaa     144
Pro Ser Phe Ala Lys Gly Ala Asp Ile Ser Trp Val Pro Gly Met Glu
5                   10                  15 gcg caa ggg tac agg tgg aag gac aag aac ggc gtg cag cgg gac atc     192
Ala Gln Gly Tyr Arg Trp Lys Asp Lys Asn Gly Val Gln Arg Asp Ile
20                  25                  30                  35 ctg gac att ctc aag aac gat tac cag atc aac tcc gtc cgc att cgg     240
Leu Asp Ile Leu Lys Asn Asp Tyr Gln Ile Asn Ser Val Arg Ile Arg
            40                  45                  50
```

```
gta tgg gtc aat cct tcg agc agc tat acg aac ggc tac ctg aac aag      288
Val Trp Val Asn Pro Ser Ser Ser Tyr Thr Asn Gly Tyr Leu Asn Lys
             55                  60                  65 gac cgg gcg gcc gcg ctc gcg aag cgg gcg aag gcg gcg ggg ctc agc      336
Asp Arg Ala Ala Ala Leu Ala Lys Arg Ala Lys Ala Ala Gly Leu Ser
         70                  75                  80 gtc atg ctg acg ctg cat tac agc gac agc tgg gcc gac ccc ggg aag      384
Val Met Leu Thr Leu His Tyr Ser Asp Ser Trp Ala Asp Pro Gly Lys
     85                  90                  95 cag acg aag ccg gcg gcg tgg gcc ggg tac aac ttc cag cag ctg atg      432
Gln Thr Lys Pro Ala Ala Trp Ala Gly Tyr Asn Phe Gln Gln Leu Met
100                 105                 110                 115 gac gcg gtg tgg aac tgg acg cgc gag gtc atg acg acg atg cag gcc      480
Asp Ala Val Trp Asn Trp Thr Arg Glu Val Met Thr Thr Met Gln Ala
                120                 125                 130 agc ggg gtg acg ccg gac tgg gtg cag atc ggc aac gag acg aac aac      528
Ser Gly Val Thr Pro Asp Trp Val Gln Ile Gly Asn Glu Thr Asn Asn
            135                 140                 145 ggc atg ctg tgg gac gac ggg aag gcc tcg ctg agc atg aag aat tac      576
Gly Met Leu Trp Asp Asp Gly Lys Ala Ser Leu Ser Met Lys Asn Tyr
        150                 155                 160 gcc tgg ctc gtc aac acg ggc aac aac gcg gtc aag tcg atc agc agc      624
Ala Trp Leu Val Asn Thr Gly Asn Asn Ala Val Lys Ser Ile Ser Ser
    165                 170                 175 ggg acg aaa acg atc gtg cat ctc gcc aac ggg tac gac aat tcg ttg      672
Gly Thr Lys Thr Ile Val His Leu Ala Asn Gly Tyr Asp Asn Ser Leu
180                 185                 190                 195 ttc gtc tgg aac atc ggc ggc ctg atc gcg aac ggc gcc acg ttc gac      720
Phe Val Trp Asn Ile Gly Gly Leu Ile Ala Asn Gly Ala Thr Phe Asp
                200                 205                 210 att atc ggc atg tcg ctg tat ccg agc gcg tcc gac tgg tcc tcg aag      768
Ile Ile Gly Met Ser Leu Tyr Pro Ser Ala Ser Asp Trp Ser Ser Lys
            215                 220                 225 gtg acg cag acg atc tcc aac gcg aac gat atg atc tcc cgg tac ggc      816
Val Thr Gln Thr Ile Ser Asn Ala Asn Asp Met Ile Ser Arg Tyr Gly
        230                 235                 240 aag ccg atc atg atc acg gag atc ggc atg gac tac aac cag ccg tcg      864
Lys Pro Ile Met Ile Thr Glu Ile Gly Met Asp Tyr Asn Gln Pro Ser
    245                 250                 255 gcg gcc aag agc ttc gtc gcg gat atc aag acg aag atc cgc agc ctg      912
Ala Ala Lys Ser Phe Val Ala Asp Ile Lys Thr Lys Ile Arg Ser Leu
260                 265                 270                 275 tcc ggc ggc cga ggg ctc ggc gtc ttc tac tgg gag ccg gag gcg acc      960
Ser Gly Gly Arg Gly Leu Gly Val Phe Tyr Trp Glu Pro Glu Ala Thr
                280                 285                 290 ccg ggt tat aac gga ggc tat aac aag gga gcc tgg cag gca gac atg     1008
Pro Gly Tyr Asn Gly Gly Tyr Asn Lys Gly Ala Trp Gln Ala Asp Met
            295                 300                 305 aag ccg acg atc gct ctc gaa ggt ttt ctg aac taa                     1044
Lys Pro Thr Ile Ala Leu Glu Gly Phe Leu Asn
        310                 315

<210> SEQ ID NO 6
<211> LENGTH: 347
<212> TYPE: PRT
<213> ORGANISM: Cohnella xylanilytica

<400> SEQUENCE: 6

Met Leu Arg Lys Ala Val Ala Val Phe Ile Thr Leu Val Leu Gly Leu
                -25                 -20                 -15
```

```
Thr Leu Leu Ser Ala Gln Gly Gly Arg Pro Gln Glu Ala Ala Ala
            -10               -5            -1   1

Pro Ser Phe Ala Lys Gly Ala Asp Ile Ser Trp Val Pro Gly Met Glu
    5                   10              15

Ala Gln Gly Tyr Arg Trp Lys Asp Lys Asn Gly Val Gln Arg Asp Ile
 20              25              30              35

Leu Asp Ile Leu Lys Asn Asp Tyr Gln Ile Asn Ser Val Arg Ile Arg
             40              45              50

Val Trp Val Asn Pro Ser Ser Tyr Thr Asn Gly Tyr Leu Asn Lys
             55              60              65

Asp Arg Ala Ala Ala Leu Ala Lys Arg Ala Lys Ala Ala Gly Leu Ser
             70              75              80

Val Met Leu Thr Leu His Tyr Ser Asp Ser Trp Ala Asp Pro Gly Lys
             85              90              95

Gln Thr Lys Pro Ala Ala Trp Ala Gly Tyr Asn Phe Gln Gln Leu Met
100             105             110             115

Asp Ala Val Trp Asn Trp Thr Arg Glu Val Met Thr Thr Met Gln Ala
                120             125             130

Ser Gly Val Thr Pro Asp Trp Val Gln Ile Gly Asn Glu Thr Asn Asn
            135             140             145

Gly Met Leu Trp Asp Asp Gly Lys Ala Ser Leu Ser Met Lys Asn Tyr
            150             155             160

Ala Trp Leu Val Asn Thr Gly Asn Asn Ala Val Lys Ser Ile Ser Ser
        165             170             175

Gly Thr Lys Thr Ile Val His Leu Ala Asn Gly Tyr Asp Asn Ser Leu
180             185             190             195

Phe Val Trp Asn Ile Gly Gly Leu Ile Ala Asn Gly Ala Thr Phe Asp
                200             205             210

Ile Ile Gly Met Ser Leu Tyr Pro Ser Ala Ser Asp Trp Ser Ser Lys
            215             220             225

Val Thr Gln Thr Ile Ser Asn Ala Asn Asp Met Ile Ser Arg Tyr Gly
        230             235             240

Lys Pro Ile Met Ile Thr Glu Ile Gly Met Asp Tyr Asn Gln Pro Ser
    245             250             255

Ala Ala Lys Ser Phe Val Ala Asp Ile Lys Thr Lys Ile Arg Ser Leu
260             265             270             275

Ser Gly Gly Arg Gly Leu Gly Val Phe Tyr Trp Glu Pro Glu Ala Thr
            280             285             290

Pro Gly Tyr Asn Gly Gly Tyr Asn Lys Gly Ala Trp Gln Ala Asp Met
            295             300             305

Lys Pro Thr Ile Ala Leu Glu Gly Phe Leu Asn
    310             315

<210> SEQ ID NO 7
<211> LENGTH: 318
<212> TYPE: PRT
<213> ORGANISM: Cohnella xylanilytica
<220> FEATURE:
<221> NAME/KEY: mat_peptide
<222> LOCATION: (1)..(318)

<400> SEQUENCE: 7

Ala Ala Ala Pro Ser Phe Ala Lys Gly Ala Asp Ile Ser Trp Val Pro
 1               5              10              15

Gly Met Glu Ala Gln Gly Tyr Arg Trp Lys Asp Lys Asn Gly Val Gln
```

```
                20                  25                  30
Arg Asp Ile Leu Asp Ile Leu Lys Asn Asp Tyr Gln Ile Asn Ser Val
            35                  40                  45
Arg Ile Arg Val Trp Val Asn Pro Ser Ser Tyr Thr Asn Gly Tyr
        50                  55                  60
Leu Asn Lys Asp Arg Ala Ala Leu Ala Lys Arg Ala Lys Ala Ala
65                  70                  75                  80
Gly Leu Ser Val Met Leu Thr Leu His Tyr Ser Asp Ser Trp Ala Asp
                85                  90                  95
Pro Gly Lys Gln Thr Lys Pro Ala Ala Trp Ala Gly Tyr Asn Phe Gln
                100                 105                 110
Gln Leu Met Asp Ala Val Trp Asn Trp Thr Arg Glu Val Met Thr Thr
                115                 120                 125
Met Gln Ala Ser Gly Val Thr Pro Asp Trp Val Gln Ile Gly Asn Glu
                130                 135                 140
Thr Asn Asn Gly Met Leu Trp Asp Asp Gly Lys Ala Ser Leu Ser Met
145                 150                 155                 160
Lys Asn Tyr Ala Trp Leu Val Asn Thr Gly Asn Asn Ala Val Lys Ser
                165                 170                 175
Ile Ser Ser Gly Thr Lys Thr Ile Val His Leu Ala Asn Gly Tyr Asp
                180                 185                 190
Asn Ser Leu Phe Val Trp Asn Ile Gly Gly Leu Ile Ala Asn Gly Ala
                195                 200                 205
Thr Phe Asp Ile Ile Gly Met Ser Leu Tyr Pro Ser Ala Ser Asp Trp
                210                 215                 220
Ser Ser Lys Val Thr Gln Thr Ile Ser Asn Ala Asn Asp Met Ile Ser
225                 230                 235                 240
Arg Tyr Gly Lys Pro Ile Met Ile Thr Glu Ile Gly Met Asp Tyr Asn
                245                 250                 255
Gln Pro Ser Ala Ala Lys Ser Phe Val Ala Asp Ile Lys Thr Lys Ile
                260                 265                 270
Arg Ser Leu Ser Gly Gly Arg Gly Leu Gly Val Phe Tyr Trp Glu Pro
                275                 280                 285
Glu Ala Thr Pro Gly Tyr Asn Gly Gly Tyr Asn Lys Gly Ala Trp Gln
                290                 295                 300
Ala Asp Met Lys Pro Thr Ile Ala Leu Glu Gly Phe Leu Asn
305                 310                 315

<210> SEQ ID NO 8
<211> LENGTH: 326
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(326)

<400> SEQUENCE: 8

His His His His His His Pro Arg Ala Ala Pro Ser Phe Ala Lys
1               5                   10                  15
Gly Ala Asp Ile Ser Trp Val Pro Gly Met Glu Ala Gln Gly Tyr Arg
                20                  25                  30
Trp Lys Asp Lys Asn Gly Val Gln Arg Asp Ile Leu Asp Ile Leu Lys
            35                  40                  45
Asn Asp Tyr Gln Ile Asn Ser Val Arg Ile Arg Val Trp Val Asn Pro
```

```
                  50                  55                  60
Ser Ser Ser Tyr Thr Asn Gly Tyr Leu Asn Lys Asp Arg Ala Ala Ala
 65                  70                  75                  80

Leu Ala Lys Arg Ala Lys Ala Ala Gly Leu Ser Val Met Leu Thr Leu
                 85                  90                  95

His Tyr Ser Asp Ser Trp Ala Asp Pro Gly Lys Gln Thr Lys Pro Ala
                 100                 105                 110

Ala Trp Ala Gly Tyr Asn Phe Gln Gln Leu Met Asp Ala Val Trp Asn
                 115                 120                 125

Trp Thr Arg Glu Val Met Thr Thr Met Gln Ala Ser Gly Val Thr Pro
130                 135                 140

Asp Trp Val Gln Ile Gly Asn Glu Thr Asn Asn Gly Met Leu Trp Asp
145                 150                 155                 160

Asp Gly Lys Ala Ser Leu Ser Met Lys Asn Tyr Ala Trp Leu Val Asn
                 165                 170                 175

Thr Gly Asn Asn Ala Val Lys Ser Ile Ser Ser Gly Thr Lys Thr Ile
                 180                 185                 190

Val His Leu Ala Asn Gly Tyr Asp Asn Ser Leu Phe Val Trp Asn Ile
                 195                 200                 205

Gly Gly Leu Ile Ala Asn Gly Ala Thr Phe Asp Ile Ile Gly Met Ser
                 210                 215                 220

Leu Tyr Pro Ser Ala Ser Asp Trp Ser Ser Lys Val Thr Gln Thr Ile
225                 230                 235                 240

Ser Asn Ala Asn Asp Met Ile Ser Arg Tyr Gly Lys Pro Ile Met Ile
                 245                 250                 255

Thr Glu Ile Gly Met Asp Tyr Asn Gln Pro Ser Ala Ala Lys Ser Phe
                 260                 265                 270

Val Ala Asp Ile Lys Thr Lys Ile Arg Ser Leu Ser Gly Gly Arg Gly
                 275                 280                 285

Leu Gly Val Phe Tyr Trp Glu Pro Glu Ala Thr Pro Gly Tyr Asn Gly
                 290                 295                 300

Gly Tyr Asn Lys Gly Ala Trp Gln Ala Asp Met Lys Pro Thr Ile Ala
305                 310                 315                 320

Leu Glu Gly Phe Leu Asn
                 325

<210> SEQ ID NO 9
<211> LENGTH: 1050
<212> TYPE: DNA
<213> ORGANISM: Paenibacillus tundrae
<220> FEATURE:
<221> NAME/KEY: CDS
<222> LOCATION: (1)..(1047)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1047)

<400> SEQUENCE: 9 atg ttc aaa aat gta agg ggt ttc aag aca tcc atc atg ttg gct ttt     48
Met Phe Lys Asn Val Arg Gly Phe Lys Thr Ser Ile Met Leu Ala Phe
            -30                 -25                 -20 gtt ttg tta ttc acc tcc atc atg ttg ccc gca ggt cag cat gcc agc     96
Val Leu Leu Phe Thr Ser Ile Met Leu Pro Ala Gly Gln His Ala Ser
        -15                 -10                  -5 gca gca cca agt ttc gcc aaa gga gcc gac atc agc tgg gtt ccc gga    144
```

| | | | | | | | | | | | | | | | |
|---|---|---|---|---|---|---|---|---|---|---|---|---|---|---|---|
| Ala | Ala | Pro | Ser | Phe | Ala | Lys | Gly | Ala | Asp | Ile | Ser | Trp | Val | Pro | Gly |
| -1 | 1 | | | | 5 | | | | 10 | | | | | | 15 |

| atg | gaa | gcc | caa | ggt | tac | aaa | tgg | aaa | gat | aaa | aac | ggg | gta | cag | cgt | 192 |
|---|---|---|---|---|---|---|---|---|---|---|---|---|---|---|---|---|
| Met | Glu | Ala | Gln | Gly | Tyr | Lys | Trp | Lys | Asp | Lys | Asn | Gly | Val | Gln | Arg | |
| | | | | 20 | | | | | 25 | | | | | 30 | | |

| gac | atc | att | gat | att | ttg | aaa | aag | gac | tat | caa | att | aac | tcc | gtt | cgc | 240 |
|---|---|---|---|---|---|---|---|---|---|---|---|---|---|---|---|---|
| Asp | Ile | Ile | Asp | Ile | Leu | Lys | Lys | Asp | Tyr | Gln | Ile | Asn | Ser | Val | Arg | |
| | | | 35 | | | | | 40 | | | | | 45 | | | |

| att | cgg | gtc | ttt | gtt | aat | cct | tcg | aat | gat | tat | ggg | aac | ggt | tac | atg | 288 |
|---|---|---|---|---|---|---|---|---|---|---|---|---|---|---|---|---|
| Ile | Arg | Val | Phe | Val | Asn | Pro | Ser | Asn | Asp | Tyr | Gly | Asn | Gly | Tyr | Met | |
| | | 50 | | | | | 55 | | | | | 60 | | | | |

| aat | aag | gaa | cgt | gcg | gct | aca | ctc | gca | caa | cgt | gct | aaa | aat | gcc | ggc | 336 |
|---|---|---|---|---|---|---|---|---|---|---|---|---|---|---|---|---|
| Asn | Lys | Glu | Arg | Ala | Ala | Thr | Leu | Ala | Gln | Arg | Ala | Lys | Asn | Ala | Gly | |
| | 65 | | | | | 70 | | | | | 75 | | | | | |

| atg | agc | gta | atg | ctt | acc | ctg | cat | tac | agc | gac | tct | tgg | gca | gac | cct | 384 |
|---|---|---|---|---|---|---|---|---|---|---|---|---|---|---|---|---|
| Met | Ser | Val | Met | Leu | Thr | Leu | His | Tyr | Ser | Asp | Ser | Trp | Ala | Asp | Pro | |
| 80 | | | | | 85 | | | | | 90 | | | | | 95 | |

| ggt | caa | cag | acc | aaa | cca | gct | gcc | tgg | aaa | aac | tat | acc | ttc | caa | cag | 432 |
|---|---|---|---|---|---|---|---|---|---|---|---|---|---|---|---|---|
| Gly | Gln | Gln | Thr | Lys | Pro | Ala | Ala | Trp | Lys | Asn | Tyr | Thr | Phe | Gln | Gln | |
| | | | 100 | | | | | 105 | | | | | 110 | | | |

| ctc | atg | gac | gca | gtg | tgg | aat | cac | aca | cgt | gat | gtc | atg | act | gcg | atg | 480 |
|---|---|---|---|---|---|---|---|---|---|---|---|---|---|---|---|---|
| Leu | Met | Asp | Ala | Val | Trp | Asn | His | Thr | Arg | Asp | Val | Met | Thr | Ala | Met | |
| | | | 115 | | | | | 120 | | | | | 125 | | | |

| caa | agc | aaa | ggc | gtt | acc | ccg | gac | tgg | gta | cag | atc | ggg | aat | gaa | aca | 528 |
|---|---|---|---|---|---|---|---|---|---|---|---|---|---|---|---|---|
| Gln | Ser | Lys | Gly | Val | Thr | Pro | Asp | Trp | Val | Gln | Ile | Gly | Asn | Glu | Thr | |
| | | | 130 | | | | | 135 | | | | | 140 | | | |

| agt | aac | ggc | atg | tta | tgg | gaa | gat | ggt | aaa | gca | tcc | acc | aac | atg | aaa | 576 |
|---|---|---|---|---|---|---|---|---|---|---|---|---|---|---|---|---|
| Ser | Asn | Gly | Met | Leu | Trp | Glu | Asp | Gly | Lys | Ala | Ser | Thr | Asn | Met | Lys | |
| | 145 | | | | | 150 | | | | | 155 | | | | | |

| aac | tat | gcg | tgg | ctg | gtg | aac | aca | ggc | cat | aat | gca | gtg | aaa | tcc | ctg | 624 |
|---|---|---|---|---|---|---|---|---|---|---|---|---|---|---|---|---|
| Asn | Tyr | Ala | Trp | Leu | Val | Asn | Thr | Gly | His | Asn | Ala | Val | Lys | Ser | Leu | |
| 160 | | | | | 165 | | | | | 170 | | | | | 175 | |

| agc | agt | ggc | acc | aaa | acc | att | gtg | cac | ctg | gca | ggt | ggg | gat | gat | aac | 672 |
|---|---|---|---|---|---|---|---|---|---|---|---|---|---|---|---|---|
| Ser | Ser | Gly | Thr | Lys | Thr | Ile | Val | His | Leu | Ala | Gly | Gly | Asp | Asp | Asn | |
| | | | 180 | | | | | 185 | | | | | 190 | | | |

| gcc | ctc | tat | gta | tgg | aat | att | ggt | ggt | ttg | atc | aat | aat | gga | gct | aac | 720 |
|---|---|---|---|---|---|---|---|---|---|---|---|---|---|---|---|---|
| Ala | Leu | Tyr | Val | Trp | Asn | Ile | Gly | Gly | Leu | Ile | Asn | Asn | Gly | Ala | Asn | |
| | | | 195 | | | | | 200 | | | | | 205 | | | |

| ttt | gac | atg | att | gcc | atg | tcc | ctc | tac | cct | tcg | gct | tcc | ggc | tgg | aac | 768 |
|---|---|---|---|---|---|---|---|---|---|---|---|---|---|---|---|---|
| Phe | Asp | Met | Ile | Ala | Met | Ser | Leu | Tyr | Pro | Ser | Ala | Ser | Gly | Trp | Asn | |
| | | | 210 | | | | | 215 | | | | | 220 | | | |

| aca | gct | gtg | acg | aat | acg | gta | aac | aat | gcc | aag | gat | atg | atc | aac | cgt | 816 |
|---|---|---|---|---|---|---|---|---|---|---|---|---|---|---|---|---|
| Thr | Ala | Val | Thr | Asn | Thr | Val | Asn | Asn | Ala | Lys | Asp | Met | Ile | Asn | Arg | |
| | 225 | | | | | 230 | | | | | 235 | | | | | |

| tat | ggc | aaa | gag | atc | atc | atc | tcc | gaa | att | ggc | atg | gat | aat | aac | cag | 864 |
|---|---|---|---|---|---|---|---|---|---|---|---|---|---|---|---|---|
| Tyr | Gly | Lys | Glu | Ile | Ile | Ile | Ser | Glu | Ile | Gly | Met | Asp | Asn | Asn | Gln | |
| 240 | | | | | 245 | | | | | 250 | | | | | 255 | |

| gct | gca | gca | ggt | aaa | agt | ttt | gtt | gcg | gcg | atg | aaa | aac | caa | atc | cgc | 912 |
|---|---|---|---|---|---|---|---|---|---|---|---|---|---|---|---|---|
| Ala | Ala | Ala | Gly | Lys | Ser | Phe | Val | Ala | Ala | Met | Lys | Asn | Gln | Ile | Arg | |
| | | | 260 | | | | | 265 | | | | | 270 | | | |

| aat | ctg | ccg | aat | ggc | aaa | gga | aaa | ggc | gta | ttc | tac | tgg | gag | cct | cag | 960 |
|---|---|---|---|---|---|---|---|---|---|---|---|---|---|---|---|---|
| Asn | Leu | Pro | Asn | Gly | Lys | Gly | Lys | Gly | Val | Phe | Tyr | Trp | Glu | Pro | Gln | |
| | | | 275 | | | | | 280 | | | | | 285 | | | |

| gct | aca | cca | ggt | tat | aac | agt | ggc | tac | ggc | aaa | ggc | gct | tgg | caa | tcg | 1008 |
|---|---|---|---|---|---|---|---|---|---|---|---|---|---|---|---|---|
| Ala | Thr | Pro | Gly | Tyr | Asn | Ser | Gly | Tyr | Gly | Lys | Gly | Ala | Trp | Gln | Ser | |
| | | | 290 | | | | | 295 | | | | | 300 | | | |

| aat | atg | atg | ccg | aca | gtt | gtc | atg | gaa | gga | ttt | att | gac | tag | | | 1050 |
|---|---|---|---|---|---|---|---|---|---|---|---|---|---|---|---|---|
| Asn | Met | Met | Pro | Thr | Val | Val | Met | Glu | Gly | Phe | Ile | Asp | | | | |
| | 305 | | | | | 310 | | | | | 315 | | | | | |

<210> SEQ ID NO 10
<211> LENGTH: 349
<212> TYPE: PRT
<213> ORGANISM: Paenibacillus tundrae

<400> SEQUENCE: 10

Met Phe Lys Asn Val Arg Gly Phe Lys Thr Ser Ile Met Leu Ala Phe
            -30                 -25                 -20

Val Leu Leu Phe Thr Ser Ile Met Leu Pro Ala Gly Gln His Ala Ser
            -15                 -10                 -5

Ala Ala Pro Ser Phe Ala Lys Gly Ala Asp Ile Ser Trp Val Pro Gly
-1  1               5                   10                  15

Met Glu Ala Gln Gly Tyr Lys Trp Lys Asp Lys Asn Gly Val Gln Arg
                20                  25                  30

Asp Ile Ile Asp Ile Leu Lys Lys Asp Tyr Gln Ile Asn Ser Val Arg
            35                  40                  45

Ile Arg Val Phe Val Asn Pro Ser Asn Asp Tyr Gly Asn Gly Tyr Met
            50                  55                  60

Asn Lys Glu Arg Ala Ala Thr Leu Ala Gln Arg Ala Lys Asn Ala Gly
65                  70                  75

Met Ser Val Met Leu Thr Leu His Tyr Ser Asp Ser Trp Ala Asp Pro
80                  85                  90                  95

Gly Gln Gln Thr Lys Pro Ala Ala Trp Lys Asn Tyr Thr Phe Gln Gln
                100                 105                 110

Leu Met Asp Ala Val Trp Asn His Thr Arg Asp Val Met Thr Ala Met
            115                 120                 125

Gln Ser Lys Gly Val Thr Pro Asp Trp Val Gln Ile Gly Asn Glu Thr
            130                 135                 140

Ser Asn Gly Met Leu Trp Glu Asp Gly Lys Ala Ser Thr Asn Met Lys
145                 150                 155

Asn Tyr Ala Trp Leu Val Asn Thr Gly His Asn Ala Val Lys Ser Leu
160                 165                 170                 175

Ser Ser Gly Thr Lys Thr Ile Val His Leu Ala Gly Gly Asp Asp Asn
            180                 185                 190

Ala Leu Tyr Val Trp Asn Ile Gly Gly Leu Ile Asn Asn Gly Ala Asn
            195                 200                 205

Phe Asp Met Ile Ala Met Ser Leu Tyr Pro Ser Ala Ser Gly Trp Asn
            210                 215                 220

Thr Ala Val Thr Asn Thr Val Asn Asn Ala Lys Asp Met Ile Asn Arg
225                 230                 235

Tyr Gly Lys Glu Ile Ile Ile Ser Glu Ile Gly Met Asp Asn Asn Gln
240                 245                 250                 255

Ala Ala Ala Gly Lys Ser Phe Val Ala Ala Met Lys Asn Gln Ile Arg
            260                 265                 270

Asn Leu Pro Asn Gly Lys Gly Lys Gly Val Phe Tyr Trp Glu Pro Gln
            275                 280                 285

Ala Thr Pro Gly Tyr Asn Ser Gly Tyr Gly Lys Gly Ala Trp Gln Ser
            290                 295                 300

Asn Met Met Pro Thr Val Val Met Glu Gly Phe Ile Asp
305                 310                 315

<210> SEQ ID NO 11
<211> LENGTH: 316
<212> TYPE: PRT
<213> ORGANISM: Paenibacillus tundrae

```
<220> FEATURE:
<221> NAME/KEY: mat_peptide
<222> LOCATION: (1)..(316)

<400> SEQUENCE: 11
```

| | | | | | | | | | | | | | | | |
|---|---|---|---|---|---|---|---|---|---|---|---|---|---|---|---|
| Ala | Pro | Ser | Phe | Ala | Lys | Gly | Ala | Asp | Ile | Ser | Trp | Val | Pro | Gly | Met |
| 1 | | | | 5 | | | | | 10 | | | | | 15 | |
| Glu | Ala | Gln | Gly | Tyr | Lys | Trp | Lys | Asp | Lys | Asn | Gly | Val | Gln | Arg | Asp |
| | | | 20 | | | | | 25 | | | | | 30 | | |
| Ile | Ile | Asp | Ile | Leu | Lys | Lys | Asp | Tyr | Gln | Ile | Asn | Ser | Val | Arg | Ile |
| | | 35 | | | | | 40 | | | | | 45 | | | |
| Arg | Val | Phe | Val | Asn | Pro | Ser | Asn | Asp | Tyr | Gly | Asn | Gly | Tyr | Met | Asn |
| | 50 | | | | | 55 | | | | | 60 | | | | |
| Lys | Glu | Arg | Ala | Ala | Thr | Leu | Ala | Gln | Arg | Ala | Lys | Asn | Ala | Gly | Met |
| 65 | | | | | 70 | | | | | 75 | | | | | 80 |
| Ser | Val | Met | Leu | Thr | Leu | His | Tyr | Ser | Asp | Ser | Trp | Ala | Asp | Pro | Gly |
| | | | | 85 | | | | | 90 | | | | | 95 | |
| Gln | Gln | Thr | Lys | Pro | Ala | Ala | Trp | Lys | Asn | Tyr | Thr | Phe | Gln | Gln | Leu |
| | | | 100 | | | | | 105 | | | | | 110 | | |
| Met | Asp | Ala | Val | Trp | Asn | His | Thr | Arg | Asp | Val | Met | Thr | Ala | Met | Gln |
| | | 115 | | | | | 120 | | | | | 125 | | | |
| Ser | Lys | Gly | Val | Thr | Pro | Asp | Trp | Val | Gln | Ile | Gly | Asn | Glu | Thr | Ser |
| | 130 | | | | | 135 | | | | | 140 | | | | |
| Asn | Gly | Met | Leu | Trp | Glu | Asp | Gly | Lys | Ala | Ser | Thr | Asn | Met | Lys | Asn |
| 145 | | | | | 150 | | | | | 155 | | | | | 160 |
| Tyr | Ala | Trp | Leu | Val | Asn | Thr | Gly | His | Asn | Ala | Val | Lys | Ser | Leu | Ser |
| | | | | 165 | | | | | 170 | | | | | 175 | |
| Ser | Gly | Thr | Lys | Thr | Ile | Val | His | Leu | Ala | Gly | Gly | Asp | Asp | Asn | Ala |
| | | | 180 | | | | | 185 | | | | | 190 | | |
| Leu | Tyr | Val | Trp | Asn | Ile | Gly | Gly | Leu | Ile | Asn | Asn | Gly | Ala | Asn | Phe |
| | | 195 | | | | | 200 | | | | | 205 | | | |
| Asp | Met | Ile | Ala | Met | Ser | Leu | Tyr | Pro | Ser | Ala | Ser | Gly | Trp | Asn | Thr |
| | 210 | | | | | 215 | | | | | 220 | | | | |
| Ala | Val | Thr | Asn | Thr | Val | Asn | Asn | Ala | Lys | Asp | Met | Ile | Asn | Arg | Tyr |
| 225 | | | | | 230 | | | | | 235 | | | | | 240 |
| Gly | Lys | Glu | Ile | Ile | Ile | Ser | Glu | Ile | Gly | Met | Asp | Asn | Asn | Gln | Ala |
| | | | | 245 | | | | | 250 | | | | | 255 | |
| Ala | Ala | Gly | Lys | Ser | Phe | Val | Ala | Ala | Met | Lys | Asn | Gln | Ile | Arg | Asn |
| | | | 260 | | | | | 265 | | | | | 270 | | |
| Leu | Pro | Asn | Gly | Lys | Gly | Lys | Gly | Val | Phe | Tyr | Trp | Glu | Pro | Gln | Ala |
| | | 275 | | | | | 280 | | | | | 285 | | | |
| Thr | Pro | Gly | Tyr | Asn | Ser | Gly | Tyr | Gly | Lys | Gly | Ala | Trp | Gln | Ser | Asn |
| | 290 | | | | | 295 | | | | | 300 | | | | |
| Met | Met | Pro | Thr | Val | Val | Met | Glu | Gly | Phe | Ile | Asp | | | | |
| 305 | | | | | 310 | | | | | 315 | | | | | |

```
<210> SEQ ID NO 12
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 12
```

His His His His His Pro Arg Ala Pro Ser Phe Ala Lys Gly Ala
1               5                   10                  15

Asp Ile Ser Trp Val Pro Gly Met Glu Ala Gln Gly Tyr Lys Trp Lys
            20                  25                  30

Asp Lys Asn Gly Val Gln Arg Asp Ile Ile Asp Ile Leu Lys Lys Asp
        35                  40                  45

Tyr Gln Ile Asn Ser Val Arg Ile Arg Val Phe Val Asn Pro Ser Asn
50                  55                  60

Asp Tyr Gly Asn Gly Tyr Met Asn Lys Glu Arg Ala Ala Thr Leu Ala
65                  70                  75                  80

Gln Arg Ala Lys Asn Ala Gly Met Ser Val Met Leu Thr Leu His Tyr
                85                  90                  95

Ser Asp Ser Trp Ala Asp Pro Gly Gln Gln Thr Lys Pro Ala Ala Trp
            100                 105                 110

Lys Asn Tyr Thr Phe Gln Gln Leu Met Asp Ala Val Trp Asn His Thr
        115                 120                 125

Arg Asp Val Met Thr Ala Met Gln Ser Lys Gly Val Thr Pro Asp Trp
130                 135                 140

Val Gln Ile Gly Asn Glu Thr Ser Asn Gly Met Leu Trp Glu Asp Gly
145                 150                 155                 160

Lys Ala Ser Thr Asn Met Lys Asn Tyr Ala Trp Leu Val Asn Thr Gly
                165                 170                 175

His Asn Ala Val Lys Ser Leu Ser Ser Gly Thr Lys Thr Ile Val His
            180                 185                 190

Leu Ala Gly Gly Asp Asp Asn Ala Leu Tyr Val Trp Asn Ile Gly Gly
        195                 200                 205

Leu Ile Asn Asn Gly Ala Asn Phe Asp Met Ile Ala Met Ser Leu Tyr
210                 215                 220

Pro Ser Ala Ser Gly Trp Asn Thr Ala Val Thr Asn Thr Val Asn Asn
225                 230                 235                 240

Ala Lys Asp Met Ile Asn Arg Tyr Gly Lys Glu Ile Ile Ile Ser Glu
                245                 250                 255

Ile Gly Met Asp Asn Asn Gln Ala Ala Ala Gly Lys Ser Phe Val Ala
            260                 265                 270

Ala Met Lys Asn Gln Ile Arg Asn Leu Pro Asn Gly Lys Gly Lys Gly
        275                 280                 285

Val Phe Tyr Trp Glu Pro Gln Ala Thr Pro Gly Tyr Asn Ser Gly Tyr
290                 295                 300

Gly Lys Gly Ala Trp Gln Ser Asn Met Met Pro Thr Val Val Met Glu
305                 310                 315                 320

Gly Phe Ile Asp

<210> SEQ ID NO 13
<211> LENGTH: 1056
<212> TYPE: DNA
<213> ORGANISM: Paenibacillus barcinonensis
<220> FEATURE:
<221> NAME/KEY: CDS
<222> LOCATION: (1)..(1053)
<220> FEATURE:
<221> NAME/KEY: sig_peptide
<222> LOCATION: (1)..(105)
<220> FEATURE:
<221> NAME/KEY: mat_peptide
<222> LOCATION: (106)..(1053)

<400> SEQUENCE: 13

-continued

| | | | | | | | | | | | | | | | | |
|---|---|---|---|---|---|---|---|---|---|---|---|---|---|---|---|---|
| atg | ttt | aaa | aat | gta | agg | ggt | ttc | aag | gtt | aag | aca | agc | gtt | ctg | ctg | 48 |
| Met | Phe | Lys | Asn | Val | Arg | Gly | Phe | Lys | Val | Lys | Thr | Ser | Val | Leu | Leu | |
| -35 | | | | -30 | | | | | -25 | | | | | -20 | | |
| gca | ttg | gtt | ttg | tta | ttt | act | tct | att | ctg | ctg | cct | gca | ggc | cag | cac | 96 |
| Ala | Leu | Val | Leu | Leu | Phe | Thr | Ser | Ile | Leu | Leu | Pro | Ala | Gly | Gln | His | |
| | | | -15 | | | | | -10 | | | | | -5 | | | |
| gcc | agc | gcc | gca | ccg | agc | ttt | gcc | aag | gga | gct | gac | atc | agc | tgg | gtt | 144 |
| Ala | Ser | Ala | Ala | Pro | Ser | Phe | Ala | Lys | Gly | Ala | Asp | Ile | Ser | Trp | Val | |
| | | -1 | 1 | | | | 5 | | | | | 10 | | | | |
| ccc | ggc | atg | gag | gct | caa | ggg | tac | aaa | tgg | aag | gat | aaa | aac | ggg | gta | 192 |
| Pro | Gly | Met | Glu | Ala | Gln | Gly | Tyr | Lys | Trp | Lys | Asp | Lys | Asn | Gly | Val | |
| | | 15 | | | | 20 | | | | | 25 | | | | | |
| caa | cgt | gat | att | att | gat | att | ttg | aaa | aag | gat | tac | caa | att | aac | tcc | 240 |
| Gln | Arg | Asp | Ile | Ile | Asp | Ile | Leu | Lys | Lys | Asp | Tyr | Gln | Ile | Asn | Ser | |
| 30 | | | | | 35 | | | | | 40 | | | | | 45 | |
| gtt | cgt | att | cgg | gta | ttc | gtt | aat | cca | tcg | aac | gat | tat | ggt | aac | ggt | 288 |
| Val | Arg | Ile | Arg | Val | Phe | Val | Asn | Pro | Ser | Asn | Asp | Tyr | Gly | Asn | Gly | |
| | | | 50 | | | | | 55 | | | | | 60 | | | |
| tac | atg | aat | aag | gat | cgc | gcg | gct | gct | ctt | gca | cag | cgt | gcc | aaa | aat | 336 |
| Tyr | Met | Asn | Lys | Asp | Arg | Ala | Ala | Ala | Leu | Ala | Gln | Arg | Ala | Lys | Asn | |
| | | 65 | | | | 70 | | | | | 75 | | | | | |
| gca | ggc | atg | agt | gtc | atg | ctc | aca | ctt | cac | tac | agc | gat | tcc | tgg | gca | 384 |
| Ala | Gly | Met | Ser | Val | Met | Leu | Thr | Leu | His | Tyr | Ser | Asp | Ser | Trp | Ala | |
| | 80 | | | | | 85 | | | | | 90 | | | | | |
| gac | cca | ggc | aaa | caa | agc | aaa | cca | gcg | gca | tgg | aaa | aat | tac | tcc | ttc | 432 |
| Asp | Pro | Gly | Lys | Gln | Ser | Lys | Pro | Ala | Ala | Trp | Lys | Asn | Tyr | Ser | Phe | |
| 95 | | | | | 100 | | | | | 105 | | | | | | |
| caa | cag | ctc | atg | gac | gct | gtc | tgg | aat | tat | aca | cgt | gaa | gtg | atg | aca | 480 |
| Gln | Gln | Leu | Met | Asp | Ala | Val | Trp | Asn | Tyr | Thr | Arg | Glu | Val | Met | Thr | |
| 110 | | | | 115 | | | | | 120 | | | | | 125 | | |
| gct | atg | caa | aac | aaa | ggg | gtt | acg | ccg | gac | tgg | gta | cag | atc | ggt | aac | 528 |
| Ala | Met | Gln | Asn | Lys | Gly | Val | Thr | Pro | Asp | Trp | Val | Gln | Ile | Gly | Asn | |
| | | | 130 | | | | | 135 | | | | | 140 | | | |
| gaa | aca | agc | aac | ggc | atg | tta | tgg | gat | gac | ggg | aaa | gcc | tct | gtt | aac | 576 |
| Glu | Thr | Ser | Asn | Gly | Met | Leu | Trp | Asp | Asp | Gly | Lys | Ala | Ser | Val | Asn | |
| | | 145 | | | | | 150 | | | | | 155 | | | | |
| atg | aaa | aac | tat | gca | tgg | ctc | gtg | aac | aca | gga | cat | aat | gcg | gta | aaa | 624 |
| Met | Lys | Asn | Tyr | Ala | Trp | Leu | Val | Asn | Thr | Gly | His | Asn | Ala | Val | Lys | |
| | 160 | | | | | 165 | | | | | 170 | | | | | |
| tcc | att | agc | agc | ggc | acc | aaa | acg | atc | gtt | cat | ctg | gcc | ggt | ggc | gac | 672 |
| Ser | Ile | Ser | Ser | Gly | Thr | Lys | Thr | Ile | Val | His | Leu | Ala | Gly | Gly | Asp | |
| | 175 | | | | | 180 | | | | | 185 | | | | | |
| gac | aat | gcg | ctg | tat | gtc | tgg | aat | att | ggc | ggc | ctg | atc | aac | aac | ggc | 720 |
| Asp | Asn | Ala | Leu | Tyr | Val | Trp | Asn | Ile | Gly | Gly | Leu | Ile | Asn | Asn | Gly | |
| 190 | | | | | 195 | | | | | 200 | | | | | 205 | |
| gct | aac | ttt | gac | atg | atc | gct | atg | tcg | ctt | tac | cct | tcc | gct | tcc | ggc | 768 |
| Ala | Asn | Phe | Asp | Met | Ile | Ala | Met | Ser | Leu | Tyr | Pro | Ser | Ala | Ser | Gly | |
| | | | 210 | | | | | 215 | | | | | 220 | | | |
| tgg | aat | act | gcg | gtg | acc | aac | acg | gtc | aac | aat | gca | aag | gat | atg | atc | 816 |
| Trp | Asn | Thr | Ala | Val | Thr | Asn | Thr | Val | Asn | Asn | Ala | Lys | Asp | Met | Ile | |
| | | 225 | | | | | 230 | | | | | 235 | | | | |
| aat | cgg | tac | ggc | aaa | gag | atc | atg | atc | tcc | gaa | att | ggc | atg | gac | aac | 864 |
| Asn | Arg | Tyr | Gly | Lys | Glu | Ile | Met | Ile | Ser | Glu | Ile | Gly | Met | Asp | Asn | |
| | 240 | | | | | 245 | | | | | 250 | | | | | |
| aat | cag | gcg | gcg | gca | ggc | aaa | agc | ttc | gta | gct | gcg | atg | aaa | aat | caa | 912 |
| Asn | Gln | Ala | Ala | Ala | Gly | Lys | Ser | Phe | Val | Ala | Ala | Met | Lys | Asn | Gln | |
| | 255 | | | | | 260 | | | | | 265 | | | | | |
| att | cgc | aat | ctg | cca | aat | ggc | aaa | gga | aaa | ggc | gta | ttc | tac | tgg | gag | 960 |
| Ile | Arg | Asn | Leu | Pro | Asn | Gly | Lys | Gly | Lys | Gly | Val | Phe | Tyr | Trp | Glu | |
| 270 | | | | | 275 | | | | | 280 | | | | | 285 | |

```
ccg cag gct aca cct ggc tat aac ggt gga tac ggt aaa ggc gct tgg       1008
Pro Gln Ala Thr Pro Gly Tyr Asn Gly Gly Tyr Gly Lys Gly Ala Trp
            290                 295                 300 cag tcc aac atg atg cca aca gcc gtc atg gaa ggg ttt att gac taa       1056
Gln Ser Asn Met Met Pro Thr Ala Val Met Glu Gly Phe Ile Asp
                305                 310                 315

<210> SEQ ID NO 14
<211> LENGTH: 351
<212> TYPE: PRT
<213> ORGANISM: Paenibacillus barcinonensis

<400> SEQUENCE: 14

Met Phe Lys Asn Val Arg Gly Phe Lys Val Lys Thr Ser Val Leu Leu
-35                 -30                 -25                 -20

Ala Leu Val Leu Leu Phe Thr Ser Ile Leu Leu Pro Ala Gly Gln His
                -15                 -10                 -5

Ala Ser Ala Ala Pro Ser Phe Ala Lys Gly Ala Asp Ile Ser Trp Val
        -1  1               5                   10

Pro Gly Met Glu Ala Gln Gly Tyr Lys Trp Lys Asp Lys Asn Gly Val
                15                  20                  25

Gln Arg Asp Ile Ile Asp Ile Leu Lys Lys Asp Tyr Gln Ile Asn Ser
30                  35                  40                  45

Val Arg Ile Arg Val Phe Val Asn Pro Ser Asn Asp Tyr Gly Asn Gly
                50                  55                  60

Tyr Met Asn Lys Asp Arg Ala Ala Ala Leu Ala Gln Arg Ala Lys Asn
                65                  70                  75

Ala Gly Met Ser Val Met Leu Thr Leu His Tyr Ser Asp Ser Trp Ala
        80                  85                  90

Asp Pro Gly Lys Gln Ser Lys Pro Ala Ala Trp Lys Asn Tyr Ser Phe
        95                  100                 105

Gln Gln Leu Met Asp Ala Val Trp Asn Tyr Thr Arg Glu Val Met Thr
110                 115                 120                 125

Ala Met Gln Asn Lys Gly Val Thr Pro Asp Trp Val Gln Ile Gly Asn
                130                 135                 140

Glu Thr Ser Asn Gly Met Leu Trp Asp Asp Gly Lys Ala Ser Val Asn
                145                 150                 155

Met Lys Asn Tyr Ala Trp Leu Val Asn Thr Gly His Asn Ala Val Lys
                160                 165                 170

Ser Ile Ser Ser Gly Thr Lys Thr Ile Val His Leu Ala Gly Gly Asp
                175                 180                 185

Asp Asn Ala Leu Tyr Val Trp Asn Ile Gly Gly Leu Ile Asn Asn Gly
190                 195                 200                 205

Ala Asn Phe Asp Met Ile Ala Met Ser Leu Tyr Pro Ser Ala Ser Gly
                210                 215                 220

Trp Asn Thr Ala Val Thr Asn Thr Val Asn Asn Ala Lys Asp Met Ile
                225                 230                 235

Asn Arg Tyr Gly Lys Glu Ile Met Ile Ser Glu Ile Gly Met Asp Asn
                240                 245                 250

Asn Gln Ala Ala Ala Gly Lys Ser Phe Val Ala Ala Met Lys Asn Gln
                255                 260                 265

Ile Arg Asn Leu Pro Asn Gly Lys Gly Lys Gly Val Phe Tyr Trp Glu
270                 275                 280                 285

Pro Gln Ala Thr Pro Gly Tyr Asn Gly Gly Tyr Gly Lys Gly Ala Trp
                290                 295                 300
```

```
Gln Ser Asn Met Met Pro Thr Ala Val Met Glu Gly Phe Ile Asp
            305                 310                 315

<210> SEQ ID NO 15
<211> LENGTH: 316
<212> TYPE: PRT
<213> ORGANISM: Paenibacillus barcinonensis

<400> SEQUENCE: 15

Ala Pro Ser Phe Ala Lys Gly Ala Asp Ile Ser Trp Val Pro Gly Met
1               5                   10                  15

Glu Ala Gln Gly Tyr Lys Trp Lys Asp Lys Asn Gly Val Gln Arg Asp
                20                  25                  30

Ile Ile Asp Ile Leu Lys Lys Asp Tyr Gln Ile Asn Ser Val Arg Ile
            35                  40                  45

Arg Val Phe Val Asn Pro Ser Asn Asp Tyr Gly Asn Gly Tyr Met Asn
        50                  55                  60

Lys Asp Arg Ala Ala Leu Ala Gln Arg Ala Lys Asn Ala Gly Met
65                  70                  75                  80

Ser Val Met Leu Thr Leu His Tyr Ser Asp Ser Trp Ala Asp Pro Gly
                85                  90                  95

Lys Gln Ser Lys Pro Ala Ala Trp Lys Asn Tyr Ser Phe Gln Gln Leu
                100                 105                 110

Met Asp Ala Val Trp Asn Tyr Thr Arg Glu Val Met Thr Ala Met Gln
            115                 120                 125

Asn Lys Gly Val Thr Pro Asp Trp Val Gln Ile Gly Asn Glu Thr Ser
130                 135                 140

Asn Gly Met Leu Trp Asp Asp Gly Lys Ala Ser Val Asn Met Lys Asn
145                 150                 155                 160

Tyr Ala Trp Leu Val Asn Thr Gly His Asn Ala Val Lys Ser Ile Ser
                165                 170                 175

Ser Gly Thr Lys Thr Ile Val His Leu Ala Gly Gly Asp Asp Asn Ala
            180                 185                 190

Leu Tyr Val Trp Asn Ile Gly Gly Leu Ile Asn Asn Gly Ala Asn Phe
        195                 200                 205

Asp Met Ile Ala Met Ser Leu Tyr Pro Ser Ala Ser Gly Trp Asn Thr
    210                 215                 220

Ala Val Thr Asn Thr Val Asn Asn Ala Lys Asp Met Ile Asn Arg Tyr
225                 230                 235                 240

Gly Lys Glu Ile Met Ile Ser Glu Ile Gly Met Asp Asn Asn Gln Ala
                245                 250                 255

Ala Ala Gly Lys Ser Phe Val Ala Ala Met Lys Asn Gln Ile Arg Asn
            260                 265                 270

Leu Pro Asn Gly Lys Gly Lys Gly Val Phe Tyr Trp Glu Pro Gln Ala
        275                 280                 285

Thr Pro Gly Tyr Asn Gly Gly Tyr Gly Lys Gly Ala Trp Gln Ser Asn
    290                 295                 300

Met Met Pro Thr Ala Val Met Glu Gly Phe Ile Asp
305                 310                 315

<210> SEQ ID NO 16
<211> LENGTH: 324
<212> TYPE: PRT
<213> ORGANISM: Artificial Sequence
<220> FEATURE:
<223> OTHER INFORMATION: Mature sequence with His-tag
```

<220> FEATURE:
<221> NAME/KEY: mat_peptide
<222> LOCATION: (1)..(324)

<400> SEQUENCE: 16

His His His His His His Pro Arg Ala Pro Ser Phe Ala Lys Gly Ala
1               5                   10                  15

Asp Ile Ser Trp Val Pro Gly Met Glu Ala Gln Gly Tyr Lys Trp Lys
            20                  25                  30

Asp Lys Asn Gly Val Gln Arg Asp Ile Ile Asp Ile Leu Lys Lys Asp
        35                  40                  45

Tyr Gln Ile Asn Ser Val Arg Ile Arg Val Phe Val Asn Pro Ser Asn
    50                  55                  60

Asp Tyr Gly Asn Gly Tyr Met Asn Lys Asp Arg Ala Ala Ala Leu Ala
65                  70                  75                  80

Gln Arg Ala Lys Asn Ala Gly Met Ser Val Met Leu Thr Leu His Tyr
                85                  90                  95

Ser Asp Ser Trp Ala Asp Pro Gly Lys Gln Ser Lys Pro Ala Ala Trp
            100                 105                 110

Lys Asn Tyr Ser Phe Gln Gln Leu Met Asp Ala Val Trp Asn Tyr Thr
        115                 120                 125

Arg Glu Val Met Thr Ala Met Gln Asn Lys Gly Val Thr Pro Asp Trp
    130                 135                 140

Val Gln Ile Gly Asn Glu Thr Ser Asn Gly Met Leu Trp Asp Asp Gly
145                 150                 155                 160

Lys Ala Ser Val Asn Met Lys Asn Tyr Ala Trp Leu Val Asn Thr Gly
                165                 170                 175

His Asn Ala Val Lys Ser Ile Ser Ser Gly Thr Lys Thr Ile Val His
            180                 185                 190

Leu Ala Gly Gly Asp Asp Asn Ala Leu Tyr Val Trp Asn Ile Gly Gly
        195                 200                 205

Leu Ile Asn Asn Gly Ala Asn Phe Asp Met Ile Ala Met Ser Leu Tyr
    210                 215                 220

Pro Ser Ala Ser Gly Trp Asn Thr Ala Val Thr Asn Thr Val Asn Asn
225                 230                 235                 240

Ala Lys Asp Met Ile Asn Arg Tyr Gly Lys Glu Ile Met Ile Ser Glu
                245                 250                 255

Ile Gly Met Asp Asn Asn Gln Ala Ala Ala Gly Lys Ser Phe Val Ala
            260                 265                 270

Ala Met Lys Asn Gln Ile Arg Asn Leu Pro Asn Gly Lys Gly Lys Gly
        275                 280                 285

Val Phe Tyr Trp Glu Pro Gln Ala Thr Pro Gly Tyr Asn Gly Gly Tyr
    290                 295                 300

Gly Lys Gly Ala Trp Gln Ser Asn Met Met Pro Thr Ala Val Met Glu
305                 310                 315                 320

Gly Phe Ile Asp

<210> SEQ ID NO 17
<211> LENGTH: 1044
<212> TYPE: DNA
<213> ORGANISM: Paenibacillus sp-62603
<220> FEATURE:
<221> NAME/KEY: CDS
<222> LOCATION: (1)..(1041)
<220> FEATURE:
<221> NAME/KEY: sig_peptide
<222> LOCATION: (1)..(93)

```
<220> FEATURE:
<221> NAME/KEY: mat_peptide
<222> LOCATION: (94)..(1041)

<400> SEQUENCE: 17 atg aaa cga agg ttt tac agt ttg acg ctt gtt gtc gcc ttg tta atg      48
Met Lys Arg Arg Phe Tyr Ser Leu Thr Leu Val Val Ala Leu Leu Met
    -30                 -25                 -20 act att ttt gga gtg aat ggg gga tct gtg ccg cag gtc agc gca gct      96
Thr Ile Phe Gly Val Asn Gly Gly Ser Val Pro Gln Val Ser Ala Ala
-15                 -10                  -5                  -1  1 cct gca ttc gcg aaa ggt gcg gac att agc tgg gta gtc ggc atg gag     144
Pro Ala Phe Ala Lys Gly Ala Asp Ile Ser Trp Val Val Gly Met Glu
            5                  10                  15 gcg caa ggg tat acg tgg aag gac aaa aac ggc gta act agg gac att     192
Ala Gln Gly Tyr Thr Trp Lys Asp Lys Asn Gly Val Thr Arg Asp Ile
        20                  25                  30 att caa att ttg aag cag gat tac caa atc aac tcc gta cgt att cga     240
Ile Gln Ile Leu Lys Gln Asp Tyr Gln Ile Asn Ser Val Arg Ile Arg
    35                  40                  45 gta ttc gtc aat cct tct tcg aac tat ggc aac ggg tat atg aat aaa     288
Val Phe Val Asn Pro Ser Ser Asn Tyr Gly Asn Gly Tyr Met Asn Lys
50                  55                  60                  65 gat cgc gct gca acc ttg gcg aag cgg gcg aag gat gct ggg atg agc     336
Asp Arg Ala Ala Thr Leu Ala Lys Arg Ala Lys Asp Ala Gly Met Ser
                70                  75                  80 gtc atg ctt aca ttg cat tac agc gat tcg tgg gcg gac ccc gga aaa     384
Val Met Leu Thr Leu His Tyr Ser Asp Ser Trp Ala Asp Pro Gly Lys
            85                  90                  95 cag aca aag cca gcg gct tgg gca agc tat tcg ttc cag cag ctg atg     432
Gln Thr Lys Pro Ala Ala Trp Ala Ser Tyr Ser Phe Gln Gln Leu Met
        100                 105                 110 gat gca gtt tat aat cat acg cgt gag gta atg aca gct atg caa agc     480
Asp Ala Val Tyr Asn His Thr Arg Glu Val Met Thr Ala Met Gln Ser
    115                 120                 125 aaa ggt gtc aca ccg gat tgg gtg caa atc ggc aac gaa acg aac gat     528
Lys Gly Val Thr Pro Asp Trp Val Gln Ile Gly Asn Glu Thr Asn Asp
130                 135                 140                 145 ggc atg ctc tgg aat gac ggg aaa gct tcc tta aac atg caa aac tac     576
Gly Met Leu Trp Asn Asp Gly Lys Ala Ser Leu Asn Met Gln Asn Tyr
                150                 155                 160 gct tgg ctg atc aac act ggc aac aat gcg gtc aag tcc att agt tca     624
Ala Trp Leu Ile Asn Thr Gly Asn Asn Ala Val Lys Ser Ile Ser Ser
            165                 170                 175 gct aca aaa acg att gtc cac ttg tcc aac ggt tat gac aac agt tta     672
Ala Thr Lys Thr Ile Val His Leu Ser Asn Gly Tyr Asp Asn Ser Leu
        180                 185                 190 ttt gtc tgg aat atc ggc gga ctg atc gct aac gga gcg acc ttc gat     720
Phe Val Trp Asn Ile Gly Gly Leu Ile Ala Asn Gly Ala Thr Phe Asp
    195                 200                 205 att atc ggg atg tca ctt tat cct acc agt gct gat tgg tcg act aag     768
Ile Ile Gly Met Ser Leu Tyr Pro Thr Ser Ala Asp Trp Ser Thr Lys
210                 215                 220                 225 gtt acg caa acg gtc agc aac tcc aac aat atg ata tcg cgt tat ggc     816
Val Thr Gln Thr Val Ser Asn Ser Asn Asn Met Ile Ser Arg Tyr Gly
                230                 235                 240 aag ccg gtt atg att acc gaa att ggt atg gat tat aac cag cct gcc     864
Lys Pro Val Met Ile Thr Glu Ile Gly Met Asp Tyr Asn Gln Pro Ala
            245                 250                 255 gct gcc aaa agc ttt gtc gct gat ata aag aca aaa ata cgt aat att     912
Ala Ala Lys Ser Phe Val Ala Asp Ile Lys Thr Lys Ile Arg Asn Ile
```

-continued

| | | | | | | | | | | | | |
|---|---|---|---|---|---|---|---|---|---|---|---|---|
| Ala | Ala | Lys | Ser | Phe | Val | Ala | Asp | Ile | Lys | Thr | Lys | Ile | Arg | Asn | Ile |
| | | | 260 | | | | 265 | | | | 270 | | | | |

```
gca ggt gga aaa ggg ctt ggc gtg ttt tat tgg gaa ccg gaa gcg acc    960
Ala Gly Gly Lys Gly Leu Gly Val Phe Tyr Trp Glu Pro Glu Ala Thr
275             280             285 cct ggt tat aac gga ggt tat aat aag gga gct tgg cag gcg gac ggc   1008
Pro Gly Tyr Asn Gly Gly Tyr Asn Lys Gly Ala Trp Gln Ala Asp Gly
290             295             300             305 aaa cca aca att gcg ctt gac ggc ttc ttg aat taa                   1044
Lys Pro Thr Ile Ala Leu Asp Gly Phe Leu Asn
                310             315
```

<210> SEQ ID NO 18
<211> LENGTH: 347
<212> TYPE: PRT
<213> ORGANISM: Paenibacillus sp-62603

<400> SEQUENCE: 18

Met Lys Arg Arg Phe Tyr Ser Leu Thr Leu Val Val Ala Leu Leu Met
        -30                 -25                 -20

Thr Ile Phe Gly Val Asn Gly Gly Ser Val Pro Gln Val Ser Ala Ala
-15                 -10                  -5                  -1  1

Pro Ala Phe Ala Lys Gly Ala Asp Ile Ser Trp Val Val Gly Met Glu
                 5                  10                  15

Ala Gln Gly Tyr Thr Trp Lys Asp Lys Asn Gly Val Thr Arg Asp Ile
             20                  25                  30

Ile Gln Ile Leu Lys Gln Asp Tyr Gln Ile Asn Ser Val Arg Ile Arg
         35                  40                  45

Val Phe Val Asn Pro Ser Ser Asn Tyr Gly Asn Gly Tyr Met Asn Lys
50                  55                  60                  65

Asp Arg Ala Ala Thr Leu Ala Lys Arg Ala Lys Asp Ala Gly Met Ser
                 70                  75                  80

Val Met Leu Thr Leu His Tyr Ser Asp Ser Trp Ala Asp Pro Gly Lys
             85                  90                  95

Gln Thr Lys Pro Ala Ala Trp Ala Ser Tyr Ser Phe Gln Gln Leu Met
         100                 105                 110

Asp Ala Val Tyr Asn His Thr Arg Glu Val Met Thr Ala Met Gln Ser
    115                 120                 125

Lys Gly Val Thr Pro Asp Trp Val Gln Ile Gly Asn Glu Thr Asn Asp
130                 135                 140                 145

Gly Met Leu Trp Asn Asp Gly Lys Ala Ser Leu Asn Met Gln Asn Tyr
                150                 155                 160

Ala Trp Leu Ile Asn Thr Gly Asn Asn Ala Val Lys Ser Ile Ser Ser
            165                 170                 175

Ala Thr Lys Thr Ile Val His Leu Ser Asn Gly Tyr Asp Asn Ser Leu
        180                 185                 190

Phe Val Trp Asn Ile Gly Gly Leu Ile Ala Asn Gly Ala Thr Phe Asp
    195                 200                 205

Ile Ile Gly Met Ser Leu Tyr Pro Thr Ser Ala Asp Trp Ser Thr Lys
210                 215                 220                 225

Val Thr Gln Thr Val Ser Asn Ser Asn Asn Met Ile Ser Arg Tyr Gly
                230                 235                 240

Lys Pro Val Met Ile Thr Glu Ile Gly Met Asp Tyr Asn Gln Pro Ala
            245                 250                 255

Ala Ala Lys Ser Phe Val Ala Asp Ile Lys Thr Lys Ile Arg Asn Ile
        260                 265                 270

Ala Gly Gly Lys Gly Leu Gly Val Phe Tyr Trp Glu Pro Glu Ala Thr
            275                 280                 285

Pro Gly Tyr Asn Gly Gly Tyr Asn Lys Gly Ala Trp Gln Ala Asp Gly
290                 295                 300                 305

Lys Pro Thr Ile Ala Leu Asp Gly Phe Leu Asn
            310                 315

<210> SEQ ID NO 19
<211> LENGTH: 316
<212> TYPE: PRT
<213> ORGANISM: Paenibacillus sp-62603
<220> FEATURE:
<221> NAME/KEY: mat_peptide
<222> LOCATION: (1)..(316)

<400> SEQUENCE: 19

Ala Pro Ala Phe Ala Lys Gly Ala Asp Ile Ser Trp Val Val Gly Met
1               5                   10                  15

Glu Ala Gln Gly Tyr Thr Trp Lys Asp Lys Asn Gly Val Thr Arg Asp
            20                  25                  30

Ile Ile Gln Ile Leu Lys Gln Asp Tyr Gln Ile Asn Ser Val Arg Ile
        35                  40                  45

Arg Val Phe Val Asn Pro Ser Ser Asn Tyr Gly Asn Gly Tyr Met Asn
    50                  55                  60

Lys Asp Arg Ala Ala Thr Leu Ala Lys Arg Ala Lys Asp Ala Gly Met
65                  70                  75                  80

Ser Val Met Leu Thr Leu His Tyr Ser Asp Ser Trp Ala Asp Pro Gly
                85                  90                  95

Lys Gln Thr Lys Pro Ala Ala Trp Ala Ser Tyr Ser Phe Gln Gln Leu
            100                 105                 110

Met Asp Ala Val Tyr Asn His Thr Arg Glu Val Met Thr Ala Met Gln
        115                 120                 125

Ser Lys Gly Val Thr Pro Asp Trp Val Gln Ile Gly Asn Glu Thr Asn
    130                 135                 140

Asp Gly Met Leu Trp Asn Asp Gly Lys Ala Ser Leu Asn Met Gln Asn
145                 150                 155                 160

Tyr Ala Trp Leu Ile Asn Thr Gly Asn Asn Ala Val Lys Ser Ile Ser
                165                 170                 175

Ser Ala Thr Lys Thr Ile Val His Leu Ser Asn Gly Tyr Asp Asn Ser
            180                 185                 190

Leu Phe Val Trp Asn Ile Gly Gly Leu Ile Ala Asn Gly Ala Thr Phe
        195                 200                 205

Asp Ile Ile Gly Met Ser Leu Tyr Pro Thr Ser Ala Asp Trp Ser Thr
    210                 215                 220

Lys Val Thr Gln Thr Val Ser Asn Ser Asn Asn Met Ile Ser Arg Tyr
225                 230                 235                 240

Gly Lys Pro Val Met Ile Thr Glu Ile Gly Met Asp Tyr Asn Gln Pro
                245                 250                 255

Ala Ala Ala Lys Ser Phe Val Ala Asp Ile Lys Thr Lys Ile Arg Asn
            260                 265                 270

Ile Ala Gly Gly Lys Gly Leu Gly Val Phe Tyr Trp Glu Pro Glu Ala
        275                 280                 285

Thr Pro Gly Tyr Asn Gly Gly Tyr Asn Lys Gly Ala Trp Gln Ala Asp
    290                 295                 300

Gly Lys Pro Thr Ile Ala Leu Asp Gly Phe Leu Asn

-continued

<210> SEQ ID NO 20
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 20

```
His His His His His His Pro Arg Ala Pro Ala Phe Ala Lys Gly Ala
1               5                   10                  15

Asp Ile Ser Trp Val Val Gly Met Glu Ala Gln Gly Tyr Thr Trp Lys
            20                  25                  30

Asp Lys Asn Gly Val Thr Arg Asp Ile Ile Gln Ile Leu Lys Gln Asp
        35                  40                  45

Tyr Gln Ile Asn Ser Val Arg Ile Arg Val Phe Val Asn Pro Ser Ser
    50                  55                  60

Asn Tyr Gly Asn Gly Tyr Met Asn Lys Asp Arg Ala Ala Thr Leu Ala
65                  70                  75                  80

Lys Arg Ala Lys Asp Ala Gly Met Ser Val Met Leu Thr Leu His Tyr
                85                  90                  95

Ser Asp Ser Trp Ala Asp Pro Gly Lys Gln Thr Lys Pro Ala Ala Trp
            100                 105                 110

Ala Ser Tyr Ser Phe Gln Gln Leu Met Asp Ala Val Tyr Asn His Thr
        115                 120                 125

Arg Glu Val Met Thr Ala Met Gln Ser Lys Gly Val Thr Pro Asp Trp
    130                 135                 140

Val Gln Ile Gly Asn Glu Thr Asn Asp Gly Met Leu Trp Asn Asp Gly
145                 150                 155                 160

Lys Ala Ser Leu Asn Met Gln Asn Tyr Ala Trp Leu Ile Asn Thr Gly
                165                 170                 175

Asn Asn Ala Val Lys Ser Ile Ser Ser Ala Thr Lys Thr Ile Val His
            180                 185                 190

Leu Ser Asn Gly Tyr Asp Asn Ser Leu Phe Val Trp Asn Ile Gly Gly
        195                 200                 205

Leu Ile Ala Asn Gly Ala Thr Phe Asp Ile Ile Gly Met Ser Leu Tyr
    210                 215                 220

Pro Thr Ser Ala Asp Trp Ser Thr Lys Val Thr Gln Thr Val Ser Asn
225                 230                 235                 240

Ser Asn Asn Met Ile Ser Arg Tyr Gly Lys Pro Val Met Ile Thr Glu
                245                 250                 255

Ile Gly Met Asp Tyr Asn Gln Pro Ala Ala Lys Ser Phe Val Ala
            260                 265                 270

Asp Ile Lys Thr Lys Ile Arg Asn Ile Ala Gly Gly Lys Gly Leu Gly
        275                 280                 285

Val Phe Tyr Trp Glu Pro Glu Ala Thr Pro Gly Tyr Asn Gly Tyr
    290                 295                 300

Asn Lys Gly Ala Trp Gln Ala Asp Gly Lys Pro Thr Ile Ala Leu Asp
305                 310                 315                 320

Gly Phe Leu Asn
```

<210> SEQ ID NO 21

<211> LENGTH: 1050
<212> TYPE: DNA
<213> ORGANISM: Paenibacillus xylanilyticus
<220> FEATURE:
<221> NAME/KEY: CDS
<222> LOCATION: (1)..(1047)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1047)

<400> SEQUENCE: 21

| | | | | | | | | | | | | | | | | |
|---|---|---|---|---|---|---|---|---|---|---|---|---|---|---|---|---|
| atg | ctt | aaa | ttt | gta | agg | ggt | tac | aaa | aca | tcg | att | gct | ctt | gtt | ctt | 48 |
| Met | Leu | Lys | Phe | Val | Arg | Gly | Tyr | Lys | Thr | Ser | Ile | Ala | Leu | Val | Leu | |
| | | | -30 | | | | -25 | | | | | -20 | | | | |
| gtg | ttg | ttg | ttc | acc | tcc | att | atg | ctg | cct | gtg | ggt | cag | cat | gtc | agc | 96 |
| Val | Leu | Leu | Phe | Thr | Ser | Ile | Met | Leu | Pro | Val | Gly | Gln | His | Val | Ser | |
| | | -15 | | | | | -10 | | | | | -5 | | | | |
| gca | gca | ccc | agc | ttc | gcc | aag | ggg | gct | gat | ata | agc | tgg | gta | cca | ggc | 144 |
| Ala | Ala | Pro | Ser | Phe | Ala | Lys | Gly | Ala | Asp | Ile | Ser | Trp | Val | Pro | Gly | |
| -1 | 1 | | | | 5 | | | | | 10 | | | | | 15 | |
| atg | gaa | gcg | caa | ggg | tac | aaa | tgg | aaa | gac | aaa | aat | ggt | gta | cag | cgt | 192 |
| Met | Glu | Ala | Gln | Gly | Tyr | Lys | Trp | Lys | Asp | Lys | Asn | Gly | Val | Gln | Arg | |
| | | | 20 | | | | | 25 | | | | | 30 | | | |
| gac | att | att | gat | att | ttg | aaa | aac | gat | tat | cag | atc | aac | tcg | gtt | cgt | 240 |
| Asp | Ile | Ile | Asp | Ile | Leu | Lys | Asn | Asp | Tyr | Gln | Ile | Asn | Ser | Val | Arg | |
| | | 35 | | | | | 40 | | | | | 45 | | | | |
| atc | cgg | gtg | ttt | gtt | aat | cct | tct | aat | gat | tac | ggc | aac | ggg | tac | atg | 288 |
| Ile | Arg | Val | Phe | Val | Asn | Pro | Ser | Asn | Asp | Tyr | Gly | Asn | Gly | Tyr | Met | |
| | 50 | | | | | 55 | | | | | 60 | | | | | |
| aat | aag | gat | cgt | gtc | gct | gct | ttg | gca | cag | cgg | gcc | aaa | aac | gcg | ggc | 336 |
| Asn | Lys | Asp | Arg | Val | Ala | Ala | Leu | Ala | Gln | Arg | Ala | Lys | Asn | Ala | Gly | |
| | 65 | | | | | 70 | | | | | 75 | | | | | |
| atg | agc | gtc | atg | ttg | act | ctg | cac | tac | agt | gat | tcc | tgg | gca | gac | cct | 384 |
| Met | Ser | Val | Met | Leu | Thr | Leu | His | Tyr | Ser | Asp | Ser | Trp | Ala | Asp | Pro | |
| 80 | | | | | 85 | | | | | 90 | | | | | 95 | |
| ggc | caa | cag | acc | aaa | ccg | gca | gcc | tgg | aaa | aac | tac | acc | ttc | cag | cag | 432 |
| Gly | Gln | Gln | Thr | Lys | Pro | Ala | Ala | Trp | Lys | Asn | Tyr | Thr | Phe | Gln | Gln | |
| | | | | 100 | | | | | 105 | | | | | 110 | | |
| ctg | atg | gat | gcc | gtt | tgg | aat | cat | aca | cgc | gat | gtg | atg | acg | gcc | atg | 480 |
| Leu | Met | Asp | Ala | Val | Trp | Asn | His | Thr | Arg | Asp | Val | Met | Thr | Ala | Met | |
| | | | | 115 | | | | | 120 | | | | | 125 | | |
| cag | agt | aaa | ggg | gtt | acg | cct | gac | tgg | gta | caa | atc | ggg | aac | gaa | aca | 528 |
| Gln | Ser | Lys | Gly | Val | Thr | Pro | Asp | Trp | Val | Gln | Ile | Gly | Asn | Glu | Thr | |
| | | 130 | | | | | 135 | | | | | 140 | | | | |
| agc | aac | ggc | atg | tta | tgg | gag | gac | ggt | aaa | gcg | tcc | acg | aac | atg | aaa | 576 |
| Ser | Asn | Gly | Met | Leu | Trp | Glu | Asp | Gly | Lys | Ala | Ser | Thr | Asn | Met | Lys | |
| | | 145 | | | | | 150 | | | | | 155 | | | | |
| aat | tac | gca | tgg | ctg | gtg | aac | acg | ggc | cat | aat | gcc | gtc | aag | tcc | atg | 624 |
| Asn | Tyr | Ala | Trp | Leu | Val | Asn | Thr | Gly | His | Asn | Ala | Val | Lys | Ser | Met | |
| 160 | | | | | 165 | | | | | 170 | | | | | 175 | |
| agt | aca | ggg | acc | aaa | acg | att | gtc | cat | ctt | gca | ggc | ggt | gac | gac | aat | 672 |
| Ser | Thr | Gly | Thr | Lys | Thr | Ile | Val | His | Leu | Ala | Gly | Gly | Asp | Asp | Asn | |
| | | | | 180 | | | | | 185 | | | | | 190 | | |
| gcc | ctt | tat | gta | tgg | aat | atc | ggc | gga | ctg | atc | aac | aac | ggt | gcc | aac | 720 |
| Ala | Leu | Tyr | Val | Trp | Asn | Ile | Gly | Gly | Leu | Ile | Asn | Asn | Gly | Ala | Asn | |
| | | | 195 | | | | | 200 | | | | | 205 | | | |
| ttc | gat | atg | att | gcc | atg | tcc | ctc | tat | cct | tcg | gct | tcc | ggc | tgg | aat | 768 |
| Phe | Asp | Met | Ile | Ala | Met | Ser | Leu | Tyr | Pro | Ser | Ala | Ser | Gly | Trp | Asn | |
| | | 210 | | | | | 215 | | | | | 220 | | | | |

```
aca gct gtc acc aat acg gtg aat aat gcc aag gac ttg atc aac cgc      816
Thr Ala Val Thr Asn Thr Val Asn Asn Ala Lys Asp Leu Ile Asn Arg
    225                 230                 235 tac ggc aaa gag att atc gtc tca gaa atc ggc atg gac aac aat cag      864
Tyr Gly Lys Glu Ile Ile Val Ser Glu Ile Gly Met Asp Asn Asn Gln
240                 245                 250                 255 ccc gca gct ggc aaa agt ttc gtt gct gcg atg aaa aat caa ttc cgc      912
Pro Ala Ala Gly Lys Ser Phe Val Ala Ala Met Lys Asn Gln Phe Arg
                260                 265                 270 aac ctg cca aat ggg aaa gga aaa ggc gta ttc tac tgg gag ccg cag      960
Asn Leu Pro Asn Gly Lys Gly Lys Gly Val Phe Tyr Trp Glu Pro Gln
                275                 280                 285 gct aca cca ggt tat aac ggt ggt tac ggc aaa ggc gct tgg cag tcg     1008
Ala Thr Pro Gly Tyr Asn Gly Gly Tyr Gly Lys Gly Ala Trp Gln Ser
            290                 295                 300 aat atg atg cca aca gcg gtc atg gaa gga ttt ata gac tag              1050
Asn Met Met Pro Thr Ala Val Met Glu Gly Phe Ile Asp
        305                 310                 315

<210> SEQ ID NO 22
<211> LENGTH: 349
<212> TYPE: PRT
<213> ORGANISM: Paenibacillus xylanilyticus

<400> SEQUENCE: 22

Met Leu Lys Phe Val Arg Gly Tyr Lys Thr Ser Ile Ala Leu Val Leu
        -30                 -25                 -20

Val Leu Leu Phe Thr Ser Ile Met Leu Pro Val Gly Gln His Val Ser
    -15                 -10                  -5

Ala Ala Pro Ser Phe Ala Lys Gly Ala Asp Ile Ser Trp Val Pro Gly
 -1  1               5                  10                  15

Met Glu Ala Gln Gly Tyr Lys Trp Lys Asp Lys Asn Gly Val Gln Arg
                20                  25                  30

Asp Ile Ile Asp Ile Leu Lys Asn Asp Tyr Gln Ile Asn Ser Val Arg
                35                  40                  45

Ile Arg Val Phe Val Asn Pro Ser Asn Asp Tyr Gly Asn Gly Tyr Met
            50                  55                  60

Asn Lys Asp Arg Val Ala Ala Leu Ala Gln Arg Ala Lys Asn Ala Gly
 65                 70                  75

Met Ser Val Met Leu Thr Leu His Tyr Ser Asp Ser Trp Ala Asp Pro
 80                 85                  90                  95

Gly Gln Gln Thr Lys Pro Ala Ala Trp Lys Asn Tyr Thr Phe Gln Gln
                100                 105                 110

Leu Met Asp Ala Val Trp Asn His Thr Arg Asp Val Met Thr Ala Met
                115                 120                 125

Gln Ser Lys Gly Val Thr Pro Asp Trp Val Gln Ile Gly Asn Glu Thr
            130                 135                 140

Ser Asn Gly Met Leu Trp Glu Asp Gly Lys Ala Ser Thr Asn Met Lys
145                 150                 155

Asn Tyr Ala Trp Leu Val Asn Thr Gly His Asn Ala Val Lys Ser Met
160                 165                 170                 175

Ser Thr Gly Thr Lys Thr Ile Val His Leu Ala Gly Gly Asp Asp Asn
                180                 185                 190

Ala Leu Tyr Val Trp Asn Ile Gly Gly Leu Ile Asn Asn Gly Ala Asn
                195                 200                 205

Phe Asp Met Ile Ala Met Ser Leu Tyr Pro Ser Ala Ser Gly Trp Asn
            210                 215                 220
```

```
Thr Ala Val Thr Asn Thr Val Asn Asn Ala Lys Asp Leu Ile Asn Arg
            225                 230                 235

Tyr Gly Lys Glu Ile Ile Val Ser Glu Ile Gly Met Asp Asn Asn Gln
240                 245                 250                 255

Pro Ala Ala Gly Lys Ser Phe Val Ala Ala Met Lys Asn Gln Phe Arg
                260                 265                 270

Asn Leu Pro Asn Gly Lys Gly Lys Gly Val Phe Tyr Trp Glu Pro Gln
            275                 280                 285

Ala Thr Pro Gly Tyr Asn Gly Gly Tyr Gly Lys Gly Ala Trp Gln Ser
            290                 295                 300

Asn Met Met Pro Thr Ala Val Met Glu Gly Phe Ile Asp
            305                 310                 315

<210> SEQ ID NO 23
<211> LENGTH: 316
<212> TYPE: PRT
<213> ORGANISM: Paenibacillus xylanilyticus
<220> FEATURE:
<221> NAME/KEY: mat_peptide
<222> LOCATION: (1)..(316)

<400> SEQUENCE: 23

Ala Pro Ser Phe Ala Lys Gly Ala Asp Ile Ser Trp Val Pro Gly Met
1               5                   10                  15

Glu Ala Gln Gly Tyr Lys Trp Lys Asp Lys Asn Gly Val Gln Arg Asp
                20                  25                  30

Ile Ile Asp Ile Leu Lys Asn Asp Tyr Gln Ile Asn Ser Val Arg Ile
            35                  40                  45

Arg Val Phe Val Asn Pro Ser Asn Asp Tyr Gly Asn Gly Tyr Met Asn
        50                  55                  60

Lys Asp Arg Val Ala Ala Leu Ala Gln Arg Ala Lys Asn Ala Gly Met
65                  70                  75                  80

Ser Val Met Leu Thr Leu His Tyr Ser Asp Ser Trp Ala Asp Pro Gly
                85                  90                  95

Gln Gln Thr Lys Pro Ala Ala Trp Lys Asn Tyr Thr Phe Gln Gln Leu
                100                 105                 110

Met Asp Ala Val Trp Asn His Thr Arg Asp Val Met Thr Ala Met Gln
            115                 120                 125

Ser Lys Gly Val Thr Pro Asp Trp Val Gln Ile Gly Asn Glu Thr Ser
        130                 135                 140

Asn Gly Met Leu Trp Glu Asp Gly Lys Ala Ser Thr Asn Met Lys Asn
145                 150                 155                 160

Tyr Ala Trp Leu Val Asn Thr Gly His Asn Ala Val Lys Ser Met Ser
                165                 170                 175

Thr Gly Thr Lys Thr Ile Val His Leu Ala Gly Gly Asp Asn Ala
            180                 185                 190

Leu Tyr Val Trp Asn Ile Gly Leu Ile Asn Gly Ala Asn Phe
        195                 200                 205

Asp Met Ile Ala Met Ser Leu Tyr Pro Ser Ala Ser Gly Trp Asn Thr
            210                 215                 220

Ala Val Thr Asn Thr Val Asn Asn Ala Lys Asp Leu Ile Asn Arg Tyr
225                 230                 235                 240

Gly Lys Glu Ile Ile Val Ser Glu Ile Gly Met Asp Asn Asn Gln Pro
                245                 250                 255

Ala Ala Gly Lys Ser Phe Val Ala Ala Met Lys Asn Gln Phe Arg Asn
```

```
                260                 265                 270
Leu Pro Asn Gly Lys Gly Lys Gly Val Phe Tyr Trp Glu Pro Gln Ala
            275                 280                 285

Thr Pro Gly Tyr Asn Gly Gly Tyr Gly Lys Gly Ala Trp Gln Ser Asn
            290                 295                 300

Met Met Pro Thr Ala Val Met Glu Gly Phe Ile Asp
305                 310                 315

<210> SEQ ID NO 24
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 24

His His His His His His Pro Arg Ala Pro Ser Phe Ala Lys Gly Ala
1               5                   10                  15

Asp Ile Ser Trp Val Pro Gly Met Glu Ala Gln Gly Tyr Lys Trp Lys
            20                  25                  30

Asp Lys Asn Gly Val Gln Arg Asp Ile Ile Asp Ile Leu Lys Asn Asp
        35                  40                  45

Tyr Gln Ile Asn Ser Val Arg Ile Arg Val Phe Val Asn Pro Ser Asn
50                  55                  60

Asp Tyr Gly Asn Gly Tyr Met Asn Lys Asp Arg Val Ala Ala Leu Ala
65                  70                  75                  80

Gln Arg Ala Lys Asn Ala Gly Met Ser Val Met Leu Thr Leu His Tyr
            85                  90                  95

Ser Asp Ser Trp Ala Asp Pro Gly Gln Gln Thr Lys Pro Ala Ala Trp
        100                 105                 110

Lys Asn Tyr Thr Phe Gln Gln Leu Met Asp Ala Val Trp Asn His Thr
    115                 120                 125

Arg Asp Val Met Thr Ala Met Gln Ser Lys Gly Val Thr Pro Asp Trp
130                 135                 140

Val Gln Ile Gly Asn Glu Thr Ser Asn Gly Met Leu Trp Glu Asp Gly
145                 150                 155                 160

Lys Ala Ser Thr Asn Met Lys Asn Tyr Ala Trp Leu Val Asn Thr Gly
            165                 170                 175

His Asn Ala Val Lys Ser Met Ser Thr Gly Thr Lys Thr Ile Val His
        180                 185                 190

Leu Ala Gly Gly Asp Asp Asn Ala Leu Tyr Val Trp Asn Ile Gly Gly
    195                 200                 205

Leu Ile Asn Asn Gly Ala Asn Phe Asp Met Ile Ala Met Ser Leu Tyr
210                 215                 220

Pro Ser Ala Ser Gly Trp Asn Thr Ala Val Thr Asn Thr Val Asn Asn
225                 230                 235                 240

Ala Lys Asp Leu Ile Asn Arg Tyr Gly Lys Glu Ile Ile Val Ser Glu
            245                 250                 255

Ile Gly Met Asp Asn Asn Gln Pro Ala Gly Lys Ser Phe Val Ala
        260                 265                 270

Ala Met Lys Asn Gln Phe Arg Asn Leu Pro Asn Gly Lys Gly Lys Gly
    275                 280                 285

Val Phe Tyr Trp Glu Pro Gln Ala Thr Pro Gly Tyr Asn Gly Gly Tyr
```

```
                    290                 295                 300
Gly Lys Gly Ala Trp Gln Ser Asn Met Met Pro Thr Ala Val Met Glu
305                 310                 315                 320

Gly Phe Ile Asp

<210> SEQ ID NO 25
<211> LENGTH: 1638
<212> TYPE: DNA
<213> ORGANISM: Paenibacillus sp-18179
<220> FEATURE:
<221> NAME/KEY: CDS
<222> LOCATION: (1)..(1635)
<220> FEATURE:
<221> NAME/KEY: misc_feature
<222> LOCATION: (1)..(3)
<223> OTHER INFORMATION: The gene has an alternative start codon gtg
      which would normally code for Val but is translated to Met when it
      is the first codon.
<220> FEATURE:
<221> NAME/KEY: sig_peptide
<222> LOCATION: (1)..(87)
<220> FEATURE:
<221> NAME/KEY: mat_peptide
<222> LOCATION: (88)..(1635)

<400> SEQUENCE: 25
```

| | | | | | | | | | | | | | | | | |
|---|---|---|---|---|---|---|---|---|---|---|---|---|---|---|---|---|
| gtg | ggt | aaa | tgg | gtt | aga | gct | att | gct | tta | gca | ggt | gta | gtt | gca | ctt | 48 |
| Val | Gly | Lys | Trp | Val | Arg | Ala | Ile | Ala | Leu | Ala | Gly | Val | Val | Ala | Leu | |
| | | | -25 | | | | -20 | | | | | -15 | | | | |

```
ttt aca tct atg atc act cct ctt caa gaa aca aag gct gct gga ggc     96
Phe Thr Ser Met Ile Thr Pro Leu Gln Glu Thr Lys Ala Ala Gly Gly
            -10                 -5                  -1   1 ttc gtt atg ggg gga gac gtt tca atg ctc cat gaa gtt gag cag tta    144
Phe Val Met Gly Gly Asp Val Ser Met Leu His Glu Val Glu Gln Leu
 5                  10                  15 ggc ggg aag ttt tac gat cag ggc act cca aag gat gct ttg caa att    192
Gly Gly Lys Phe Tyr Asp Gln Gly Thr Pro Lys Asp Ala Leu Gln Ile
20                  25                  30                  35 tta agc gca cat ggc atg aat gct gtc cga ttg cgt cta tgg gtt gac    240
Leu Ser Ala His Gly Met Asn Ala Val Arg Leu Arg Leu Trp Val Asp
                40                  45                  50 ccg tat gac agt ttc gga aat cct tat ggc ggt gga aca aac gat ctg    288
Pro Tyr Asp Ser Phe Gly Asn Pro Tyr Gly Gly Gly Thr Asn Asp Leu
            55                  60                  65 gct acg act ata tct ctt gca cag cga gcg aag gca caa ggt atg gag    336
Ala Thr Thr Ile Ser Leu Ala Gln Arg Ala Lys Ala Gln Gly Met Glu
        70                  75                  80 gtg ctg ctg gat ttt cac ttc agt gat ttc tgg gca gac cca ggg aag    384
Val Leu Leu Asp Phe His Phe Ser Asp Phe Trp Ala Asp Pro Gly Lys
85                  90                  95 cag aac aag cct aaa gct tgg cag agc tta acg tac aac cag ctg ctt    432
Gln Asn Lys Pro Lys Ala Trp Gln Ser Leu Thr Tyr Asn Gln Leu Leu
100                 105                 110                 115 act acg gta tat gat tat acg cat agt gta att acg caa atg aaa gcg    480
Thr Thr Val Tyr Asp Tyr Thr His Ser Val Ile Thr Gln Met Lys Ala
                120                 125                 130 gct ggc gtg atg cct gat atg gtt cag gta gga aac gag gca agc agc    528
Ala Gly Val Met Pro Asp Met Val Gln Val Gly Asn Glu Ala Ser Ser
            135                 140                 145 ggc atc ctc tgg aat gat ggc aag gtg ggg gga ggc att gat gat ttt    576
Gly Ile Leu Trp Asn Asp Gly Lys Val Gly Gly Gly Ile Asp Asp Phe
        150                 155                 160 acg aaa ctc gga gaa ctg ttt acc tct gct att aat ggg att aat gcg    624
Thr Lys Leu Gly Glu Leu Phe Thr Ser Ala Ile Asn Gly Ile Asn Ala
```

```
                Thr Lys Leu Gly Glu Leu Phe Thr Ser Ala Ile Asn Gly Ile Asn Ala
                    165                 170                 175 gcc ctc agc tct agt gag aac att gag att gtt ctg cat ttg gat cat          672
Ala Leu Ser Ser Ser Glu Asn Ile Glu Ile Val Leu His Leu Asp His
180                 185                 190                 195 ggc ggc gac aac aat tta tac act tgg tgg ttc gat aaa att gaa gcg          720
Gly Gly Asp Asn Asn Leu Tyr Thr Trp Trp Phe Asp Lys Ile Glu Ala
                    200                 205                 210 gag aac gtg gat tac gat att atc ggc ttg acc tac tat ccg ttt tgg          768
Glu Asn Val Asp Tyr Asp Ile Ile Gly Leu Thr Tyr Tyr Pro Phe Trp
                215                 220                 225 cat gga acg atg gga gaa ttg gcg tat aat ctt aat gcg atc agc agt          816
His Gly Thr Met Gly Glu Leu Ala Tyr Asn Leu Asn Ala Ile Ser Ser
            230                 235                 240 cgt tac aat aag gac gta atg att gtg gaa acg tcg tat ggc ttt acg          864
Arg Tyr Asn Lys Asp Val Met Ile Val Glu Thr Ser Tyr Gly Phe Thr
        245                 250                 255 ctg gat gat ggt gat ggt tta ggc aac tct ttt tac acg gcg gaa gaa          912
Leu Asp Asp Gly Asp Gly Leu Gly Asn Ser Phe Tyr Thr Ala Glu Glu
260                 265                 270                 275 agc att ggg ggt tac ccg gct aca gta gaa ggc cag acg gcg tat ttg          960
Ser Ile Gly Gly Tyr Pro Ala Thr Val Glu Gly Gln Thr Ala Tyr Leu
                    280                 285                 290 cgg gat ttg aag gaa att gtt agg gat gtc cca aac aac cgc ggc cgc         1008
Arg Asp Leu Lys Glu Ile Val Arg Asp Val Pro Asn Asn Arg Gly Arg
                295                 300                 305 ggc att ttc tgg tgg gag ccg aca tgg ctg cct gtt gca ggg gct aac         1056
Gly Ile Phe Trp Trp Glu Pro Thr Trp Leu Pro Val Ala Gly Ala Asn
            310                 315                 320 tgg ggg acg gat gca ggc aag ctg tac aac aat gat act gga cta cta         1104
Trp Gly Thr Asp Ala Gly Lys Leu Tyr Asn Asn Asp Thr Gly Leu Leu
        325                 330                 335 tct aat cct tgg gac aat cag acc ttg ttt gat ttt aat gga aat gtg         1152
Ser Asn Pro Trp Asp Asn Gln Thr Leu Phe Asp Phe Asn Gly Asn Val
340                 345                 350                 355 ttg tct aca gtt tca gta ttt aca caa agt gct cca acc aac ctt gtt         1200
Leu Ser Thr Val Ser Val Phe Thr Gln Ser Ala Pro Thr Asn Leu Val
                    360                 365                 370 gct aat cat agc ttt gag gcc gat ggt tgg aca aca aca cca tct agc         1248
Ala Asn His Ser Phe Glu Ala Asp Gly Trp Thr Thr Thr Pro Ser Ser
                375                 380                 385 tgg aat cgc tgg gca gcc gat acg gca tcc tat aat gct att aag gtt         1296
Trp Asn Arg Trp Ala Ala Asp Thr Ala Ser Tyr Asn Ala Ile Lys Val
            390                 395                 400 gaa gaa aac ggt att acg ggc agc tat aag ctg acg cat tgg agt gat         1344
Glu Glu Asn Gly Ile Thr Gly Ser Tyr Lys Leu Thr His Trp Ser Asp
        405                 410                 415 tct gct tat gag gcc tct acg tac cag act gtt tca gga tta agc aat         1392
Ser Ala Tyr Glu Ala Ser Thr Tyr Gln Thr Val Ser Gly Leu Ser Asn
420                 425                 430                 435 ggt acc tat act tta tcc gct tgg gtg ctt aac agt ggc gga caa aat         1440
Gly Thr Tyr Thr Leu Ser Ala Trp Val Leu Asn Ser Gly Gly Gln Asn
                    440                 445                 450 acg ctg cag ctt tac gct aaa aat tac ggg ggt tca gaa cgg aac gtc         1488
Thr Leu Gln Leu Tyr Ala Lys Asn Tyr Gly Gly Ser Glu Arg Asn Val
                455                 460                 465 aat ctt cct gtt agc cca aca aag tgg gta aaa gta aaa att gaa aac         1536
Asn Leu Pro Val Ser Pro Thr Lys Trp Val Lys Val Lys Ile Glu Asn
            470                 475                 480
```

-continued

| | | | | | | | | | | | | | | |
|---|---|---|---|---|---|---|---|---|---|---|---|---|---|---|
| atc | agt | gtt | aca | aat | ggt | caa | atc | gaa | tta | ggc | att | tat | tca | gat | gcg | 1584 |
| Ile | Ser | Val | Thr | Asn | Gly | Gln | Ile | Glu | Leu | Gly | Ile | Tyr | Ser | Asp | Ala | |
| 485 | | | | 490 | | | | | 495 | | | | | | | |

| aat | gct | gat | aat | tgg | atg | aac | ctc | gat | aac | gtc | aaa | ctt | tat | aaa | aca | 1632 |
|---|---|---|---|---|---|---|---|---|---|---|---|---|---|---|---|---|
| Asn | Ala | Asp | Asn | Trp | Met | Asn | Leu | Asp | Asn | Val | Lys | Leu | Tyr | Lys | Thr | |
| 500 | | | | 505 | | | | | 510 | | | | | 515 | | |

| aac | tag | | | | | | | | | | | | | | | 1638 |
|---|---|---|---|---|---|---|---|---|---|---|---|---|---|---|---|---|
| Asn | | | | | | | | | | | | | | | | |

<210> SEQ ID NO 26
<211> LENGTH: 545
<212> TYPE: PRT
<213> ORGANISM: Paenibacillus sp-18179

<400> SEQUENCE: 26

Val Gly Lys Trp Val Arg Ala Ile Ala Leu Ala Gly Val Ala Leu
            -25                 -20                 -15

Phe Thr Ser Met Ile Thr Pro Leu Gln Glu Thr Lys Ala Ala Gly Gly
            -10                  -5                  -1   1

Phe Val Met Gly Gly Asp Val Ser Met Leu His Glu Val Glu Gln Leu
    5                   10                  15

Gly Gly Lys Phe Tyr Asp Gln Gly Thr Pro Lys Asp Ala Leu Gln Ile
 20                  25                  30                  35

Leu Ser Ala His Gly Met Asn Ala Val Arg Leu Arg Leu Trp Val Asp
                 40                  45                  50

Pro Tyr Asp Ser Phe Gly Asn Pro Tyr Gly Gly Thr Asn Asp Leu
                 55                  60                  65

Ala Thr Thr Ile Ser Leu Ala Gln Arg Ala Lys Ala Gln Gly Met Glu
                 70                  75                  80

Val Leu Leu Asp Phe His Phe Ser Asp Phe Trp Ala Asp Pro Gly Lys
 85                  90                  95

Gln Asn Lys Pro Lys Ala Trp Gln Ser Leu Thr Tyr Asn Gln Leu Leu
100                 105                 110                 115

Thr Thr Val Tyr Asp Tyr Thr His Ser Val Ile Thr Gln Met Lys Ala
                120                 125                 130

Ala Gly Val Met Pro Asp Met Val Gln Val Gly Asn Glu Ala Ser Ser
                135                 140                 145

Gly Ile Leu Trp Asn Asp Gly Lys Val Gly Gly Ile Asp Asp Phe
150                 155                 160

Thr Lys Leu Gly Glu Leu Phe Thr Ser Ala Ile Asn Gly Ile Asn Ala
165                 170                 175

Ala Leu Ser Ser Ser Glu Asn Ile Glu Ile Val Leu His Leu Asp His
180                 185                 190                 195

Gly Gly Asp Asn Asn Leu Tyr Thr Trp Trp Phe Asp Lys Ile Glu Ala
                200                 205                 210

Glu Asn Val Asp Tyr Asp Ile Ile Gly Leu Thr Tyr Tyr Pro Phe Trp
                215                 220                 225

His Gly Thr Met Gly Glu Leu Ala Tyr Asn Leu Asn Ala Ile Ser Ser
            230                 235                 240

Arg Tyr Asn Lys Asp Val Met Ile Val Glu Thr Ser Tyr Gly Phe Thr
245                 250                 255

Leu Asp Asp Gly Asp Gly Leu Gly Asn Ser Phe Tyr Thr Ala Glu Glu
260                 265                 270                 275

Ser Ile Gly Gly Tyr Pro Ala Thr Val Glu Gly Gln Thr Ala Tyr Leu
            280                 285                 290

Arg Asp Leu Lys Glu Ile Val Arg Asp Val Pro Asn Asn Arg Gly Arg
            295                 300                 305

Gly Ile Phe Trp Trp Glu Pro Thr Trp Leu Pro Val Ala Gly Ala Asn
            310                 315                 320

Trp Gly Thr Asp Ala Gly Lys Leu Tyr Asn Asn Asp Thr Gly Leu Leu
            325                 330                 335

Ser Asn Pro Trp Asp Asn Gln Thr Leu Phe Asp Phe Asn Gly Asn Val
340                 345                 350                 355

Leu Ser Thr Val Ser Val Phe Thr Gln Ser Ala Pro Thr Asn Leu Val
            360                 365                 370

Ala Asn His Ser Phe Glu Ala Asp Gly Trp Thr Thr Thr Pro Ser Ser
            375                 380                 385

Trp Asn Arg Trp Ala Ala Asp Thr Ala Ser Tyr Asn Ala Ile Lys Val
            390                 395                 400

Glu Glu Asn Gly Ile Thr Gly Ser Tyr Lys Leu Thr His Trp Ser Asp
            405                 410                 415

Ser Ala Tyr Glu Ala Ser Thr Tyr Gln Thr Val Ser Gly Leu Ser Asn
420                 425                 430                 435

Gly Thr Tyr Thr Leu Ser Ala Trp Val Leu Asn Ser Gly Gly Gln Asn
            440                 445                 450

Thr Leu Gln Leu Tyr Ala Lys Asn Tyr Gly Gly Ser Glu Arg Asn Val
            455                 460                 465

Asn Leu Pro Val Ser Pro Thr Lys Trp Val Lys Val Lys Ile Glu Asn
            470                 475                 480

Ile Ser Val Thr Asn Gly Gln Ile Glu Leu Gly Ile Tyr Ser Asp Ala
485                 490                 495

Asn Ala Asp Asn Trp Met Asn Leu Asp Asn Val Lys Leu Tyr Lys Thr
500                 505                 510                 515

Asn

<210> SEQ ID NO 27
<211> LENGTH: 516
<212> TYPE: PRT
<213> ORGANISM: Paenibacillus sp-18179
<220> FEATURE:
<221> NAME/KEY: mat_peptide
<222> LOCATION: (1)..(516)

<400> SEQUENCE: 27

Ala Gly Gly Phe Val Met Gly Gly Asp Val Ser Met Leu His Glu Val
1               5                   10                  15

Glu Gln Leu Gly Gly Lys Phe Tyr Asp Gln Gly Thr Pro Lys Asp Ala
            20                  25                  30

Leu Gln Ile Leu Ser Ala His Gly Met Asn Ala Val Arg Leu Arg Leu
            35                  40                  45

Trp Val Asp Pro Tyr Asp Ser Phe Gly Asn Pro Tyr Gly Gly Gly Thr
        50                  55                  60

Asn Asp Leu Ala Thr Thr Ile Ser Leu Ala Gln Arg Ala Lys Ala Gln
65                  70                  75                  80

Gly Met Glu Val Leu Leu Asp Phe His Phe Ser Asp Phe Trp Ala Asp
                85                  90                  95

Pro Gly Lys Gln Asn Lys Pro Lys Ala Trp Gln Ser Leu Thr Tyr Asn
            100                 105                 110

Gln Leu Leu Thr Thr Val Tyr Asp Tyr Thr His Ser Val Ile Thr Gln
            115                 120                 125

```
Met Lys Ala Ala Gly Val Met Pro Asp Met Val Gln Val Gly Asn Glu
    130                 135                 140
Ala Ser Ser Gly Ile Leu Trp Asn Asp Gly Lys Val Gly Gly Gly Ile
145                 150                 155                 160
Asp Asp Phe Thr Lys Leu Gly Glu Leu Phe Thr Ser Ala Ile Asn Gly
                165                 170                 175
Ile Asn Ala Ala Leu Ser Ser Glu Asn Ile Glu Ile Val Leu His
            180                 185                 190
Leu Asp His Gly Asp Asn Asn Leu Tyr Thr Trp Trp Phe Asp Lys
        195                 200                 205
Ile Glu Ala Glu Asn Val Asp Tyr Asp Ile Ile Gly Leu Thr Tyr Tyr
    210                 215                 220
Pro Phe Trp His Gly Thr Met Gly Glu Leu Ala Tyr Asn Leu Asn Ala
225                 230                 235                 240
Ile Ser Ser Arg Tyr Asn Lys Asp Val Met Ile Val Glu Thr Ser Tyr
                245                 250                 255
Gly Phe Thr Leu Asp Asp Gly Asp Gly Leu Gly Asn Ser Phe Tyr Thr
                260                 265                 270
Ala Glu Glu Ser Ile Gly Gly Tyr Pro Ala Thr Val Glu Gly Gln Thr
            275                 280                 285
Ala Tyr Leu Arg Asp Leu Lys Glu Ile Val Arg Asp Val Pro Asn Asn
        290                 295                 300
Arg Gly Arg Gly Ile Phe Trp Trp Glu Pro Thr Trp Leu Pro Val Ala
305                 310                 315                 320
Gly Ala Asn Trp Gly Thr Asp Ala Gly Lys Leu Tyr Asn Asn Asp Thr
                325                 330                 335
Gly Leu Leu Ser Asn Pro Trp Asp Asn Gln Thr Leu Phe Asp Phe Asn
            340                 345                 350
Gly Asn Val Leu Ser Thr Val Ser Val Phe Thr Gln Ser Ala Pro Thr
        355                 360                 365
Asn Leu Val Ala Asn His Ser Phe Glu Ala Asp Gly Trp Thr Thr Thr
    370                 375                 380
Pro Ser Ser Trp Asn Arg Trp Ala Ala Asp Thr Ala Ser Tyr Asn Ala
385                 390                 395                 400
Ile Lys Val Glu Glu Asn Gly Ile Thr Gly Ser Tyr Lys Leu Thr His
                405                 410                 415
Trp Ser Asp Ser Ala Tyr Glu Ala Ser Thr Tyr Gln Thr Val Ser Gly
            420                 425                 430
Leu Ser Asn Gly Thr Tyr Thr Leu Ser Ala Trp Val Leu Asn Ser Gly
        435                 440                 445
Gly Gln Asn Thr Leu Gln Leu Tyr Ala Lys Asn Tyr Gly Gly Ser Glu
    450                 455                 460
Arg Asn Val Asn Leu Pro Val Ser Pro Thr Lys Trp Val Lys Val Lys
465                 470                 475                 480
Ile Glu Asn Ile Ser Val Thr Asn Gly Gln Ile Glu Leu Gly Ile Tyr
                485                 490                 495
Ser Asp Ala Asn Ala Asp Asn Trp Met Asn Leu Asp Asn Val Lys Leu
            500                 505                 510
Tyr Lys Thr Asn
        515

<210> SEQ ID NO 28
<211> LENGTH: 524
<212> TYPE: PRT
```

<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(524)

<400> SEQUENCE: 28

```
His His His His His His Pro Arg Ala Gly Gly Phe Val Met Gly Gly
1               5                   10                  15

Asp Val Ser Met Leu His Glu Val Glu Gln Leu Gly Gly Lys Phe Tyr
            20                  25                  30

Asp Gln Gly Thr Pro Lys Asp Ala Leu Gln Ile Leu Ser Ala His Gly
        35                  40                  45

Met Asn Ala Val Arg Leu Arg Leu Trp Val Asp Pro Tyr Asp Ser Phe
    50                  55                  60

Gly Asn Pro Tyr Gly Gly Thr Asn Asp Leu Ala Thr Thr Ile Ser
65                  70                  75                  80

Leu Ala Gln Arg Ala Lys Ala Gln Gly Met Glu Val Leu Leu Asp Phe
                85                  90                  95

His Phe Ser Asp Phe Trp Ala Asp Pro Gly Lys Gln Asn Lys Pro Lys
            100                 105                 110

Ala Trp Gln Ser Leu Thr Tyr Asn Gln Leu Leu Thr Thr Val Tyr Asp
        115                 120                 125

Tyr Thr His Ser Val Ile Thr Gln Met Lys Ala Ala Gly Val Met Pro
    130                 135                 140

Asp Met Val Gln Val Gly Asn Glu Ala Ser Ser Gly Ile Leu Trp Asn
145                 150                 155                 160

Asp Gly Lys Val Gly Gly Ile Asp Asp Phe Thr Lys Leu Gly Glu
                165                 170                 175

Leu Phe Thr Ser Ala Ile Asn Gly Ile Asn Ala Ala Leu Ser Ser Ser
            180                 185                 190

Glu Asn Ile Glu Ile Val Leu His Leu Asp His Gly Gly Asp Asn Asn
        195                 200                 205

Leu Tyr Thr Trp Trp Phe Asp Lys Ile Glu Ala Glu Asn Val Asp Tyr
    210                 215                 220

Asp Ile Ile Gly Leu Thr Tyr Tyr Pro Phe Trp His Gly Thr Met Gly
225                 230                 235                 240

Glu Leu Ala Tyr Asn Leu Asn Ala Ile Ser Ser Arg Tyr Asn Lys Asp
                245                 250                 255

Val Met Ile Val Glu Thr Ser Tyr Gly Phe Thr Leu Asp Asp Gly Asp
            260                 265                 270

Gly Leu Gly Asn Ser Phe Tyr Thr Ala Glu Glu Ser Ile Gly Gly Tyr
        275                 280                 285

Pro Ala Thr Val Glu Gly Gln Thr Ala Tyr Leu Arg Asp Leu Lys Glu
    290                 295                 300

Ile Val Arg Asp Val Pro Asn Arg Gly Arg Gly Ile Phe Trp Trp
305                 310                 315                 320

Glu Pro Thr Trp Leu Pro Val Ala Gly Ala Asn Trp Gly Thr Asp Ala
                325                 330                 335

Gly Lys Leu Tyr Asn Asn Asp Thr Gly Leu Leu Ser Asn Pro Trp Asp
            340                 345                 350

Asn Gln Thr Leu Phe Asp Phe Asn Gly Asn Val Leu Ser Thr Val Ser
        355                 360                 365

Val Phe Thr Gln Ser Ala Pro Thr Asn Leu Val Ala Asn His Ser Phe
```

```
                    370                 375                 380
Glu Ala Asp Gly Trp Thr Thr Thr Pro Ser Ser Trp Asn Arg Trp Ala
385                 390                 395                 400

Ala Asp Thr Ala Ser Tyr Asn Ala Ile Lys Val Glu Asn Gly Ile
                405                 410                 415

Thr Gly Ser Tyr Lys Leu Thr His Trp Ser Asp Ser Ala Tyr Glu Ala
                420                 425                 430

Ser Thr Tyr Gln Thr Val Ser Gly Leu Ser Asn Gly Thr Tyr Thr Leu
            435                 440                 445

Ser Ala Trp Val Leu Asn Ser Gly Gln Asn Thr Leu Gln Leu Tyr
        450                 455                 460

Ala Lys Asn Tyr Gly Gly Ser Glu Arg Asn Val Asn Leu Pro Val Ser
465                 470                 475                 480

Pro Thr Lys Trp Val Lys Val Lys Ile Glu Asn Ile Ser Val Thr Asn
                485                 490                 495

Gly Gln Ile Glu Leu Gly Ile Tyr Ser Asp Ala Asn Ala Asp Asn Trp
            500                 505                 510

Met Asn Leu Asp Asn Val Lys Leu Tyr Lys Thr Asn
        515                 520
```

<210> SEQ ID NO 29
<211> LENGTH: 1053
<212> TYPE: DNA
<213> ORGANISM: Paenibacillus peoriae
<220> FEATURE:
<221> NAME/KEY: CDS
<222> LOCATION: (1)..(1050)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1050)

<400> SEQUENCE: 29

```
atg aaa aca ggt aac cgc acg atg gta ttt gcg atg ttg atc ttg ctt    48
Met Lys Thr Gly Asn Arg Thr Met Val Phe Ala Met Leu Ile Leu Leu
            -30                 -25                 -20 tcc agc tta ttg tat ccg ttc ggc tct gta ggg ttg ggt gcg gct tcg    96
Ser Ser Leu Leu Tyr Pro Phe Gly Ser Val Gly Leu Gly Ala Ala Ser
        -15                 -10                  -5 gcc gcc cct gct ttc gcc aaa gga gca gat ata agc tgg gta gca gga   144
Ala Ala Pro Ala Phe Ala Lys Gly Ala Asp Ile Ser Trp Val Ala Gly
 -1   1               5                  10                  15 atg gaa gcg caa ggt atg act tgg aag gat aaa aag ggt gtt cgt cga   192
Met Glu Ala Gln Gly Met Thr Trp Lys Asp Lys Lys Gly Val Arg Arg
                20                  25                  30 gat ata ctg caa att ttg cga gat gac tat cag atc aac tcg gta cgt   240
Asp Ile Leu Gln Ile Leu Arg Asp Asp Tyr Gln Ile Asn Ser Val Arg
            35                  40                  45 atc cgt gtg tgg gta aac ccc gac atg aaa gat tat gca agc gga tac   288
Ile Arg Val Trp Val Asn Pro Asp Met Lys Asp Tyr Ala Ser Gly Tyr
        50                  55                  60 atg aat gcc gaa aag gca gca gaa ctg gcg cag cga gct aaa aaa ttg   336
Met Asn Ala Glu Lys Ala Ala Glu Leu Ala Gln Arg Ala Lys Lys Leu
65                  70                  75 ggt atg agc gtt atg ctg act cta cat tat agt gat tcc tgg gca gat   384
Gly Met Ser Val Met Leu Thr Leu His Tyr Ser Asp Ser Trp Ala Asp
80                  85                  90                  95 cca ggg caa cag aac aaa cct tat gcg tgg cgc aat ttt aca ttt aca   432
```

```
Pro Gly Gln Gln Asn Lys Pro Tyr Ala Trp Arg Asn Phe Thr Phe Thr
                100                 105                 110 caa ctc atg gat gca gtc tgg tct cat acg gtt tat gtt atg aac acg      480
Gln Leu Met Asp Ala Val Trp Ser His Thr Val Tyr Val Met Asn Thr
        115                 120                 125 atg aaa agc aag ggg gta aca ccg gac tgg gtg cag atc ggt aat gag      528
Met Lys Ser Lys Gly Val Thr Pro Asp Trp Val Gln Ile Gly Asn Glu
        130                 135                 140 acg aac aat gga atg ctc tgg gaa gac ggc aaa gct tcg gtg aac atg      576
Thr Asn Asn Gly Met Leu Trp Glu Asp Gly Lys Ala Ser Val Asn Met
145                 150                 155 aaa aac tat gcc tgg ctc gtc aat aca ggt aat aat gct gta aaa tcg      624
Lys Asn Tyr Ala Trp Leu Val Asn Thr Gly Asn Asn Ala Val Lys Ser
160                 165                 170                 175 gta agc agc agt act aaa acg ata gta cat tta gcc aac ggg gat aac      672
Val Ser Ser Ser Thr Lys Thr Ile Val His Leu Ala Asn Gly Asp Asn
                180                 185                 190 ggt tcc gtg ttg aac tgg aat atc ggc gga ctg att gat aat gga gct      720
Gly Ser Val Leu Asn Trp Asn Ile Gly Gly Leu Ile Asp Asn Gly Ala
            195                 200                 205 cag ttt gat ctc atc ggg ctg tct ctg tat ccg tct cct tct gac tgg      768
Gln Phe Asp Leu Ile Gly Leu Ser Leu Tyr Pro Ser Pro Ser Asp Trp
        210                 215                 220 cag ggc aag gtg gat cag acg att acg aat gcc aat aac ctc att gcc      816
Gln Gly Lys Val Asp Gln Thr Ile Thr Asn Ala Asn Asn Leu Ile Ala
225                 230                 235 aaa tac ggt aaa ggt att gtc atc agt gaa atc ggg atg gaa tat aac      864
Lys Tyr Gly Lys Gly Ile Val Ile Ser Glu Ile Gly Met Glu Tyr Asn
240                 245                 250                 255 gaa cct gca gct tcc aag gca ttt att tct gca atc aaa aca aag gtt      912
Glu Pro Ala Ala Ser Lys Ala Phe Ile Ser Ala Ile Lys Thr Lys Val
                260                 265                 270 cgg aac atg gga ggc ggc aaa ggc aca ggg gta ttt tat tgg gag ccg      960
Arg Asn Met Gly Gly Gly Lys Gly Thr Gly Val Phe Tyr Trp Glu Pro
            275                 280                 285 gct gca act cca ggt tac aat caa ggt tat aac aaa ggt gct tgg cag     1008
Ala Ala Thr Pro Gly Tyr Asn Gln Gly Tyr Asn Lys Gly Ala Trp Gln
        290                 295                 300 gct gac ggt aaa cca acc tca gct ttg gag gga ttt gta aat taa         1053
Ala Asp Gly Lys Pro Thr Ser Ala Leu Glu Gly Phe Val Asn
305                 310                 315

<210> SEQ ID NO 30
<211> LENGTH: 350
<212> TYPE: PRT
<213> ORGANISM: Paenibacillus peoriae

<400> SEQUENCE: 30

Met Lys Thr Gly Asn Arg Thr Met Val Phe Ala Met Leu Ile Leu Leu
            -30                 -25                 -20

Ser Ser Leu Leu Tyr Pro Phe Gly Ser Val Gly Leu Gly Ala Ala Ser
        -15                 -10                  -5

Ala Ala Pro Ala Phe Ala Lys Gly Ala Asp Ile Ser Trp Val Ala Gly
 -1   1               5                  10                  15

Met Glu Ala Gln Gly Met Thr Trp Lys Asp Lys Lys Gly Val Arg Arg
                20                  25                  30

Asp Ile Leu Gln Ile Leu Arg Asp Asp Tyr Gln Ile Asn Ser Val Arg
            35                  40                  45

Ile Arg Val Trp Val Asn Pro Asp Met Lys Asp Tyr Ala Ser Gly Tyr
```

```
                50                   55                   60
Met Asn Ala Glu Lys Ala Ala Glu Leu Ala Gln Arg Ala Lys Lys Leu
 65                  70                   75

Gly Met Ser Val Met Leu Thr Leu His Tyr Ser Asp Ser Trp Ala Asp
 80                  85                   90                   95

Pro Gly Gln Gln Asn Lys Pro Tyr Ala Trp Arg Asn Phe Thr Phe Thr
                100                 105                  110

Gln Leu Met Asp Ala Val Trp Ser His Thr Val Tyr Val Met Asn Thr
                115                 120                  125

Met Lys Ser Lys Gly Val Thr Pro Asp Trp Val Gln Ile Gly Asn Glu
                130                 135                  140

Thr Asn Asn Gly Met Leu Trp Glu Asp Gly Lys Ala Ser Val Asn Met
                145                 150                  155

Lys Asn Tyr Ala Trp Leu Val Asn Thr Gly Asn Asn Ala Val Lys Ser
160                 165                  170                  175

Val Ser Ser Ser Thr Lys Thr Ile Val His Leu Ala Asn Gly Asp Asn
                180                 185                  190

Gly Ser Val Leu Asn Trp Asn Ile Gly Gly Leu Ile Asp Asn Gly Ala
                195                 200                  205

Gln Phe Asp Leu Ile Gly Leu Ser Leu Tyr Pro Ser Pro Ser Asp Trp
                210                 215                  220

Gln Gly Lys Val Asp Gln Thr Ile Thr Asn Ala Asn Asn Leu Ile Ala
                225                 230                  235

Lys Tyr Gly Lys Gly Ile Val Ile Ser Glu Ile Gly Met Glu Tyr Asn
240                 245                  250                  255

Glu Pro Ala Ala Ser Lys Ala Phe Ile Ser Ala Ile Lys Thr Lys Val
                260                 265                  270

Arg Asn Met Gly Gly Lys Gly Thr Gly Val Phe Tyr Trp Glu Pro
                275                 280                  285

Ala Ala Thr Pro Gly Tyr Asn Gln Gly Tyr Asn Lys Gly Ala Trp Gln
                290                 295                  300

Ala Asp Gly Lys Pro Thr Ser Ala Leu Glu Gly Phe Val Asn
                305                 310                  315

<210> SEQ ID NO 31
<211> LENGTH: 317
<212> TYPE: PRT
<213> ORGANISM: Paenibacillus peoriae
<220> FEATURE:
<221> NAME/KEY: mat_peptide
<222> LOCATION: (1)..(317)

<400> SEQUENCE: 31

Ala Pro Ala Phe Ala Lys Gly Asp Ile Ser Trp Val Ala Gly Met
 1               5                   10                   15

Glu Ala Gln Gly Met Thr Trp Lys Asp Lys Lys Gly Val Arg Arg Asp
                20                  25                   30

Ile Leu Gln Ile Leu Arg Asp Asp Tyr Gln Ile Asn Ser Val Arg Ile
                35                  40                   45

Arg Val Trp Val Asn Pro Asp Met Lys Asp Tyr Ala Ser Gly Tyr Met
 50                  55                   60

Asn Ala Glu Lys Ala Ala Glu Leu Ala Gln Arg Ala Lys Lys Leu Gly
 65                  70                   75                   80

Met Ser Val Met Leu Thr Leu His Tyr Ser Asp Ser Trp Ala Asp Pro
                85                  90                   95
```

Gly Gln Gln Asn Lys Pro Tyr Ala Trp Arg Asn Phe Thr Phe Thr Gln
            100                 105                 110

Leu Met Asp Ala Val Trp Ser His Thr Val Tyr Val Met Asn Thr Met
        115                 120                 125

Lys Ser Lys Gly Val Thr Pro Asp Trp Val Gln Ile Gly Asn Glu Thr
130                 135                 140

Asn Asn Gly Met Leu Trp Glu Asp Gly Lys Ala Ser Val Asn Met Lys
145                 150                 155                 160

Asn Tyr Ala Trp Leu Val Asn Thr Gly Asn Asn Ala Val Lys Ser Val
                165                 170                 175

Ser Ser Ser Thr Lys Thr Ile Val His Leu Ala Asn Gly Asp Asn Gly
            180                 185                 190

Ser Val Leu Asn Trp Asn Ile Gly Gly Leu Ile Asp Asn Gly Ala Gln
        195                 200                 205

Phe Asp Leu Ile Gly Leu Ser Leu Tyr Pro Ser Pro Ser Asp Trp Gln
210                 215                 220

Gly Lys Val Asp Gln Thr Ile Thr Asn Ala Asn Asn Leu Ile Ala Lys
225                 230                 235                 240

Tyr Gly Lys Gly Ile Val Ile Ser Glu Ile Gly Met Glu Tyr Asn Glu
                245                 250                 255

Pro Ala Ala Ser Lys Ala Phe Ile Ser Ala Ile Lys Thr Lys Val Arg
            260                 265                 270

Asn Met Gly Gly Lys Gly Thr Gly Val Phe Tyr Trp Glu Pro Ala
        275                 280                 285

Ala Thr Pro Gly Tyr Asn Gln Gly Tyr Asn Lys Gly Ala Trp Gln Ala
290                 295                 300

Asp Gly Lys Pro Thr Ser Ala Leu Glu Gly Phe Val Asn
305                 310                 315

<210> SEQ ID NO 32
<211> LENGTH: 325
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(325)

<400> SEQUENCE: 32

His His His His His His Pro Arg Ala Pro Ala Phe Ala Lys Gly Ala
1               5                   10                  15

Asp Ile Ser Trp Val Ala Gly Met Glu Ala Gln Gly Met Thr Trp Lys
                20                  25                  30

Asp Lys Lys Gly Val Arg Arg Asp Ile Leu Gln Ile Leu Arg Asp Asp
            35                  40                  45

Tyr Gln Ile Asn Ser Val Arg Ile Arg Val Trp Val Asn Pro Asp Met
        50                  55                  60

Lys Asp Tyr Ala Ser Gly Tyr Met Asn Ala Glu Lys Ala Ala Glu Leu
65                  70                  75                  80

Ala Gln Arg Ala Lys Lys Leu Gly Met Ser Val Met Leu Thr Leu His
                85                  90                  95

Tyr Ser Asp Ser Trp Ala Asp Pro Gly Gln Gln Asn Lys Pro Tyr Ala
            100                 105                 110

Trp Arg Asn Phe Thr Phe Thr Gln Leu Met Asp Ala Val Trp Ser His
        115                 120                 125

```
Thr Val Tyr Val Met Asn Thr Met Lys Ser Lys Gly Val Thr Pro Asp
130                 135                 140

Trp Val Gln Ile Gly Asn Glu Thr Asn Gly Met Leu Trp Glu Asp
145                 150                 155                 160

Gly Lys Ala Ser Val Asn Met Lys Asn Tyr Ala Trp Leu Val Asn Thr
                165                 170                 175

Gly Asn Asn Ala Val Lys Ser Val Ser Ser Thr Lys Thr Ile Val
                180                 185                 190

His Leu Ala Asn Gly Asp Asn Gly Ser Val Leu Asn Trp Asn Ile Gly
                195                 200                 205

Gly Leu Ile Asp Asn Gly Ala Gln Phe Asp Leu Ile Gly Leu Ser Leu
210                 215                 220

Tyr Pro Ser Pro Ser Asp Trp Gln Gly Lys Val Asp Gln Thr Ile Thr
225                 230                 235                 240

Asn Ala Asn Asn Leu Ile Ala Lys Tyr Gly Lys Gly Ile Val Ile Ser
                245                 250                 255

Glu Ile Gly Met Glu Tyr Asn Glu Pro Ala Ala Ser Lys Ala Phe Ile
                260                 265                 270

Ser Ala Ile Lys Thr Lys Val Arg Asn Met Gly Gly Lys Gly Thr
275                 280                 285

Gly Val Phe Tyr Trp Glu Pro Ala Ala Thr Pro Gly Tyr Asn Gln Gly
290                 295                 300

Tyr Asn Lys Gly Ala Trp Gln Ala Asp Gly Lys Pro Thr Ser Ala Leu
305                 310                 315                 320

Glu Gly Phe Val Asn
                325

<210> SEQ ID NO 33
<211> LENGTH: 1050
<212> TYPE: DNA
<213> ORGANISM: Paenibacillus xylanexedens
<220> FEATURE:
<221> NAME/KEY: CDS
<222> LOCATION: (1)..(1047)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1047)

<400> SEQUENCE: 33 atg ttc aaa aat gta agg ggt ttc agg ata tcc atc atg ttg gct ttt      48
Met Phe Lys Asn Val Arg Gly Phe Arg Ile Ser Ile Met Leu Ala Phe
        -30                 -25                 -20 gtt ttg tta ttc acc tcc atc atg ttg ccc gca ggt cag cat gcc agc      96
Val Leu Leu Phe Thr Ser Ile Met Leu Pro Ala Gly Gln His Ala Ser
    -15                 -10                 -5 gca gca cca agt ttc gcc aaa gga gcc gac atc agt tgg gtt ccc gga     144
Ala Ala Pro Ser Phe Ala Lys Gly Ala Asp Ile Ser Trp Val Pro Gly
-1   1               5                  10                  15 atg gaa gct caa ggc tac aaa tgg aaa gat aaa aac ggg gta cag cgt     192
Met Glu Ala Gln Gly Tyr Lys Trp Lys Asp Lys Asn Gly Val Gln Arg
                20                  25                  30 gac atc att gat att ttg aaa aat gac tat caa atc aat tcc gtt cgt     240
Asp Ile Ile Asp Ile Leu Lys Asn Asp Tyr Gln Ile Asn Ser Val Arg
            35                  40                  45 att cgg gtc ttt gtt aat cct tcg aac gat tat ggg aac ggt tac atg     288
Ile Arg Val Phe Val Asn Pro Ser Asn Asp Tyr Gly Asn Gly Tyr Met
        50                  55                  60
```

```
aac aag gat cgt gcg gct gca ctc gca caa cgt gcc aag aat gcc ggc    336
Asn Lys Asp Arg Ala Ala Ala Leu Ala Gln Arg Ala Lys Asn Ala Gly
         65                  70                  75 atg agc gta atg ctc acc ctg cac tac agc gat tcc tgg gca gac cct    384
Met Ser Val Met Leu Thr Leu His Tyr Ser Asp Ser Trp Ala Asp Pro
 80                  85                  90                  95 ggt caa cag acc aaa cca gct gcc tgg aaa aac tac acg ttc cag cag    432
Gly Gln Gln Thr Lys Pro Ala Ala Trp Lys Asn Tyr Thr Phe Gln Gln
                100                 105                 110 ctc atg gat gcg gtg tgg aat cac aca cgt gat gtc atg act gca atg    480
Leu Met Asp Ala Val Trp Asn His Thr Arg Asp Val Met Thr Ala Met
            115                 120                 125 caa agc aaa ggc gtt acc ccg gac tgg gta cag atc ggg aat gaa aca    528
Gln Ser Lys Gly Val Thr Pro Asp Trp Val Gln Ile Gly Asn Glu Thr
        130                 135                 140 agc aac ggc atg tta tgg gaa gat ggc aaa gca tct acc aac atg aaa    576
Ser Asn Gly Met Leu Trp Glu Asp Gly Lys Ala Ser Thr Asn Met Lys
    145                 150                 155 aac tat gcg tgg ctg gta aac aca ggc cat aat gca gtg aaa tcc ctg    624
Asn Tyr Ala Trp Leu Val Asn Thr Gly His Asn Ala Val Lys Ser Leu
160                 165                 170                 175 agc agc ggc acc aaa acc att gtg cat ctg gca ggt gga gat gat aac    672
Ser Ser Gly Thr Lys Thr Ile Val His Leu Ala Gly Gly Asp Asp Asn
                180                 185                 190 gcc ctc tat gta tgg aat att gga ggc ctg atc aat aac gga gcc aac    720
Ala Leu Tyr Val Trp Asn Ile Gly Gly Leu Ile Asn Asn Gly Ala Asn
            195                 200                 205 ttt gac atg att gcg atg tcc ctc tac cct tcg gct tcc ggc tgg aac    768
Phe Asp Met Ile Ala Met Ser Leu Tyr Pro Ser Ala Ser Gly Trp Asn
        210                 215                 220 aca gct gtg acg aat aca gta aac aat gcc aag gat atg atc aac cgt    816
Thr Ala Val Thr Asn Thr Val Asn Asn Ala Lys Asp Met Ile Asn Arg
    225                 230                 235 tat ggc aaa gag atc att atc tcc gaa att ggt atg gac aat aac cag    864
Tyr Gly Lys Glu Ile Ile Ile Ser Glu Ile Gly Met Asp Asn Asn Gln
240                 245                 250                 255 gct gca gct ggt aaa agt ttt gtt gcg gcg atg aaa aac caa atc cgc    912
Ala Ala Ala Gly Lys Ser Phe Val Ala Ala Met Lys Asn Gln Ile Arg
                260                 265                 270 aat ctg ccg aat ggt aaa ggc aaa ggc gta ttc tac tgg gag cct cag    960
Asn Leu Pro Asn Gly Lys Gly Lys Gly Val Phe Tyr Trp Glu Pro Gln
            275                 280                 285 gct aca cca gga tac aac agc ggc tat ggc aaa ggt gca tgg caa tcg   1008
Ala Thr Pro Gly Tyr Asn Ser Gly Tyr Gly Lys Gly Ala Trp Gln Ser
        290                 295                 300 aat atg atg ccg acg gta gtc atg gaa gga ttt att gac tag             1050
Asn Met Met Pro Thr Val Val Met Glu Gly Phe Ile Asp
    305                 310                 315

<210> SEQ ID NO 34
<211> LENGTH: 349
<212> TYPE: PRT
<213> ORGANISM: Paenibacillus xylanexedens

<400> SEQUENCE: 34

Met Phe Lys Asn Val Arg Gly Phe Arg Ile Ser Ile Met Leu Ala Phe
             -30                 -25                 -20

Val Leu Leu Phe Thr Ser Ile Met Leu Pro Ala Gly Gln His Ala Ser
        -15                 -10                  -5
```

```
Ala Ala Pro Ser Phe Ala Lys Gly Ala Asp Ile Ser Trp Val Pro Gly
 -1   1               5                  10                  15

Met Glu Ala Gln Gly Tyr Lys Trp Lys Asp Lys Asn Gly Val Gln Arg
                 20                  25                  30

Asp Ile Ile Asp Ile Leu Lys Asn Asp Tyr Gln Ile Asn Ser Val Arg
             35                  40                  45

Ile Arg Val Phe Val Asn Pro Ser Asn Asp Tyr Gly Asn Gly Tyr Met
         50                  55                  60

Asn Lys Asp Arg Ala Ala Leu Ala Gln Arg Ala Lys Asn Ala Gly
 65                  70                  75

Met Ser Val Met Leu Thr Leu His Tyr Ser Asp Ser Trp Ala Asp Pro
 80                  85                  90                  95

Gly Gln Gln Thr Lys Pro Ala Ala Trp Lys Asn Tyr Thr Phe Gln Gln
                100                 105                 110

Leu Met Asp Ala Val Trp Asn His Thr Arg Asp Val Met Thr Ala Met
                115                 120                 125

Gln Ser Lys Gly Val Thr Pro Asp Trp Val Gln Ile Gly Asn Glu Thr
            130                 135                 140

Ser Asn Gly Met Leu Trp Glu Asp Gly Lys Ala Ser Thr Asn Met Lys
145                 150                 155

Asn Tyr Ala Trp Leu Val Asn Thr Gly His Asn Ala Val Lys Ser Leu
160                 165                 170                 175

Ser Ser Gly Thr Lys Thr Ile Val His Leu Ala Gly Asp Asp Asn
                180                 185                 190

Ala Leu Tyr Val Trp Asn Ile Gly Gly Leu Ile Asn Asn Gly Ala Asn
            195                 200                 205

Phe Asp Met Ile Ala Met Ser Leu Tyr Pro Ser Ala Ser Gly Trp Asn
210                 215                 220

Thr Ala Val Thr Asn Thr Val Asn Asn Ala Lys Asp Met Ile Asn Arg
225                 230                 235

Tyr Gly Lys Glu Ile Ile Ile Ser Glu Ile Gly Met Asp Asn Asn Gln
240                 245                 250                 255

Ala Ala Ala Gly Lys Ser Phe Val Ala Ala Met Lys Asn Gln Ile Arg
            260                 265                 270

Asn Leu Pro Asn Gly Lys Gly Lys Gly Val Phe Tyr Trp Glu Pro Gln
            275                 280                 285

Ala Thr Pro Gly Tyr Asn Ser Gly Tyr Gly Lys Gly Ala Trp Gln Ser
            290                 295                 300

Asn Met Met Pro Thr Val Val Met Glu Gly Phe Ile Asp
305                 310                 315
```

<210> SEQ ID NO 35
<211> LENGTH: 316
<212> TYPE: PRT
<213> ORGANISM: Paenibacillus xylanexedens
<220> FEATURE:
<221> NAME/KEY: mat_peptide
<222> LOCATION: (1)..(316)

<400> SEQUENCE: 35

```
Ala Pro Ser Phe Ala Lys Gly Ala Asp Ile Ser Trp Val Pro Gly Met
 1               5                  10                  15

Glu Ala Gln Gly Tyr Lys Trp Lys Asp Lys Asn Gly Val Gln Arg Asp
             20                  25                  30

Ile Ile Asp Ile Leu Lys Asn Asp Tyr Gln Ile Asn Ser Val Arg Ile
         35                  40                  45
```

```
Arg Val Phe Val Asn Pro Ser Asn Asp Tyr Gly Asn Gly Tyr Met Asn
         50                  55                  60

Lys Asp Arg Ala Ala Ala Leu Ala Gln Arg Ala Lys Asn Ala Gly Met
 65                  70                  75                  80

Ser Val Met Leu Thr Leu His Tyr Ser Asp Ser Trp Ala Asp Pro Gly
                 85                  90                  95

Gln Gln Thr Lys Pro Ala Ala Trp Lys Asn Tyr Thr Phe Gln Gln Leu
                100                 105                 110

Met Asp Ala Val Trp Asn His Thr Arg Asp Val Met Thr Ala Met Gln
                115                 120                 125

Ser Lys Gly Val Thr Pro Asp Trp Val Gln Ile Gly Asn Glu Thr Ser
130                 135                 140

Asn Gly Met Leu Trp Glu Asp Gly Lys Ala Ser Thr Asn Met Lys Asn
145                 150                 155                 160

Tyr Ala Trp Leu Val Asn Thr Gly His Asn Ala Val Lys Ser Leu Ser
                165                 170                 175

Ser Gly Thr Lys Thr Ile Val His Leu Ala Gly Gly Asp Asp Asn Ala
                180                 185                 190

Leu Tyr Val Trp Asn Ile Gly Gly Leu Ile Asn Asn Gly Ala Asn Phe
                195                 200                 205

Asp Met Ile Ala Met Ser Leu Tyr Pro Ser Ala Ser Gly Trp Asn Thr
                210                 215                 220

Ala Val Thr Asn Thr Val Asn Asn Ala Lys Asp Met Ile Asn Arg Tyr
225                 230                 235                 240

Gly Lys Glu Ile Ile Ile Ser Glu Ile Gly Met Asp Asn Asn Gln Ala
                245                 250                 255

Ala Ala Gly Lys Ser Phe Val Ala Ala Met Lys Asn Gln Ile Arg Asn
                260                 265                 270

Leu Pro Asn Gly Lys Gly Lys Gly Val Phe Tyr Trp Glu Pro Gln Ala
                275                 280                 285

Thr Pro Gly Tyr Asn Ser Gly Tyr Gly Lys Gly Ala Trp Gln Ser Asn
                290                 295                 300

Met Met Pro Thr Val Val Met Glu Gly Phe Ile Asp
305                 310                 315

<210> SEQ ID NO 36
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 36

His His His His His His Pro Arg Ala Pro Ser Phe Ala Lys Gly Ala
  1               5                  10                  15

Asp Ile Ser Trp Val Pro Gly Met Glu Ala Gln Gly Tyr Lys Trp Lys
                 20                  25                  30

Asp Lys Asn Gly Val Gln Arg Asp Ile Ile Asp Ile Leu Lys Asn Asp
                 35                  40                  45

Tyr Gln Ile Asn Ser Val Arg Ile Arg Val Phe Val Asn Pro Ser Asn
         50                  55                  60

Asp Tyr Gly Asn Gly Tyr Met Asn Lys Asp Arg Ala Ala Ala Leu Ala
 65                  70                  75                  80
```

```
Gln Arg Ala Lys Asn Ala Gly Met Ser Val Met Leu Thr Leu His Tyr
             85                  90                  95

Ser Asp Ser Trp Ala Asp Pro Gly Gln Gln Thr Lys Pro Ala Ala Trp
        100                 105                 110

Lys Asn Tyr Thr Phe Gln Gln Leu Met Asp Ala Val Trp Asn His Thr
    115                 120                 125

Arg Asp Val Met Thr Ala Met Gln Ser Lys Gly Val Thr Pro Asp Trp
130                 135                 140

Val Gln Ile Gly Asn Glu Thr Ser Asn Gly Met Leu Trp Glu Asp Gly
145                 150                 155                 160

Lys Ala Ser Thr Asn Met Lys Asn Tyr Ala Trp Leu Val Asn Thr Gly
                165                 170                 175

His Asn Ala Val Lys Ser Leu Ser Ser Gly Thr Lys Thr Ile Val His
            180                 185                 190

Leu Ala Gly Gly Asp Asp Asn Ala Leu Tyr Val Trp Asn Ile Gly Gly
        195                 200                 205

Leu Ile Asn Asn Gly Ala Asn Phe Asp Met Ile Ala Met Ser Leu Tyr
210                 215                 220

Pro Ser Ala Ser Gly Trp Asn Thr Ala Val Thr Asn Thr Val Asn Asn
225                 230                 235                 240

Ala Lys Asp Met Ile Asn Arg Tyr Gly Lys Glu Ile Ile Ser Glu
                245                 250                 255

Ile Gly Met Asp Asn Asn Gln Ala Ala Ala Gly Lys Ser Phe Val Ala
            260                 265                 270

Ala Met Lys Asn Gln Ile Arg Asn Leu Pro Asn Gly Lys Gly Lys Gly
        275                 280                 285

Val Phe Tyr Trp Glu Pro Gln Ala Thr Pro Gly Tyr Asn Ser Gly Tyr
290                 295                 300

Gly Lys Gly Ala Trp Gln Ser Asn Met Met Pro Thr Val Val Met Glu
305                 310                 315                 320

Gly Phe Ile Asp

<210> SEQ ID NO 37
<211> LENGTH: 1044
<212> TYPE: DNA
<213> ORGANISM: Cohnella laeviribosi
<220> FEATURE:
<221> NAME/KEY: CDS
<222> LOCATION: (1)..(1041)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1041)

<400> SEQUENCE: 37 atg aaa aga aaa acg ttc gga tgg ctg ttg acg gcg ctg ctc ggt ttg      48
Met Lys Arg Lys Thr Phe Gly Trp Leu Leu Thr Ala Leu Leu Gly Leu
    -30                 -25                 -20 acc ctg gcg ctc ggc aac gcc gtg tct ccc ggc gac gcg aaa gcc gcc      96
Thr Leu Ala Leu Gly Asn Ala Val Ser Pro Gly Asp Ala Lys Ala Ala
-15                 -10                  -5                 -1  1 ccg gca ttt gcg aaa ggc gcg gac atc agc tgg gtt ccg ggc atg gag     144
Pro Ala Phe Ala Lys Gly Ala Asp Ile Ser Trp Val Pro Gly Met Glu
                5                  10                  15 gcg caa ggg tac aaa tgg aag gac aaa aac ggc gtg cag cgg gac atc     192
Ala Gln Gly Tyr Lys Trp Lys Asp Lys Asn Gly Val Gln Arg Asp Ile
```

```
                  20                  25                  30
att gat att tta aag cag gat tac cag atc aac tcc gtc cgg atc cgc         240
Ile Asp Ile Leu Lys Gln Asp Tyr Gln Ile Asn Ser Val Arg Ile Arg
 35                  40                  45 gtg ttt gtc aat ccg tca agc gat tac ggc aac ggc tac ttg aac aag         288
Val Phe Val Asn Pro Ser Ser Asp Tyr Gly Asn Gly Tyr Leu Asn Lys
 50                  55                  60                  65 gaa cgc gcg gcc gac ttg gcc cag cgg gcg aaa aac gcc ggc atg agc         336
Glu Arg Ala Ala Asp Leu Ala Gln Arg Ala Lys Asn Ala Gly Met Ser
                 70                  75                  80 gtc atg ctg acg ctg cac tac agc gat tcg tgg gcg gac ccc ggc aag         384
Val Met Leu Thr Leu His Tyr Ser Asp Ser Trp Ala Asp Pro Gly Lys
                     85                  90                  95 caa acc aag ccg gcc gcg tgg caa aat tat acg ttc gag caa ttg atg         432
Gln Thr Lys Pro Ala Ala Trp Gln Asn Tyr Thr Phe Glu Gln Leu Met
                         100                 105                 110 gac gcc gta tgg aac tgg acg cgc gat gtg atg acg acg atg cag agc         480
Asp Ala Val Trp Asn Trp Thr Arg Asp Val Met Thr Thr Met Gln Ser
            115                 120                 125 aga ggc gtt acg ccg gac tgg gtg cag atc ggc aac gag acg aac aac         528
Arg Gly Val Thr Pro Asp Trp Val Gln Ile Gly Asn Glu Thr Asn Asn
130                 135                 140                 145 ggc atg ctg tgg gat gac ggc aag gcg tcc gtc aac atg cgt aat tac         576
Gly Met Leu Trp Asp Asp Gly Lys Ala Ser Val Asn Met Arg Asn Tyr
                150                 155                 160 gcc tgg ctc gtc aat acc ggc aac aat gcg gtc aag tcg atc agc agc         624
Ala Trp Leu Val Asn Thr Gly Asn Asn Ala Val Lys Ser Ile Ser Ser
                    165                 170                 175 tcc acg aag acg atc gtc cat ctt tcc aac ggc tac gac aat tcg ctg         672
Ser Thr Lys Thr Ile Val His Leu Ser Asn Gly Tyr Asp Asn Ser Leu
                        180                 185                 190 ttc gtc tgg aac atc ggt ggg ctg atc agc aac ggc gcg acg ttt gac         720
Phe Val Trp Asn Ile Gly Gly Leu Ile Ser Asn Gly Ala Thr Phe Asp
            195                 200                 205 att atc ggc atg tcg ctg tac ccg tcc gcg tcc gac tgg cag acg aag         768
Ile Ile Gly Met Ser Leu Tyr Pro Ser Ala Ser Asp Trp Gln Thr Lys
210                 215                 220                 225 gtc aat cag acg atc agc aac gcg aac gat ctg att tcg cgc tac ggc         816
Val Asn Gln Thr Ile Ser Asn Ala Asn Asp Leu Ile Ser Arg Tyr Gly
                230                 235                 240 aag agc atc atg atc tcc gaa atc ggc atg gac tac aac cag cct tcg         864
Lys Ser Ile Met Ile Ser Glu Ile Gly Met Asp Tyr Asn Gln Pro Ser
                    245                 250                 255 gcc gcg aag agc ttc atc tcc gac atc aag acg aag gtc cgg aat ctt         912
Ala Ala Lys Ser Phe Ile Ser Asp Ile Lys Thr Lys Val Arg Asn Leu
                        260                 265                 270 tcc gga ggc aaa ggg ctt ggc gtg ttt tat tgg gag ccc gag gct acc         960
Ser Gly Gly Lys Gly Leu Gly Val Phe Tyr Trp Glu Pro Glu Ala Thr
            275                 280                 285 ccc ggc tac aac ggc ggc tac aac aag ggc gcc tgg cag tcc gac atg        1008
Pro Gly Tyr Asn Gly Gly Tyr Asn Lys Gly Ala Trp Gln Ser Asp Met
290                 295                 300                 305 aag ccg acg atc gcg ctg gaa ggc ttc ctg aac tga                        1044
Lys Pro Thr Ile Ala Leu Glu Gly Phe Leu Asn
                310                 315

<210> SEQ ID NO 38
<211> LENGTH: 347
<212> TYPE: PRT
<213> ORGANISM: Cohnella laeviribosi
```

<400> SEQUENCE: 38

```
Met Lys Arg Lys Thr Phe Gly Trp Leu Leu Thr Ala Leu Leu Gly Leu
-30                 -25                 -20
Thr Leu Ala Leu Gly Asn Ala Val Ser Pro Gly Asp Ala Lys Ala Ala
-15                 -10                  -5                  -1   1
Pro Ala Phe Ala Lys Gly Ala Asp Ile Ser Trp Val Pro Gly Met Glu
                 5                  10                  15
Ala Gln Gly Tyr Lys Trp Lys Asp Lys Asn Gly Val Gln Arg Asp Ile
             20                  25                  30
Ile Asp Ile Leu Lys Gln Asp Tyr Gln Ile Asn Ser Val Arg Ile Arg
         35                  40                  45
Val Phe Val Asn Pro Ser Ser Asp Tyr Gly Asn Gly Tyr Leu Asn Lys
50                  55                  60                  65
Glu Arg Ala Ala Asp Leu Ala Gln Arg Ala Lys Asn Ala Gly Met Ser
                 70                  75                  80
Val Met Leu Thr Leu His Tyr Ser Asp Ser Trp Ala Asp Pro Gly Lys
             85                  90                  95
Gln Thr Lys Pro Ala Ala Trp Gln Asn Tyr Thr Phe Glu Gln Leu Met
            100                 105                 110
Asp Ala Val Trp Asn Trp Thr Arg Asp Val Met Thr Thr Met Gln Ser
        115                 120                 125
Arg Gly Val Thr Pro Asp Trp Val Gln Ile Gly Asn Glu Thr Asn Asn
130                 135                 140                 145
Gly Met Leu Trp Asp Asp Gly Lys Ala Ser Val Asn Met Arg Asn Tyr
                150                 155                 160
Ala Trp Leu Val Asn Thr Gly Asn Asn Ala Val Lys Ser Ile Ser Ser
            165                 170                 175
Ser Thr Lys Thr Ile Val His Leu Ser Asn Gly Tyr Asp Asn Ser Leu
        180                 185                 190
Phe Val Trp Asn Ile Gly Gly Leu Ile Ser Asn Gly Ala Thr Phe Asp
    195                 200                 205
Ile Ile Gly Met Ser Leu Tyr Pro Ser Ala Ser Asp Trp Gln Thr Lys
210                 215                 220                 225
Val Asn Gln Thr Ile Ser Asn Ala Asn Asp Leu Ile Ser Arg Tyr Gly
                230                 235                 240
Lys Ser Ile Met Ile Ser Glu Ile Gly Met Asp Tyr Asn Gln Pro Ser
            245                 250                 255
Ala Ala Lys Ser Phe Ile Ser Asp Ile Lys Thr Lys Val Arg Asn Leu
        260                 265                 270
Ser Gly Gly Lys Gly Leu Gly Val Phe Tyr Trp Glu Pro Glu Ala Thr
    275                 280                 285
Pro Gly Tyr Asn Gly Gly Tyr Asn Lys Gly Ala Trp Gln Ser Asp Met
290                 295                 300                 305
Lys Pro Thr Ile Ala Leu Glu Gly Phe Leu Asn
                310                 315
```

<210> SEQ ID NO 39
<211> LENGTH: 316
<212> TYPE: PRT
<213> ORGANISM: Cohnella laeviribosi
<220> FEATURE:
<221> NAME/KEY: mat_peptide
<222> LOCATION: (1)..(316)

<400> SEQUENCE: 39

-continued

```
Ala Pro Ala Phe Ala Lys Gly Ala Asp Ile Ser Trp Val Pro Gly Met
1               5                   10                  15

Glu Ala Gln Gly Tyr Lys Trp Lys Asp Lys Asn Gly Val Gln Arg Asp
            20                  25                  30

Ile Ile Asp Ile Leu Lys Gln Asp Tyr Gln Ile Asn Ser Val Arg Ile
        35                  40                  45

Arg Val Phe Val Asn Pro Ser Ser Asp Tyr Gly Asn Gly Tyr Leu Asn
    50                  55                  60

Lys Glu Arg Ala Ala Asp Leu Ala Gln Arg Ala Lys Asn Ala Gly Met
65                  70                  75                  80

Ser Val Met Leu Thr Leu His Tyr Ser Asp Ser Trp Ala Asp Pro Gly
                85                  90                  95

Lys Gln Thr Lys Pro Ala Ala Trp Gln Asn Tyr Thr Phe Glu Gln Leu
            100                 105                 110

Met Asp Ala Val Trp Asn Trp Thr Arg Asp Val Met Thr Thr Met Gln
        115                 120                 125

Ser Arg Gly Val Thr Pro Asp Trp Val Gln Ile Gly Asn Glu Thr Asn
    130                 135                 140

Asn Gly Met Leu Trp Asp Gly Lys Ala Ser Val Asn Met Arg Asn
145                 150                 155                 160

Tyr Ala Trp Leu Val Asn Thr Gly Asn Asn Ala Val Lys Ser Ile Ser
                165                 170                 175

Ser Ser Thr Lys Thr Ile Val His Leu Ser Asn Gly Tyr Asp Asn Ser
            180                 185                 190

Leu Phe Val Trp Asn Ile Gly Gly Leu Ile Ser Asn Gly Ala Thr Phe
        195                 200                 205

Asp Ile Ile Gly Met Ser Leu Tyr Pro Ser Ala Ser Asp Trp Gln Thr
    210                 215                 220

Lys Val Asn Gln Thr Ile Ser Asn Ala Asn Asp Leu Ile Ser Arg Tyr
225                 230                 235                 240

Gly Lys Ser Ile Met Ile Ser Glu Ile Gly Met Asp Tyr Asn Gln Pro
                245                 250                 255

Ser Ala Ala Lys Ser Phe Ile Ser Asp Ile Lys Thr Lys Val Arg Asn
            260                 265                 270

Leu Ser Gly Gly Lys Gly Leu Gly Val Phe Tyr Trp Glu Pro Glu Ala
        275                 280                 285

Thr Pro Gly Tyr Asn Gly Gly Tyr Asn Lys Gly Ala Trp Gln Ser Asp
    290                 295                 300

Met Lys Pro Thr Ile Ala Leu Glu Gly Phe Leu Asn
305                 310                 315
```

<210> SEQ ID NO 40
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 40

```
His His His His His His Pro Arg Ala Pro Ala Phe Ala Lys Gly Ala
1               5                   10                  15

Asp Ile Ser Trp Val Pro Gly Met Glu Ala Gln Gly Tyr Lys Trp Lys
            20                  25                  30
```

```
Asp Lys Asn Gly Val Gln Arg Asp Ile Ile Asp Ile Leu Lys Gln Asp
         35                  40                  45

Tyr Gln Ile Asn Ser Val Arg Ile Arg Val Phe Val Asn Pro Ser Ser
 50                  55                  60

Asp Tyr Gly Asn Gly Tyr Leu Asn Lys Glu Arg Ala Ala Asp Leu Ala
 65                  70                  75                  80

Gln Arg Ala Lys Asn Ala Gly Met Ser Val Met Leu Thr Leu His Tyr
                 85                  90                  95

Ser Asp Ser Trp Ala Asp Pro Gly Lys Gln Thr Lys Pro Ala Ala Trp
                100                 105                 110

Gln Asn Tyr Thr Phe Glu Gln Leu Met Asp Ala Val Trp Asn Trp Thr
            115                 120                 125

Arg Asp Val Met Thr Thr Met Gln Ser Arg Gly Val Thr Pro Asp Trp
130                 135                 140

Val Gln Ile Gly Asn Glu Thr Asn Asn Gly Met Leu Trp Asp Asp Gly
145                 150                 155                 160

Lys Ala Ser Val Asn Met Arg Asn Tyr Ala Trp Leu Val Asn Thr Gly
                165                 170                 175

Asn Asn Ala Val Lys Ser Ile Ser Ser Thr Lys Thr Ile Val His
            180                 185                 190

Leu Ser Asn Gly Tyr Asp Asn Ser Leu Phe Val Trp Asn Ile Gly Gly
            195                 200                 205

Leu Ile Ser Asn Gly Ala Thr Phe Asp Ile Ile Gly Met Ser Leu Tyr
210                 215                 220

Pro Ser Ala Ser Asp Trp Gln Thr Lys Val Asn Gln Thr Ile Ser Asn
225                 230                 235                 240

Ala Asn Asp Leu Ile Ser Arg Tyr Gly Lys Ser Ile Met Ile Ser Glu
                245                 250                 255

Ile Gly Met Asp Tyr Asn Gln Pro Ser Ala Ala Lys Ser Phe Ile Ser
            260                 265                 270

Asp Ile Lys Thr Lys Val Arg Asn Leu Ser Gly Gly Lys Gly Leu Gly
            275                 280                 285

Val Phe Tyr Trp Glu Pro Glu Ala Thr Pro Gly Tyr Asn Gly Gly Tyr
290                 295                 300

Asn Lys Gly Ala Trp Gln Ser Asp Met Lys Pro Thr Ile Ala Leu Glu
305                 310                 315                 320

Gly Phe Leu Asn

<210> SEQ ID NO 41
<211> LENGTH: 2058
<212> TYPE: DNA
<213> ORGANISM: Paenibacillus sp-18026
<220> FEATURE:
<221> NAME/KEY: CDS
<222> LOCATION: (1)..(2055)
<220> FEATURE:
<221> NAME/KEY: mat_peptide
<222> LOCATION: (1)..(2055)

<400> SEQUENCE: 41 atg acg aag caa cat gca ccc att agc agc aag ctt ccc gtc ctc atg      48
Met Thr Lys Gln His Ala Pro Ile Ser Ser Lys Leu Pro Val Leu Met
 1               5                  10                  15 cat ggg gcg gac tat aac ccg gat cag tgg ctg cac gac ccg gca gtg      96
His Gly Ala Asp Tyr Asn Pro Asp Gln Trp Leu His Asp Pro Ala Val
            20                  25                  30
```

-continued

| | | |
|---|---|---|
| ctg gag gag gac atc cgt ctg atg aag ctg gcg ggc tgc aat gtc atg<br>Leu Glu Glu Asp Ile Arg Leu Met Lys Leu Ala Gly Cys Asn Val Met<br>35                         40                      45 | | 144 |
| gcc gtc ggt att ttc tca tgg gcg gct ttg gag cct gcg gag ggc agc<br>Ala Val Gly Ile Phe Ser Trp Ala Ala Leu Glu Pro Ala Glu Gly Ser<br>    50                      55                      60 | | 192 |
| ttt acg ttc gaa tgg ctg gat ggg gta ctg aac cgt ttt gct gag aat<br>Phe Thr Phe Glu Trp Leu Asp Gly Val Leu Asn Arg Phe Ala Glu Asn<br>65                         70                      75                 80 | | 240 |
| gga atc tat gcg tgg ctg gcg aca ccg agc gga gcg cgt ccg gcc tgg<br>Gly Ile Tyr Ala Trp Leu Ala Thr Pro Ser Gly Ala Arg Pro Ala Trp<br>                      85                      90                      95 | | 288 |
| atg tcg gag aaa tac ccg gag gtc aga cgc gtg gag gcc aac cgg gtg<br>Met Ser Glu Lys Tyr Pro Glu Val Arg Arg Val Glu Ala Asn Arg Val<br>                    100                    105                    110 | | 336 |
| cgc aat ctg cac ggc atg cgt cac aac cac tgc tat aca tcg ccg gtg<br>Arg Asn Leu His Gly Met Arg His Asn His Cys Tyr Thr Ser Pro Val<br>               115                    120                    125 | | 384 |
| tac cgt gag aaa acg gca atc atc aat gcc aag ctg gcg gag cgc tac<br>Tyr Arg Glu Lys Thr Ala Ile Ile Asn Ala Lys Leu Ala Glu Arg Tyr<br>130                       135                    140 | | 432 |
| ggc agc cat ccg gcc gtc atc ggc tgg cat atc tcc aat gaa ttc ggc<br>Gly Ser His Pro Ala Val Ile Gly Trp His Ile Ser Asn Glu Phe Gly<br>145                       150                    155                    160 | | 480 |
| ggc gac tgc cac tgc gat tac tgc cag gat gcg ttc cgc ggg tgg ctg<br>Gly Asp Cys His Cys Asp Tyr Cys Gln Asp Ala Phe Arg Gly Trp Leu<br>                       165                    170                    175 | | 528 |
| cag aag aaa tat gga acg ctg gaa gca ctc aat atg gcg tgg tgg acg<br>Gln Lys Lys Tyr Gly Thr Leu Glu Ala Leu Asn Met Ala Trp Trp Thr<br>                    180                    185                    190 | | 576 |
| tcc ttc tgg gcg cat aca tac acg gat tgg agc cag gtg gaa tca ccg<br>Ser Phe Trp Ala His Thr Tyr Thr Asp Trp Ser Gln Val Glu Ser Pro<br>               195                    200                    205 | | 624 |
| gcc cgc cat ggc gaa atg atg gtg cac ggc cat aat ctg gat tgg cgc<br>Ala Arg His Gly Glu Met Met Val His Gly His Asn Leu Asp Trp Arg<br>210                       215                    220 | | 672 |
| cga ttt gtg acg gat caa acc gta gac ttc tgc cgg cat gag atc gat<br>Arg Phe Val Thr Asp Gln Thr Val Asp Phe Cys Arg His Glu Ile Asp<br>225                       230                    235                    240 | | 720 |
| gcg gtg cgc ggc gcg aat tct tcg ctg ccg gtc acg acg aat atg cac<br>Ala Val Arg Gly Ala Asn Ser Ser Leu Pro Val Thr Thr Asn Met His<br>                       245                    250                    255 | | 768 |
| atg atc gaa gga ctg gat tac cgg aag ttc tcc gag atc ctg gac gtc<br>Met Ile Glu Gly Leu Asp Tyr Arg Lys Phe Ser Glu Ile Leu Asp Val<br>                    260                    265                    270 | | 816 |
| atc tcc tgg gat gcg tac ccg acc tgg cat gag cac aag gac gac agc<br>Ile Ser Trp Asp Ala Tyr Pro Thr Trp His Glu His Lys Asp Asp Ser<br>               275                    280                    285 | | 864 |
| cag ctg gcg gcg tct gtg gcg ttc tac cac gac ctg tac cgc tcg ctg<br>Gln Leu Ala Ala Ser Val Ala Phe Tyr His Asp Leu Tyr Arg Ser Leu<br>290                       295                    300 | | 912 |
| aag caa aag ccg ttt ctg ctg atg gag agc acg cca tcg ctg acg aac<br>Lys Gln Lys Pro Phe Leu Leu Met Glu Ser Thr Pro Ser Leu Thr Asn<br>305                       310                    315                    320 | | 960 |
| tgg cag ccg gta agc aag ctg aag cag ccg ggc atg cac cag ctg tcc<br>Trp Gln Pro Val Ser Lys Leu Lys Gln Pro Gly Met His Gln Leu Ser<br>                       325                    330                    335 | | 1008 |
| tcg ctg cag gcg att gcg cac ggc tcg gat tcc gtc caa tat ttt cag<br>Ser Leu Gln Ala Ile Ala His Gly Ser Asp Ser Val Gln Tyr Phe Gln<br>                    340                    345                    350 | | 1056 |

| | | |
|---|---|---|
| tgg cgc aaa agc cgc ggc tcc agt gag aag ttc cac ggc gcg gtg gtc<br>Trp Arg Lys Ser Arg Gly Ser Ser Glu Lys Phe His Gly Ala Val Val<br>            355                  360                  365 | | 1104 |
| gac cat gcg ggt cat gcg cat acg cgc gta ttc cgc gat gtg gcc cat<br>Asp His Ala Gly His Ala His Thr Arg Val Phe Arg Asp Val Ala His<br>370                  375                  380 | | 1152 |
| ctg ggg caa atg ctg gcg aat ata tcc gaa gtc gcc gga aca gcc aca<br>Leu Gly Gln Met Leu Ala Asn Ile Ser Glu Val Ala Gly Thr Ala Thr<br>385                  390                  395                  400 | | 1200 |
| ccg tcg gaa acg gcg att ctc ttc gat tgg gac aac cgc tgg gcc gtc<br>Pro Ser Glu Thr Ala Ile Leu Phe Asp Trp Asp Asn Arg Trp Ala Val<br>            405                  410                  415 | | 1248 |
| aag gat gcg cag ggg ccc cgt aat atg ggg atc cat tac gag gaa acc<br>Lys Asp Ala Gln Gly Pro Arg Asn Met Gly Ile His Tyr Glu Glu Thr<br>                  420                  425                  430 | | 1296 |
| gtg tat gcc cat cac cgg gcg ctg tgg cag cag ggc atc gca gcc gat<br>Val Tyr Ala His His Arg Ala Leu Trp Gln Gln Gly Ile Ala Ala Asp<br>            435                  440                  445 | | 1344 |
| gtg att ggc tca gag gac ggc ttt gca ggc tac aag ctg atc att gcc<br>Val Ile Gly Ser Glu Asp Gly Phe Ala Gly Tyr Lys Leu Ile Ile Ala<br>450                  455                  460 | | 1392 |
| ccg atg ctg tat ctt tgc cgg gag gaa acc ggc cgg aag ctg gag cag<br>Pro Met Leu Tyr Leu Cys Arg Glu Glu Thr Gly Arg Lys Leu Glu Gln<br>465                  470                  475                  480 | | 1440 |
| ttt gtg gag cag ggc ggg acc ctc gtg tca acc tat tgg tct ggc gtt<br>Phe Val Glu Gln Gly Gly Thr Leu Val Ser Thr Tyr Trp Ser Gly Val<br>                  485                  490                  495 | | 1488 |
| gtc aac gag aac gat ttg tgc cat ctg ggc gga ttc cct gga ccg ctg<br>Val Asn Glu Asn Asp Leu Cys His Leu Gly Gly Phe Pro Gly Pro Leu<br>                  500                  505                  510 | | 1536 |
| cgg aag acg ctc ggc gta tgg gcc gag gag atc gag gga ttg tac gac<br>Arg Lys Thr Leu Gly Val Trp Ala Glu Glu Ile Glu Gly Leu Tyr Asp<br>            515                  520                  525 | | 1584 |
| cat gac cgc aac ggg gta tcg atg gcc gaa ggc aat ccg ctc gga ttg<br>His Asp Arg Asn Gly Val Ser Met Ala Glu Gly Asn Pro Leu Gly Leu<br>        530                  535                  540 | | 1632 |
| gcc ggc acc ttc gaa gcc cac gaa att tgc gag ctg atc cat acg gaa<br>Ala Gly Thr Phe Glu Ala His Glu Ile Cys Glu Leu Ile His Thr Glu<br>545                  550                  555                  560 | | 1680 |
| ggc gcg gag gtg ctg ggc gtg tac act gac agt ttc tat gcg ggc cgg<br>Gly Ala Glu Val Leu Gly Val Tyr Thr Asp Ser Phe Tyr Ala Gly Arg<br>                  565                  570                  575 | | 1728 |
| ccg gcg ctg acg ctg aac cgg ttc gga caa ggc cgg gcc tat cat atg<br>Pro Ala Leu Thr Leu Asn Arg Phe Gly Gln Gly Arg Ala Tyr His Met<br>                  580                  585                  590 | | 1776 |
| gcc acc cgg ctc aag gac gat ttc ctg ggg gcg ttc tac aag tcg gtc<br>Ala Thr Arg Leu Lys Asp Asp Phe Leu Gly Ala Phe Tyr Lys Ser Val<br>            595                  600                  605 | | 1824 |
| acc gag gaa gca gga ata tcc cgt gcg ctg cag acc gag ctg ccg cag<br>Thr Glu Glu Ala Gly Ile Ser Arg Ala Leu Gln Thr Glu Leu Pro Gln<br>        610                  615                  620 | | 1872 |
| ggg gtt agc gca cag gtg cgc acc aac gga aca acg gat tac gtg ttc<br>Gly Val Ser Ala Gln Val Arg Thr Asn Gly Thr Thr Asp Tyr Val Phe<br>625                  630                  635                  640 | | 1920 |
| ctg atg aac ttc agc ggc cgg gca cag cag gtc ctg ctg gac gaa cgc<br>Leu Met Asn Phe Ser Gly Arg Ala Gln Gln Val Leu Leu Asp Glu Arg<br>                  645                  650                  655 | | 1968 |
| gcc tac agc gat atg gaa tcc ggg gca ccc gca gac cgc aag ctg gag<br>Ala Tyr Ser Asp Met Glu Ser Gly Ala Pro Ala Asp Arg Lys Leu Glu | | 2016 |

```
                660               665               670
ctg ccg gtt aac ggc gtg aag ctg ttg aag cgg aac gct taa      2058
Leu Pro Val Asn Gly Val Lys Leu Leu Lys Arg Asn Ala
        675               680               685
```

<210> SEQ ID NO 42
<211> LENGTH: 685
<212> TYPE: PRT
<213> ORGANISM: Paenibacillus sp-18026

<400> SEQUENCE: 42

```
Met Thr Lys Gln His Ala Pro Ile Ser Ser Lys Leu Pro Val Leu Met
1               5                   10                  15

His Gly Ala Asp Tyr Asn Pro Asp Gln Trp Leu His Asp Pro Ala Val
            20                  25                  30

Leu Glu Glu Asp Ile Arg Leu Met Lys Leu Ala Gly Cys Asn Val Met
        35                  40                  45

Ala Val Gly Ile Phe Ser Trp Ala Ala Leu Glu Pro Ala Glu Gly Ser
    50                  55                  60

Phe Thr Phe Glu Trp Leu Asp Gly Val Leu Asn Arg Phe Ala Glu Asn
65                  70                  75                  80

Gly Ile Tyr Ala Trp Leu Ala Thr Pro Ser Gly Ala Arg Pro Ala Trp
                85                  90                  95

Met Ser Glu Lys Tyr Pro Glu Val Arg Arg Val Glu Ala Asn Arg Val
            100                 105                 110

Arg Asn Leu His Gly Met Arg His Asn His Cys Tyr Thr Ser Pro Val
        115                 120                 125

Tyr Arg Glu Lys Thr Ala Ile Ile Asn Ala Lys Leu Ala Glu Arg Tyr
    130                 135                 140

Gly Ser His Pro Ala Val Ile Gly Trp His Ile Ser Asn Glu Phe Gly
145                 150                 155                 160

Gly Asp Cys His Cys Asp Tyr Cys Gln Asp Ala Phe Arg Gly Trp Leu
                165                 170                 175

Gln Lys Lys Tyr Gly Thr Leu Glu Ala Leu Asn Met Ala Trp Trp Thr
            180                 185                 190

Ser Phe Trp Ala His Thr Tyr Thr Asp Trp Ser Gln Val Glu Ser Pro
        195                 200                 205

Ala Arg His Gly Glu Met Met Val His Gly His Asn Leu Asp Trp Arg
    210                 215                 220

Arg Phe Val Thr Asp Gln Thr Val Asp Phe Cys Arg His Glu Ile Asp
225                 230                 235                 240

Ala Val Arg Gly Ala Asn Ser Ser Leu Pro Val Thr Asn Met His
                245                 250                 255

Met Ile Glu Gly Leu Asp Tyr Arg Lys Phe Ser Glu Ile Leu Asp Val
            260                 265                 270

Ile Ser Trp Asp Ala Tyr Pro Thr Trp His Glu His Lys Asp Asp Ser
        275                 280                 285

Gln Leu Ala Ala Ser Val Ala Phe Tyr His Asp Leu Tyr Arg Ser Leu
    290                 295                 300

Lys Gln Lys Pro Phe Leu Leu Met Glu Ser Thr Pro Ser Leu Thr Asn
305                 310                 315                 320

Trp Gln Pro Val Ser Lys Leu Lys Gln Pro Gly Met His Gln Leu Ser
                325                 330                 335

Ser Leu Gln Ala Ile Ala His Gly Ser Asp Ser Val Gln Tyr Phe Gln
            340                 345                 350
```

```
Trp Arg Lys Ser Arg Gly Ser Glu Lys Phe His Gly Ala Val Val
        355                 360                 365

Asp His Ala Gly His Ala His Thr Arg Val Phe Arg Asp Val Ala His
        370                 375                 380

Leu Gly Gln Met Leu Ala Asn Ile Ser Glu Val Ala Gly Thr Ala Thr
385                 390                 395                 400

Pro Ser Glu Thr Ala Ile Leu Phe Asp Trp Asp Asn Arg Trp Ala Val
                405                 410                 415

Lys Asp Ala Gln Gly Pro Arg Asn Met Gly Ile His Tyr Glu Glu Thr
                420                 425                 430

Val Tyr Ala His His Arg Ala Leu Trp Gln Gln Gly Ile Ala Ala Asp
                435                 440                 445

Val Ile Gly Ser Glu Asp Gly Phe Ala Gly Tyr Lys Leu Ile Ile Ala
                450                 455                 460

Pro Met Leu Tyr Leu Cys Arg Glu Glu Thr Gly Arg Lys Leu Glu Gln
465                 470                 475                 480

Phe Val Glu Gln Gly Gly Thr Leu Val Ser Thr Tyr Trp Ser Gly Val
                485                 490                 495

Val Asn Glu Asn Asp Leu Cys His Leu Gly Gly Phe Pro Gly Pro Leu
                500                 505                 510

Arg Lys Thr Leu Gly Val Trp Ala Glu Glu Ile Glu Gly Leu Tyr Asp
                515                 520                 525

His Asp Arg Asn Gly Val Ser Met Ala Glu Gly Asn Pro Leu Gly Leu
                530                 535                 540

Ala Gly Thr Phe Glu Ala His Glu Ile Cys Glu Leu Ile His Thr Glu
545                 550                 555                 560

Gly Ala Glu Val Leu Gly Val Tyr Thr Asp Ser Phe Tyr Ala Gly Arg
                565                 570                 575

Pro Ala Leu Thr Leu Asn Arg Phe Gly Gln Gly Arg Ala Tyr His Met
                580                 585                 590

Ala Thr Arg Leu Lys Asp Asp Phe Leu Gly Ala Phe Tyr Lys Ser Val
                595                 600                 605

Thr Glu Glu Ala Gly Ile Ser Arg Ala Leu Gln Thr Glu Leu Pro Gln
        610                 615                 620

Gly Val Ser Ala Gln Val Arg Thr Asn Gly Thr Thr Asp Tyr Val Phe
625                 630                 635                 640

Leu Met Asn Phe Ser Gly Arg Ala Gln Gln Val Leu Leu Asp Glu Arg
                645                 650                 655

Ala Tyr Ser Asp Met Glu Ser Gly Ala Pro Ala Asp Arg Lys Leu Glu
                660                 665                 670

Leu Pro Val Asn Gly Val Lys Leu Leu Lys Arg Asn Ala
                675                 680                 685

<210> SEQ ID NO 43
<211> LENGTH: 2067
<212> TYPE: DNA
<213> ORGANISM: Bacillus pumilus
<220> FEATURE:
<221> NAME/KEY: CDS
<222> LOCATION: (1)..(2064)
<220> FEATURE:
<221> NAME/KEY: mat_peptide
<222> LOCATION: (1)..(2064)

<400> SEQUENCE: 43 atg gga aag cgt tac cca ctc gtt cac cca aat gtg aaa ggc ttt ttg       48
```

-continued

```
Met Gly Lys Arg Tyr Pro Leu Val His Pro Asn Val Lys Gly Phe Leu
 1               5                  10                  15 cat ggt ggc gat tat aat cca gat caa tgg ctc cat atg ccg gag atc          96
His Gly Gly Asp Tyr Asn Pro Asp Gln Trp Leu His Met Pro Glu Ile
             20                  25                  30 att gac gaa gat ttt cga tta atg aag ctt gca cac tgt caa aca ttc         144
Ile Asp Glu Asp Phe Arg Leu Met Lys Leu Ala His Cys Gln Thr Phe
             35                  40                  45 tcc atc aac att ttc gca tgg agt aag cta gag cca aaa gaa ggg cag         192
Ser Ile Asn Ile Phe Ala Trp Ser Lys Leu Glu Pro Lys Glu Gly Gln
 50                  55                  60 tat gat ttt gca tgg ctg gat gac atc atg gac cgc ttg gca gct cag         240
Tyr Asp Phe Ala Trp Leu Asp Asp Ile Met Asp Arg Leu Ala Ala Gln
 65                  70                  75                  80 ggg gct cac gcc att ctc gca acg cca agc ggg gca aga cct gct tgg         288
Gly Ala His Ala Ile Leu Ala Thr Pro Ser Gly Ala Arg Pro Ala Trp
                 85                  90                  95 ctg tca caa gca tat cca gag gta ttg cgc gtc gaa gcg aac cgt cag         336
Leu Ser Gln Ala Tyr Pro Glu Val Leu Arg Val Glu Ala Asn Arg Gln
                100                 105                 110 cgt aat tta cat gga ctg cgc cat aat cat tgc ttc acc tca ccg gtt         384
Arg Asn Leu His Gly Leu Arg His Asn His Cys Phe Thr Ser Pro Val
            115                 120                 125 tat cga gaa aaa acg aat aca ctc aac cgg ctg ctg gct gaa cgc tac         432
Tyr Arg Glu Lys Thr Asn Thr Leu Asn Arg Leu Leu Ala Glu Arg Tyr
            130                 135                 140 aag gat cat ccg gca ctg att atg tgg cac att tcg aat gag tac ggc         480
Lys Asp His Pro Ala Leu Ile Met Trp His Ile Ser Asn Glu Tyr Gly
145                 150                 155                 160 ggc gaa tgt cat tgt gat ctt tgc cag gaa gca ttt cgg gac tat ttg         528
Gly Glu Cys His Cys Asp Leu Cys Gln Glu Ala Phe Arg Asp Tyr Leu
                165                 170                 175 aaa gac aaa tac aat cat gac ctt gaa gtt ttg aat caa gca tgg tgg         576
Lys Asp Lys Tyr Asn His Asp Leu Glu Val Leu Asn Gln Ala Trp Trp
            180                 185                 190 acg ggt ttt tgg agc cac acg tat agt gac tgg tca caa atc gaa tca         624
Thr Gly Phe Trp Ser His Thr Tyr Ser Asp Trp Ser Gln Ile Glu Ser
            195                 200                 205 cct gca ccg cac ggg gag cac atg att cac ggg atg aac cta gac tgg         672
Pro Ala Pro His Gly Glu His Met Ile His Gly Met Asn Leu Asp Trp
210                 215                 220 aag cgc ttt gtc aca gcg caa acg atc aat ttt tat caa aat gaa att         720
Lys Arg Phe Val Thr Ala Gln Thr Ile Asn Phe Tyr Gln Asn Glu Ile
225                 230                 235                 240 gaa ccg ctg cgg gaa ttg acg cct cat atc cca gtg acc acc aac ttt         768
Glu Pro Leu Arg Glu Leu Thr Pro His Ile Pro Val Thr Thr Asn Phe
                245                 250                 255 atg ggc gac tac ccg cat atg cgc cca ttc ctt ggg ctg gat tat cat         816
Met Gly Asp Tyr Pro His Met Arg Pro Phe Leu Gly Leu Asp Tyr His
            260                 265                 270 caa ttt gca aaa gag gtc gac gtg att tca tgg gat agc tat cca gca         864
Gln Phe Ala Lys Glu Val Asp Val Ile Ser Trp Asp Ser Tyr Pro Ala
            275                 280                 285 tgg cat agc ggc agg gaa aca acc tcc gaa tta gcg tca aac gtc gcc         912
Trp His Ser Gly Arg Glu Thr Thr Ser Glu Leu Ala Ser Asn Val Ala
            290                 295                 300 ttc gtt cac gat tta tat cgt tca tta aag gac ggt cag cca ttt ctc         960
Phe Val His Asp Leu Tyr Arg Ser Leu Lys Asp Gly Gln Pro Phe Leu
305                 310                 315                 320
```

```
gtt atg gag agt aca ccg agc ctt gtg aac tgg cat gaa gtg aat aag    1008
Val Met Glu Ser Thr Pro Ser Leu Val Asn Trp His Glu Val Asn Lys
            325                 330                 335 gtc aaa cac aaa gga atg gca cac ctt tct gcc ata cag gcg att gcc    1056
Val Lys His Lys Gly Met Ala His Leu Ser Ala Ile Gln Ala Ile Ala
            340                 345                 350 cat gga tca gac tcc gtg ctt tac ttc cag tgg cgc caa ggc cga ggt    1104
His Gly Ser Asp Ser Val Leu Tyr Phe Gln Trp Arg Gln Gly Arg Gly
            355                 360                 365 gcc tcc gag aaa ttc cat ggc gcc gta gtt gat cat tcc gga cat gaa    1152
Ala Ser Glu Lys Phe His Gly Ala Val Val Asp His Ser Gly His Glu
        370                 375                 380 cat acg cgg gtg ttt caa gaa gtc gct gat cta gga aaa caa ttg gag    1200
His Thr Arg Val Phe Gln Glu Val Ala Asp Leu Gly Lys Gln Leu Glu
385                 390                 395                 400 cag ctg cag ccc att gcg ggc acg tcc gta caa cca gaa gtc gcc atc    1248
Gln Leu Gln Pro Ile Ala Gly Thr Ser Val Gln Pro Glu Val Ala Ile
                405                 410                 415 ata tac gat tgg gaa aac cac tgg gcc att gat gat gca caa ggc tta    1296
Ile Tyr Asp Trp Glu Asn His Trp Ala Ile Asp Asp Ala Gln Gly Leu
            420                 425                 430 aat aat aca aac aaa cgc tat gta gag gct tgt caa act cac tat cga    1344
Asn Asn Thr Asn Lys Arg Tyr Val Glu Ala Cys Gln Thr His Tyr Arg
            435                 440                 445 agc ttt tgg aaa aaa ggc atc cct gtt gac att gtc ggc atg gaa aag    1392
Ser Phe Trp Lys Lys Gly Ile Pro Val Asp Ile Val Gly Met Glu Lys
            450                 455                 460 gat ttc tca tcc tat cgt gtg ctg gtt gct cca atg ctc tac atg atc    1440
Asp Phe Ser Ser Tyr Arg Val Leu Val Ala Pro Met Leu Tyr Met Ile
465                 470                 475                 480 aaa cca ggc gtc gca gaa aaa atc gaa gcc ttt gtc aaa aag ggc ggt    1488
Lys Pro Gly Val Ala Glu Lys Ile Glu Ala Phe Val Lys Lys Gly Gly
                485                 490                 495 att ttt atc gcg aca tat tgg agc ggc atg gtc gac gaa aat gac cta    1536
Ile Phe Ile Ala Thr Tyr Trp Ser Gly Met Val Asp Glu Asn Asp Leu
            500                 505                 510 tgt ttc ctc ggt ggt ttc ccc ggc cct ctc cgt cat gta ctt ggc ata    1584
Cys Phe Leu Gly Gly Phe Pro Gly Pro Leu Arg His Val Leu Gly Ile
            515                 520                 525 tgg gct gag gaa atc aac aca ttg atg cca gat gaa cat gtg tta ata    1632
Trp Ala Glu Glu Ile Asn Thr Leu Met Pro Asp Glu His Val Leu Ile
    530                 535                 540 acc aca ggg aat gga cgc acc tac cat gtc ggg caa tat tgc gaa tcc    1680
Thr Thr Gly Asn Gly Arg Thr Tyr His Val Gly Gln Tyr Cys Glu Ser
545                 550                 555                 560 att cat cct gaa acg gcc tct gtg tta ggg cat ttt gag aat ggc tgc    1728
Ile His Pro Glu Thr Ala Ser Val Leu Gly His Phe Glu Asn Gly Cys
                565                 570                 575 tat gaa gga cag cca gcc ctt act gtt cat cct ttt gga gat gga aaa    1776
Tyr Glu Gly Gln Pro Ala Leu Thr Val His Pro Phe Gly Asp Gly Lys
            580                 585                 590 gca tac tat atg gct tcc gaa aat gag cag att ttt tat gat gag ttt    1824
Ala Tyr Tyr Met Ala Ser Glu Asn Glu Gln Ile Phe Tyr Asp Glu Phe
            595                 600                 605 tac gag gat ctc atc gca gga atg ggt ata cag ccc gtc cta tca tct    1872
Tyr Glu Asp Leu Ile Ala Gly Met Gly Ile Gln Pro Val Leu Ser Ser
610                 615                 620 gtc att cca gag gga gtt agt gta caa aaa cga aca gat ggc acg caa    1920
Val Ile Pro Glu Gly Val Ser Val Gln Lys Arg Thr Asp Gly Thr Gln
                625                 630                 635                 640
```

| | | | | | | | | | | | | | | | |
|---|---|---|---|---|---|---|---|---|---|---|---|---|---|---|---|
| gac | tat | gta | ttt | atg | atg | aat | ttt | aca | gaa | gag | ctg | cag | aac | ata | tca | 1968 |
| Asp | Tyr | Val | Phe | Met | Met | Asn | Phe | Thr | Glu | Glu | Leu | Gln | Asn | Ile | Ser | |
| | | | | 645 | | | | | 650 | | | | | 655 | | |
| cta | gat | tca | gcg | gaa | agc | tat | gaa | aat | atg | ctg | act | gaa | gag | cag | gtg | 2016 |
| Leu | Asp | Ser | Ala | Glu | Ser | Tyr | Glu | Asn | Met | Leu | Thr | Glu | Glu | Gln | Val | |
| | | | 660 | | | | | 665 | | | | | 670 | | | |
| cca | gac | cag | ctt | cag | ctt | gac | cct | tac | gag | tac | gtc | atc | ttg | aaa | aaa | 2064 |
| Pro | Asp | Gln | Leu | Gln | Leu | Asp | Pro | Tyr | Glu | Tyr | Val | Ile | Leu | Lys | Lys | |
| | | 675 | | | | | 680 | | | | | 685 | | | | |
| taa | | | | | | | | | | | | | | | | 2067 |

<210> SEQ ID NO 44
<211> LENGTH: 688
<212> TYPE: PRT
<213> ORGANISM: Bacillus pumilus

<400> SEQUENCE: 44

Met Gly Lys Arg Tyr Pro Leu Val His Pro Asn Val Lys Gly Phe Leu
1               5                   10                  15

His Gly Gly Asp Tyr Asn Pro Asp Gln Trp Leu His Met Pro Glu Ile
            20                  25                  30

Ile Asp Glu Asp Phe Arg Leu Met Lys Leu Ala His Cys Gln Thr Phe
        35                  40                  45

Ser Ile Asn Ile Phe Ala Trp Ser Lys Leu Glu Pro Lys Glu Gly Gln
    50                  55                  60

Tyr Asp Phe Ala Trp Leu Asp Asp Ile Met Asp Arg Leu Ala Ala Gln
65                  70                  75                  80

Gly Ala His Ala Ile Leu Ala Thr Pro Ser Gly Ala Arg Pro Ala Trp
                85                  90                  95

Leu Ser Gln Ala Tyr Pro Glu Val Leu Arg Val Glu Ala Asn Arg Gln
            100                 105                 110

Arg Asn Leu His Gly Leu Arg His Asn His Cys Phe Thr Ser Pro Val
        115                 120                 125

Tyr Arg Glu Lys Thr Asn Thr Leu Asn Arg Leu Leu Ala Glu Arg Tyr
    130                 135                 140

Lys Asp His Pro Ala Leu Ile Met Trp His Ile Ser Asn Glu Tyr Gly
145                 150                 155                 160

Gly Glu Cys His Cys Asp Leu Cys Gln Glu Ala Phe Arg Asp Tyr Leu
                165                 170                 175

Lys Asp Lys Tyr Asn His Asp Leu Glu Val Leu Asn Gln Ala Trp Trp
            180                 185                 190

Thr Gly Phe Trp Ser His Thr Tyr Ser Asp Trp Ser Gln Ile Glu Ser
        195                 200                 205

Pro Ala Pro His Gly Glu His Met Ile His Gly Met Asn Leu Asp Trp
    210                 215                 220

Lys Arg Phe Val Thr Ala Gln Thr Ile Asn Phe Tyr Gln Asn Glu Ile
225                 230                 235                 240

Glu Pro Leu Arg Glu Leu Thr Pro His Ile Pro Val Thr Thr Asn Phe
                245                 250                 255

Met Gly Asp Tyr Pro His Met Arg Pro Phe Leu Gly Leu Asp Tyr His
            260                 265                 270

Gln Phe Ala Lys Glu Val Asp Val Ile Ser Trp Asp Ser Tyr Pro Ala
        275                 280                 285

Trp His Ser Gly Arg Glu Thr Thr Ser Glu Leu Ala Ser Asn Val Ala
    290                 295                 300

Phe Val His Asp Leu Tyr Arg Ser Leu Lys Asp Gly Gln Pro Phe Leu
305                 310                 315                 320

Val Met Glu Ser Thr Pro Ser Leu Val Asn Trp His Glu Val Asn Lys
            325                 330                 335

Val Lys His Lys Gly Met Ala His Leu Ser Ala Ile Gln Ala Ile Ala
        340                 345                 350

His Gly Ser Asp Ser Val Leu Tyr Phe Gln Trp Arg Gln Gly Arg Gly
    355                 360                 365

Ala Ser Glu Lys Phe His Gly Ala Val Val Asp His Ser Gly His Glu
370                 375                 380

His Thr Arg Val Phe Gln Glu Val Ala Asp Leu Gly Lys Gln Leu Glu
385                 390                 395                 400

Gln Leu Gln Pro Ile Ala Gly Thr Ser Val Gln Pro Glu Val Ala Ile
            405                 410                 415

Ile Tyr Asp Trp Glu Asn His Trp Ala Ile Asp Asp Ala Gln Gly Leu
        420                 425                 430

Asn Asn Thr Asn Lys Arg Tyr Val Glu Ala Cys Gln Thr His Tyr Arg
    435                 440                 445

Ser Phe Trp Lys Lys Gly Ile Pro Val Asp Ile Val Gly Met Glu Lys
450                 455                 460

Asp Phe Ser Ser Tyr Arg Val Leu Val Ala Pro Met Leu Tyr Met Ile
465                 470                 475                 480

Lys Pro Gly Val Ala Glu Lys Ile Glu Ala Phe Val Lys Lys Gly Gly
            485                 490                 495

Ile Phe Ile Ala Thr Tyr Trp Ser Gly Met Val Asp Glu Asn Asp Leu
        500                 505                 510

Cys Phe Leu Gly Gly Phe Pro Gly Pro Leu Arg His Val Leu Gly Ile
    515                 520                 525

Trp Ala Glu Glu Ile Asn Thr Leu Met Pro Asp Glu His Val Leu Ile
530                 535                 540

Thr Thr Gly Asn Gly Arg Thr Tyr His Val Gly Gln Tyr Cys Glu Ser
545                 550                 555                 560

Ile His Pro Glu Thr Ala Ser Val Leu Gly His Phe Glu Asn Gly Cys
            565                 570                 575

Tyr Glu Gly Gln Pro Ala Leu Thr Val His Pro Phe Gly Asp Gly Lys
        580                 585                 590

Ala Tyr Tyr Met Ala Ser Glu Asn Glu Gln Ile Phe Tyr Asp Glu Phe
    595                 600                 605

Tyr Glu Asp Leu Ile Ala Gly Met Gly Ile Gln Pro Val Leu Ser Ser
610                 615                 620

Val Ile Pro Glu Gly Val Ser Val Gln Lys Arg Thr Asp Gly Thr Gln
625                 630                 635                 640

Asp Tyr Val Phe Met Met Asn Phe Thr Glu Glu Leu Gln Asn Ile Ser
            645                 650                 655

Leu Asp Ser Ala Glu Ser Tyr Glu Asn Met Leu Thr Glu Glu Gln Val
        660                 665                 670

Pro Asp Gln Leu Gln Leu Asp Pro Tyr Glu Tyr Val Ile Leu Lys Lys
    675                 680                 685

<210> SEQ ID NO 45
<211> LENGTH: 695
<212> TYPE: PRT
<213> ORGANISM: Artificial Sequence
<220> FEATURE:

-continued

```
<223> OTHER INFORMATION: Mature sequence with His-tag
<220> FEATURE:
<221> NAME/KEY: mat_peptide
<222> LOCATION: (1)..(695)

<400> SEQUENCE: 45
```

| Met | His | His | His | His | His | Met | Gly | Lys | Arg | Tyr | Pro | Leu | Val | His |
|---|---|---|---|---|---|---|---|---|---|---|---|---|---|---|
| 1 | | | | 5 | | | | | 10 | | | | | 15 |

| Pro | Asn | Val | Lys | Gly | Phe | Leu | His | Gly | Gly | Asp | Tyr | Asn | Pro | Asp | Gln |
| | | | 20 | | | | | 25 | | | | | 30 | | |

| Trp | Leu | His | Met | Pro | Glu | Ile | Ile | Asp | Glu | Asp | Phe | Arg | Leu | Met | Lys |
| | | | 35 | | | | 40 | | | | | 45 | | | |

| Leu | Ala | His | Cys | Gln | Thr | Phe | Ser | Ile | Asn | Ile | Phe | Ala | Trp | Ser | Lys |
| | 50 | | | | | 55 | | | | | 60 | | | | |

| Leu | Glu | Pro | Lys | Glu | Gly | Gln | Tyr | Asp | Phe | Ala | Trp | Leu | Asp | Asp | Ile |
| 65 | | | | | 70 | | | | | 75 | | | | | 80 |

| Met | Asp | Arg | Leu | Ala | Ala | Gln | Gly | Ala | His | Ala | Ile | Leu | Ala | Thr | Pro |
| | | | | 85 | | | | | 90 | | | | | 95 | |

| Ser | Gly | Ala | Arg | Pro | Ala | Trp | Leu | Ser | Gln | Ala | Tyr | Pro | Glu | Val | Leu |
| | | | 100 | | | | | 105 | | | | | 110 | | |

| Arg | Val | Glu | Ala | Asn | Arg | Gln | Arg | Asn | Leu | His | Gly | Leu | Arg | His | Asn |
| | | 115 | | | | | 120 | | | | | 125 | | | |

| His | Cys | Phe | Thr | Ser | Pro | Val | Tyr | Arg | Glu | Lys | Thr | Asn | Thr | Leu | Asn |
| 130 | | | | | 135 | | | | | 140 | | | | | |

| Arg | Leu | Leu | Ala | Glu | Arg | Tyr | Lys | Asp | His | Pro | Ala | Leu | Ile | Met | Trp |
| 145 | | | | | 150 | | | | | 155 | | | | | 160 |

| His | Ile | Ser | Asn | Glu | Tyr | Gly | Gly | Glu | Cys | His | Cys | Asp | Leu | Cys | Gln |
| | | | | 165 | | | | | 170 | | | | | 175 | |

| Glu | Ala | Phe | Arg | Asp | Tyr | Leu | Lys | Asp | Lys | Tyr | Asn | His | Asp | Leu | Glu |
| | | | 180 | | | | | 185 | | | | | 190 | | |

| Val | Leu | Asn | Gln | Ala | Trp | Trp | Thr | Gly | Phe | Trp | Ser | His | Thr | Tyr | Ser |
| | | 195 | | | | | 200 | | | | | 205 | | | |

| Asp | Trp | Ser | Gln | Ile | Glu | Ser | Pro | Ala | Pro | His | Gly | Glu | His | Met | Ile |
| 210 | | | | | 215 | | | | | 220 | | | | | |

| His | Gly | Met | Asn | Leu | Asp | Trp | Lys | Arg | Phe | Val | Thr | Ala | Gln | Thr | Ile |
| 225 | | | | | 230 | | | | | 235 | | | | | 240 |

| Asn | Phe | Tyr | Gln | Asn | Glu | Ile | Glu | Pro | Leu | Arg | Glu | Leu | Thr | Pro | His |
| | | | | 245 | | | | | 250 | | | | | 255 | |

| Ile | Pro | Val | Thr | Thr | Asn | Phe | Met | Gly | Asp | Tyr | Pro | His | Met | Arg | Pro |
| | | | 260 | | | | | 265 | | | | | 270 | | |

| Phe | Leu | Gly | Leu | Asp | Tyr | His | Gln | Phe | Ala | Lys | Glu | Val | Asp | Val | Ile |
| | | 275 | | | | | 280 | | | | | 285 | | | |

| Ser | Trp | Asp | Ser | Tyr | Pro | Ala | Trp | His | Ser | Gly | Arg | Glu | Thr | Thr | Ser |
| 290 | | | | | 295 | | | | | 300 | | | | | |

| Glu | Leu | Ala | Ser | Asn | Val | Ala | Phe | Val | His | Asp | Leu | Tyr | Arg | Ser | Leu |
| 305 | | | | | 310 | | | | | 315 | | | | | 320 |

| Lys | Asp | Gly | Gln | Pro | Phe | Leu | Val | Met | Glu | Ser | Thr | Pro | Ser | Leu | Val |
| | | | | 325 | | | | | 330 | | | | | 335 | |

| Asn | Trp | His | Glu | Val | Asn | Lys | Val | Lys | His | Lys | Gly | Met | Ala | His | Leu |
| | | | 340 | | | | | 345 | | | | | 350 | | |

| Ser | Ala | Ile | Gln | Ala | Ile | Ala | His | Gly | Ser | Asp | Ser | Val | Leu | Tyr | Phe |
| | | 355 | | | | | 360 | | | | | 365 | | | |

| Gln | Trp | Arg | Gln | Gly | Arg | Gly | Ala | Ser | Glu | Lys | Phe | His | Gly | Ala | Val |
| 370 | | | | | 375 | | | | | 380 | | | | | |

| | | | | | | | | | | | | | | |
|---|---|---|---|---|---|---|---|---|---|---|---|---|---|---|
|Val|Asp|His|Ser|Gly|His|Glu|His|Thr|Arg|Val|Phe|Gln|Glu|Val|Ala|
|385| | | |390| | | | |395| | | | |400|

Asp Leu Gly Lys Gln Leu Glu Gln Leu Gln Pro Ile Ala Gly Thr Ser
                405                 410                 415

Val Gln Pro Glu Val Ala Ile Ile Tyr Asp Trp Glu Asn His Trp Ala
            420                 425                 430

Ile Asp Asp Ala Gln Gly Leu Asn Asn Thr Asn Lys Arg Tyr Val Glu
        435                 440                 445

Ala Cys Gln Thr His Tyr Arg Ser Phe Trp Lys Lys Gly Ile Pro Val
    450                 455                 460

Asp Ile Val Gly Met Glu Lys Asp Phe Ser Ser Tyr Arg Val Leu Val
465                 470                 475                 480

Ala Pro Met Leu Tyr Met Ile Lys Pro Gly Val Ala Glu Lys Ile Glu
                485                 490                 495

Ala Phe Val Lys Lys Gly Gly Ile Phe Ile Ala Thr Tyr Trp Ser Gly
            500                 505                 510

Met Val Asp Glu Asn Asp Leu Cys Phe Leu Gly Gly Phe Pro Gly Pro
        515                 520                 525

Leu Arg His Val Leu Gly Ile Trp Ala Glu Glu Ile Asn Thr Leu Met
    530                 535                 540

Pro Asp Glu His Val Leu Ile Thr Thr Gly Asn Gly Arg Thr Tyr His
545                 550                 555                 560

Val Gly Gln Tyr Cys Glu Ser Ile His Pro Glu Thr Ala Ser Val Leu
                565                 570                 575

Gly His Phe Glu Asn Gly Cys Tyr Glu Gly Gln Pro Ala Leu Thr Val
            580                 585                 590

His Pro Phe Gly Asp Gly Lys Ala Tyr Tyr Met Ala Ser Glu Asn Glu
        595                 600                 605

Gln Ile Phe Tyr Asp Glu Phe Tyr Glu Asp Leu Ile Ala Gly Met Gly
    610                 615                 620

Ile Gln Pro Val Leu Ser Ser Val Ile Pro Gly Val Ser Val Gln
625                 630                 635                 640

Lys Arg Thr Asp Gly Thr Gln Asp Tyr Val Phe Met Met Asn Phe Thr
                645                 650                 655

Glu Glu Leu Gln Asn Ile Ser Leu Asp Ser Ala Glu Ser Tyr Glu Asn
            660                 665                 670

Met Leu Thr Glu Glu Gln Val Pro Asp Gln Leu Gln Leu Asp Pro Tyr
        675                 680                 685

Glu Tyr Val Ile Leu Lys Lys
    690                 695

<210> SEQ ID NO 46
<211> LENGTH: 2064
<212> TYPE: DNA
<213> ORGANISM: Bacillus nealsonii
<220> FEATURE:
<221> NAME/KEY: CDS
<222> LOCATION: (1)..(2061)
<220> FEATURE:
<221> NAME/KEY: mat_peptide
<222> LOCATION: (1)..(2061)

<400> SEQUENCE: 46 atg gca aac aaa gag aaa aca ttt gtt aca gat gct aaa ttt atg ctg      48
Met Ala Asn Lys Glu Lys Thr Phe Val Thr Asp Ala Lys Phe Met Leu
1               5                   10                  15 cat ggc ggc gat tat aac cct gat cag tgg ctg gac cgt cca gat att      96

-continued

```
                His Gly Gly Asp Tyr Asn Pro Asp Gln Trp Leu Asp Arg Pro Asp Ile
                             20                  25                  30 tta gcg gat gac att aag ctg atg cag ctg tcc cac aca aac act ttc        144
Leu Ala Asp Asp Ile Lys Leu Met Gln Leu Ser His Thr Asn Thr Phe
             35                  40                  45 tcg ctt ggg ata ttt gcg tgg agc gcc ttg gaa cca gag gaa ggt gtc        192
Ser Leu Gly Ile Phe Ala Trp Ser Ala Leu Glu Pro Glu Glu Gly Val
 50                  55                  60 tat cat ttt gaa tgg ctt gat gag gta ata gaa aga att cat ggt att        240
Tyr His Phe Glu Trp Leu Asp Glu Val Ile Glu Arg Ile His Gly Ile
 65                  70                  75                  80 ggc ggc aaa gtg att ttg gct acg cca agc ggt gca aga cct gca tgg        288
Gly Gly Lys Val Ile Leu Ala Thr Pro Ser Gly Ala Arg Pro Ala Trp
             85                  90                  95 atg tcc cat aaa tat ccg gag gtg ctg cgt gtt gac ggc gct aga agg        336
Met Ser His Lys Tyr Pro Glu Val Leu Arg Val Asp Gly Ala Arg Arg
            100                 105                 110 aag cag ctc cat ggc ggg cgc cat aat cac tgc ttc tct tct agt gtt        384
Lys Gln Leu His Gly Gly Arg His Asn His Cys Phe Ser Ser Ser Val
            115                 120                 125 tat aga gaa aaa aca cag cag att aac aga ttg ctt gct gaa aga tac        432
Tyr Arg Glu Lys Thr Gln Gln Ile Asn Arg Leu Leu Ala Glu Arg Tyr
130                 135                 140 ggc agc cat ccg gct ttg ctg atg tgg cat att tcc aat gaa tat ggc        480
Gly Ser His Pro Ala Leu Leu Met Trp His Ile Ser Asn Glu Tyr Gly
145                 150                 155                 160 ggg gaa tgt cat tgt gat acc tgt cag gaa gcc ttc cga caa tgg ctg        528
Gly Glu Cys His Cys Asp Thr Cys Gln Glu Ala Phe Arg Gln Trp Leu
            165                 170                 175 aag aaa aag tac gac aat aac ttg aag gct gtc aat gat gct tgg tgg        576
Lys Lys Lys Tyr Asp Asn Asn Leu Lys Ala Val Asn Asp Ala Trp Trp
            180                 185                 190 ggg ccg ttt tgg agc cac aca tac agt gac tgg tca cag att gaa tct        624
Gly Pro Phe Trp Ser His Thr Tyr Ser Asp Trp Ser Gln Ile Glu Ser
            195                 200                 205 cct tct cca gtc ggt gag aat gca gtg cac ggc tta aac ttg gat tgg        672
Pro Ser Pro Val Gly Glu Asn Ala Val His Gly Leu Asn Leu Asp Trp
210                 215                 220 cgc cga ttt gtg aca gac cag aca att gac ttt ttt gag aat gaa att        720
Arg Arg Phe Val Thr Asp Gln Thr Ile Asp Phe Phe Glu Asn Glu Ile
225                 230                 235                 240 gtt cca att aaa gag att tca cca gat att ccg att act aca aat ttg        768
Val Pro Ile Lys Glu Ile Ser Pro Asp Ile Pro Ile Thr Thr Asn Leu
            245                 250                 255 atg gca gat aca ttt gat ttg att cca ttc caa agt ctt gat tac agc        816
Met Ala Asp Thr Phe Asp Leu Ile Pro Phe Gln Ser Leu Asp Tyr Ser
            260                 265                 270 aag ttt gcg cgt cac gta gat gtg ata agc tgg gat gca tat cct gct        864
Lys Phe Ala Arg His Val Asp Val Ile Ser Trp Asp Ala Tyr Pro Ala
            275                 280                 285 tgg cat aat gat tgg gaa aca aca gcg gat tta gcg gtg aag gtt ggc        912
Trp His Asn Asp Trp Glu Thr Thr Ala Asp Leu Ala Val Lys Val Gly
290                 295                 300 ttc att aat gat tta ttc cgc agt tta aaa gag cag ccg ttt ttg ctg        960
Phe Ile Asn Asp Leu Phe Arg Ser Leu Lys Glu Gln Pro Phe Leu Leu
305                 310                 315                 320 atg gag tca aca cca agt gct gtc aac tgg cat aaa gtc aat aaa gcg       1008
Met Glu Ser Thr Pro Ser Ala Val Asn Trp His Lys Val Asn Lys Ala
            325                 330                 335
```

| | | |
|---|---|---|
| aaa cgt cca ggc atg cat ttg ctt tct tct atg cag atg gtt gcc cat<br>Lys Arg Pro Gly Met His Leu Leu Ser Ser Met Gln Met Val Ala His<br>340 345 350 | 1056 | |
| ggt tct gac agc gtt cta tac ttc cag tgg cgc aaa tcg cgt ggg tcg<br>Gly Ser Asp Ser Val Leu Tyr Phe Gln Trp Arg Lys Ser Arg Gly Ser<br>355 360 365 | 1104 | |
| tca gag aag ttt cac ggt gca gtt gtt gac cat gat aac agc ccg gat<br>Ser Glu Lys Phe His Gly Ala Val Val Asp His Asp Asn Ser Pro Asp<br>370 375 380 | 1152 | |
| aac cgg gtg ttc cag gaa gtc gcc aag gtc ggt aca acg ctg gaa aag<br>Asn Arg Val Phe Gln Glu Val Ala Lys Val Gly Thr Thr Leu Glu Lys<br>385 390 395 400 | 1200 | |
| ctg acc gat att gtc ggt aca aat cgt gta gca gat aca gcc atc ctg<br>Leu Thr Asp Ile Val Gly Thr Asn Arg Val Ala Asp Thr Ala Ile Leu<br>405 410 415 | 1248 | |
| tat gat tgg gaa aat aac tgg gcg ctg aat gat gcg caa ggc tac gga<br>Tyr Asp Trp Glu Asn Asn Trp Ala Leu Asn Asp Ala Gln Gly Tyr Gly<br>420 425 430 | 1296 | |
| tta gac acg aag cgc tat ccg caa aca ttg cag cag cat tat cgc aca<br>Leu Asp Thr Lys Arg Tyr Pro Gln Thr Leu Gln Gln His Tyr Arg Thr<br>435 440 445 | 1344 | |
| ttt tgg gag cag gat gtt cca gtt gat gtg atc aca aag gaa aac gat<br>Phe Trp Glu Gln Asp Val Pro Val Asp Val Ile Thr Lys Glu Asn Asp<br>450 455 460 | 1392 | |
| ttt tct aaa tac cgt ctg ttg att gtg ccg atg ctc tat tta gca agt<br>Phe Ser Lys Tyr Arg Leu Leu Ile Val Pro Met Leu Tyr Leu Ala Ser<br>465 470 475 480 | 1440 | |
| gaa gag acg att gcc cgc tta aaa gcg tat gta gca aat ggc ggt acg<br>Glu Glu Thr Ile Ala Arg Leu Lys Ala Tyr Val Ala Asn Gly Gly Thr<br>485 490 495 | 1488 | |
| tta atc atg aca tat ata agc gga atc gtg aat gag cat gac tta acg<br>Leu Ile Met Thr Tyr Ile Ser Gly Ile Val Asn Glu His Asp Leu Thr<br>500 505 510 | 1536 | |
| tat atg gaa ggc tgg cat caa gat ctg caa gac atg ttt ggc cta aat<br>Tyr Met Glu Gly Trp His Gln Asp Leu Gln Asp Met Phe Gly Leu Asn<br>515 520 525 | 1584 | |
| cca att gaa aca gat aca ctt tat ccg aaa gat gct aac act gtc cat<br>Pro Ile Glu Thr Asp Thr Leu Tyr Pro Lys Asp Ala Asn Thr Val His<br>530 535 540 | 1632 | |
| tac gaa ggc aag gat tat gta ctg aag gat tat gca acc gtt gta aat<br>Tyr Glu Gly Lys Asp Tyr Val Leu Lys Asp Tyr Ala Thr Val Val Asn<br>545 550 555 560 | 1680 | |
| att gcc tct gct aat gtg gaa ggt gta tat aaa gaa gat ttt tat gca<br>Ile Ala Ser Ala Asn Val Glu Gly Val Tyr Lys Glu Asp Phe Tyr Ala<br>565 570 575 | 1728 | |
| aac aca gca gca gta aca agc aat gct tat gag aat ggg aaa gct tac<br>Asn Thr Ala Ala Val Thr Ser Asn Ala Tyr Glu Asn Gly Lys Ala Tyr<br>580 585 590 | 1776 | |
| tat att ggc ggc cga tta gat gat gag ttt cat ctt gct ttc tac ggc<br>Tyr Ile Gly Gly Arg Leu Asp Asp Glu Phe His Leu Ala Phe Tyr Gly<br>595 600 605 | 1824 | |
| aag ctt att gaa gaa ttg tca tta aag cca gat tac gcg ata aca cat<br>Lys Leu Ile Glu Glu Leu Ser Leu Lys Pro Asp Tyr Ala Ile Thr His<br>610 615 620 | 1872 | |
| ggc agc gga gta tct gtt caa gca aga caa gat gaa ggt aaa gag tat<br>Gly Ser Gly Val Ser Val Gln Ala Arg Gln Asp Glu Gly Lys Glu Tyr<br>625 630 635 640 | 1920 | |
| ctc ttt att atg aac ttt aca gaa gat acg cag cca gtt gtc ctt ggc<br>Leu Phe Ile Met Asn Phe Thr Glu Asp Thr Gln Pro Val Val Leu Gly<br>645 650 655 | 1968 | |

```
agt gaa gta aag gat gtt att act ggt gag cag ctt cat ggc agt ata    2016
Ser Glu Val Lys Asp Val Ile Thr Gly Glu Gln Leu His Gly Ser Ile
        660             665             670 aag cta gat aag tat gaa gtg aga ata gta gag aaa gta aaa ggc taa    2064
Lys Leu Asp Lys Tyr Glu Val Arg Ile Val Glu Lys Val Lys Gly
        675             680             685

<210> SEQ ID NO 47
<211> LENGTH: 687
<212> TYPE: PRT
<213> ORGANISM: Bacillus nealsonii

<400> SEQUENCE: 47

Met Ala Asn Lys Glu Lys Thr Phe Val Thr Asp Ala Lys Phe Met Leu
1               5                   10                  15

His Gly Gly Asp Tyr Asn Pro Asp Gln Trp Leu Asp Arg Pro Asp Ile
                20                  25                  30

Leu Ala Asp Asp Ile Lys Leu Met Gln Leu Ser His Thr Asn Thr Phe
            35                  40                  45

Ser Leu Gly Ile Phe Ala Trp Ser Ala Leu Glu Pro Glu Glu Gly Val
        50                  55                  60

Tyr His Phe Glu Trp Leu Asp Glu Val Ile Glu Arg Ile His Gly Ile
65                  70                  75                  80

Gly Gly Lys Val Ile Leu Ala Thr Pro Ser Gly Ala Arg Pro Ala Trp
                85                  90                  95

Met Ser His Lys Tyr Pro Glu Val Leu Arg Val Asp Gly Ala Arg Arg
                100                 105                 110

Lys Gln Leu His Gly Gly Arg His Asn His Cys Phe Ser Ser Ser Val
            115                 120                 125

Tyr Arg Glu Lys Thr Gln Gln Ile Asn Arg Leu Leu Ala Glu Arg Tyr
        130                 135                 140

Gly Ser His Pro Ala Leu Leu Met Trp His Ile Ser Asn Glu Tyr Gly
145                 150                 155                 160

Gly Glu Cys His Cys Asp Thr Cys Gln Glu Ala Phe Arg Gln Trp Leu
                165                 170                 175

Lys Lys Lys Tyr Asp Asn Asn Leu Lys Ala Val Asn Asp Ala Trp Trp
                180                 185                 190

Gly Pro Phe Trp Ser His Thr Tyr Ser Asp Trp Ser Gln Ile Glu Ser
            195                 200                 205

Pro Ser Pro Val Gly Glu Asn Ala Val His Gly Leu Asn Leu Asp Trp
        210                 215                 220

Arg Arg Phe Val Thr Asp Gln Thr Ile Asp Phe Phe Glu Asn Glu Ile
225                 230                 235                 240

Val Pro Ile Lys Glu Ile Ser Pro Asp Ile Pro Ile Thr Thr Asn Leu
                245                 250                 255

Met Ala Asp Thr Phe Asp Leu Ile Pro Phe Gln Ser Leu Asp Tyr Ser
                260                 265                 270

Lys Phe Ala Arg His Val Asp Val Ile Ser Trp Asp Ala Tyr Pro Ala
            275                 280                 285

Trp His Asn Asp Trp Glu Thr Thr Ala Asp Leu Ala Val Lys Val Gly
        290                 295                 300

Phe Ile Asn Asp Leu Phe Arg Ser Leu Lys Glu Gln Pro Phe Leu Leu
305                 310                 315                 320

Met Glu Ser Thr Pro Ser Ala Val Asn Trp His Lys Val Asn Lys Ala
                325                 330                 335
```

```
Lys Arg Pro Gly Met His Leu Leu Ser Ser Met Gln Met Val Ala His
                340                 345                 350

Gly Ser Asp Ser Val Leu Tyr Phe Gln Trp Arg Lys Ser Arg Gly Ser
            355                 360                 365

Ser Glu Lys Phe His Gly Ala Val Val Asp His Asp Asn Ser Pro Asp
        370                 375                 380

Asn Arg Val Phe Gln Glu Val Ala Lys Val Gly Thr Thr Leu Glu Lys
385                 390                 395                 400

Leu Thr Asp Ile Val Gly Thr Asn Arg Val Ala Asp Thr Ala Ile Leu
                405                 410                 415

Tyr Asp Trp Glu Asn Asn Trp Ala Leu Asn Asp Ala Gln Gly Tyr Gly
                420                 425                 430

Leu Asp Thr Lys Arg Tyr Pro Gln Thr Leu Gln Gln His Tyr Arg Thr
            435                 440                 445

Phe Trp Glu Gln Asp Val Pro Val Asp Val Ile Thr Lys Glu Asn Asp
        450                 455                 460

Phe Ser Lys Tyr Arg Leu Leu Ile Val Pro Met Leu Tyr Leu Ala Ser
465                 470                 475                 480

Glu Glu Thr Ile Ala Arg Leu Lys Ala Tyr Val Ala Asn Gly Gly Thr
                485                 490                 495

Leu Ile Met Thr Tyr Ile Ser Gly Ile Val Asn Glu His Asp Leu Thr
                500                 505                 510

Tyr Met Glu Gly Trp His Gln Asp Leu Gln Asp Met Phe Gly Leu Asn
            515                 520                 525

Pro Ile Glu Thr Asp Thr Leu Tyr Pro Lys Asp Ala Asn Thr Val His
        530                 535                 540

Tyr Glu Gly Lys Asp Tyr Val Leu Lys Asp Tyr Ala Thr Val Val Asn
545                 550                 555                 560

Ile Ala Ser Ala Asn Val Glu Gly Val Tyr Lys Glu Asp Phe Tyr Ala
                565                 570                 575

Asn Thr Ala Ala Val Thr Ser Asn Ala Tyr Glu Asn Gly Lys Ala Tyr
                580                 585                 590

Tyr Ile Gly Gly Arg Leu Asp Asp Glu Phe His Leu Ala Phe Tyr Gly
            595                 600                 605

Lys Leu Ile Glu Glu Leu Ser Leu Lys Pro Asp Tyr Ala Ile Thr His
        610                 615                 620

Gly Ser Gly Val Ser Val Gln Ala Arg Gln Asp Glu Gly Lys Glu Tyr
625                 630                 635                 640

Leu Phe Ile Met Asn Phe Thr Glu Asp Thr Gln Pro Val Val Leu Gly
                645                 650                 655

Ser Glu Val Lys Asp Val Ile Thr Gly Glu Gln Leu His Gly Ser Ile
            660                 665                 670

Lys Leu Asp Lys Tyr Glu Val Arg Ile Val Glu Lys Val Lys Gly
        675                 680                 685

<210> SEQ ID NO 48
<211> LENGTH: 694
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(694)

<400> SEQUENCE: 48
```

-continued

```
Met His His His His His Met Ala Asn Lys Glu Lys Thr Phe Val
1               5                  10                 15

Thr Asp Ala Lys Phe Met Leu His Gly Gly Asp Tyr Asn Pro Asp Gln
                20                 25                 30

Trp Leu Asp Arg Pro Asp Ile Leu Ala Asp Ile Lys Leu Met Gln
             35                  40                 45

Leu Ser His Thr Asn Thr Phe Ser Leu Gly Ile Phe Ala Trp Ser Ala
    50                  55                  60

Leu Glu Pro Glu Glu Gly Val Tyr His Phe Glu Trp Leu Asp Glu Val
65                  70                  75                  80

Ile Glu Arg Ile His Gly Ile Gly Gly Lys Val Ile Leu Ala Thr Pro
                85                  90                  95

Ser Gly Ala Arg Pro Ala Trp Met Ser His Lys Tyr Pro Glu Val Leu
            100                 105                 110

Arg Val Asp Gly Ala Arg Arg Lys Gln Leu His Gly Arg His Asn
            115                 120                 125

His Cys Phe Ser Ser Val Tyr Arg Glu Lys Thr Gln Gln Ile Asn
    130                 135                 140

Arg Leu Leu Ala Glu Arg Tyr Gly Ser His Pro Ala Leu Leu Met Trp
145                 150                 155                 160

His Ile Ser Asn Glu Tyr Gly Gly Glu Cys His Cys Asp Thr Cys Gln
                165                 170                 175

Glu Ala Phe Arg Gln Trp Leu Lys Lys Tyr Asp Asn Asn Leu Lys
            180                 185                 190

Ala Val Asn Asp Ala Trp Trp Gly Pro Phe Trp Ser His Thr Tyr Ser
    195                 200                 205

Asp Trp Ser Gln Ile Glu Ser Pro Ser Pro Val Gly Glu Asn Ala Val
210                 215                 220

His Gly Leu Asn Leu Asp Trp Arg Arg Phe Val Thr Asp Gln Thr Ile
225                 230                 235                 240

Asp Phe Phe Glu Asn Glu Ile Val Pro Ile Lys Glu Ile Ser Pro Asp
                245                 250                 255

Ile Pro Ile Thr Thr Asn Leu Met Ala Asp Thr Phe Asp Leu Ile Pro
            260                 265                 270

Phe Gln Ser Leu Asp Tyr Ser Lys Phe Ala Arg His Val Asp Val Ile
        275                 280                 285

Ser Trp Asp Ala Tyr Pro Ala Trp His Asn Asp Trp Glu Thr Thr Ala
    290                 295                 300

Asp Leu Ala Val Lys Val Gly Phe Ile Asn Asp Leu Phe Arg Ser Leu
305                 310                 315                 320

Lys Glu Gln Pro Phe Leu Leu Met Glu Ser Thr Pro Ser Ala Val Asn
                325                 330                 335

Trp His Lys Val Asn Lys Ala Lys Arg Pro Gly Met His Leu Leu Ser
            340                 345                 350

Ser Met Gln Met Val Ala His Gly Ser Asp Ser Val Leu Tyr Phe Gln
    355                 360                 365

Trp Arg Lys Ser Arg Gly Ser Ser Glu Lys Phe His Gly Ala Val Val
370                 375                 380

Asp His Asp Asn Ser Pro Asp Asn Arg Val Phe Gln Glu Val Ala Lys
385                 390                 395                 400

Val Gly Thr Thr Leu Glu Lys Leu Thr Asp Ile Val Gly Thr Asn Arg
                405                 410                 415
```

```
Val Ala Asp Thr Ala Ile Leu Tyr Asp Trp Glu Asn Asn Trp Ala Leu
            420                 425                 430

Asn Asp Ala Gln Gly Tyr Gly Leu Asp Thr Lys Arg Tyr Pro Gln Thr
                435                 440                 445

Leu Gln Gln His Tyr Arg Thr Phe Trp Glu Gln Asp Val Pro Val Asp
        450                 455                 460

Val Ile Thr Lys Glu Asn Asp Phe Ser Lys Tyr Arg Leu Leu Ile Val
465                 470                 475                 480

Pro Met Leu Tyr Leu Ala Ser Glu Glu Thr Ile Ala Arg Leu Lys Ala
                485                 490                 495

Tyr Val Ala Asn Gly Gly Thr Leu Ile Met Thr Tyr Ile Ser Gly Ile
            500                 505                 510

Val Asn Glu His Asp Leu Thr Tyr Met Glu Gly Trp His Gln Asp Leu
        515                 520                 525

Gln Asp Met Phe Gly Leu Asn Pro Ile Glu Thr Asp Thr Leu Tyr Pro
    530                 535                 540

Lys Asp Ala Asn Thr Val His Tyr Glu Gly Lys Asp Tyr Val Leu Lys
545                 550                 555                 560

Asp Tyr Ala Thr Val Val Asn Ile Ala Ser Ala Asn Val Glu Gly Val
                565                 570                 575

Tyr Lys Glu Asp Phe Tyr Ala Asn Thr Ala Ala Val Thr Ser Asn Ala
            580                 585                 590

Tyr Glu Asn Gly Lys Ala Tyr Tyr Ile Gly Gly Arg Leu Asp Asp Glu
        595                 600                 605

Phe His Leu Ala Phe Tyr Gly Lys Leu Ile Glu Glu Leu Ser Leu Lys
    610                 615                 620

Pro Asp Tyr Ala Ile Thr His Gly Ser Gly Val Ser Val Gln Ala Arg
625                 630                 635                 640

Gln Asp Glu Gly Lys Glu Tyr Leu Phe Ile Met Asn Phe Thr Glu Asp
                645                 650                 655

Thr Gln Pro Val Val Leu Gly Ser Glu Val Lys Asp Val Ile Thr Gly
            660                 665                 670

Glu Gln Leu His Gly Ser Ile Lys Leu Asp Lys Tyr Glu Val Arg Ile
        675                 680                 685

Val Glu Lys Val Lys Gly
    690

<210> SEQ ID NO 49
<211> LENGTH: 1965
<212> TYPE: DNA
<213> ORGANISM: Burkholderia sediminicola
<220> FEATURE:
<221> NAME/KEY: CDS
<222> LOCATION: (1)..(1962)
<220> FEATURE:
<221> NAME/KEY: mat_peptide
<222> LOCATION: (1)..(1962)

<400> SEQUENCE: 49 atg caa ctt ggt gtt tgc tac tac ccc gaa caa tgg ccg cgt tcg atg      48
Met Gln Leu Gly Val Cys Tyr Tyr Pro Glu Gln Trp Pro Arg Ser Met
1               5                   10                  15 tgg gcc gac gat gcg aaa cgt atg gtc gag ctc ggc atc acg cat gtg      96
Trp Ala Asp Asp Ala Lys Arg Met Val Glu Leu Gly Ile Thr His Val
                20                  25                  30 cgg atc gcc gaa ttc gcg tgg agc cgg atg gaa ccg cgc gcc ggc gaa     144
Arg Ile Ala Glu Phe Ala Trp Ser Arg Met Glu Pro Arg Ala Gly Glu
        35                  40                  45
```

| | | |
|---|---|---|
| ttc gcc tgg gac tgg ctc gat gaa gcc gtt gag acg ctc gcg gcc gaa<br>Phe Ala Trp Asp Trp Leu Asp Glu Ala Val Glu Thr Leu Ala Ala Glu<br>50                            55                         60 | 192 |
| ggg ctg aaa ctc gtg cta ggc aca ccg acc gcg tcg ccg ccg aaa tgg<br>Gly Leu Lys Leu Val Leu Gly Thr Pro Thr Ala Ser Pro Pro Lys Trp<br>65                         70                   75                   80 | 240 |
| ctg atc gat gcg cac ccg gat gtt ttg ccg gta cgt gcg gac ggc gtg<br>Leu Ile Asp Ala His Pro Asp Val Leu Pro Val Arg Ala Asp Gly Val<br>                       85                   90                   95 | 288 |
| cgc tgg aat ttc ggc tcg cgt cgc cac tac gat att tcc agc gaa acc<br>Arg Trp Asn Phe Gly Ser Arg Arg His Tyr Asp Ile Ser Ser Glu Thr<br>               100                 105                110 | 336 |
| tat cgg cgt gag tgc gta cgt att gtc acc gcg atg gcg gag cgc tat<br>Tyr Arg Arg Glu Cys Val Arg Ile Val Thr Ala Met Ala Glu Arg Tyr<br>      115                 120                125 | 384 |
| gga cgg cac ccg tct atc gtt gcg tgg cag acc gac aac gaa ctc ggc<br>Gly Arg His Pro Ser Ile Val Ala Trp Gln Thr Asp Asn Glu Leu Gly<br>130                         135                140 | 432 |
| tgc cac gag acc gtg ccg agt tat tcg ggc gcg gca ctg gcg cgc ttt<br>Cys His Glu Thr Val Pro Ser Tyr Ser Gly Ala Ala Leu Ala Arg Phe<br>145                         150                155              160 | 480 |
| cag acg tgg ttg cag cat cgc tac gag cgc gtc gag gcg ttg aac gat<br>Gln Thr Trp Leu Gln His Arg Tyr Glu Arg Val Glu Ala Leu Asn Asp<br>                 165                170                175 | 528 |
| gca tgg ggc aat gtg ttc tgg agc atg gag tat ccg tcg ttc gat acg<br>Ala Trp Gly Asn Val Phe Trp Ser Met Glu Tyr Pro Ser Phe Asp Thr<br>             180                 185                190 | 576 |
| atc ggc ctg ccg aac cgc acg ccc acc gac gcc aat ccg atc cat ttg<br>Ile Gly Leu Pro Asn Arg Thr Pro Thr Asp Ala Asn Pro Ile His Leu<br>      195                 200                205 | 624 |
| ctc gac ttc cgc cgt ttc atg tcg gat gag gtg gcg agc ttc cat cgc<br>Leu Asp Phe Arg Arg Phe Met Ser Asp Glu Val Ala Ser Phe His Arg<br>210                         215                220 | 672 |
| gag cag atc gac gtg ctg cgt cag cat gcg ccc aag gcg gat ctt ctg<br>Glu Gln Ile Asp Val Leu Arg Gln His Ala Pro Lys Ala Asp Leu Leu<br>225                         230                235              240 | 720 |
| cat aac ttc atg ggc ttc ttc acg acc ttc gat cat tac cgc ttc gcc<br>His Asn Phe Met Gly Phe Phe Thr Thr Phe Asp His Tyr Arg Phe Ala<br>             245                 250                255 | 768 |
| gaa gac aac gcg ctc gac gtg gcg acg tgg gat agc tat ccg atc gcg<br>Glu Asp Asn Ala Leu Asp Val Ala Thr Trp Asp Ser Tyr Pro Ile Ala<br>                 260                265                270 | 816 |
| cgc acg gaa tcg atc gca ctg cct gaa gag cag aag gcg cgt tac gca<br>Arg Thr Glu Ser Ile Ala Leu Pro Glu Glu Gln Lys Ala Arg Tyr Ala<br>      275                 280                285 | 864 |
| cgt acc gcg cat ccg gac gtc tcg gcg ttc gat cac gac cgc tac cgc<br>Arg Thr Ala His Pro Asp Val Ser Ala Phe Asp His Asp Arg Tyr Arg<br>290                         295                300 | 912 |
| gcg atc ggc gcc ggc cgt ttc tgg gtg atg gag caa cag gca ggg ccg<br>Ala Ile Gly Ala Gly Arg Phe Trp Val Met Glu Gln Gln Ala Gly Pro<br>305                         310                315              320 | 960 |
| gtg aac tgg gcg ccg tgg aat ccg gtg ccg gcg aag ggc atg gtc agg<br>Val Asn Trp Ala Pro Trp Asn Pro Val Pro Ala Lys Gly Met Val Arg<br>             325                 330                335 | 1008 |
| ctg tgg gca tac gaa gca ttc gcg cat ggg gcg gaa ctg gtg tcg tat<br>Leu Trp Ala Tyr Glu Ala Phe Ala His Gly Ala Glu Leu Val Ser Tyr<br>                 340                345                350 | 1056 |
| ttc cgc tgg cgt cag tgt ccg tat gcg cag gaa cag atg cat tcg ggt<br>Phe Arg Trp Arg Gln Cys Pro Tyr Ala Gln Glu Gln Met His Ser Gly | 1104 |

|  |  |  |  |  |  |  |  |  |  |  |  |  |  |  |  |  |
|---|---|---|---|---|---|---|---|---|---|---|---|---|---|---|---|---|
|  |  | 355 |  |  |  | 360 |  |  |  |  | 365 |  |  |  |  |  |
| ctc | aac | ttg | ccg | aac | aac | gaa | ctg | tcg | cct | ggc | ggc | atc | gaa | gtg | cag |  1152 |
| Leu | Asn | Leu | Pro | Asn | Asn | Glu | Leu | Ser | Pro | Gly | Gly | Ile | Glu | Val | Gln |  |
|  |  | 370 |  |  |  | 375 |  |  |  |  | 380 |  |  |  |  |  |
| cag | gcg | gcg | cat | gaa | att | gcc | tcg | tcc | gca | gcg | cta | tcc | gga | ctc | ggt |  1200 |
| Gln | Ala | Ala | His | Glu | Ile | Ala | Ser | Ser | Ala | Ala | Leu | Ser | Gly | Leu | Gly |  |
| 385 |  |  |  |  | 390 |  |  |  |  | 395 |  |  |  |  | 400 |  |
| gcg | ccg | acg | cgc | gcg | gcc | acc | gcg | atc | gtg | ttc | gac | tac | gag | acg | cag |  1248 |
| Ala | Pro | Thr | Arg | Ala | Ala | Thr | Ala | Ile | Val | Phe | Asp | Tyr | Glu | Thr | Gln |  |
|  |  |  |  | 405 |  |  |  |  | 410 |  |  |  |  | 415 |  |  |
| tgg | atg | ttc | gag | att | cag | cgt | cat | ggc | aaa | acc | ttc | gat | tac | cag | acg |  1296 |
| Trp | Met | Phe | Glu | Ile | Gln | Arg | His | Gly | Lys | Thr | Phe | Asp | Tyr | Gln | Thr |  |
|  |  |  | 420 |  |  |  |  | 425 |  |  |  |  | 430 |  |  |  |
| ctg | gcg | ttc | gac | tac | tac | gag | gcg | ctg | cgt | gaa | ctc | ggc | ctc | gac | gtc |  1344 |
| Leu | Ala | Phe | Asp | Tyr | Tyr | Glu | Ala | Leu | Arg | Glu | Leu | Gly | Leu | Asp | Val |  |
|  |  |  | 435 |  |  |  |  | 440 |  |  |  |  | 445 |  |  |  |
| gat | atc | gtg | tcg | agc | aag | gcc | gat | ctt | tcg | ccg | tac | cgg | tta | gtg | gtg |  1392 |
| Asp | Ile | Val | Ser | Ser | Lys | Ala | Asp | Leu | Ser | Pro | Tyr | Arg | Leu | Val | Val |  |
|  | 450 |  |  |  |  | 455 |  |  |  |  | 460 |  |  |  |  |  |
| gtg | ccg | agt | att | gcc | gtg | atc | aac | gac | acg | ctc | gtc | gac | cag | atc | gag |  1440 |
| Val | Pro | Ser | Ile | Ala | Val | Ile | Asn | Asp | Thr | Leu | Val | Asp | Gln | Ile | Glu |  |
| 465 |  |  |  |  | 470 |  |  |  |  | 475 |  |  |  |  | 480 |  |
| cag | agt | tcg | gcg | caa | tgg | gta | ttc | ggt | ccg | agg | agc | ggt | tcg | aag | acc |  1488 |
| Gln | Ser | Ser | Ala | Gln | Trp | Val | Phe | Gly | Pro | Arg | Ser | Gly | Ser | Lys | Thr |  |
|  |  |  |  | 485 |  |  |  |  | 490 |  |  |  |  | 495 |  |  |
| acg | acc | ttt | gcc | att | cct | tcg | agc | ttg | ccg | ccc | ggc | gcg | ttg | caa | cgc |  1536 |
| Thr | Thr | Phe | Ala | Ile | Pro | Ser | Ser | Leu | Pro | Pro | Gly | Ala | Leu | Gln | Arg |  |
|  |  |  | 500 |  |  |  |  | 505 |  |  |  |  | 510 |  |  |  |
| gtt | ctg | ccg | atg | cag | gtg | ctc | gaa | gtc | gaa | acg | ctg | cgt | ccg | acg | ctt |  1584 |
| Val | Leu | Pro | Met | Gln | Val | Leu | Glu | Val | Glu | Thr | Leu | Arg | Pro | Thr | Leu |  |
|  |  | 515 |  |  |  |  | 520 |  |  |  |  | 525 |  |  |  |  |
| acg | cca | gcg | ctt | tcg | atc | gga | gac | acg | cag | ggc | gtt | gca | ctg | cat | tgg |  1632 |
| Thr | Pro | Ala | Leu | Ser | Ile | Gly | Asp | Thr | Gln | Gly | Val | Ala | Leu | His | Trp |  |
|  | 530 |  |  |  |  | 535 |  |  |  |  | 540 |  |  |  |  |  |
| cgc | gag | cac | gtt | cgc | gcc | aat | ggc | gag | aca | acc | gtc | gac | gcg | caa | ttc |  1680 |
| Arg | Glu | His | Val | Arg | Ala | Asn | Gly | Glu | Thr | Thr | Val | Asp | Ala | Gln | Phe |  |
| 545 |  |  |  |  | 550 |  |  |  |  | 555 |  |  |  |  | 560 |  |
| gac | gac | acg | tgg | ccc | gcg | atc | ctc | acc | cac | gga | aga | gtt | cgc | tat | gtg |  1728 |
| Asp | Asp | Thr | Trp | Pro | Ala | Ile | Leu | Thr | His | Gly | Arg | Val | Arg | Tyr | Val |  |
|  |  |  | 565 |  |  |  |  | 570 |  |  |  |  | 575 |  |  |  |
| gcg | ggt | tgg | ttg | tcg | cac | gcg | ttg | cat | cgc | gag | gtg | ttg | cag | cgg | gcc |  1776 |
| Ala | Gly | Trp | Leu | Ser | His | Ala | Leu | His | Arg | Glu | Val | Leu | Gln | Arg | Ala |  |
|  |  | 580 |  |  |  |  | 585 |  |  |  |  | 590 |  |  |  |  |
| gcg | aaa | gat | gcc | ggc | atc | gag | acg | cag | cac | ctg | gct | gat | ggc | ttg | cgc |  1824 |
| Ala | Lys | Asp | Ala | Gly | Ile | Glu | Thr | Gln | His | Leu | Ala | Asp | Gly | Leu | Arg |  |
|  | 595 |  |  |  |  | 600 |  |  |  |  | 605 |  |  |  |  |  |
| att | cgc | cgg | cgc | ggc | gat | ctg | acc | ttc | gcg | ttc | aac | ttc | ggg | ccg | gag |  1872 |
| Ile | Arg | Arg | Arg | Gly | Asp | Leu | Thr | Phe | Ala | Phe | Asn | Phe | Gly | Pro | Glu |  |
| 610 |  |  |  |  | 615 |  |  |  |  | 620 |  |  |  |  |  |  |
| cca | gtg | caa | gcg | cct | gcg | cca | gcc | aat | gcg | acg | ttt | gtg | ctg | gga | cat |  1920 |
| Pro | Val | Gln | Ala | Pro | Ala | Pro | Ala | Asn | Ala | Thr | Phe | Val | Leu | Gly | His |  |
| 625 |  |  |  |  | 630 |  |  |  |  | 635 |  |  |  |  | 640 |  |
| tcg | gaa | ttg | aaa | acc | ggc | gac | gtc | tgc | gcg | tgg | agg | aac | acg | tag |  |  1965 |
| Ser | Glu | Leu | Lys | Thr | Gly | Asp | Val | Cys | Ala | Trp | Arg | Asn | Thr |  |  |  |
|  |  |  | 645 |  |  |  |  | 650 |  |  |  |  |  |  |  |  |

<210> SEQ ID NO 50
<211> LENGTH: 654
<212> TYPE: PRT
<213> ORGANISM: Burkholderia sediminicola

<400> SEQUENCE: 50

```
Met Gln Leu Gly Val Cys Tyr Tyr Pro Glu Gln Trp Pro Arg Ser Met
1               5                   10                  15

Trp Ala Asp Asp Ala Lys Arg Met Val Glu Leu Gly Ile Thr His Val
            20                  25                  30

Arg Ile Ala Glu Phe Ala Trp Ser Arg Met Glu Pro Arg Ala Gly Glu
        35                  40                  45

Phe Ala Trp Asp Trp Leu Asp Glu Ala Val Glu Thr Leu Ala Ala Glu
50                  55                  60

Gly Leu Lys Leu Val Leu Gly Thr Pro Thr Ala Ser Pro Pro Lys Trp
65                  70                  75                  80

Leu Ile Asp Ala His Pro Asp Val Leu Pro Val Arg Ala Asp Gly Val
                85                  90                  95

Arg Trp Asn Phe Gly Ser Arg Arg His Tyr Asp Ile Ser Ser Glu Thr
            100                 105                 110

Tyr Arg Arg Glu Cys Val Arg Ile Val Thr Ala Met Ala Glu Arg Tyr
        115                 120                 125

Gly Arg His Pro Ser Ile Val Ala Trp Gln Thr Asp Asn Glu Leu Gly
    130                 135                 140

Cys His Glu Thr Val Pro Ser Tyr Ser Gly Ala Ala Leu Ala Arg Phe
145                 150                 155                 160

Gln Thr Trp Leu Gln His Arg Tyr Glu Arg Val Glu Ala Leu Asn Asp
                165                 170                 175

Ala Trp Gly Asn Val Phe Trp Ser Met Glu Tyr Pro Ser Phe Asp Thr
            180                 185                 190

Ile Gly Leu Pro Asn Arg Thr Pro Thr Asp Ala Asn Pro Ile His Leu
        195                 200                 205

Leu Asp Phe Arg Arg Phe Met Ser Asp Glu Val Ala Ser Phe His Arg
210                 215                 220

Glu Gln Ile Asp Val Leu Arg Gln His Ala Pro Lys Ala Asp Leu Leu
225                 230                 235                 240

His Asn Phe Met Gly Phe Phe Thr Thr Phe Asp His Tyr Arg Phe Ala
                245                 250                 255

Glu Asp Asn Ala Leu Asp Val Ala Thr Trp Asp Ser Tyr Pro Ile Ala
            260                 265                 270

Arg Thr Glu Ser Ile Ala Leu Pro Glu Glu Gln Lys Ala Arg Tyr Ala
        275                 280                 285

Arg Thr Ala His Pro Asp Val Ser Ala Phe Asp His Asp Arg Tyr Arg
    290                 295                 300

Ala Ile Gly Ala Gly Arg Phe Trp Val Met Glu Gln Gln Ala Gly Pro
305                 310                 315                 320

Val Asn Trp Ala Pro Trp Asn Pro Val Pro Ala Lys Gly Met Val Arg
                325                 330                 335

Leu Trp Ala Tyr Glu Ala Phe Ala His Gly Ala Glu Leu Val Ser Tyr
            340                 345                 350

Phe Arg Trp Arg Gln Cys Pro Tyr Ala Gln Glu Gln Met His Ser Gly
        355                 360                 365

Leu Asn Leu Pro Asn Asn Glu Leu Ser Pro Gly Gly Ile Glu Val Gln
    370                 375                 380

Gln Ala Ala His Glu Ile Ala Ser Ser Ala Ala Leu Ser Gly Leu Gly
385                 390                 395                 400

Ala Pro Thr Arg Ala Ala Thr Ala Ile Val Phe Asp Tyr Glu Thr Gln
```

```
                    405                 410                 415
Trp Met Phe Glu Ile Gln Arg His Gly Lys Thr Phe Asp Tyr Gln Thr
                420                 425                 430

Leu Ala Phe Asp Tyr Tyr Glu Ala Leu Arg Glu Leu Gly Leu Asp Val
            435                 440                 445

Asp Ile Val Ser Ser Lys Ala Asp Leu Ser Pro Tyr Arg Leu Val Val
        450                 455                 460

Val Pro Ser Ile Ala Val Ile Asn Asp Thr Leu Val Asp Gln Ile Glu
465                 470                 475                 480

Gln Ser Ser Ala Gln Trp Val Phe Gly Pro Arg Ser Gly Ser Lys Thr
                485                 490                 495

Thr Thr Phe Ala Ile Pro Ser Ser Leu Pro Pro Gly Ala Leu Gln Arg
            500                 505                 510

Val Leu Pro Met Gln Val Leu Glu Val Glu Thr Leu Arg Pro Thr Leu
        515                 520                 525

Thr Pro Ala Leu Ser Ile Gly Asp Thr Gln Gly Val Ala Leu His Trp
530                 535                 540

Arg Glu His Val Arg Ala Asn Gly Glu Thr Thr Val Asp Ala Gln Phe
545                 550                 555                 560

Asp Asp Thr Trp Pro Ala Ile Leu Thr His Gly Arg Val Arg Tyr Val
                565                 570                 575

Ala Gly Trp Leu Ser His Ala Leu His Arg Glu Val Leu Gln Arg Ala
            580                 585                 590

Ala Lys Asp Ala Gly Ile Glu Thr Gln His Leu Ala Asp Gly Leu Arg
        595                 600                 605

Ile Arg Arg Arg Gly Asp Leu Thr Phe Ala Phe Asn Phe Gly Pro Glu
610                 615                 620

Pro Val Gln Ala Pro Ala Pro Ala Asn Ala Thr Phe Val Leu Gly His
625                 630                 635                 640

Ser Glu Leu Lys Thr Gly Asp Val Cys Ala Trp Arg Asn Thr
                645                 650

<210> SEQ ID NO 51
<211> LENGTH: 661
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(661)

<400> SEQUENCE: 51

Met His His His His His Met Gln Leu Gly Val Cys Tyr Tyr Pro
1               5                   10                  15

Glu Gln Trp Pro Arg Ser Met Trp Ala Asp Asp Ala Lys Arg Met Val
                20                  25                  30

Glu Leu Gly Ile Thr His Val Arg Ile Ala Glu Phe Ala Trp Ser Arg
            35                  40                  45

Met Glu Pro Arg Ala Gly Glu Phe Ala Trp Asp Trp Leu Asp Glu Ala
        50                  55                  60

Val Glu Thr Leu Ala Ala Glu Gly Leu Lys Leu Val Leu Gly Thr Pro
65                  70                  75                  80

Thr Ala Ser Pro Pro Lys Trp Leu Ile Asp Ala His Pro Asp Val Leu
                85                  90                  95

Pro Val Arg Ala Asp Gly Val Arg Trp Asn Phe Gly Ser Arg Arg His
```

```
               100                 105                 110
Tyr Asp Ile Ser Ser Glu Thr Tyr Arg Arg Glu Cys Val Arg Ile Val
                115                 120                 125
Thr Ala Met Ala Glu Arg Tyr Gly Arg His Pro Ser Ile Val Ala Trp
                130                 135                 140
Gln Thr Asp Asn Glu Leu Gly Cys His Glu Thr Val Pro Ser Tyr Ser
145                 150                 155                 160
Gly Ala Ala Leu Ala Arg Phe Gln Thr Trp Leu Gln His Arg Tyr Glu
                165                 170                 175
Arg Val Glu Ala Leu Asn Asp Ala Trp Gly Asn Val Phe Trp Ser Met
                180                 185                 190
Glu Tyr Pro Ser Phe Asp Thr Ile Gly Leu Pro Asn Arg Thr Pro Thr
                195                 200                 205
Asp Ala Asn Pro Ile His Leu Leu Asp Phe Arg Arg Phe Met Ser Asp
210                 215                 220
Glu Val Ala Ser Phe His Arg Glu Gln Ile Asp Val Leu Arg Gln His
225                 230                 235                 240
Ala Pro Lys Ala Asp Leu Leu His Asn Phe Met Gly Phe Phe Thr Thr
                245                 250                 255
Phe Asp His Tyr Arg Phe Ala Glu Asp Asn Ala Leu Asp Val Ala Thr
                260                 265                 270
Trp Asp Ser Tyr Pro Ile Ala Arg Thr Glu Ser Ile Ala Leu Pro Glu
                275                 280                 285
Glu Gln Lys Ala Arg Tyr Ala Arg Thr Ala His Pro Asp Val Ser Ala
                290                 295                 300
Phe Asp His Asp Arg Tyr Arg Ala Ile Gly Ala Gly Arg Phe Trp Val
305                 310                 315                 320
Met Glu Gln Gln Ala Gly Pro Val Asn Trp Ala Pro Trp Asn Pro Val
                325                 330                 335
Pro Ala Lys Gly Met Val Arg Leu Trp Ala Tyr Glu Ala Phe Ala His
                340                 345                 350
Gly Ala Glu Leu Val Ser Tyr Phe Arg Trp Arg Gln Cys Pro Tyr Ala
                355                 360                 365
Gln Glu Gln Met His Ser Gly Leu Asn Leu Pro Asn Asn Glu Leu Ser
                370                 375                 380
Pro Gly Gly Ile Glu Val Gln Gln Ala Ala His Glu Ile Ala Ser Ser
385                 390                 395                 400
Ala Ala Leu Ser Gly Leu Gly Ala Pro Thr Arg Ala Ala Thr Ala Ile
                405                 410                 415
Val Phe Asp Tyr Glu Thr Gln Trp Met Phe Glu Ile Gln Arg His Gly
                420                 425                 430
Lys Thr Phe Asp Tyr Gln Thr Leu Ala Phe Asp Tyr Tyr Glu Ala Leu
                435                 440                 445
Arg Glu Leu Gly Leu Asp Val Asp Ile Val Ser Ser Lys Ala Asp Leu
                450                 455                 460
Ser Pro Tyr Arg Leu Val Val Pro Ser Ile Ala Val Ile Asn Asp
465                 470                 475                 480
Thr Leu Val Asp Gln Ile Glu Gln Ser Ser Ala Gln Trp Val Phe Gly
                485                 490                 495
Pro Arg Ser Gly Ser Lys Thr Thr Thr Phe Ala Ile Pro Ser Ser Leu
                500                 505                 510
Pro Pro Gly Ala Leu Gln Arg Val Leu Pro Met Gln Val Leu Glu Val
                515                 520                 525
```

```
Glu Thr Leu Arg Pro Thr Leu Thr Pro Ala Leu Ser Ile Gly Asp Thr
    530                 535                 540

Gln Gly Val Ala Leu His Trp Arg Glu His Val Arg Ala Asn Gly Glu
545                 550                 555                 560

Thr Thr Val Asp Ala Gln Phe Asp Asp Thr Trp Pro Ala Ile Leu Thr
                565                 570                 575

His Gly Arg Val Arg Tyr Val Ala Gly Trp Leu Ser His Ala Leu His
            580                 585                 590

Arg Glu Val Leu Gln Arg Ala Ala Lys Asp Ala Gly Ile Glu Thr Gln
            595                 600                 605

His Leu Ala Asp Gly Leu Arg Ile Arg Arg Arg Gly Asp Leu Thr Phe
610                 615                 620

Ala Phe Asn Phe Gly Pro Glu Pro Val Gln Ala Pro Ala Pro Ala Asn
625                 630                 635                 640

Ala Thr Phe Val Leu Gly His Ser Glu Leu Lys Thr Gly Asp Val Cys
                645                 650                 655

Ala Trp Arg Asn Thr
            660

<210> SEQ ID NO 52
<211> LENGTH: 2064
<212> TYPE: DNA
<213> ORGANISM: Bacillus alcalophilus
<220> FEATURE:
<221> NAME/KEY: CDS
<222> LOCATION: (1)..(2061)
<220> FEATURE:
<221> NAME/KEY: mat_peptide
<222> LOCATION: (1)..(2061)

<400> SEQUENCE: 52 atg tca aac ttt gag aaa tca cga gtt act aac gca gaa ttt atg ctc      48
Met Ser Asn Phe Glu Lys Ser Arg Val Thr Asn Ala Glu Phe Met Leu
1               5                   10                  15 cat ggc gga gat tac aac ccc gat caa tgg tta gat cga cct gat ata      96
His Gly Gly Asp Tyr Asn Pro Asp Gln Trp Leu Asp Arg Pro Asp Ile
                20                  25                  30 tta gcg gat gat ttg cag ttg atg aaa ttg tcc gat tcg aat aca ttc     144
Leu Ala Asp Asp Leu Gln Leu Met Lys Leu Ser Asp Ser Asn Thr Phe
            35                  40                  45 tcc att ggt att ttt gcc tgg agt gcc ctt gag cca gaa gaa ggt gtt     192
Ser Ile Gly Ile Phe Ala Trp Ser Ala Leu Glu Pro Glu Glu Gly Val
        50                  55                  60 tat cag ttt gaa tgg atg gat gag att ttt aac aat att cac gaa ata     240
Tyr Gln Phe Glu Trp Met Asp Glu Ile Phe Asn Asn Ile His Glu Ile
65                  70                  75                  80 ggt gga aaa gtc att ttg gcg aca ccg agc ggg gct cgt cct gct tgg     288
Gly Gly Lys Val Ile Leu Ala Thr Pro Ser Gly Ala Arg Pro Ala Trp
                85                  90                  95 atg tca caa aag tat cca gaa gtg ttg cgt gtc aat gaa aag cgg atg     336
Met Ser Gln Lys Tyr Pro Glu Val Leu Arg Val Asn Glu Lys Arg Met
                100                 105                 110 aag caa ctg cat ggt gga aga cat aat cat tgt ttt agc tct aaa gtg     384
Lys Gln Leu His Gly Gly Arg His Asn His Cys Phe Ser Ser Lys Val
            115                 120                 125 tac cgc gag aag act caa caa atg aat cgt cta tta gcc aaa aga tat     432
Tyr Arg Glu Lys Thr Gln Gln Met Asn Arg Leu Leu Ala Lys Arg Tyr
        130                 135                 140 gga aac cat cct gct ctt tta atg tgg cat att tcc aat gaa tat ggt     480
Gly Asn His Pro Ala Leu Leu Met Trp His Ile Ser Asn Glu Tyr Gly
```

```
                Gly Asn His Pro Ala Leu Leu Met Trp His Ile Ser Asn Glu Tyr Gly
                145                 150                 155                 160 ggc gaa tgc cat tgt gac aac tgt caa cat gct ttt aga gaa tgg ttg         528
Gly Glu Cys His Cys Asp Asn Cys Gln His Ala Phe Arg Glu Trp Leu
                165                 170                 175 aag tca aag tat aac aat gat tta aaa gca tta aac gac gca tgg tgg         576
Lys Ser Lys Tyr Asn Asn Asp Leu Lys Ala Leu Asn Asp Ala Trp Trp
            180                 185                 190 gga cca ttc tgg agt cat aca ttc agc aat tgg tca caa att gaa tct         624
Gly Pro Phe Trp Ser His Thr Phe Ser Asn Trp Ser Gln Ile Glu Ser
        195                 200                 205 cca tca cca att ggg gaa agt atg gtt cat ggc tta aac tta gat tgg         672
Pro Ser Pro Ile Gly Glu Ser Met Val His Gly Leu Asn Leu Asp Trp
    210                 215                 220 cga cga ttc gta act gac caa acg att tcc ttt tat gaa aat gaa gtg         720
Arg Arg Phe Val Thr Asp Gln Thr Ile Ser Phe Tyr Glu Asn Glu Val
225                 230                 235                 240 gtg cca tta aga gaa gta tcg cct acc att ccg att aca aca aat ttt         768
Val Pro Leu Arg Glu Val Ser Pro Thr Ile Pro Ile Thr Thr Asn Phe
                245                 250                 255 atg gct gat aca ttc gat ttg att cca ttc caa ggt ctc gat tat agt         816
Met Ala Asp Thr Phe Asp Leu Ile Pro Phe Gln Gly Leu Asp Tyr Ser
            260                 265                 270 aag ttt gcc aaa cac tta gat gtc atc agt tgg gat gct tat ccg gct         864
Lys Phe Ala Lys His Leu Asp Val Ile Ser Trp Asp Ala Tyr Pro Ala
        275                 280                 285 tgg cat aat gat tgg gaa acg acc gcc aat tta gcg atg aaa gtc ggc         912
Trp His Asn Asp Trp Glu Thr Thr Ala Asn Leu Ala Met Lys Val Gly
    290                 295                 300 ttt att aat gat tta tat cga agc atg aag cag caa ccg ttc ttg ttg         960
Phe Ile Asn Asp Leu Tyr Arg Ser Met Lys Gln Gln Pro Phe Leu Leu
305                 310                 315                 320 atg gag tct acg cca agc ggg gtt aac tgg cat agt gtg aat aaa gtc        1008
Met Glu Ser Thr Pro Ser Gly Val Asn Trp His Ser Val Asn Lys Val
                325                 330                 335 aaa cgt cct gga atg cat tta ctt tcc tcg atg caa atg att gcc cat        1056
Lys Arg Pro Gly Met His Leu Leu Ser Ser Met Gln Met Ile Ala His
            340                 345                 350 ggt tct gat agt gtg ctt tat ttc cag tgg aga aaa tca aga ggt tct        1104
Gly Ser Asp Ser Val Leu Tyr Phe Gln Trp Arg Lys Ser Arg Gly Ser
        355                 360                 365 tct gag aag ttt cat ggt gca gtg gtg gac cat gat aat agt gct gag        1152
Ser Glu Lys Phe His Gly Ala Val Val Asp His Asp Asn Ser Ala Glu
    370                 375                 380 aat cgt gtg ttt aag gaa gtc gct caa gtt ggc gaa act tta aaa gca        1200
Asn Arg Val Phe Lys Glu Val Ala Gln Val Gly Glu Thr Leu Lys Ala
385                 390                 395                 400 ctt cct aat gtt gtc ggt act aac cgt ccg tcg gaa gtg gcg att ttg        1248
Leu Pro Asn Val Val Gly Thr Asn Arg Pro Ser Glu Val Ala Ile Leu
                405                 410                 415 tat gat tgg gaa aac aat tgg gca ctc aat gat gca caa ggg ttt ggc        1296
Tyr Asp Trp Glu Asn Asn Trp Ala Leu Asn Asp Ala Gln Gly Phe Gly
            420                 425                 430 atg gag aca aaa cgt tat cca caa acg ttg caa gaa cat tat cgt cca        1344
Met Glu Thr Lys Arg Tyr Pro Gln Thr Leu Gln Glu His Tyr Arg Pro
        435                 440                 445 ttt tgg gaa aag gac att cca gtt gat gtc att acg aaa gaa caa gat        1392
Phe Trp Glu Lys Asp Ile Pro Val Asp Val Ile Thr Lys Glu Gln Asp
    450                 455                 460
```

-continued

| | | |
|---|---|---|
| ttt tct gcg tat aaa ttg tta atc gtt ccg atg ttg tat tta gtg agt<br>Phe Ser Ala Tyr Lys Leu Leu Ile Val Pro Met Leu Tyr Leu Val Ser<br>465                             470                      475                      480 | 1440 |
| gaa gat acg att tca cga tta aaa gcg ttt gtc gca aat ggc ggt aga<br>Glu Asp Thr Ile Ser Arg Leu Lys Ala Phe Val Ala Asn Gly Gly Arg<br>                           485                         490                      495 | 1488 |
| ttg gtc atg act tat ata agt gga att gta aat gaa tac gat ttg acg<br>Leu Val Met Thr Tyr Ile Ser Gly Ile Val Asn Glu Tyr Asp Leu Thr<br>500                           505                      510 | 1536 |
| tat tta ggt gga tgg cat tca gct ctt caa gaa atg ttt gga att aag<br>Tyr Leu Gly Gly Trp His Ser Ala Leu Gln Glu Met Phe Gly Ile Lys<br>         515                      520                      525 | 1584 |
| cca ctt gaa acg gat acg tat tat cca aat gat aaa aat tac gtt cag<br>Pro Leu Glu Thr Asp Thr Tyr Tyr Pro Asn Asp Lys Asn Tyr Val Gln<br>530                           535                      540 | 1632 |
| tat cat aat aag tcg tat gta tta aaa gat tat gca acg gta ctt gag<br>Tyr His Asn Lys Ser Tyr Val Leu Lys Asp Tyr Ala Thr Val Leu Glu<br>545                           550                      555                      560 | 1680 |
| gtt cat tct gca aaa gta gaa ggg caa tac ctt gaa gat ttt tat gca<br>Val His Ser Ala Lys Val Glu Gly Gln Tyr Leu Glu Asp Phe Tyr Ala<br>                         565                      570                      575 | 1728 |
| cat aca cca gcc gta aca agc cat tct tat aaa gaa gga aaa act tat<br>His Thr Pro Ala Val Thr Ser His Ser Tyr Lys Glu Gly Lys Thr Tyr<br>                   580                      585                      590 | 1776 |
| tat att ggg gca cgt tta gaa gcc gat ttc caa cgc gat ttt tat aat<br>Tyr Ile Gly Ala Arg Leu Glu Ala Asp Phe Gln Arg Asp Phe Tyr Asn<br>595                           600                      605 | 1824 |
| caa gtg att gag gat ttg gca tta gag tct gta agt caa gtg aaa cat<br>Gln Val Ile Glu Asp Leu Ala Leu Glu Ser Val Ser Gln Val Lys His<br>         610                      615                      620 | 1872 |
| gga aaa ggc gtc tcc gtt caa gca aga caa gac gaa gaa aat gat tat<br>Gly Lys Gly Val Ser Val Gln Ala Arg Gln Asp Glu Glu Asn Asp Tyr<br>625                           630                      635                      640 | 1920 |
| cta ttt gtt atg aat ttt acg gaa gaa agt caa aca gta gag ttt cca<br>Leu Phe Val Met Asn Phe Thr Glu Glu Ser Gln Thr Val Glu Phe Pro<br>                         645                      650                      655 | 1968 |
| tca acc gtt caa gat ctt gtc acc aat gaa aag ctg tac ggg gat gtc<br>Ser Thr Val Gln Asp Leu Val Thr Asn Glu Lys Leu Tyr Gly Asp Val<br>660                           665                      670 | 2016 |
| acc cta gag aag tat gaa gta aga att gtt caa caa cca aga gtt taa<br>Thr Leu Glu Lys Tyr Glu Val Arg Ile Val Gln Gln Pro Arg Val<br>         675                      680                      685 | 2064 |

<210> SEQ ID NO 53
<211> LENGTH: 687
<212> TYPE: PRT
<213> ORGANISM: Bacillus alcalophilus

<400> SEQUENCE: 53

Met Ser Asn Phe Glu Lys Ser Arg Val Thr Asn Ala Glu Phe Met Leu
1                 5                     10                   15

His Gly Gly Asp Tyr Asn Pro Asp Gln Trp Leu Asp Arg Pro Asp Ile
                 20                     25                     30

Leu Ala Asp Asp Leu Gln Leu Met Lys Leu Ser Asp Ser Asn Thr Phe
            35                     40                     45

Ser Ile Gly Ile Phe Ala Trp Ser Ala Leu Glu Pro Glu Glu Gly Val
       50                     55                     60

Tyr Gln Phe Glu Trp Met Asp Glu Ile Phe Asn Asn Ile His Glu Ile
65                70                     75                   80

-continued

Gly Gly Lys Val Ile Leu Ala Thr Pro Ser Gly Ala Arg Pro Ala Trp
            85                  90                  95
Met Ser Gln Lys Tyr Pro Glu Val Leu Arg Val Asn Glu Lys Arg Met
            100                 105                 110
Lys Gln Leu His Gly Gly Arg His Asn His Cys Phe Ser Ser Lys Val
            115                 120                 125
Tyr Arg Glu Lys Thr Gln Gln Met Asn Arg Leu Leu Ala Lys Arg Tyr
            130                 135                 140
Gly Asn His Pro Ala Leu Leu Met Trp His Ile Ser Asn Glu Tyr Gly
145                 150                 155                 160
Gly Glu Cys His Cys Asp Asn Cys Gln His Ala Phe Arg Glu Trp Leu
            165                 170                 175
Lys Ser Lys Tyr Asn Asn Asp Leu Lys Ala Leu Asn Asp Ala Trp Trp
            180                 185                 190
Gly Pro Phe Trp Ser His Thr Phe Ser Asn Trp Ser Gln Ile Glu Ser
            195                 200                 205
Pro Ser Pro Ile Gly Glu Ser Met Val His Gly Leu Asn Leu Asp Trp
            210                 215                 220
Arg Arg Phe Val Thr Asp Gln Thr Ile Ser Phe Tyr Glu Asn Glu Val
225                 230                 235                 240
Val Pro Leu Arg Glu Val Ser Pro Thr Ile Pro Ile Thr Thr Asn Phe
            245                 250                 255
Met Ala Asp Thr Phe Asp Leu Ile Pro Phe Gln Gly Leu Asp Tyr Ser
            260                 265                 270
Lys Phe Ala Lys His Leu Asp Val Ile Ser Trp Asp Ala Tyr Pro Ala
            275                 280                 285
Trp His Asn Asp Trp Glu Thr Thr Ala Asn Leu Ala Met Lys Val Gly
            290                 295                 300
Phe Ile Asn Asp Leu Tyr Arg Ser Met Lys Gln Gln Pro Phe Leu Leu
305                 310                 315                 320
Met Glu Ser Thr Pro Ser Gly Val Asn Trp His Ser Val Asn Lys Val
            325                 330                 335
Lys Arg Pro Gly Met His Leu Leu Ser Ser Met Gln Met Ile Ala His
            340                 345                 350
Gly Ser Asp Ser Val Leu Tyr Phe Gln Trp Arg Lys Ser Arg Gly Ser
            355                 360                 365
Ser Glu Lys Phe His Gly Ala Val Asp His Asp Asn Ser Ala Glu
            370                 375                 380
Asn Arg Val Phe Lys Glu Val Ala Gln Val Gly Glu Thr Leu Lys Ala
385                 390                 395                 400
Leu Pro Asn Val Val Gly Thr Asn Arg Pro Ser Glu Val Ala Ile Leu
            405                 410                 415
Tyr Asp Trp Glu Asn Asn Trp Ala Leu Asn Asp Ala Gln Gly Phe Gly
            420                 425                 430
Met Glu Thr Lys Arg Tyr Pro Gln Thr Leu Gln Glu His Tyr Arg Pro
            435                 440                 445
Phe Trp Glu Lys Asp Ile Pro Val Asp Val Ile Thr Lys Glu Gln Asp
            450                 455                 460
Phe Ser Ala Tyr Lys Leu Leu Ile Val Pro Met Leu Tyr Leu Val Ser
465                 470                 475                 480
Glu Asp Thr Ile Ser Arg Leu Lys Ala Phe Val Ala Asn Gly Gly Arg
            485                 490                 495
Leu Val Met Thr Tyr Ile Ser Gly Ile Val Asn Glu Tyr Asp Leu Thr

-continued

```
                500                 505                 510
Tyr Leu Gly Gly Trp His Ser Ala Leu Gln Glu Met Phe Gly Ile Lys
            515                 520                 525

Pro Leu Glu Thr Asp Thr Tyr Tyr Pro Asn Asp Lys Asn Tyr Val Gln
        530                 535                 540

Tyr His Asn Lys Ser Tyr Val Leu Lys Asp Tyr Ala Thr Val Leu Glu
545                 550                 555                 560

Val His Ser Ala Lys Val Glu Gly Gln Tyr Leu Glu Asp Phe Tyr Ala
                565                 570                 575

His Thr Pro Ala Val Thr Ser His Ser Tyr Lys Glu Gly Lys Thr Tyr
            580                 585                 590

Tyr Ile Gly Ala Arg Leu Glu Ala Asp Phe Gln Arg Asp Phe Tyr Asn
        595                 600                 605

Gln Val Ile Glu Asp Leu Ala Leu Glu Ser Val Ser Gln Val Lys His
            610                 615                 620

Gly Lys Gly Val Ser Val Gln Ala Arg Gln Asp Glu Glu Asn Asp Tyr
625                 630                 635                 640

Leu Phe Val Met Asn Phe Thr Glu Gly Ser Gln Thr Val Glu Phe Pro
                645                 650                 655

Ser Thr Val Gln Asp Leu Val Thr Asn Glu Lys Leu Tyr Gly Asp Val
            660                 665                 670

Thr Leu Glu Lys Tyr Glu Val Arg Ile Val Gln Pro Arg Val
        675                 680                 685

<210> SEQ ID NO 54
<211> LENGTH: 694
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(694)

<400> SEQUENCE: 54

Met His His His His His Met Ser Asn Phe Glu Lys Ser Arg Val
1               5                   10                  15

Thr Asn Ala Glu Phe Met Leu His Gly Gly Asp Tyr Asn Pro Asp Gln
            20                  25                  30

Trp Leu Asp Arg Pro Asp Ile Leu Ala Asp Leu Gln Leu Met Lys
        35                  40                  45

Leu Ser Asp Ser Asn Thr Phe Ser Ile Gly Ile Phe Ala Trp Ser Ala
 50                  55                  60

Leu Glu Pro Glu Glu Gly Val Tyr Gln Phe Glu Trp Met Asp Glu Ile
65                  70                  75                  80

Phe Asn Asn Ile His Glu Ile Gly Gly Lys Val Ile Leu Ala Thr Pro
                85                  90                  95

Ser Gly Ala Arg Pro Ala Trp Met Ser Gln Lys Tyr Pro Glu Val Leu
            100                 105                 110

Arg Val Asn Glu Lys Arg Met Lys Gln Leu His Gly Arg His Asn
        115                 120                 125

His Cys Phe Ser Ser Lys Val Tyr Arg Glu Lys Thr Gln Gln Met Asn
    130                 135                 140

Arg Leu Leu Ala Lys Arg Tyr Gly Asn His Pro Ala Leu Leu Met Trp
145                 150                 155                 160

His Ile Ser Asn Glu Tyr Gly Gly Glu Cys His Cys Asp Asn Cys Gln
```

```
                165                 170                 175
His Ala Phe Arg Glu Trp Leu Lys Ser Lys Tyr Asn Asn Asp Leu Lys
                180                 185                 190

Ala Leu Asn Asp Ala Trp Trp Gly Pro Phe Trp Ser His Thr Phe Ser
                195                 200                 205

Asn Trp Ser Gln Ile Glu Ser Pro Ser Pro Ile Gly Glu Ser Met Val
                210                 215                 220

His Gly Leu Asn Leu Asp Trp Arg Arg Phe Val Thr Asp Gln Thr Ile
225                 230                 235                 240

Ser Phe Tyr Glu Asn Glu Val Val Pro Leu Arg Glu Val Ser Pro Thr
                245                 250                 255

Ile Pro Ile Thr Thr Asn Phe Met Ala Asp Thr Phe Asp Leu Ile Pro
                260                 265                 270

Phe Gln Gly Leu Asp Tyr Ser Lys Phe Ala Lys His Leu Asp Val Ile
                275                 280                 285

Ser Trp Asp Ala Tyr Pro Ala Trp His Asn Asp Trp Glu Thr Thr Ala
                290                 295                 300

Asn Leu Ala Met Lys Val Gly Phe Ile Asn Asp Leu Tyr Arg Ser Met
305                 310                 315                 320

Lys Gln Gln Pro Phe Leu Leu Met Glu Ser Thr Pro Ser Gly Val Asn
                325                 330                 335

Trp His Ser Val Asn Lys Val Lys Arg Pro Gly Met His Leu Leu Ser
                340                 345                 350

Ser Met Gln Met Ile Ala His Gly Ser Asp Ser Val Leu Tyr Phe Gln
                355                 360                 365

Trp Arg Lys Ser Arg Gly Ser Ser Glu Lys Phe His Gly Ala Val Val
                370                 375                 380

Asp His Asp Asn Ser Ala Glu Asn Arg Val Phe Lys Glu Val Ala Gln
385                 390                 395                 400

Val Gly Glu Thr Leu Lys Ala Leu Pro Asn Val Val Gly Thr Asn Arg
                405                 410                 415

Pro Ser Glu Val Ala Ile Leu Tyr Asp Trp Glu Asn Asn Trp Ala Leu
                420                 425                 430

Asn Asp Ala Gln Gly Phe Gly Met Glu Thr Lys Arg Tyr Pro Gln Thr
                435                 440                 445

Leu Gln Glu His Tyr Arg Pro Phe Trp Glu Lys Asp Ile Pro Val Asp
                450                 455                 460

Val Ile Thr Lys Glu Gln Asp Phe Ser Ala Tyr Lys Leu Leu Ile Val
465                 470                 475                 480

Pro Met Leu Tyr Leu Val Ser Glu Asp Thr Ile Ser Arg Leu Lys Ala
                485                 490                 495

Phe Val Ala Asn Gly Gly Arg Leu Val Met Thr Tyr Ile Ser Gly Ile
                500                 505                 510

Val Asn Glu Tyr Asp Leu Thr Tyr Leu Gly Gly Trp His Ser Ala Leu
                515                 520                 525

Gln Glu Met Phe Gly Ile Lys Pro Leu Glu Thr Asp Thr Tyr Tyr Pro
                530                 535                 540

Asn Asp Lys Asn Tyr Val Gln Tyr His Asn Lys Ser Tyr Val Leu Lys
545                 550                 555                 560

Asp Tyr Ala Thr Val Leu Glu Val His Ser Ala Lys Val Glu Gly Gln
                565                 570                 575

Tyr Leu Glu Asp Phe Tyr Ala His Thr Pro Ala Val Thr Ser His Ser
                580                 585                 590
```

```
Tyr Lys Glu Gly Lys Thr Tyr Tyr Ile Gly Ala Arg Leu Glu Ala Asp
        595                 600                 605

Phe Gln Arg Asp Phe Tyr Asn Gln Val Ile Glu Asp Leu Ala Leu Glu
        610                 615                 620

Ser Val Ser Gln Val Lys His Gly Lys Gly Val Ser Val Gln Ala Arg
625                 630                 635                 640

Gln Asp Glu Glu Asn Asp Tyr Leu Phe Val Met Asn Phe Thr Glu Glu
                645                 650                 655

Ser Gln Thr Val Glu Phe Pro Ser Thr Val Gln Asp Leu Val Thr Asn
        660                 665                 670

Glu Lys Leu Tyr Gly Asp Val Thr Leu Glu Lys Tyr Glu Val Arg Ile
        675                 680                 685

Val Gln Gln Pro Arg Val
        690

<210> SEQ ID NO 55
<211> LENGTH: 2061
<212> TYPE: DNA
<213> ORGANISM: Bacillus sp-11182
<220> FEATURE:
<221> NAME/KEY: CDS
<222> LOCATION: (1)..(2058)
<220> FEATURE:
<221> NAME/KEY: mat_peptide
<222> LOCATION: (1)..(2058)

<400> SEQUENCE: 55
```

| | | | | | | | | | | | | | | | | |
|---|---|---|---|---|---|---|---|---|---|---|---|---|---|---|---|---|
| atg | tca | aca | cta | aag | aaa | aca | caa | gtg | aca | aaa | gcg | gat | ttt | atg | ctt | 48 |
| Met | Ser | Thr | Leu | Lys | Lys | Thr | Gln | Val | Thr | Lys | Ala | Asp | Phe | Met | Leu | |
| 1 | | | | 5 | | | | | 10 | | | | | 15 | | |
| cat | gga | ggc | gat | tat | aat | cct | gat | cag | tgg | ctg | gac | cgc | cct | gat | ata | 96 |
| His | Gly | Gly | Asp | Tyr | Asn | Pro | Asp | Gln | Trp | Leu | Asp | Arg | Pro | Asp | Ile | |
| | | | 20 | | | | | 25 | | | | | 30 | | | |
| ctg | gca | gat | gac | atc | aaa | ctg | atg | aag | ctt | gcg | cat | aca | aat | acc | ttt | 144 |
| Leu | Ala | Asp | Asp | Ile | Lys | Leu | Met | Lys | Leu | Ala | His | Thr | Asn | Thr | Phe | |
| | | 35 | | | | | 40 | | | | | 45 | | | | |
| tca | gtg | ggg | atc | ttc | gcc | tgg | agc | gcc | ctt | gaa | cct | gag | gaa | ggg | cat | 192 |
| Ser | Val | Gly | Ile | Phe | Ala | Trp | Ser | Ala | Leu | Glu | Pro | Glu | Glu | Gly | His | |
| | 50 | | | | | 55 | | | | | 60 | | | | | |
| ttt | acc | ttc | gaa | tgg | ctt | gat | gag | atc | atc | aat | aat | atc | gac | gga | atc | 240 |
| Phe | Thr | Phe | Glu | Trp | Leu | Asp | Glu | Ile | Ile | Asn | Asn | Ile | Asp | Gly | Ile | |
| 65 | | | | | 70 | | | | | 75 | | | | | 80 | |
| ggc | ggc | aag | gta | atc | ctt | gct | act | cca | agc | ggc | gcc | cgc | cct | gca | tgg | 288 |
| Gly | Gly | Lys | Val | Ile | Leu | Ala | Thr | Pro | Ser | Gly | Ala | Arg | Pro | Ala | Trp | |
| | | | | 85 | | | | | 90 | | | | | 95 | | |
| atg | tcg | cag | aag | tat | cct | gag | gtc | ctc | agg | gta | aac | ggg | gag | agg | gtc | 336 |
| Met | Ser | Gln | Lys | Tyr | Pro | Glu | Val | Leu | Arg | Val | Asn | Gly | Glu | Arg | Val | |
| | | | 100 | | | | | 105 | | | | | 110 | | | |
| aaa | cag | ctt | cat | ggc | ggc | agg | cac | aac | cat | tgc | ttt | acg | tct | gag | gtc | 384 |
| Lys | Gln | Leu | His | Gly | Gly | Arg | His | Asn | His | Cys | Phe | Thr | Ser | Glu | Val | |
| | | 115 | | | | | 120 | | | | | 125 | | | | |
| tac | cgc | gag | aaa | act | cgg | aag | atc | aac | agg | ctc | ctt | gct | gaa | aga | tat | 432 |
| Tyr | Arg | Glu | Lys | Thr | Arg | Lys | Ile | Asn | Arg | Leu | Leu | Ala | Glu | Arg | Tyr | |
| | 130 | | | | | 135 | | | | | 140 | | | | | |
| gca | ggc | cac | cct | gcg | ctc | ctg | atg | tgg | cac | att | tcc | aat | gag | tat | ggc | 480 |
| Ala | Gly | His | Pro | Ala | Leu | Leu | Met | Trp | His | Ile | Ser | Asn | Glu | Tyr | Gly | |
| 145 | | | | | 150 | | | | | 155 | | | | | 160 | |
| ggg | gaa | tgc | cac | tgc | agc | agc | tgc | cag | gca | gcc | ttc | cgg | aac | tgg | ctg | 528 |
| Gly | Glu | Cys | His | Cys | Ser | Ser | Cys | Gln | Ala | Ala | Phe | Arg | Asn | Trp | Leu | |
| | | | | 165 | | | | | 170 | | | | | 175 | | |

```
aaa gag aaa tac aat cat aat ctc aaa gca ttg aat gac gcc tgg tgg      576
Lys Glu Lys Tyr Asn His Asn Leu Lys Ala Leu Asn Asp Ala Trp Trp
            180                 185                 190 ggt cct ttc tgg agc cat act ttc agc gat tgg gaa cag atc gag tcc      624
Gly Pro Phe Trp Ser His Thr Phe Ser Asp Trp Glu Gln Ile Glu Ser
        195                 200                 205 cct tcg ccg atc ggg gaa aat gct gtt cac ggc ctt aac ctg gat tgg      672
Pro Ser Pro Ile Gly Glu Asn Ala Val His Gly Leu Asn Leu Asp Trp
    210                 215                 220 cgc cgc ttt ata aca gac cag acg atc tct ttt tat aaa aac gaa atc      720
Arg Arg Phe Ile Thr Asp Gln Thr Ile Ser Phe Tyr Lys Asn Glu Ile
225                 230                 235                 240 gta cct tta agg gag att aca ccc ggt att cca atc aca acc aat ttc      768
Val Pro Leu Arg Glu Ile Thr Pro Gly Ile Pro Ile Thr Thr Asn Phe
                245                 250                 255 atg gca gat aca atg gat ctt atc ccg ttc cag gcc ctt gat tat tcc      816
Met Ala Asp Thr Met Asp Leu Ile Pro Phe Gln Ala Leu Asp Tyr Ser
            260                 265                 270 aag ttt gcc aag cat ctg gat gtc atc agc tgg gat gcc tat cct gcc      864
Lys Phe Ala Lys His Leu Asp Val Ile Ser Trp Asp Ala Tyr Pro Ala
        275                 280                 285 tgg cat aat gac tgg gag tcc aca gcg aat ctt gcc atg aag aca gct      912
Trp His Asn Asp Trp Glu Ser Thr Ala Asn Leu Ala Met Lys Thr Ala
    290                 295                 300 ttt atc gat gat tta tat cgc agt ctg aaa cag cag ccg ttt ctg ctg      960
Phe Ile Asp Asp Leu Tyr Arg Ser Leu Lys Gln Gln Pro Phe Leu Leu
305                 310                 315                 320 atg gag tct acg cca agc gct gta aac tgg cac cct gtc aat aaa gcg     1008
Met Glu Ser Thr Pro Ser Ala Val Asn Trp His Pro Val Asn Lys Ala
                325                 330                 335 aag cgt ccc ggc atg cac ctt tta tct tcc atg cag atg atc gcc cac     1056
Lys Arg Pro Gly Met His Leu Leu Ser Ser Met Gln Met Ile Ala His
            340                 345                 350 gga tct gac agc gtt atg tat ttt caa tgg cgc aag tca agg ggg tca     1104
Gly Ser Asp Ser Val Met Tyr Phe Gln Trp Arg Lys Ser Arg Gly Ser
        355                 360                 365 tct gag aag ttc cat gga gcg gtt gta gac cat gat aat agt gcc gat     1152
Ser Glu Lys Phe His Gly Ala Val Val Asp His Asp Asn Ser Ala Asp
    370                 375                 380 aac cgg gtc ttc aag gaa gtc gcg gca gtg ggt gaa act ctt gaa aag     1200
Asn Arg Val Phe Lys Glu Val Ala Ala Val Gly Glu Thr Leu Glu Lys
385                 390                 395                 400 ctt tct gct gtc gta gga acc agc cgc cct gct gaa gct gcc atc ctg     1248
Leu Ser Ala Val Val Gly Thr Ser Arg Pro Ala Glu Ala Ala Ile Leu
                405                 410                 415 tat gac tgg gaa agc aat tgg gcc ctg aac gat gcc cag ggg ttc ggt     1296
Tyr Asp Trp Glu Ser Asn Trp Ala Leu Asn Asp Ala Gln Gly Phe Gly
            420                 425                 430 ctg gaa acg aaa caa tat ccg caa aca ctg cag gaa cat tac cgc acc     1344
Leu Glu Thr Lys Gln Tyr Pro Gln Thr Leu Gln Glu His Tyr Arg Thr
        435                 440                 445 ttc tgg gaa aaa gat att cca gtg gat gtc atc aca aaa gag cag gat     1392
Phe Trp Glu Lys Asp Ile Pro Val Asp Val Ile Thr Lys Glu Gln Asp
    450                 455                 460 ttt acg gca tac aag ctg att atc gcc ccg atg ctg tat ctg gca agc     1440
Phe Thr Ala Tyr Lys Leu Ile Ile Ala Pro Met Leu Tyr Leu Ala Ser
465                 470                 475                 480 aaa gaa acg att gca agg ctg aaa tcc ttt gtg gcc ggc ggc ggt aca     1488
Lys Glu Thr Ile Ala Arg Leu Lys Ser Phe Val Ala Gly Gly Gly Thr
```

```
                         485                 490                 495
ctg gtt atg tcc tat atc agc ggt gtg gtt gac gaa aat gat ctt gtc     1536
Leu Val Met Ser Tyr Ile Ser Gly Val Val Asp Glu Asn Asp Leu Val
            500                 505                 510 cat ttt ggc gga tgg ccg ctg gac ctt cag gaa acc ttc ggg ctg aag     1584
His Phe Gly Gly Trp Pro Leu Asp Leu Gln Glu Thr Phe Gly Leu Lys
        515                 520                 525 cct gtc gag act gat act tta tat cct ggg gac agc aac cag gta act     1632
Pro Val Glu Thr Asp Thr Leu Tyr Pro Gly Asp Ser Asn Gln Val Thr
    530                 535                 540 tat aaa gac aaa caa tat atg ctg aaa gat tat gcg act gtt att gag     1680
Tyr Lys Asp Lys Gln Tyr Met Leu Lys Asp Tyr Ala Thr Val Ile Glu
545                 550                 555                 560 ctg gcc ggc gca aaa gcc gac ggg aca tat gaa cag gat ttc tat gct     1728
Leu Ala Gly Ala Lys Ala Asp Gly Thr Tyr Glu Gln Asp Phe Tyr Ala
            565                 570                 575 ggc ctc ccg gct gtc aca agc cac cag tat aaa gaa gga aac gct tat     1776
Gly Leu Pro Ala Val Thr Ser His Gln Tyr Lys Glu Gly Asn Ala Tyr
        580                 585                 590 tat atc gga ggc cgc ctg gat gca gaa ttc cac cgg gat ttt tac agc     1824
Tyr Ile Gly Gly Arg Leu Asp Ala Glu Phe His Arg Asp Phe Tyr Ser
    595                 600                 605 aga ttg atg gcc gga ttg agc ttg aag gct gcc ttc cct gtc aag cat     1872
Arg Leu Met Ala Gly Leu Ser Leu Lys Ala Ala Phe Pro Val Lys His
610                 615                 620 gag agc ggg gtt tct gtg cag gta agg caa gat ggg gaa aag gat tat     1920
Glu Ser Gly Val Ser Val Gln Val Arg Gln Asp Gly Glu Lys Asp Tyr
625                 630                 635                 640 ata ttt gtc atg aac ttc act gaa gag aag cag act gcg gtt ttt gag     1968
Ile Phe Val Met Asn Phe Thr Glu Glu Lys Gln Thr Ala Val Phe Glu
            645                 650                 655 cag cag gca aaa gat att ctg act aac gaa gaa ctg tcc ggt gaa gtc     2016
Gln Gln Ala Lys Asp Ile Leu Thr Asn Glu Glu Leu Ser Gly Glu Val
        660                 665                 670 agt ttg aat cct tac gaa gtt aag ata gca gaa aga acc aga taa         2061
Ser Leu Asn Pro Tyr Glu Val Lys Ile Ala Glu Arg Thr Arg
    675                 680                 685
```

<210> SEQ ID NO 56
<211> LENGTH: 686
<212> TYPE: PRT
<213> ORGANISM: Bacillus sp-11182

<400> SEQUENCE: 56

```
Met Ser Thr Leu Lys Lys Thr Gln Val Thr Lys Ala Asp Phe Met Leu
1               5                   10                  15

His Gly Gly Asp Tyr Asn Pro Asp Gln Trp Leu Asp Arg Pro Asp Ile
            20                  25                  30

Leu Ala Asp Asp Ile Lys Leu Met Lys Leu Ala His Thr Asn Thr Phe
        35                  40                  45

Ser Val Gly Ile Phe Ala Trp Ser Ala Leu Glu Pro Glu Glu Gly His
    50                  55                  60

Phe Thr Phe Glu Trp Leu Asp Glu Ile Ile Asn Asn Ile Asp Gly Ile
65                  70                  75                  80

Gly Gly Lys Val Ile Leu Ala Thr Pro Ser Gly Ala Arg Pro Ala Trp
                85                  90                  95

Met Ser Gln Lys Tyr Pro Glu Val Leu Arg Val Asn Gly Glu Arg Val
            100                 105                 110
```

```
Lys Gln Leu His Gly Gly Arg His Asn His Cys Phe Thr Ser Glu Val
            115                 120                 125
Tyr Arg Glu Lys Thr Arg Lys Ile Asn Arg Leu Leu Ala Glu Arg Tyr
130                 135                 140
Ala Gly His Pro Ala Leu Leu Met Trp His Ile Ser Asn Glu Tyr Gly
145                 150                 155                 160
Gly Glu Cys His Cys Ser Ser Cys Gln Ala Ala Phe Arg Asn Trp Leu
                165                 170                 175
Lys Glu Lys Tyr Asn His Asn Leu Lys Ala Leu Asn Asp Ala Trp Trp
            180                 185                 190
Gly Pro Phe Trp Ser His Thr Phe Ser Asp Trp Glu Gln Ile Glu Ser
        195                 200                 205
Pro Ser Pro Ile Gly Glu Asn Ala Val His Gly Leu Asn Leu Asp Trp
210                 215                 220
Arg Arg Phe Ile Thr Asp Gln Thr Ile Ser Phe Tyr Lys Asn Glu Ile
225                 230                 235                 240
Val Pro Leu Arg Glu Ile Thr Pro Gly Ile Pro Ile Thr Thr Asn Phe
                245                 250                 255
Met Ala Asp Thr Met Asp Leu Ile Pro Phe Gln Ala Leu Asp Tyr Ser
            260                 265                 270
Lys Phe Ala Lys His Leu Asp Val Ile Ser Trp Asp Ala Tyr Pro Ala
        275                 280                 285
Trp His Asn Asp Trp Glu Ser Thr Ala Asn Leu Ala Met Lys Thr Ala
        290                 295                 300
Phe Ile Asp Asp Leu Tyr Arg Ser Leu Lys Gln Gln Pro Phe Leu Leu
305                 310                 315                 320
Met Glu Ser Thr Pro Ser Ala Val Asn Trp His Pro Val Asn Lys Ala
                325                 330                 335
Lys Arg Pro Gly Met His Leu Leu Ser Ser Met Gln Met Ile Ala His
            340                 345                 350
Gly Ser Asp Ser Val Met Tyr Phe Gln Trp Arg Lys Ser Arg Gly Ser
        355                 360                 365
Ser Glu Lys Phe His Gly Ala Val Val Asp His Asp Asn Ser Ala Asp
370                 375                 380
Asn Arg Val Phe Lys Glu Val Ala Ala Val Gly Glu Thr Leu Glu Lys
385                 390                 395                 400
Leu Ser Ala Val Val Gly Thr Ser Arg Pro Ala Glu Ala Ala Ile Leu
                405                 410                 415
Tyr Asp Trp Glu Ser Asn Trp Ala Leu Asn Asp Ala Gln Gly Phe Gly
            420                 425                 430
Leu Glu Thr Lys Gln Tyr Pro Gln Thr Leu Gln Glu His Tyr Arg Thr
        435                 440                 445
Phe Trp Glu Lys Asp Ile Pro Val Asp Val Ile Thr Lys Glu Gln Asp
        450                 455                 460
Phe Thr Ala Tyr Lys Leu Ile Ile Ala Pro Met Leu Tyr Leu Ala Ser
465                 470                 475                 480
Lys Glu Thr Ile Ala Arg Leu Lys Ser Phe Val Ala Gly Gly Thr
                485                 490                 495
Leu Val Met Ser Tyr Ile Ser Gly Val Val Asp Glu Asn Asp Leu Val
            500                 505                 510
His Phe Gly Gly Trp Pro Leu Asp Leu Gln Glu Thr Phe Gly Leu Lys
        515                 520                 525
Pro Val Glu Thr Asp Thr Leu Tyr Pro Gly Asp Ser Asn Gln Val Thr
```

```
                530             535             540
Tyr Lys Asp Lys Gln Tyr Met Leu Lys Asp Tyr Ala Thr Val Ile Glu
545                 550             555                 560

Leu Ala Gly Ala Lys Ala Asp Gly Thr Tyr Glu Gln Asp Phe Tyr Ala
                565             570             575

Gly Leu Pro Ala Val Thr Ser His Gln Tyr Lys Glu Gly Asn Ala Tyr
            580             585             590

Tyr Ile Gly Gly Arg Leu Asp Ala Glu Phe His Arg Asp Phe Tyr Ser
        595             600             605

Arg Leu Met Ala Gly Leu Ser Leu Lys Ala Ala Phe Pro Val Lys His
            610             615             620

Glu Ser Gly Val Ser Val Gln Val Arg Gln Asp Gly Glu Lys Asp Tyr
625             630             635             640

Ile Phe Val Met Asn Phe Thr Glu Glu Lys Gln Thr Ala Val Phe Glu
                645             650             655

Gln Gln Ala Lys Asp Ile Leu Thr Asn Glu Glu Leu Ser Gly Glu Val
                660             665             670

Ser Leu Asn Pro Tyr Glu Val Lys Ile Ala Glu Arg Thr Arg
            675             680             685

<210> SEQ ID NO 57
<211> LENGTH: 695
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(695)

<400> SEQUENCE: 57

Met His His His His His Pro Arg Met Ser Thr Leu Lys Lys Thr
1               5                   10                  15

Gln Val Thr Lys Ala Asp Phe Met Leu His Gly Gly Asp Tyr Asn Pro
                20                  25                  30

Asp Gln Trp Leu Asp Arg Pro Asp Ile Leu Ala Asp Asp Ile Lys Leu
            35                  40                  45

Met Lys Leu Ala His Thr Asn Thr Phe Ser Val Gly Ile Phe Ala Trp
        50                  55                  60

Ser Ala Leu Glu Pro Glu Glu Gly His Phe Thr Phe Glu Trp Leu Asp
65                  70                  75                  80

Glu Ile Ile Asn Asn Ile Asp Gly Ile Gly Lys Val Ile Leu Ala
                85                  90                  95

Thr Pro Ser Gly Ala Arg Pro Ala Trp Met Ser Gln Lys Tyr Pro Glu
                100                 105                 110

Val Leu Arg Val Asn Gly Glu Arg Val Lys Gln Leu His Gly Gly Arg
            115                 120                 125

His Asn His Cys Phe Thr Ser Glu Val Tyr Arg Glu Lys Thr Arg Lys
        130                 135                 140

Ile Asn Arg Leu Leu Ala Glu Arg Tyr Ala Gly His Pro Ala Leu Leu
145                 150                 155                 160

Met Trp His Ile Ser Asn Glu Tyr Gly Gly Glu Cys His Cys Ser Ser
                165                 170                 175

Cys Gln Ala Ala Phe Arg Asn Trp Leu Lys Glu Lys Tyr Asn His Asn
                180                 185                 190

Leu Lys Ala Leu Asn Asp Ala Trp Trp Gly Pro Phe Trp Ser His Thr
```

```
                195                 200                 205
Phe Ser Asp Trp Glu Gln Ile Glu Ser Pro Ser Pro Ile Gly Glu Asn
    210                 215                 220

Ala Val His Gly Leu Asn Leu Asp Trp Arg Arg Phe Ile Thr Asp Gln
225                 230                 235                 240

Thr Ile Ser Phe Tyr Lys Asn Glu Ile Val Pro Leu Arg Glu Ile Thr
                245                 250                 255

Pro Gly Ile Pro Ile Thr Thr Asn Phe Met Ala Asp Thr Met Asp Leu
            260                 265                 270

Ile Pro Phe Gln Ala Leu Asp Tyr Ser Lys Phe Ala Lys His Leu Asp
        275                 280                 285

Val Ile Ser Trp Asp Ala Tyr Pro Ala Trp His Asn Asp Trp Glu Ser
    290                 295                 300

Thr Ala Asn Leu Ala Met Lys Thr Ala Phe Ile Asp Asp Leu Tyr Arg
305                 310                 315                 320

Ser Leu Lys Gln Gln Pro Phe Leu Leu Met Glu Ser Thr Pro Ser Ala
                325                 330                 335

Val Asn Trp His Pro Val Asn Lys Ala Lys Arg Pro Gly Met His Leu
            340                 345                 350

Leu Ser Ser Met Gln Met Ile Ala His Gly Ser Asp Ser Val Met Tyr
        355                 360                 365

Phe Gln Trp Arg Lys Ser Arg Gly Ser Ser Glu Lys Phe His Gly Ala
    370                 375                 380

Val Val Asp His Asp Asn Ser Ala Asp Asn Arg Val Phe Lys Glu Val
385                 390                 395                 400

Ala Ala Val Gly Glu Thr Leu Glu Lys Leu Ser Ala Val Val Gly Thr
                405                 410                 415

Ser Arg Pro Ala Glu Ala Ala Ile Leu Tyr Asp Trp Glu Ser Asn Trp
            420                 425                 430

Ala Leu Asn Asp Ala Gln Gly Phe Gly Leu Glu Thr Lys Gln Tyr Pro
        435                 440                 445

Gln Thr Leu Gln Glu His Tyr Arg Thr Phe Trp Glu Lys Asp Ile Pro
    450                 455                 460

Val Asp Val Ile Thr Lys Glu Gln Asp Phe Thr Ala Tyr Lys Leu Ile
465                 470                 475                 480

Ile Ala Pro Met Leu Tyr Leu Ala Ser Lys Glu Thr Ile Ala Arg Leu
                485                 490                 495

Lys Ser Phe Val Ala Gly Gly Thr Leu Val Met Ser Tyr Ile Ser
            500                 505                 510

Gly Val Val Asp Glu Asn Asp Leu Val His Phe Gly Trp Pro Leu
    515                 520                 525

Asp Leu Gln Glu Thr Phe Gly Leu Lys Pro Val Glu Thr Asp Thr Leu
    530                 535                 540

Tyr Pro Gly Asp Ser Asn Gln Val Thr Tyr Lys Asp Lys Gln Tyr Met
545                 550                 555                 560

Leu Lys Asp Tyr Ala Thr Val Ile Glu Leu Ala Gly Ala Lys Ala Asp
                565                 570                 575

Gly Thr Tyr Glu Gln Asp Phe Tyr Ala Gly Leu Pro Ala Val Thr Ser
            580                 585                 590

His Gln Tyr Lys Glu Gly Asn Ala Tyr Tyr Ile Gly Gly Arg Leu Asp
        595                 600                 605

Ala Glu Phe His Arg Asp Phe Tyr Ser Arg Leu Met Ala Gly Leu Ser
    610                 615                 620
```

| | | | | | | | | | | | | |
|---|---|---|---|---|---|---|---|---|---|---|---|---|
|Leu|Lys|Ala|Ala|Phe|Pro|Val|Lys|His|Glu|Ser|Gly|Val|Ser|Val|Gln|
|625| | | |630| | | |635| | | |640|

| | | | | | | | | | | | |
|---|---|---|---|---|---|---|---|---|---|---|---|
|Val|Arg|Gln|Asp|Gly|Glu|Lys|Asp|Tyr|Ile|Phe|Val|Met|Asn|Phe|Thr|
| | | | |645| | | |650| | | |655|

|Glu|Glu|Lys|Gln|Thr|Ala|Val|Phe|Glu|Gln|Gln|Ala|Lys|Asp|Ile|Leu|
| | | |660| | | | |665| | | |670|

|Thr|Asn|Glu|Glu|Leu|Ser|Gly|Glu|Val|Ser|Leu|Asn|Pro|Tyr|Glu|Val|
| | | |675| | | | |680| | | |685|

|Lys|Ile|Ala|Glu|Arg|Thr|Arg|
| | |690| | | |695|

<210> SEQ ID NO 58
<211> LENGTH: 2067
<212> TYPE: DNA
<213> ORGANISM: Bacillus sp-62759
<220> FEATURE:
<221> NAME/KEY: CDS
<222> LOCATION: (1)..(2064)
<220> FEATURE:
<221> NAME/KEY: mat_peptide
<222> LOCATION: (1)..(2064)

<400> SEQUENCE: 58

```
atg cct gac aat gaa aaa act tac gtg aca aaa gca aac ttt atg ctt      48
Met Pro Asp Asn Glu Lys Thr Tyr Val Thr Lys Ala Asn Phe Met Leu
1               5                  10                  15 cat ggt ggc gat tat aac cca gat cag tgg tta gac cga cct gat atc      96
His Gly Gly Asp Tyr Asn Pro Asp Gln Trp Leu Asp Arg Pro Asp Ile
                20                  25                  30 ctt gcc gat gat gtg aag tta atg aag cta tca cat tca aat act ttt     144
Leu Ala Asp Asp Val Lys Leu Met Lys Leu Ser His Ser Asn Thr Phe
            35                  40                  45 tcg gtt gga att ttt gca tgg agt gca ctt gaa cca caa gaa ggt gtc     192
Ser Val Gly Ile Phe Ala Trp Ser Ala Leu Glu Pro Gln Glu Gly Val
        50                  55                  60 tac caa ttt gaa tgg tta gat gag atc ttc gag aat att tac aaa att     240
Tyr Gln Phe Glu Trp Leu Asp Glu Ile Phe Glu Asn Ile Tyr Lys Ile
65                  70                  75                  80 ggt ggt cgt gtg att ttg gcg acc cca agt ggt gct cgt cca gcg tgg     288
Gly Gly Arg Val Ile Leu Ala Thr Pro Ser Gly Ala Arg Pro Ala Trp
                85                  90                  95 atg tca gca aag tac cca gaa gtg ctt cgc gtt aat agt tca aga gtg     336
Met Ser Ala Lys Tyr Pro Glu Val Leu Arg Val Asn Ser Ser Arg Val
                100                 105                 110 aaa cag cta cat ggg ggg cga cat aat cat tgt ttc aca tca gaa gtg     384
Lys Gln Leu His Gly Gly Arg His Asn His Cys Phe Thr Ser Glu Val
            115                 120                 125 tac cgt gat aaa acc cag gaa atg aat cga tta tta gct gag aga tat     432
Tyr Arg Asp Lys Thr Gln Glu Met Asn Arg Leu Leu Ala Glu Arg Tyr
        130                 135                 140 gga agt cat cca gcc tta ctg atg tgg cat atc tca aat gag tat ggt     480
Gly Ser His Pro Ala Leu Leu Met Trp His Ile Ser Asn Glu Tyr Gly
145                 150                 155                 160 ggc gag tgt cac tgt gat aag tgt cag act gca ttt aga agc tgg gtt     528
Gly Glu Cys His Cys Asp Lys Cys Gln Thr Ala Phe Arg Ser Trp Val
                165                 170                 175 aag cga aaa tat aat gat gat tta aaa gcg tta aat gac gca tgg tgg     576
Lys Arg Lys Tyr Asn Asp Asp Leu Lys Ala Leu Asn Asp Ala Trp Trp
                180                 185                 190 gga ccg ttc tgg agc cat aca att agt gat tgg tca cag gta gaa tct     624
```

```
Gly Pro Phe Trp Ser His Thr Ile Ser Asp Trp Ser Gln Val Glu Ser
            195                 200                 205 cct tct ccg att ggg gaa aat atg gtt cat ggc ctg aac ttg gat tgg        672
Pro Ser Pro Ile Gly Glu Asn Met Val His Gly Leu Asn Leu Asp Trp
210                 215                 220 cgt aga ttt att aca gac caa acg atc tca ttc tat caa aac gaa att        720
Arg Arg Phe Ile Thr Asp Gln Thr Ile Ser Phe Tyr Gln Asn Glu Ile
225                 230                 235                 240 gta ccg ctc aga aag ttg act cca gaa att cca att aca acg aat ttc        768
Val Pro Leu Arg Lys Leu Thr Pro Glu Ile Pro Ile Thr Thr Asn Phe
            245                 250                 255 atg gca gac aca cat gat ctt att cct ttt cag gca ttg gat tac agc        816
Met Ala Asp Thr His Asp Leu Ile Pro Phe Gln Ala Leu Asp Tyr Ser
            260                 265                 270 aag ttt gct aag cat tta gat gtg att agc tgg gat gcg tat cca gct        864
Lys Phe Ala Lys His Leu Asp Val Ile Ser Trp Asp Ala Tyr Pro Ala
            275                 280                 285 tgg cat aat gat tgg gaa acc aca gct gac tta gcg gca aaa gta gcg        912
Trp His Asn Asp Trp Glu Thr Thr Ala Asp Leu Ala Ala Lys Val Ala
            290                 295                 300 ttt ata aat gat ttg tat cgt agc cta aag caa caa ccg ttc ttg tta        960
Phe Ile Asn Asp Leu Tyr Arg Ser Leu Lys Gln Gln Pro Phe Leu Leu
305                 310                 315                 320 atg gag tca acc cct agt gga gtt aat tgg cat gaa gta aat aag gct       1008
Met Glu Ser Thr Pro Ser Gly Val Asn Trp His Glu Val Asn Lys Ala
            325                 330                 335 aaa agg ccg gga atg cac cta tta tca tca ctc caa atg gta gca cat       1056
Lys Arg Pro Gly Met His Leu Leu Ser Ser Leu Gln Met Val Ala His
            340                 345                 350 gga tct gat agt gtc ctt tat ttc cag tgg cga aag tct cgg gga tct       1104
Gly Ser Asp Ser Val Leu Tyr Phe Gln Trp Arg Lys Ser Arg Gly Ser
            355                 360                 365 tca gag aaa ttt cat ggt gcg gtt gtt gat cat gat aac agc tcg gaa       1152
Ser Glu Lys Phe His Gly Ala Val Val Asp His Asp Asn Ser Ser Glu
            370                 375                 380 aat cgt gta ttt aaa gaa gtt gct agc tta gga gaa aaa ttg gag aaa       1200
Asn Arg Val Phe Lys Glu Val Ala Ser Leu Gly Glu Lys Leu Glu Lys
385                 390                 395                 400 ctc acg gat gtt gta ggt gcg aat cgt cct gct gat gtt gct gta ctg       1248
Leu Thr Asp Val Val Gly Ala Asn Arg Pro Ala Asp Val Ala Val Leu
            405                 410                 415 tat gac tgg gag agt aat tgg gcg tta aat gat gcc caa ggc ttc ggg       1296
Tyr Asp Trp Glu Ser Asn Trp Ala Leu Asn Asp Ala Gln Gly Phe Gly
            420                 425                 430 gta aag acg aag ctg tat cct caa aca ctt caa caa cat cac aaa tca       1344
Val Lys Thr Lys Leu Tyr Pro Gln Thr Leu Gln Gln His His Lys Ser
            435                 440                 445 ttc tgg gag agg gat att cca gtt gat gta att aca aag gaa cag gat       1392
Phe Trp Glu Arg Asp Ile Pro Val Asp Val Ile Thr Lys Glu Gln Asp
450                 455                 460 ttc gcg gct tac aaa cta ctt att gtt cca atg ctc tac ctt gta agt       1440
Phe Ala Ala Tyr Lys Leu Leu Ile Val Pro Met Leu Tyr Leu Val Ser
465                 470                 475                 480 gaa gaa acc att tca cgc ttg aaa acc tat gtt gcc aac ggt ggc act       1488
Glu Glu Thr Ile Ser Arg Leu Lys Thr Tyr Val Ala Asn Gly Gly Thr
            485                 490                 495 ttg gtg atg act tat att agt ggt ttg gtt aat gag cat gac tta acg       1536
Leu Val Met Thr Tyr Ile Ser Gly Leu Val Asn Glu His Asp Leu Thr
            500                 505                 510
```

| | | | | | | | | | | | | | | | | |
|---|---|---|---|---|---|---|---|---|---|---|---|---|---|---|---|---|
| tat | tta | ggt | ggg | tgg | cat | aag | gat | ctt | caa | gaa | atc | ttt | gga | atg | aag | 1584 |
| Tyr | Leu | Gly | Gly | Trp | His | Lys | Asp | Leu | Gln | Glu | Ile | Phe | Gly | Met | Lys | |
| | 515 | | | | | 520 | | | | | 525 | | | | | |
| cca | gtt | gaa | aca | gat | aca | tta | tat | cca | tct | gat | tct | aat | acg | gtg | aat | 1632 |
| Pro | Val | Glu | Thr | Asp | Thr | Leu | Tyr | Pro | Ser | Asp | Ser | Asn | Thr | Val | Asn | |
| | 530 | | | | | 535 | | | | | 540 | | | | | |
| tac | cac | ggt | gac | act | tat | caa | tta | aag | gat | tat | gca | agt | att | cta | gaa | 1680 |
| Tyr | His | Gly | Asp | Thr | Tyr | Gln | Leu | Lys | Asp | Tyr | Ala | Ser | Ile | Leu | Glu | |
| 545 | | | | | 550 | | | | | 555 | | | | | 560 | |
| gtc | gat | acg | gct | act | gtt | gaa | ggt | atg | tat | gtt | gat | gac | ttc | tat | gca | 1728 |
| Val | Asp | Thr | Ala | Thr | Val | Glu | Gly | Met | Tyr | Val | Asp | Asp | Phe | Tyr | Ala | |
| | | | | 565 | | | | | 570 | | | | | 575 | | |
| aat | aca | gct | gct | att | aca | agc | aat | caa | tat | caa | aat | ggc | aaa | acg | tat | 1776 |
| Asn | Thr | Ala | Ala | Ile | Thr | Ser | Asn | Gln | Tyr | Gln | Asn | Gly | Lys | Thr | Tyr | |
| | | | 580 | | | | | 585 | | | | | 590 | | | |
| tat | att | ggt | gct | cgc | atg | gaa | cat | gga | ttt | cag | cag | gcc | ttt | tat | caa | 1824 |
| Tyr | Ile | Gly | Ala | Arg | Met | Glu | His | Gly | Phe | Gln | Gln | Ala | Phe | Tyr | Gln | |
| | | 595 | | | | | 600 | | | | | 605 | | | | |
| gaa | tta | att | gaa | gaa | tta | tca | ctg | gcc | cct | gtt | gca | tca | gtt | aaa | cat | 1872 |
| Glu | Leu | Ile | Glu | Glu | Leu | Ser | Leu | Ala | Pro | Val | Ala | Ser | Val | Lys | His | |
| 610 | | | | | 615 | | | | | 620 | | | | | | |
| aat | gaa | ggt | gtt | tca | gtg | caa | gta | aga | caa | ggt | cca | gaa | agt | gat | tat | 1920 |
| Asn | Glu | Gly | Val | Ser | Val | Gln | Val | Arg | Gln | Gly | Pro | Glu | Ser | Asp | Tyr | |
| 625 | | | | | 630 | | | | | 635 | | | | | 640 | |
| atc | ttt | gtt | atg | aac | ttt | act | gaa | aag | aaa | caa | tca | gtc | acc | ttc | gac | 1968 |
| Ile | Phe | Val | Met | Asn | Phe | Thr | Glu | Lys | Lys | Gln | Ser | Val | Thr | Phe | Asp | |
| | | | | 645 | | | | | 650 | | | | | 655 | | |
| tca | cag | gtt | aca | gat | ctg | ctg | acg | gga | gaa | gct | gtt | tct | agc | gag | gtt | 2016 |
| Ser | Gln | Val | Thr | Asp | Leu | Leu | Thr | Gly | Glu | Ala | Val | Ser | Ser | Glu | Val | |
| | | | 660 | | | | | 665 | | | | | 670 | | | |
| gtg | ttg | gat | ata | tat | gag | gtg | aaa | att | gta | gag | aag | gtt | aga | ggt | aag | 2064 |
| Val | Leu | Asp | Ile | Tyr | Glu | Val | Lys | Ile | Val | Glu | Lys | Val | Arg | Gly | Lys | |
| | | 675 | | | | | 680 | | | | | 685 | | | | |
| tag | | | | | | | | | | | | | | | | 2067 |

<210> SEQ ID NO 59
<211> LENGTH: 688
<212> TYPE: PRT
<213> ORGANISM: Bacillus sp-62759

<400> SEQUENCE: 59

Met Pro Asp Asn Glu Lys Thr Tyr Val Thr Lys Ala Asn Phe Met Leu
1               5                   10                  15

His Gly Gly Asp Tyr Asn Pro Asp Gln Trp Leu Asp Arg Pro Asp Ile
            20                  25                  30

Leu Ala Asp Asp Val Lys Leu Met Lys Leu Ser His Ser Asn Thr Phe
        35                  40                  45

Ser Val Gly Ile Phe Ala Trp Ser Ala Leu Glu Pro Gln Glu Gly Val
    50                  55                  60

Tyr Gln Phe Glu Trp Leu Asp Glu Ile Phe Glu Asn Ile Tyr Lys Ile
65                  70                  75                  80

Gly Gly Arg Val Ile Leu Ala Thr Pro Ser Gly Ala Arg Pro Ala Trp
                85                  90                  95

Met Ser Ala Lys Tyr Pro Glu Val Leu Arg Val Asn Ser Ser Arg Val
            100                 105                 110

Lys Gln Leu His Gly Gly Arg His Asn His Cys Phe Thr Ser Glu Val
        115                 120                 125

Tyr Arg Asp Lys Thr Gln Glu Met Asn Arg Leu Leu Ala Glu Arg Tyr

```
            130                 135                 140
Gly Ser His Pro Ala Leu Leu Met Trp His Ile Ser Asn Glu Tyr Gly
145                 150                 155                 160

Gly Glu Cys His Cys Asp Lys Cys Gln Thr Ala Phe Arg Ser Trp Val
                165                 170                 175

Lys Arg Lys Tyr Asn Asp Asp Leu Lys Ala Leu Asn Asp Ala Trp Trp
                180                 185                 190

Gly Pro Phe Trp Ser His Thr Ile Ser Asp Trp Ser Gln Val Glu Ser
                195                 200                 205

Pro Ser Pro Ile Gly Glu Asn Met Val His Gly Leu Asn Leu Asp Trp
            210                 215                 220

Arg Arg Phe Ile Thr Asp Gln Thr Ile Ser Phe Tyr Gln Asn Glu Ile
225                 230                 235                 240

Val Pro Leu Arg Lys Leu Thr Pro Glu Ile Pro Ile Thr Thr Asn Phe
                245                 250                 255

Met Ala Asp Thr His Asp Leu Ile Pro Phe Gln Ala Leu Asp Tyr Ser
                260                 265                 270

Lys Phe Ala Lys His Leu Asp Val Ile Ser Trp Asp Ala Tyr Pro Ala
                275                 280                 285

Trp His Asn Asp Trp Glu Thr Thr Ala Asp Leu Ala Ala Lys Val Ala
            290                 295                 300

Phe Ile Asn Asp Leu Tyr Arg Ser Leu Lys Gln Gln Pro Phe Leu Leu
305                 310                 315                 320

Met Glu Ser Thr Pro Ser Gly Val Asn Trp His Glu Val Asn Lys Ala
                325                 330                 335

Lys Arg Pro Gly Met His Leu Leu Ser Ser Leu Gln Met Val Ala His
                340                 345                 350

Gly Ser Asp Ser Val Leu Tyr Phe Gln Trp Arg Lys Ser Arg Gly Ser
            355                 360                 365

Ser Glu Lys Phe His Gly Ala Val Val Asp His Asp Asn Ser Ser Glu
            370                 375                 380

Asn Arg Val Phe Lys Glu Val Ala Ser Leu Gly Glu Lys Leu Glu Lys
385                 390                 395                 400

Leu Thr Asp Val Val Gly Ala Asn Arg Pro Ala Asp Val Ala Val Leu
                405                 410                 415

Tyr Asp Trp Glu Ser Asn Trp Ala Leu Asn Asp Ala Gln Gly Phe Gly
                420                 425                 430

Val Lys Thr Lys Leu Tyr Pro Gln Thr Leu Gln Gln His His Lys Ser
            435                 440                 445

Phe Trp Glu Arg Asp Ile Pro Val Asp Val Ile Thr Lys Glu Gln Asp
450                 455                 460

Phe Ala Ala Tyr Lys Leu Leu Ile Val Pro Met Leu Tyr Leu Val Ser
465                 470                 475                 480

Glu Glu Thr Ile Ser Arg Leu Lys Thr Tyr Val Ala Asn Gly Gly Thr
                485                 490                 495

Leu Val Met Thr Tyr Ile Ser Gly Leu Val Asn Glu His Asp Leu Thr
                500                 505                 510

Tyr Leu Gly Gly Trp His Lys Asp Leu Gln Glu Ile Phe Gly Met Lys
            515                 520                 525

Pro Val Glu Thr Asp Thr Leu Tyr Pro Ser Asp Ser Asn Thr Val Asn
            530                 535                 540

Tyr His Gly Asp Thr Tyr Gln Leu Lys Asp Tyr Ala Ser Ile Leu Glu
545                 550                 555                 560
```

```
Val Asp Thr Ala Thr Val Glu Gly Met Tyr Val Asp Phe Tyr Ala
                565                 570                 575

Asn Thr Ala Ala Ile Thr Ser Asn Gln Tyr Gln Asn Gly Lys Thr Tyr
                580                 585                 590

Tyr Ile Gly Ala Arg Met Glu His Gly Phe Gln Gln Ala Phe Tyr Gln
                595                 600                 605

Glu Leu Ile Glu Glu Leu Ser Leu Ala Pro Val Ala Ser Val Lys His
            610                 615                 620

Asn Glu Gly Val Ser Val Gln Val Arg Gln Gly Pro Glu Ser Asp Tyr
625                 630                 635                 640

Ile Phe Val Met Asn Phe Thr Glu Lys Lys Gln Ser Val Thr Phe Asp
                645                 650                 655

Ser Gln Val Thr Asp Leu Leu Thr Gly Glu Ala Val Ser Ser Glu Val
                660                 665                 670

Val Leu Asp Ile Tyr Glu Val Lys Ile Val Glu Lys Val Arg Gly Lys
                675                 680                 685

<210> SEQ ID NO 60
<211> LENGTH: 697
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(697)

<400> SEQUENCE: 60

Met His His His His His Pro Arg Met Pro Asp Asn Glu Lys Thr
1               5                   10                  15

Tyr Val Thr Lys Ala Asn Phe Met Leu His Gly Gly Asp Tyr Asn Pro
                20                  25                  30

Asp Gln Trp Leu Asp Arg Pro Asp Ile Leu Ala Asp Val Lys Leu
            35                  40                  45

Met Lys Leu Ser His Ser Asn Thr Phe Ser Val Gly Ile Phe Ala Trp
50                  55                  60

Ser Ala Leu Glu Pro Gln Glu Gly Val Tyr Gln Phe Glu Trp Leu Asp
65                  70                  75                  80

Glu Ile Phe Glu Asn Ile Tyr Lys Ile Gly Gly Arg Val Ile Leu Ala
                85                  90                  95

Thr Pro Ser Gly Ala Arg Pro Ala Trp Met Ser Ala Lys Tyr Pro Glu
            100                 105                 110

Val Leu Arg Val Asn Ser Ser Arg Val Lys Gln Leu His Gly Gly Arg
        115                 120                 125

His Asn His Cys Phe Thr Ser Glu Val Tyr Arg Asp Lys Thr Gln Glu
    130                 135                 140

Met Asn Arg Leu Leu Ala Glu Arg Tyr Gly Ser His Pro Ala Leu Leu
145                 150                 155                 160

Met Trp His Ile Ser Asn Glu Tyr Gly Gly Glu Cys His Cys Asp Lys
                165                 170                 175

Cys Gln Thr Ala Phe Arg Ser Trp Val Lys Arg Lys Tyr Asn Asp Asp
            180                 185                 190

Leu Lys Ala Leu Asn Asp Ala Trp Trp Gly Pro Phe Trp Ser His Thr
        195                 200                 205

Ile Ser Asp Trp Ser Gln Val Glu Ser Pro Ser Pro Ile Gly Glu Asn
    210                 215                 220
```

-continued

```
Met Val His Gly Leu Asn Leu Asp Trp Arg Arg Phe Ile Thr Asp Gln
225                 230                 235                 240

Thr Ile Ser Phe Tyr Gln Asn Glu Ile Val Pro Leu Arg Lys Leu Thr
            245                 250                 255

Pro Glu Ile Pro Ile Thr Thr Asn Phe Met Ala Asp Thr His Asp Leu
                260                 265                 270

Ile Pro Phe Gln Ala Leu Asp Tyr Ser Lys Phe Ala Lys His Leu Asp
            275                 280                 285

Val Ile Ser Trp Asp Ala Tyr Pro Ala Trp His Asn Asp Trp Glu Thr
        290                 295                 300

Thr Ala Asp Leu Ala Ala Lys Val Ala Phe Ile Asn Asp Leu Tyr Arg
305                 310                 315                 320

Ser Leu Lys Gln Gln Pro Phe Leu Leu Met Glu Ser Thr Pro Ser Gly
                325                 330                 335

Val Asn Trp His Glu Val Asn Lys Ala Lys Arg Pro Gly Met His Leu
            340                 345                 350

Leu Ser Ser Leu Gln Met Val Ala His Gly Ser Asp Ser Val Leu Tyr
        355                 360                 365

Phe Gln Trp Arg Lys Ser Arg Gly Ser Ser Glu Lys Phe His Gly Ala
370                 375                 380

Val Val Asp His Asp Asn Ser Ser Glu Asn Arg Val Phe Lys Glu Val
385                 390                 395                 400

Ala Ser Leu Gly Glu Lys Leu Glu Lys Leu Thr Asp Val Val Gly Ala
                405                 410                 415

Asn Arg Pro Ala Asp Val Ala Val Leu Tyr Asp Trp Glu Ser Asn Trp
            420                 425                 430

Ala Leu Asn Asp Ala Gln Gly Phe Gly Val Lys Thr Lys Leu Tyr Pro
        435                 440                 445

Gln Thr Leu Gln Gln His His Lys Ser Phe Trp Glu Arg Asp Ile Pro
450                 455                 460

Val Asp Val Ile Thr Lys Glu Gln Asp Phe Ala Ala Tyr Lys Leu Leu
465                 470                 475                 480

Ile Val Pro Met Leu Tyr Leu Val Ser Glu Glu Thr Ile Ser Arg Leu
                485                 490                 495

Lys Thr Tyr Val Ala Asn Gly Gly Thr Leu Val Met Thr Tyr Ile Ser
            500                 505                 510

Gly Leu Val Asn Glu His Asp Leu Thr Tyr Leu Gly Gly Trp His Lys
        515                 520                 525

Asp Leu Gln Glu Ile Phe Gly Met Lys Pro Val Glu Thr Asp Thr Leu
530                 535                 540

Tyr Pro Ser Asp Ser Asn Thr Val Asn Tyr His Gly Asp Thr Tyr Gln
545                 550                 555                 560

Leu Lys Asp Tyr Ala Ser Ile Leu Glu Val Asp Thr Ala Thr Val Glu
                565                 570                 575

Gly Met Tyr Val Asp Asp Phe Tyr Ala Asn Thr Ala Ala Ile Thr Ser
            580                 585                 590

Asn Gln Tyr Gln Asn Gly Lys Thr Tyr Tyr Ile Gly Ala Arg Met Glu
        595                 600                 605

His Gly Phe Gln Gln Ala Phe Tyr Gln Glu Leu Ile Glu Glu Leu Ser
610                 615                 620

Leu Ala Pro Val Ala Ser Val Lys His Asn Glu Gly Val Ser Val Gln
625                 630                 635                 640
```

-continued

```
Val Arg Gln Gly Pro Glu Ser Asp Tyr Ile Phe Val Met Asn Phe Thr
            645                 650                 655

Glu Lys Lys Gln Ser Val Thr Phe Asp Ser Gln Val Thr Asp Leu Leu
        660                 665                 670

Thr Gly Glu Ala Val Ser Ser Glu Val Val Leu Asp Ile Tyr Glu Val
    675                 680                 685

Lys Ile Val Glu Lys Val Arg Gly Lys
690                 695

<210> SEQ ID NO 61
<211> LENGTH: 2076
<212> TYPE: DNA
<213> ORGANISM: Paenibacillus sp-18054
<220> FEATURE:
<221> NAME/KEY: CDS
<222> LOCATION: (1)..(2073)
<220> FEATURE:
<221> NAME/KEY: mat_peptide
<222> LOCATION: (1)..(2073)

<400> SEQUENCE: 61
```

| | | | | | | | | | | | | | | | | |
|---|---|---|---|---|---|---|---|---|---|---|---|---|---|---|---|---|
| atg | aca | aaa | ccg | aaa | cgt | tat | tcg | ccg | atc | agc | gcc | aag | ctg | ccg | gta | 48 |
| Met | Thr | Lys | Pro | Lys | Arg | Tyr | Ser | Pro | Ile | Ser | Ala | Lys | Leu | Pro | Val | |
| 1 | | | 5 | | | | | 10 | | | | | 15 | | | |
| ttt | atg | cac | gga | gcg | gac | tat | aac | ccg | gat | caa | tgg | ctg | gac | cgg | ccc | 96 |
| Phe | Met | His | Gly | Ala | Asp | Tyr | Asn | Pro | Asp | Gln | Trp | Leu | Asp | Arg | Pro | |
| | | | 20 | | | | | 25 | | | | | 30 | | | |
| gat | gtg | ctt | gag | gaa | gat | atc | cgg | ctg | atg | aag | ctc | gcc | ggc | tgc | aat | 144 |
| Asp | Val | Leu | Glu | Glu | Asp | Ile | Arg | Leu | Met | Lys | Leu | Ala | Gly | Cys | Asn | |
| | | 35 | | | | | 40 | | | | | 45 | | | | |
| gtg | atg | gcc | gta | ggc | ata | ttc | ggc | tgg | acc | gcg | att | gag | ccg | gag | gaa | 192 |
| Val | Met | Ala | Val | Gly | Ile | Phe | Gly | Trp | Thr | Ala | Ile | Glu | Pro | Glu | Glu | |
| | 50 | | | | | 55 | | | | | 60 | | | | | |
| ggc | cga | ttt | aca | ttc | gaa | tgg | ctc | gac | gaa | gta | ttg | gac | cgc | ttt | gcc | 240 |
| Gly | Arg | Phe | Thr | Phe | Glu | Trp | Leu | Asp | Glu | Val | Leu | Asp | Arg | Phe | Ala | |
| 65 | | | | | 70 | | | | | 75 | | | | | 80 | |
| gcc | aac | ggc | att | tat | gcc | tgg | ctt | gcg | acg | ccg | agc | ggc | gcg | cgt | ccc | 288 |
| Ala | Asn | Gly | Ile | Tyr | Ala | Trp | Leu | Ala | Thr | Pro | Ser | Gly | Ala | Arg | Pro | |
| | | | 85 | | | | | 90 | | | | | 95 | | | |
| gca | tgg | atg | tcg | gcc | cgt | tac | ccg | gag | gtg | ctg | cgg | gta | gct | gca | aat | 336 |
| Ala | Trp | Met | Ser | Ala | Arg | Tyr | Pro | Glu | Val | Leu | Arg | Val | Ala | Ala | Asn | |
| | | | 100 | | | | | 105 | | | | | 110 | | | |
| cgc | gtc | cgc | aat | ttg | cac | gga | gca | aga | cat | aat | cat | tgc | tac | tct | tcg | 384 |
| Arg | Val | Arg | Asn | Leu | His | Gly | Ala | Arg | His | Asn | His | Cys | Tyr | Ser | Ser | |
| | | 115 | | | | | 120 | | | | | 125 | | | | |
| ccg | gtc | tat | cgc | gag | aaa | gcg | gcg | ttg | atg | aac | ggc | aag | ctg | gcg | gag | 432 |
| Pro | Val | Tyr | Arg | Glu | Lys | Ala | Ala | Leu | Met | Asn | Gly | Lys | Leu | Ala | Glu | |
| | 130 | | | | | 135 | | | | | 140 | | | | | |
| cgc | tac | gcg | cag | cat | ccg | gca | gtc | gtc | ggc | tgg | cat | atc | tcg | aat | gaa | 480 |
| Arg | Tyr | Ala | Gln | His | Pro | Ala | Val | Val | Gly | Trp | His | Ile | Ser | Asn | Glu | |
| 145 | | | | | 150 | | | | | 155 | | | | | 160 | |
| tac | ggc | gga | gat | tgc | cat | tgc | gag | tat | tgc | cag | gat | gct | ttc | cgc | gac | 528 |
| Tyr | Gly | Gly | Asp | Cys | His | Cys | Glu | Tyr | Cys | Gln | Asp | Ala | Phe | Arg | Asp | |
| | | | 165 | | | | | 170 | | | | | 175 | | | |
| tgg | ctg | cag | cgc | aag | tac | ggc | agt | ctg | gag | gcg | ctc | aac | aaa | gcg | tgg | 576 |
| Trp | Leu | Gln | Arg | Lys | Tyr | Gly | Ser | Leu | Glu | Ala | Leu | Asn | Lys | Ala | Trp | |
| | | | 180 | | | | | 185 | | | | | 190 | | | |
| tgg | gca | gca | ttc | tgg | agc | cat | acg | tat | acg | gat | tgg | tcg | cag | gtg | gag | 624 |
| Trp | Ala | Ala | Phe | Trp | Ser | His | Thr | Tyr | Thr | Asp | Trp | Ser | Gln | Val | Glu | |
| | | 195 | | | | | 200 | | | | | 205 | | | | |
| tcg | ccg | gct | ccg | cat | gga | gaa | aat | gcc | gtt | cac | gcg | atg | aat | ctg | gac | 672 |

```
Ser Pro Ala Pro His Gly Glu Asn Ala Val His Ala Met Asn Leu Asp
    210             215                 220 tgg aag cga ttc gtc acg gac caa acc gtc gac ttc tgc cgc cat gag       720
Trp Lys Arg Phe Val Thr Asp Gln Thr Val Asp Phe Cys Arg His Glu
225             230                 235                 240 atc gca ccg ctt cga gcg ctc aat ccg gcg ctg ccg gtt acg acc aat       768
Ile Ala Pro Leu Arg Ala Leu Asn Pro Ala Leu Pro Val Thr Thr Asn
                245                 250                 255 atg atg gac ctg ttc gag ggg ttg gac tac tgg aag ttt gcc gat gtg       816
Met Met Asp Leu Phe Glu Gly Leu Asp Tyr Trp Lys Phe Ala Asp Val
            260                 265                 270 ctg gac gtc att tca tgg gac gct tat ccg acc tgg cat gcg ggc aag       864
Leu Asp Val Ile Ser Trp Asp Ala Tyr Pro Thr Trp His Ala Gly Lys
        275                 280                 285 gat gac agc cgt ctc gca gcc tgg ttt gcc atg aac cat gat ata ttc       912
Asp Asp Ser Arg Leu Ala Ala Trp Phe Ala Met Asn His Asp Ile Phe
    290                 295                 300 cgg tcg ctt aag ggc ggt cag cct ttt atg ctg atg gaa agc acg cct       960
Arg Ser Leu Lys Gly Gly Gln Pro Phe Met Leu Met Glu Ser Thr Pro
305                 310                 315                 320 agc ctg acg aat tgg cag gcg gtg agc aag ctg aag cgc ccg ggc atg      1008
Ser Leu Thr Asn Trp Gln Ala Val Ser Lys Leu Lys Arg Pro Gly Met
                325                 330                 335 cat aag ctg tcg tcg ctg cag gcc gtt gcg cat ggg gcg gat acg gtg      1056
His Lys Leu Ser Ser Leu Gln Ala Val Ala His Gly Ala Asp Thr Val
            340                 345                 350 caa tat ttt caa tgg cgc aaa agc aga ggc tcc agc gag aaa ttt cac      1104
Gln Tyr Phe Gln Trp Arg Lys Ser Arg Gly Ser Ser Glu Lys Phe His
        355                 360                 365 gga gcg gtc gtc gat cat gtc gga cat gaa cat acg cgc gtg ttt cgc      1152
Gly Ala Val Val Asp His Val Gly His Glu His Thr Arg Val Phe Arg
    370                 375                 380 gat gtg gcg gag ctt ggc gag acg ctc ggc aaa ctg acg gat att atc      1200
Asp Val Ala Glu Leu Gly Glu Thr Leu Gly Lys Leu Thr Asp Ile Ile
385                 390                 395                 400 ggg acc ggc gtg ccg gcg gaa gcg gct att att ttc gac tgg gaa aat      1248
Gly Thr Gly Val Pro Ala Glu Ala Ala Ile Ile Phe Asp Trp Glu Asn
                405                 410                 415 cgc tgg gcg gtc aag gat gcg caa ggc ccg cgc aat atg ggc att cac      1296
Arg Trp Ala Val Lys Asp Ala Gln Gly Pro Arg Asn Met Gly Ile His
            420                 425                 430 tac gag gat acg gtg ctg ctt cat tat aaa gca ttg tgg gag aaa ggc      1344
Tyr Glu Asp Thr Val Leu Leu His Tyr Lys Ala Leu Trp Glu Lys Gly
        435                 440                 445 att tcc gtc gat gtt gtg tcg atg gat gcg gac ttg tcc ggc tac aag      1392
Ile Ser Val Asp Val Val Ser Met Asp Ala Asp Leu Ser Gly Tyr Lys
    450                 455                 460 ctc gta atc gct cct atg ctg tac atg gtg cgt ccc ggc gtc ggg gaa      1440
Leu Val Ile Ala Pro Met Leu Tyr Met Val Arg Pro Gly Val Gly Glu
465                 470                 475                 480 aaa atc gag cga ttt gtc gaa gaa gga ggc aca ttc gtc tcc acc tat      1488
Lys Ile Glu Arg Phe Val Glu Glu Gly Gly Thr Phe Val Ser Thr Tyr
                485                 490                 495 tgg tca ggc atc gtg gac gac aac gat ctt tgt tat ctt ggc ggt ttt      1536
Trp Ser Gly Ile Val Asp Asp Asn Asp Leu Cys Tyr Leu Gly Gly Phe
            500                 505                 510 cca ggt ccg ctg cgc aag acg ctc ggc ata tgg gcc gag gag gcg gaa      1584
Pro Gly Pro Leu Arg Lys Thr Leu Gly Ile Trp Ala Glu Glu Ala Glu
        515                 520                 525
```

| | | |
|---|---|---|
| ggg ctg tac gat gag gat cgc aac gaa atc gca ttg acc tca ggc gga<br>Gly Leu Tyr Asp Glu Asp Arg Asn Glu Ile Ala Leu Thr Ser Gly Gly<br>530                 535                 540 | | 1632 |
| aga ctg gca ggc atg gaa ggg cca tac gag gtg cat gag ctt tgc gag<br>Arg Leu Ala Gly Met Glu Gly Pro Tyr Glu Val His Glu Leu Cys Glu<br>545                 550                 555                 560 | | 1680 |
| ctt gtc cat gcc gag acg gcc gag gtg ctg ggc gtg tac acg gac gat<br>Leu Val His Ala Glu Thr Ala Glu Val Leu Gly Val Tyr Thr Asp Asp<br>                 565                 570                 575 | | 1728 |
| ttc tac gcc ggc aga ccg gcg ctg acc gtc aac aag ctg ggc aaa ggc<br>Phe Tyr Ala Gly Arg Pro Ala Leu Thr Val Asn Lys Leu Gly Lys Gly<br>                   580                 585                 590 | | 1776 |
| cgt gcc tac tac ttg gcg gcc agg gcg aaa gag cct ttc tac gaa cag<br>Arg Ala Tyr Tyr Leu Ala Ala Arg Ala Lys Glu Pro Phe Tyr Glu Gln<br>             595                 600                 605 | | 1824 |
| ttc tac cgg atc gtt gtc gag gag gcg ggt gta cgg gga gcg ttg gaa<br>Phe Tyr Arg Ile Val Val Glu Glu Ala Gly Val Arg Gly Ala Leu Glu<br>610                 615                 620 | | 1872 |
| gcg gaa ctt ccg gca ggt gtt acc gcc cag ctg cgg acg gac ggg gaa<br>Ala Glu Leu Pro Ala Gly Val Thr Ala Gln Leu Arg Thr Asp Gly Glu<br>625                 630                 635                 640 | | 1920 |
| gcc gac tat atc ttt ctg ctg aac ttc agc ggc aag ccg cag cag gtt<br>Ala Asp Tyr Ile Phe Leu Leu Asn Phe Ser Gly Lys Pro Gln Gln Val<br>                   645                 650                 655 | | 1968 |
| gcg ctg gat cat cgg caa tac gac gat atg gag tcg ggc aat aga tta<br>Ala Leu Asp His Arg Gln Tyr Asp Asp Met Glu Ser Gly Asn Arg Leu<br>             660                 665                 670 | | 2016 |
| ctc gaa aac atg gcg tac ctt ccg gct aac ggc gcc aag gtg ctg cga<br>Leu Glu Asn Met Ala Tyr Leu Pro Ala Asn Gly Ala Lys Val Leu Arg<br>675                 680                 685 | | 2064 |
| aga aaa agc taa<br>Arg Lys Ser<br>    690 | | 2076 |

<210> SEQ ID NO 62
<211> LENGTH: 691
<212> TYPE: PRT
<213> ORGANISM: Paenibacillus sp-18054

<400> SEQUENCE: 62

Met Thr Lys Pro Lys Arg Tyr Ser Pro Ile Ser Ala Lys Leu Pro Val
1                5                 10                 15

Phe Met His Gly Ala Asp Tyr Asn Pro Asp Gln Trp Leu Asp Arg Pro
                20                 25                 30

Asp Val Leu Glu Glu Asp Ile Arg Leu Met Lys Leu Ala Gly Cys Asn
         35                   40                 45

Val Met Ala Val Gly Ile Phe Gly Trp Thr Ala Ile Glu Pro Glu Glu
50                55                 60

Gly Arg Phe Thr Phe Glu Trp Leu Asp Glu Val Leu Asp Arg Phe Ala
65                70                 75                 80

Ala Asn Gly Ile Tyr Ala Trp Leu Ala Thr Pro Ser Gly Ala Arg Pro
                85                 90                 95

Ala Trp Met Ser Ala Arg Tyr Pro Glu Val Leu Arg Val Ala Ala Asn
                   100               105               110

Arg Val Arg Asn Leu His Gly Ala Arg His Asn His Cys Tyr Ser Ser
         115                   120               125

Pro Val Tyr Arg Glu Lys Ala Ala Leu Met Asn Gly Lys Leu Ala Glu
130                135                 140

```
Arg Tyr Ala Gln His Pro Ala Val Val Gly Trp His Ile Ser Asn Glu
145                 150                 155                 160

Tyr Gly Gly Asp Cys His Cys Glu Tyr Cys Gln Asp Ala Phe Arg Asp
            165                 170                 175

Trp Leu Gln Arg Lys Tyr Gly Ser Leu Glu Ala Leu Asn Lys Ala Trp
        180                 185                 190

Trp Ala Ala Phe Trp Ser His Thr Tyr Thr Asp Trp Ser Gln Val Glu
    195                 200                 205

Ser Pro Ala Pro His Gly Glu Asn Ala Val His Ala Met Asn Leu Asp
210                 215                 220

Trp Lys Arg Phe Val Thr Asp Gln Thr Val Asp Phe Cys Arg His Glu
225                 230                 235                 240

Ile Ala Pro Leu Arg Ala Leu Asn Pro Ala Leu Pro Val Thr Thr Asn
                245                 250                 255

Met Met Asp Leu Phe Glu Gly Leu Asp Tyr Trp Lys Phe Ala Asp Val
            260                 265                 270

Leu Asp Val Ile Ser Trp Asp Ala Tyr Pro Thr Trp His Ala Gly Lys
        275                 280                 285

Asp Asp Ser Arg Leu Ala Ala Trp Phe Ala Met Asn His Asp Ile Phe
290                 295                 300

Arg Ser Leu Lys Gly Gly Gln Pro Phe Met Leu Met Glu Ser Thr Pro
305                 310                 315                 320

Ser Leu Thr Asn Trp Gln Ala Val Ser Lys Leu Lys Arg Pro Gly Met
                325                 330                 335

His Lys Leu Ser Ser Leu Gln Ala Val Ala His Gly Ala Asp Thr Val
            340                 345                 350

Gln Tyr Phe Gln Trp Arg Lys Ser Arg Gly Ser Ser Glu Lys Phe His
        355                 360                 365

Gly Ala Val Val Asp His Val Gly His Glu His Thr Arg Val Phe Arg
370                 375                 380

Asp Val Ala Glu Leu Gly Glu Thr Leu Gly Lys Leu Thr Asp Ile Ile
385                 390                 395                 400

Gly Thr Gly Val Pro Ala Glu Ala Ala Ile Ile Phe Asp Trp Glu Asn
                405                 410                 415

Arg Trp Ala Val Lys Asp Ala Gln Gly Pro Arg Asn Met Gly Ile His
            420                 425                 430

Tyr Glu Asp Thr Val Leu Leu His Tyr Lys Ala Leu Trp Glu Lys Gly
        435                 440                 445

Ile Ser Val Asp Val Val Ser Met Asp Ala Asp Leu Ser Gly Tyr Lys
450                 455                 460

Leu Val Ile Ala Pro Met Leu Tyr Met Val Arg Pro Gly Val Gly Glu
465                 470                 475                 480

Lys Ile Glu Arg Phe Val Glu Glu Gly Gly Thr Phe Val Ser Thr Tyr
                485                 490                 495

Trp Ser Gly Ile Val Asp Asp Asn Asp Leu Cys Tyr Leu Gly Gly Phe
            500                 505                 510

Pro Gly Pro Leu Arg Lys Thr Leu Gly Ile Trp Ala Glu Glu Ala Glu
        515                 520                 525

Gly Leu Tyr Asp Glu Asp Arg Asn Glu Ile Ala Leu Thr Ser Gly Gly
530                 535                 540

Arg Leu Ala Gly Met Glu Gly Pro Tyr Glu Val His Glu Leu Cys Glu
545                 550                 555                 560

Leu Val His Ala Glu Thr Ala Glu Val Leu Gly Val Tyr Thr Asp Asp
```

Phe Tyr Ala Gly Arg Pro Ala Leu Thr Val Asn Lys Leu Gly Lys Gly
            565                 570                 575
                580                     585                 590

Arg Ala Tyr Tyr Leu Ala Ala Arg Ala Lys Glu Pro Phe Tyr Glu Gln
            595                 600                 605

Phe Tyr Arg Ile Val Val Glu Glu Ala Gly Val Arg Gly Ala Leu Glu
            610                 615                 620

Ala Glu Leu Pro Ala Gly Val Thr Ala Gln Leu Arg Thr Asp Gly Glu
625                 630                 635                 640

Ala Asp Tyr Ile Phe Leu Leu Asn Phe Ser Gly Lys Pro Gln Gln Val
            645                 650                 655

Ala Leu Asp His Arg Gln Tyr Asp Asp Met Glu Ser Gly Asn Arg Leu
            660                 665                 670

Leu Glu Asn Met Ala Tyr Leu Pro Ala Asn Gly Ala Lys Val Leu Arg
            675                 680                 685

Arg Lys Ser
    690

<210> SEQ ID NO 63
<211> LENGTH: 700
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(700)

<400> SEQUENCE: 63

Met His His His His His Pro Arg Met Thr Lys Pro Lys Arg Tyr
1               5                   10                  15

Ser Pro Ile Ser Ala Lys Leu Pro Val Phe Met His Gly Ala Asp Tyr
            20                  25                  30

Asn Pro Asp Gln Trp Leu Asp Arg Pro Asp Val Leu Glu Glu Asp Ile
        35                  40                  45

Arg Leu Met Lys Leu Ala Gly Cys Asn Val Met Ala Val Gly Ile Phe
50                  55                  60

Gly Trp Thr Ala Ile Glu Pro Glu Glu Gly Arg Phe Thr Phe Glu Trp
65                  70                  75                  80

Leu Asp Glu Val Leu Asp Arg Phe Ala Ala Asn Gly Ile Tyr Ala Trp
            85                  90                  95

Leu Ala Thr Pro Ser Gly Ala Arg Pro Ala Trp Met Ser Ala Arg Tyr
            100                 105                 110

Pro Glu Val Leu Arg Val Ala Ala Asn Arg Val Arg Asn Leu His Gly
        115                 120                 125

Ala Arg His Asn His Cys Tyr Ser Ser Pro Val Tyr Arg Glu Lys Ala
130                 135                 140

Ala Leu Met Asn Gly Lys Leu Ala Glu Arg Tyr Ala Gln His Pro Ala
145                 150                 155                 160

Val Val Gly Trp His Ile Ser Asn Glu Tyr Gly Gly Asp Cys His Cys
            165                 170                 175

Glu Tyr Cys Gln Asp Ala Phe Arg Asp Trp Leu Gln Arg Lys Tyr Gly
        180                 185                 190

Ser Leu Glu Ala Leu Asn Lys Ala Trp Trp Ala Ala Phe Trp Ser His
    195                 200                 205

Thr Tyr Thr Asp Trp Ser Gln Val Glu Ser Pro Ala Pro His Gly Glu

-continued

```
            210                 215                 220
Asn Ala Val His Ala Met Asn Leu Asp Trp Lys Arg Phe Val Thr Asp
225                 230                 235                 240

Gln Thr Val Asp Phe Cys Arg His Glu Ile Ala Pro Leu Arg Ala Leu
                245                 250                 255

Asn Pro Ala Leu Pro Val Thr Thr Asn Met Met Asp Leu Phe Glu Gly
                260                 265                 270

Leu Asp Tyr Trp Lys Phe Ala Asp Val Leu Asp Val Ile Ser Trp Asp
            275                 280                 285

Ala Tyr Pro Thr Trp His Ala Gly Lys Asp Asp Ser Arg Leu Ala Ala
        290                 295                 300

Trp Phe Ala Met Asn His Asp Ile Phe Arg Ser Leu Lys Gly Gly Gln
305                 310                 315                 320

Pro Phe Met Leu Met Glu Ser Thr Pro Ser Leu Thr Asn Trp Gln Ala
                325                 330                 335

Val Ser Lys Leu Lys Arg Pro Gly Met His Lys Leu Ser Ser Leu Gln
                340                 345                 350

Ala Val Ala His Gly Ala Asp Thr Val Gln Tyr Phe Gln Trp Arg Lys
            355                 360                 365

Ser Arg Gly Ser Ser Glu Lys Phe His Gly Ala Val Val Asp His Val
        370                 375                 380

Gly His Glu His Thr Arg Val Phe Arg Asp Val Ala Glu Leu Gly Glu
385                 390                 395                 400

Thr Leu Gly Lys Leu Thr Asp Ile Ile Gly Thr Gly Val Pro Ala Glu
                405                 410                 415

Ala Ala Ile Ile Phe Asp Trp Glu Asn Arg Trp Ala Val Lys Asp Ala
                420                 425                 430

Gln Gly Pro Arg Asn Met Gly Ile His Tyr Glu Asp Thr Val Leu Leu
            435                 440                 445

His Tyr Lys Ala Leu Trp Glu Lys Gly Ile Ser Val Asp Val Val Ser
        450                 455                 460

Met Asp Ala Asp Leu Ser Gly Tyr Lys Leu Val Ile Ala Pro Met Leu
465                 470                 475                 480

Tyr Met Val Arg Pro Gly Val Gly Glu Lys Ile Glu Arg Phe Val Glu
                485                 490                 495

Glu Gly Gly Thr Phe Val Ser Thr Tyr Trp Ser Gly Ile Val Asp Asp
                500                 505                 510

Asn Asp Leu Cys Tyr Leu Gly Gly Phe Pro Gly Pro Leu Arg Lys Thr
            515                 520                 525

Leu Gly Ile Trp Ala Glu Glu Ala Gly Leu Tyr Asp Glu Asp Arg
        530                 535                 540

Asn Glu Ile Ala Leu Thr Ser Gly Gly Arg Leu Ala Gly Met Glu Gly
545                 550                 555                 560

Pro Tyr Glu Val His Glu Leu Cys Glu Leu Val His Ala Glu Thr Ala
                565                 570                 575

Glu Val Leu Gly Val Tyr Thr Asp Asp Phe Tyr Ala Gly Arg Pro Ala
                580                 585                 590

Leu Thr Val Asn Lys Leu Gly Lys Gly Arg Ala Tyr Tyr Leu Ala Ala
            595                 600                 605

Arg Ala Lys Glu Pro Phe Tyr Glu Gln Phe Tyr Arg Ile Val Val Glu
        610                 615                 620

Glu Ala Gly Val Arg Gly Ala Leu Glu Ala Glu Leu Pro Ala Gly Val
625                 630                 635                 640
```

```
Thr Ala Gln Leu Arg Thr Asp Gly Glu Ala Asp Tyr Ile Phe Leu Leu
                645                 650                 655

Asn Phe Ser Gly Lys Pro Gln Val Ala Leu Asp His Arg Gln Tyr
            660                 665                 670

Asp Asp Met Glu Ser Gly Asn Arg Leu Leu Glu Asn Met Ala Tyr Leu
        675                 680                 685

Pro Ala Asn Gly Ala Lys Val Leu Arg Arg Lys Ser
    690                 695                 700

<210> SEQ ID NO 64
<211> LENGTH: 2073
<212> TYPE: DNA
<213> ORGANISM: Paenibacillus sp- 62047
<220> FEATURE:
<221> NAME/KEY: CDS
<222> LOCATION: (1)..(2070)
<220> FEATURE:
<221> NAME/KEY: mat_peptide
<222> LOCATION: (1)..(2070)

<400> SEQUENCE: 64 atg act tta aaa tac ccg ccg atc agc acg aaa ata ccg caa atg ctg      48
Met Thr Leu Lys Tyr Pro Pro Ile Ser Thr Lys Ile Pro Gln Met Leu
1               5                  10                  15 cat ggg gcc gat tat aat ccg gat cag tgg cag aaa tat ccc gag gtg      96
His Gly Ala Asp Tyr Asn Pro Asp Gln Trp Gln Lys Tyr Pro Glu Val
                20                  25                  30 ctg gag gaa gat atc cgg ctt atg aag ctt gcg ggc tgc aat gtt atg     144
Leu Glu Glu Asp Ile Arg Leu Met Lys Leu Ala Gly Cys Asn Val Met
            35                  40                  45 tcc gta ggc atc ttc gcg tgg gcg gct atc gag ccg gaa gag ggc gtt     192
Ser Val Gly Ile Phe Ala Trp Ala Ala Ile Glu Pro Glu Glu Gly Val
        50                  55                  60 ttc acg ttc gaa tgg ctc gac tcg ctg ctt gac aaa ttc gcg gct aac     240
Phe Thr Phe Glu Trp Leu Asp Ser Leu Leu Asp Lys Phe Ala Ala Asn
65                  70                  75                  80 ggc att tac gcc ttg ctt gca acg cca agc ggc gcc cgt ccg gcc tgg     288
Gly Ile Tyr Ala Leu Leu Ala Thr Pro Ser Gly Ala Arg Pro Ala Trp
                85                  90                  95 atg tcc cag aaa tat ccg gag gtg ctc cgc gtg gcg cca acc ggc atc     336
Met Ser Gln Lys Tyr Pro Glu Val Leu Arg Val Ala Pro Thr Gly Ile
                100                 105                 110 cgc aac ctg cat ggc gcg cgc cac aat cac tgc ttc acc tcg ccg gta     384
Arg Asn Leu His Gly Ala Arg His Asn His Cys Phe Thr Ser Pro Val
            115                 120                 125 tac cgc gag aag gtc aac atc atg aat acg aag ctt gcc gag cgt tat     432
Tyr Arg Glu Lys Val Asn Ile Met Asn Thr Lys Leu Ala Glu Arg Tyr
        130                 135                 140 gca cag cat ccc gct gtc atc ggc tgg cac att tcc aac gag tac ggc     480
Ala Gln His Pro Ala Val Ile Gly Trp His Ile Ser Asn Glu Tyr Gly
145                 150                 155                 160 ggc gaa tgc cac tgt tcg tac tgc gag gag gcg ttc cgc ggc tgg ctg     528
Gly Glu Cys His Cys Ser Tyr Cys Glu Glu Ala Phe Arg Gly Trp Leu
                165                 170                 175 aaa aac aaa tac ggc acg ctt gag gct ctt aac gac gcc tgg tgg acc     576
Lys Asn Lys Tyr Gly Thr Leu Glu Ala Leu Asn Asp Ala Trp Trp Thr
                180                 185                 190 acg ttc tgg agc cat act tac aca gac tgg agc cag gtt gag tct cct     624
Thr Phe Trp Ser His Thr Tyr Thr Asp Trp Ser Gln Val Glu Ser Pro
            195                 200                 205
```

| | | |
|---|---|---|
| act ccg cgc ggc gag aac gcg gtt cac ggc cag aac gtc gat tgg aga<br>Thr Pro Arg Gly Glu Asn Ala Val His Gly Gln Asn Val Asp Trp Arg<br>210                       215                     220 | | 672 |
| agg ttt gta acc gat caa acc gtc gat ttc tgc cgc aaa gag atc gag<br>Arg Phe Val Thr Asp Gln Thr Val Asp Phe Cys Arg Lys Glu Ile Glu<br>225                       230                     235                     240 | | 720 |
| cct ttg cgc gcc gca aac agc gag ctt ccg atc acg acc aac ttc atg<br>Pro Leu Arg Ala Ala Asn Ser Glu Leu Pro Ile Thr Thr Asn Phe Met<br>                     245                     250                     255 | | 768 |
| ctg gat ttc gag ccg ttg aat tac tgg aag ttt acg gag gtg ctc gat<br>Leu Asp Phe Glu Pro Leu Asn Tyr Trp Lys Phe Thr Glu Val Leu Asp<br>                     260                     265                     270 | | 816 |
| gtc att tcg tgg gat gcg tat ccg act tgg cac gac aac aac ggc gat<br>Val Ile Ser Trp Asp Ala Tyr Pro Thr Trp His Asp Asn Asn Gly Asp<br>               275                     280                     285 | | 864 |
| gag gcc gag ctt gcc gca tgg atc gcc tta aac cat gat gta ttc cga<br>Glu Ala Glu Leu Ala Ala Trp Ile Ala Leu Asn His Asp Val Phe Arg<br>       290                     295                     300 | | 912 |
| tcc ctg aag ggc ggc aag ccg ttc atg ctg atg gag agc acg ccg agc<br>Ser Leu Lys Gly Gly Lys Pro Phe Met Leu Met Glu Ser Thr Pro Ser<br>305                       310                     315                     320 | | 960 |
| atg acg aac tgg cag ccg atc agc aag ctg aag cgt ccg ggc atg cat<br>Met Thr Asn Trp Gln Pro Ile Ser Lys Leu Lys Arg Pro Gly Met His<br>                     325                     330                     335 | | 1008 |
| atg ctc tcc tcc ctg cag gcg gtt gcg cac ggc tcg gac acg gta caa<br>Met Leu Ser Ser Leu Gln Ala Val Ala His Gly Ser Asp Thr Val Gln<br>               340                     345                     350 | | 1056 |
| tat ttc caa tgg cgc aag agc aga ggc tcg agc gag aag ctg cac ggc<br>Tyr Phe Gln Trp Arg Lys Ser Arg Gly Ser Ser Glu Lys Leu His Gly<br>       355                     360                     365 | | 1104 |
| gcg gtg gtt gac cat gtc ggc cac gag cat acg cgc gtg ttc cgc gat<br>Ala Val Val Asp His Val Gly His Glu His Thr Arg Val Phe Arg Asp<br>370                       375                     380 | | 1152 |
| gtg gcg gag ctg ggc gag agg ctg tcc aag ctg acg gag gtt gtc ggc<br>Val Ala Glu Leu Gly Glu Arg Leu Ser Lys Leu Thr Glu Val Val Gly<br>385                       390                     395                     400 | | 1200 |
| acg acg gtg aag ccg gag gtc gcc ctc atc tat gac tgg gag aac cgc<br>Thr Thr Val Lys Pro Glu Val Ala Leu Ile Tyr Asp Trp Glu Asn Arg<br>                     405                     410                     415 | | 1248 |
| tgg gca gtg aag gat tct caa ggt ccg cgc aac agc ggc ctg aaa tac<br>Trp Ala Val Lys Asp Ser Gln Gly Pro Arg Asn Ser Gly Leu Lys Tyr<br>               420                     425                     430 | | 1296 |
| gag gaa acg gcg aag cgc cat tac cgt cca tta tgg gat ctt ggc gtg<br>Glu Glu Thr Ala Lys Arg His Tyr Arg Pro Leu Trp Asp Leu Gly Val<br>                     435                     440                     445 | | 1344 |
| ccc gtt gac gtc atc gat tcg gag tgc agc ttc gat tcg tac aag ctg<br>Pro Val Asp Val Ile Asp Ser Glu Cys Ser Phe Asp Ser Tyr Lys Leu<br>       450                     455                     460 | | 1392 |
| gtc atc gcg cct atg ctg tat atg gtg cgc cct ggc gtc ggc gag aaa<br>Val Ile Ala Pro Met Leu Tyr Met Val Arg Pro Gly Val Gly Glu Lys<br>465                       470                     475                     480 | | 1440 |
| atc gaa cgg ttc gtg gaa aac ggc ggt aca ttc gtg gcg act tac tgg<br>Ile Glu Arg Phe Val Glu Asn Gly Gly Thr Phe Val Ala Thr Tyr Trp<br>                     485                     490                     495 | | 1488 |
| agc ggc atc gtg gac gag aac gat ctt tgc ttc ctg acc ggc ttc ccg<br>Ser Gly Ile Val Asp Glu Asn Asp Leu Cys Phe Leu Thr Gly Phe Pro<br>               500                     505                     510 | | 1536 |
| ggc ccg ctt cgc aag acg ctg ggc atc tgg tcg gag gaa atc gac tcg<br>Gly Pro Leu Arg Lys Thr Leu Gly Ile Trp Ser Glu Glu Ile Asp Ser<br>       515                     520                     525 | | 1584 |

```
ctg cac gat cac gat tcg aac cgg gtc gtc atg aac gac ggc aac tcg    1632
Leu His Asp His Asp Ser Asn Arg Val Val Met Asn Asp Gly Asn Ser
    530                 535                 540 ctc gga ctt ggc ggc gag tat gaa gct cgc gag ctt tgc gac ctg att    1680
Leu Gly Leu Gly Gly Glu Tyr Glu Ala Arg Glu Leu Cys Asp Leu Ile
545                 550                 555                 560 cat ctg gag ggg gcg gag gcg ctg gcc gtg tac ggc gac gat ttc tac    1728
His Leu Glu Gly Ala Glu Ala Leu Ala Val Tyr Gly Asp Asp Phe Tyr
                565                 570                 575 gcc gga aga cct gct ctt acg gtg aat aag ctt ggc aag ggc aaa gcg    1776
Ala Gly Arg Pro Ala Leu Thr Val Asn Lys Leu Gly Lys Gly Lys Ala
            580                 585                 590 tat tat atc gcc tcc cgc aac gaa gcg gcg ttt aca aag cag ctg ctt    1824
Tyr Tyr Ile Ala Ser Arg Asn Glu Ala Ala Phe Thr Lys Gln Leu Leu
        595                 600                 605 gcc gcc ctc gtg tcg gaa gcg ggc atc aag cgc gtg ctc gaa tcc gag    1872
Ala Ala Leu Val Ser Glu Ala Gly Ile Lys Arg Val Leu Glu Ser Glu
    610                 615                 620 ctc ccg tat ggc gta acc gcc cag ctt cgc acg gac gga agg aac gac    1920
Leu Pro Tyr Gly Val Thr Ala Gln Leu Arg Thr Asp Gly Arg Asn Asp
625                 630                 635                 640 tac gtc ttc gta tcc aac ttt agc aac aaa gac gtt acc gtg ccg ctc    1968
Tyr Val Phe Val Ser Asn Phe Ser Asn Lys Asp Val Thr Val Pro Leu
                645                 650                 655 gac gga aga aac tat acc gat ctg ctg aca ggc gat ccg gaa ggt gcc    2016
Asp Gly Arg Asn Tyr Thr Asp Leu Leu Thr Gly Asp Pro Glu Gly Ala
            660                 665                 670 gca ctg gaa cta agc gcg tat agc tgc cgg att ttg aag cgt tct tcg    2064
Ala Leu Glu Leu Ser Ala Tyr Ser Cys Arg Ile Leu Lys Arg Ser Ser
        675                 680                 685 aat gca taa                                                         2073
Asn Ala
    690

<210> SEQ ID NO 65
<211> LENGTH: 690
<212> TYPE: PRT
<213> ORGANISM: Paenibacillus sp- 62047

<400> SEQUENCE: 65

Met Thr Leu Lys Tyr Pro Pro Ile Ser Thr Lys Ile Pro Gln Met Leu
1               5                   10                  15

His Gly Ala Asp Tyr Asn Pro Asp Gln Trp Gln Lys Tyr Pro Glu Val
            20                  25                  30

Leu Glu Glu Asp Ile Arg Leu Met Lys Leu Ala Gly Cys Asn Val Met
        35                  40                  45

Ser Val Gly Ile Phe Ala Trp Ala Ala Ile Glu Pro Glu Glu Gly Val
    50                  55                  60

Phe Thr Phe Glu Trp Leu Asp Ser Leu Asp Lys Phe Ala Ala Asn
65                  70                  75                  80

Gly Ile Tyr Ala Leu Leu Ala Thr Pro Ser Gly Ala Arg Pro Ala Trp
                85                  90                  95

Met Ser Gln Lys Tyr Pro Glu Val Leu Arg Val Ala Pro Thr Gly Ile
            100                 105                 110

Arg Asn Leu His Gly Ala Arg His Asn His Cys Phe Thr Ser Pro Val
        115                 120                 125

Tyr Arg Glu Lys Val Asn Ile Met Asn Thr Lys Leu Ala Glu Arg Tyr
    130                 135                 140
```

```
Ala Gln His Pro Ala Val Ile Gly Trp His Ile Ser Asn Glu Tyr Gly
145                 150                 155                 160

Gly Glu Cys His Cys Ser Tyr Cys Glu Glu Ala Phe Arg Gly Trp Leu
            165                 170                 175

Lys Asn Lys Tyr Gly Thr Leu Glu Ala Leu Asn Asp Ala Trp Trp Thr
        180                 185                 190

Thr Phe Trp Ser His Thr Tyr Thr Asp Trp Ser Gln Val Glu Ser Pro
    195                 200                 205

Thr Pro Arg Gly Glu Asn Ala Val His Gly Gln Asn Val Asp Trp Arg
210                 215                 220

Arg Phe Val Thr Asp Gln Thr Val Asp Phe Cys Arg Lys Glu Ile Glu
225                 230                 235                 240

Pro Leu Arg Ala Ala Asn Ser Glu Leu Pro Ile Thr Thr Asn Phe Met
            245                 250                 255

Leu Asp Phe Glu Pro Leu Asn Tyr Trp Lys Phe Thr Glu Val Leu Asp
        260                 265                 270

Val Ile Ser Trp Asp Ala Tyr Pro Thr Trp His Asp Asn Asn Gly Asp
    275                 280                 285

Glu Ala Glu Leu Ala Ala Trp Ile Ala Leu Asn His Asp Val Phe Arg
290                 295                 300

Ser Leu Lys Gly Gly Lys Pro Phe Met Leu Met Glu Ser Thr Pro Ser
305                 310                 315                 320

Met Thr Asn Trp Gln Pro Ile Ser Lys Leu Lys Arg Pro Gly Met His
            325                 330                 335

Met Leu Ser Ser Leu Gln Ala Val Ala His Gly Ser Asp Thr Val Gln
        340                 345                 350

Tyr Phe Gln Trp Arg Lys Ser Arg Gly Ser Ser Glu Lys Leu His Gly
    355                 360                 365

Ala Val Val Asp His Val Gly His Glu His Thr Arg Val Phe Arg Asp
370                 375                 380

Val Ala Glu Leu Gly Glu Arg Leu Ser Lys Leu Thr Glu Val Val Gly
385                 390                 395                 400

Thr Thr Val Lys Pro Glu Val Ala Leu Ile Tyr Asp Trp Glu Asn Arg
            405                 410                 415

Trp Ala Val Lys Asp Ser Gln Gly Pro Arg Asn Ser Gly Leu Lys Tyr
        420                 425                 430

Glu Glu Thr Ala Lys Arg His Tyr Arg Pro Leu Trp Asp Leu Gly Val
    435                 440                 445

Pro Val Asp Val Ile Asp Ser Glu Cys Ser Phe Asp Ser Tyr Lys Leu
450                 455                 460

Val Ile Ala Pro Met Leu Tyr Met Val Arg Pro Gly Val Gly Glu Lys
465                 470                 475                 480

Ile Glu Arg Phe Val Glu Asn Gly Gly Thr Phe Val Ala Thr Tyr Trp
            485                 490                 495

Ser Gly Ile Val Asp Glu Asn Asp Leu Cys Phe Leu Thr Gly Phe Pro
        500                 505                 510

Gly Pro Leu Arg Lys Thr Leu Gly Ile Trp Ser Glu Glu Ile Asp Ser
    515                 520                 525

Leu His Asp His Asp Ser Asn Arg Val Val Met Asn Asp Gly Asn Ser
530                 535                 540

Leu Gly Leu Gly Gly Glu Tyr Glu Ala Arg Glu Leu Cys Asp Leu Ile
545                 550                 555                 560
```

```
His Leu Glu Gly Ala Glu Ala Leu Ala Val Tyr Gly Asp Asp Phe Tyr
            565                 570                 575

Ala Gly Arg Pro Ala Leu Thr Val Asn Lys Leu Gly Lys Gly Lys Ala
            580                 585                 590

Tyr Tyr Ile Ala Ser Arg Asn Glu Ala Ala Phe Thr Lys Gln Leu Leu
            595                 600                 605

Ala Ala Leu Val Ser Glu Ala Gly Ile Lys Arg Val Leu Glu Ser Glu
610                 615                 620

Leu Pro Tyr Gly Val Thr Ala Gln Leu Arg Thr Asp Gly Arg Asn Asp
625                 630                 635                 640

Tyr Val Phe Val Ser Asn Phe Ser Asn Lys Asp Val Thr Val Pro Leu
            645                 650                 655

Asp Gly Arg Asn Tyr Thr Asp Leu Leu Thr Gly Asp Pro Glu Gly Ala
            660                 665                 670

Ala Leu Glu Leu Ser Ala Tyr Ser Cys Arg Ile Leu Lys Arg Ser Ser
            675                 680                 685

Asn Ala
    690

<210> SEQ ID NO 66
<211> LENGTH: 699
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(699)

<400> SEQUENCE: 66

Met His His His His His His Pro Arg Met Thr Leu Lys Tyr Pro Pro
1               5                   10                  15

Ile Ser Thr Lys Ile Pro Gln Met Leu His Gly Ala Asp Tyr Asn Pro
            20                  25                  30

Asp Gln Trp Gln Lys Tyr Pro Glu Val Leu Glu Glu Asp Ile Arg Leu
        35                  40                  45

Met Lys Leu Ala Gly Cys Asn Val Met Ser Val Gly Ile Phe Ala Trp
50                  55                  60

Ala Ala Ile Glu Pro Glu Glu Gly Val Phe Thr Phe Glu Trp Leu Asp
65                  70                  75                  80

Ser Leu Leu Asp Lys Phe Ala Ala Asn Gly Ile Tyr Ala Leu Leu Ala
                85                  90                  95

Thr Pro Ser Gly Ala Arg Pro Ala Trp Met Ser Gln Lys Tyr Pro Glu
            100                 105                 110

Val Leu Arg Val Ala Pro Thr Gly Ile Arg Asn Leu His Gly Ala Arg
        115                 120                 125

His Asn His Cys Phe Thr Ser Pro Val Tyr Arg Glu Lys Val Asn Ile
    130                 135                 140

Met Asn Thr Lys Leu Ala Glu Arg Tyr Ala Gln His Pro Ala Val Ile
145                 150                 155                 160

Gly Trp His Ile Ser Asn Glu Tyr Gly Gly Glu Cys His Cys Ser Tyr
                165                 170                 175

Cys Glu Glu Ala Phe Arg Gly Trp Leu Lys Asn Lys Tyr Gly Thr Leu
            180                 185                 190

Glu Ala Leu Asn Asp Ala Trp Trp Thr Thr Phe Trp Ser His Thr Tyr
        195                 200                 205
```

```
Thr Asp Trp Ser Gln Val Glu Ser Pro Thr Pro Arg Gly Glu Asn Ala
210                 215                 220

Val His Gly Gln Asn Val Asp Trp Arg Phe Val Thr Asp Gln Thr
225                 230                 235                 240

Val Asp Phe Cys Arg Lys Glu Ile Glu Pro Leu Arg Ala Ala Asn Ser
                245                 250                 255

Glu Leu Pro Ile Thr Thr Asn Phe Met Leu Asp Phe Glu Pro Leu Asn
            260                 265                 270

Tyr Trp Lys Phe Thr Glu Val Leu Asp Val Ile Ser Trp Asp Ala Tyr
        275                 280                 285

Pro Thr Trp His Asp Asn Asn Gly Asp Glu Ala Glu Leu Ala Ala Trp
    290                 295                 300

Ile Ala Leu Asn His Asp Val Phe Arg Ser Leu Lys Gly Gly Lys Pro
305                 310                 315                 320

Phe Met Leu Met Glu Ser Thr Pro Ser Met Thr Asn Trp Gln Pro Ile
                325                 330                 335

Ser Lys Leu Lys Arg Pro Gly Met His Met Leu Ser Ser Leu Gln Ala
            340                 345                 350

Val Ala His Gly Ser Asp Thr Val Gln Tyr Phe Gln Trp Arg Lys Ser
        355                 360                 365

Arg Gly Ser Ser Glu Lys Leu His Gly Ala Val Val Asp His Val Gly
    370                 375                 380

His Glu His Thr Arg Val Phe Arg Asp Val Ala Glu Leu Gly Glu Arg
385                 390                 395                 400

Leu Ser Lys Leu Thr Glu Val Val Gly Thr Thr Val Lys Pro Glu Val
                405                 410                 415

Ala Leu Ile Tyr Asp Trp Glu Asn Arg Trp Ala Val Lys Asp Ser Gln
            420                 425                 430

Gly Pro Arg Asn Ser Gly Leu Lys Tyr Glu Glu Thr Ala Lys Arg His
        435                 440                 445

Tyr Arg Pro Leu Trp Asp Leu Gly Val Pro Val Asp Val Ile Asp Ser
    450                 455                 460

Glu Cys Ser Phe Asp Ser Tyr Lys Leu Val Ile Ala Pro Met Leu Tyr
465                 470                 475                 480

Met Val Arg Pro Gly Val Gly Glu Lys Ile Glu Arg Phe Val Glu Asn
                485                 490                 495

Gly Gly Thr Phe Val Ala Thr Tyr Trp Ser Gly Ile Val Asp Glu Asn
            500                 505                 510

Asp Leu Cys Phe Leu Thr Gly Phe Pro Gly Pro Leu Arg Lys Thr Leu
        515                 520                 525

Gly Ile Trp Ser Glu Glu Ile Asp Ser Leu His Asp His Asp Ser Asn
    530                 535                 540

Arg Val Val Met Asn Asp Gly Asn Ser Leu Gly Leu Gly Gly Glu Tyr
545                 550                 555                 560

Glu Ala Arg Glu Leu Cys Asp Leu Ile His Leu Glu Gly Ala Glu Ala
                565                 570                 575

Leu Ala Val Tyr Gly Asp Asp Phe Tyr Ala Gly Arg Pro Ala Leu Thr
            580                 585                 590

Val Asn Lys Leu Gly Lys Gly Lys Ala Tyr Tyr Ile Ala Ser Arg Asn
        595                 600                 605

Glu Ala Ala Phe Thr Lys Gln Leu Leu Ala Ala Leu Val Ser Glu Ala
    610                 615                 620

Gly Ile Lys Arg Val Leu Glu Ser Glu Leu Pro Tyr Gly Val Thr Ala
```

```
             625                 630                 635                 640
Gln Leu Arg Thr Asp Gly Arg Asn Asp Tyr Val Phe Val Ser Asn Phe
                     645                 650                 655

Ser Asn Lys Asp Val Thr Val Pro Leu Asp Gly Arg Asn Tyr Thr Asp
             660                 665                 670

Leu Leu Thr Gly Asp Pro Glu Gly Ala Ala Leu Glu Leu Ser Ala Tyr
             675                 680                 685

Ser Cys Arg Ile Leu Lys Arg Ser Ser Asn Ala
             690                 695

<210> SEQ ID NO 67
<211> LENGTH: 2070
<212> TYPE: DNA
<213> ORGANISM: Paenibacillus sp- 62603
<220> FEATURE:
<221> NAME/KEY: CDS
<222> LOCATION: (1)..(2067)
<220> FEATURE:
<221> NAME/KEY: mat_peptide
<222> LOCATION: (1)..(2067)

<400> SEQUENCE: 67 atg agt atg aaa ttt ccc ccg ata agt gca aaa att ccg caa atg ctg      48
Met Ser Met Lys Phe Pro Pro Ile Ser Ala Lys Ile Pro Gln Met Leu
1               5                   10                  15 cat ggt gca gat tat aat cca gat caa tgg cag aag tat cct gag gtg      96
His Gly Ala Asp Tyr Asn Pro Asp Gln Trp Gln Lys Tyr Pro Glu Val
            20                  25                  30 ctg gag gaa gac atc cgc ctc atg aag ctt gca cat tgc aac gtg atg     144
Leu Glu Glu Asp Ile Arg Leu Met Lys Leu Ala His Cys Asn Val Met
        35                  40                  45 tct gta ggc att ttt gca tgg atg gcg atc gag ccg gag gaa ggc gta     192
Ser Val Gly Ile Phe Ala Trp Met Ala Ile Glu Pro Glu Glu Gly Val
    50                  55                  60 ttt aca ttt gaa tgg ctg gac acg ttg ctt gat aaa ttt gct gct aac     240
Phe Thr Phe Glu Trp Leu Asp Thr Leu Leu Asp Lys Phe Ala Ala Asn
65                  70                  75                  80 ggc atc tat gcc ttg ctt gct aca cca agc gga gca cgc ccg gtt tgg     288
Gly Ile Tyr Ala Leu Leu Ala Thr Pro Ser Gly Ala Arg Pro Val Trp
                85                  90                  95 atg tct caa aaa tat ccg gaa gtg ctg cgc gtt gca cct aac gga att     336
Met Ser Gln Lys Tyr Pro Glu Val Leu Arg Val Ala Pro Asn Gly Ile
            100                 105                 110 cgt aat ttg cat ggt gcg cgt cat aac cac tgc ttc agc tca cct gta     384
Arg Asn Leu His Gly Ala Arg His Asn His Cys Phe Ser Ser Pro Val
        115                 120                 125 tat cgc gag aag gta acg atc atg aac tcg aag ctg gca gaa cgt tat     432
Tyr Arg Glu Lys Val Thr Ile Met Asn Ser Lys Leu Ala Glu Arg Tyr
    130                 135                 140 tcg gat cat cct gcg gtc atc ggc tgg cat ata tca aat gaa tat ggc     480
Ser Asp His Pro Ala Val Ile Gly Trp His Ile Ser Asn Glu Tyr Gly
145                 150                 155                 160 ggc gaa tgt cac tgc tcg tat tgt gaa gac gct ttc cgc gac tgg ttg     528
Gly Glu Cys His Cys Ser Tyr Cys Glu Asp Ala Phe Arg Asp Trp Leu
                165                 170                 175 aaa aat aaa tac ggt aca cta gaa gca ctt aac gat gct tgg tgg acg     576
Lys Asn Lys Tyr Gly Thr Leu Glu Ala Leu Asn Asp Ala Trp Trp Thr
            180                 185                 190 acg ttc tgg agc cat acg tat acc gat tgg agc caa gtc gag tcg cca     624
Thr Phe Trp Ser His Thr Tyr Thr Asp Trp Ser Gln Val Glu Ser Pro
        195                 200                 205
```

| | | |
|---|---|---|
| acc gag cgt ggc gag aaa gcg gtt cac ggc cag aat gtt gac tgg aga<br>Thr Glu Arg Gly Glu Lys Ala Val His Gly Gln Asn Val Asp Trp Arg<br>210                            215                           220 | 672 |
| aga ttc gtt acg gat caa acg gtt gat ttc tgc cgc aac gaa att gct<br>Arg Phe Val Thr Asp Gln Thr Val Asp Phe Cys Arg Asn Glu Ile Ala<br>225                        230                        235                  240 | 720 |
| ccg ctg cgc gcc gct aat agt gag ctt ccg att acg acg aac ttt atg<br>Pro Leu Arg Ala Ala Asn Ser Glu Leu Pro Ile Thr Thr Asn Phe Met<br>                       245                       250                       255 | 768 |
| ctt gat ttt gag ccg ctt aac tat tgg aag ttt aca gag ctg ctc gat<br>Leu Asp Phe Glu Pro Leu Asn Tyr Trp Lys Phe Thr Glu Leu Leu Asp<br>              260                       265                       270 | 816 |
| atg att tcg tgg gat gct tat cca act tgg cac gac aat ggc gga gac<br>Met Ile Ser Trp Asp Ala Tyr Pro Thr Trp His Asp Asn Gly Gly Asp<br>        275                       280                       285 | 864 |
| gac agc gag caa gcg gcg tgg atc ggc ttt aac cat gat gtg ttt cgt<br>Asp Ser Glu Gln Ala Ala Trp Ile Gly Phe Asn His Asp Val Phe Arg<br>290                            295                       300 | 912 |
| tcg ctt ggc ggc gga aag ccg ttc atg ctg atg gaa agc acg ccg agc<br>Ser Leu Gly Gly Gly Lys Pro Phe Met Leu Met Glu Ser Thr Pro Ser<br>305                        310                      315                  320 | 960 |
| atg acg aac tgg cag ccg atc agc aaa gtg aag cgt cca ggg atg cac<br>Met Thr Asn Trp Gln Pro Ile Ser Lys Val Lys Arg Pro Gly Met His<br>                     325                       330                       335 | 1008 |
| atg ctg tca tcg cta caa gcg gtg gca cat ggc tca gat act gtt cag<br>Met Leu Ser Ser Leu Gln Ala Val Ala His Gly Ser Asp Thr Val Gln<br>              340                       345                       350 | 1056 |
| tat ttc cag tgg cgc aag agc aga ggc tca agc gag aag ctg cat ggt<br>Tyr Phe Gln Trp Arg Lys Ser Arg Gly Ser Ser Glu Lys Leu His Gly<br>        355                       360                       365 | 1104 |
| gca gta gtg gac cat gtc ggc cat gag cat act cgc gtt ttc cgc gat<br>Ala Val Val Asp His Val Gly His Glu His Thr Arg Val Phe Arg Asp<br>370                            375                       380 | 1152 |
| gtg gct gag ctt ggc gaa gct ttg gag aaa ctt act gaa gta gta ggt<br>Val Ala Glu Leu Gly Glu Ala Leu Glu Lys Leu Thr Glu Val Val Gly<br>385                            390                        395                  400 | 1200 |
| aca act gtg aag cca gag gta gcg ctt atc tat gat tgg gaa aat cgc<br>Thr Thr Val Lys Pro Glu Val Ala Leu Ile Tyr Asp Trp Glu Asn Arg<br>                     405                       410                       415 | 1248 |
| tgg gca gta aag gat tcg caa ggc ccg cgc aat agc ggt ctt cat tat<br>Trp Ala Val Lys Asp Ser Gln Gly Pro Arg Asn Ser Gly Leu His Tyr<br>              420                       425                       430 | 1296 |
| gaa gaa acg gct aaa cgc cat tac cgt ccg ttc tgg gat ctg ggt gta<br>Glu Glu Thr Ala Lys Arg His Tyr Arg Pro Phe Trp Asp Leu Gly Val<br>        435                       440                       445 | 1344 |
| cca gtg gac att att gat tcg gaa tgc agc ttt gat tcg tac aag ctt<br>Pro Val Asp Ile Ile Asp Ser Glu Cys Ser Phe Asp Ser Tyr Lys Leu<br>450                            455                       460 | 1392 |
| ctt att gct ccg atg tta tat atg gtg cgt cca ggt gta ggc gag cgc<br>Leu Ile Ala Pro Met Leu Tyr Met Val Arg Pro Gly Val Gly Glu Arg<br>465                            470                        475                  480 | 1440 |
| att gaa cgt ttt gtt gaa aat ggc ggt act ttc atc gct act tat tgg<br>Ile Glu Arg Phe Val Glu Asn Gly Gly Thr Phe Ile Ala Thr Tyr Trp<br>                     485                       490                       495 | 1488 |
| aca ggc atc gtt gat gag aat gat cta tgc ttc ctt aca ggt ttc cca<br>Thr Gly Ile Val Asp Glu Asn Asp Leu Cys Phe Leu Thr Gly Phe Pro<br>              500                       505                       510 | 1536 |
| gga ccg ctg cgc aag acg ctt ggg atc tgg tcc gag gag atc gat tcg<br>Gly Pro Leu Arg Lys Thr Leu Gly Ile Trp Ser Glu Glu Ile Asp Ser | 1584 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 515 |     |     |     |     | 520 |     |     |     |     | 525 |     |     |     |     |      |
| ctg | cat | gat | cat | gat | tcc | aat | cag | gtc | gtg | ctg | aag | gac | gga | aat | aag | 1632 |
| Leu | His | Asp | His | Asp | Ser | Asn | Gln | Val | Val | Leu | Lys | Asp | Gly | Asn | Lys |      |
|     | 530 |     |     |     |     | 535 |     |     |     |     | 540 |     |     |     |     |      |
| ctt | gga | ctg | agc | ggc | caa | tat | aca | gca | cgc | gag | ctg | tgt | gat | ctc | atc | 1680 |
| Leu | Gly | Leu | Ser | Gly | Gln | Tyr | Thr | Ala | Arg | Glu | Leu | Cys | Asp | Leu | Ile |      |
| 545 |     |     |     |     | 550 |     |     |     |     | 555 |     |     |     |     | 560 |      |
| cat | ctt | gaa | ggg | gcg | gag | gca | ctt | gct | gta | tat | gga | gag | gat | ttc | tat | 1728 |
| His | Leu | Glu | Gly | Ala | Glu | Ala | Leu | Ala | Val | Tyr | Gly | Glu | Asp | Phe | Tyr |      |
|     |     |     |     | 565 |     |     |     |     | 570 |     |     |     |     | 575 |     |      |
| gcg | ggt | cgc | cct | gcc | tta | acg | gta | aat | cat | ttg | ggt | gca | ggc | aaa | gcc | 1776 |
| Ala | Gly | Arg | Pro | Ala | Leu | Thr | Val | Asn | His | Leu | Gly | Ala | Gly | Lys | Ala |      |
|     |     |     | 580 |     |     |     |     | 585 |     |     |     |     | 590 |     |     |      |
| tac | tat | gtt | gca | tcg | cgc | aac | gaa | gca | tct | ttt | aca | aac | gat | ttt | ctg | 1824 |
| Tyr | Tyr | Val | Ala | Ser | Arg | Asn | Glu | Ala | Ser | Phe | Thr | Asn | Asp | Phe | Leu |      |
|     |     | 595 |     |     |     |     | 600 |     |     |     |     | 605 |     |     |     |      |
| act | cga | att | ata | gag | caa | gag | ggg | ata | aag | cga | gtt | ctt | gat | tcc | gag | 1872 |
| Thr | Arg | Ile | Ile | Glu | Gln | Glu | Gly | Ile | Lys | Arg | Val | Leu | Asp | Ser | Glu |      |
| 610 |     |     |     |     | 615 |     |     |     |     | 620 |     |     |     |     |     |      |
| ctg | ccg | caa | ggc | gta | act | gca | caa | tta | aga | acg | gat | ggg | gtg | aac | gac | 1920 |
| Leu | Pro | Gln | Gly | Val | Thr | Ala | Gln | Leu | Arg | Thr | Asp | Gly | Val | Asn | Asp |      |
| 625 |     |     |     |     | 630 |     |     |     |     | 635 |     |     |     |     | 640 |      |
| tac | gtc | ttt | gta | tcc | aat | ttc | agt | gca | aat | gag | gct | tcg | gtt | gct | tta | 1968 |
| Tyr | Val | Phe | Val | Ser | Asn | Phe | Ser | Ala | Asn | Glu | Ala | Ser | Val | Ala | Leu |      |
|     |     |     |     |     | 645 |     |     |     |     | 650 |     |     |     |     | 655 |      |
| gat | gct | cag | cag | tat | aca | gat | ttg | ttg | acg | ggt | tcg | gct | cta | aac | aac | 2016 |
| Asp | Ala | Gln | Gln | Tyr | Thr | Asp | Leu | Leu | Thr | Gly | Ser | Ala | Leu | Asn | Asn |      |
|     |     |     | 660 |     |     |     |     | 665 |     |     |     |     | 670 |     |     |      |
| agt | gtt | gaa | ttg | aag | cct | tac | ggc | tgc | cgg | atc | ttg | aaa | cga | gtt | tcg | 2064 |
| Ser | Val | Glu | Leu | Lys | Pro | Tyr | Gly | Cys | Arg | Ile | Leu | Lys | Arg | Val | Ser |      |
|     |     | 675 |     |     |     |     | 680 |     |     |     |     | 685 |     |     |     |      |
| aaa | taa |     |     |     |     |     |     |     |     |     |     |     |     |     |     | 2070 |
| Lys |     |     |     |     |     |     |     |     |     |     |     |     |     |     |     |      |

<210> SEQ ID NO 68
<211> LENGTH: 689
<212> TYPE: PRT
<213> ORGANISM: Paenibacillus sp- 62603

<400> SEQUENCE: 68

Met Ser Met Lys Phe Pro Pro Ile Ser Ala Lys Ile Pro Gln Met Leu
1               5                   10                  15

His Gly Ala Asp Tyr Asn Pro Asp Gln Trp Gln Lys Tyr Pro Glu Val
                20                  25                  30

Leu Glu Glu Asp Ile Arg Leu Met Lys Leu Ala His Cys Asn Val Met
            35                  40                  45

Ser Val Gly Ile Phe Ala Trp Met Ala Ile Glu Pro Glu Glu Gly Val
        50                  55                  60

Phe Thr Phe Glu Trp Leu Asp Thr Leu Asp Lys Phe Ala Ala Asn
65                  70                  75                  80

Gly Ile Tyr Ala Leu Leu Ala Thr Pro Ser Gly Ala Arg Pro Val Trp
                85                  90                  95

Met Ser Gln Lys Tyr Pro Glu Val Leu Arg Val Ala Pro Asn Gly Ile
            100                 105                 110

Arg Asn Leu His Gly Ala Arg His Asn His Cys Phe Ser Ser Pro Val
        115                 120                 125

Tyr Arg Glu Lys Val Thr Ile Met Asn Ser Lys Leu Ala Glu Arg Tyr
    130                 135                 140

```
Ser Asp His Pro Ala Val Ile Gly Trp His Ile Ser Asn Glu Tyr Gly
145                 150                 155                 160

Gly Glu Cys His Cys Ser Tyr Cys Glu Asp Ala Phe Arg Asp Trp Leu
            165                 170                 175

Lys Asn Lys Tyr Gly Thr Leu Glu Ala Leu Asn Asp Ala Trp Trp Thr
            180                 185                 190

Thr Phe Trp Ser His Thr Tyr Thr Asp Trp Ser Gln Val Glu Ser Pro
        195                 200                 205

Thr Glu Arg Gly Glu Lys Ala Val His Gly Gln Asn Val Asp Trp Arg
    210                 215                 220

Arg Phe Val Thr Asp Gln Thr Val Asp Phe Cys Arg Asn Glu Ile Ala
225                 230                 235                 240

Pro Leu Arg Ala Ala Asn Ser Glu Leu Pro Ile Thr Thr Asn Phe Met
                245                 250                 255

Leu Asp Phe Glu Pro Leu Asn Tyr Trp Lys Phe Thr Glu Leu Leu Asp
            260                 265                 270

Met Ile Ser Trp Asp Ala Tyr Pro Thr Trp His Asp Asn Gly Gly Asp
        275                 280                 285

Asp Ser Glu Gln Ala Ala Trp Ile Gly Phe Asn His Asp Val Phe Arg
    290                 295                 300

Ser Leu Gly Gly Gly Lys Pro Phe Met Leu Met Glu Ser Thr Pro Ser
305                 310                 315                 320

Met Thr Asn Trp Gln Pro Ile Ser Lys Val Lys Arg Pro Gly Met His
                325                 330                 335

Met Leu Ser Ser Leu Gln Ala Val Ala His Gly Ser Asp Thr Val Gln
            340                 345                 350

Tyr Phe Gln Trp Arg Lys Ser Arg Gly Ser Ser Glu Lys Leu His Gly
        355                 360                 365

Ala Val Val Asp His Val Gly His Glu His Thr Arg Val Phe Arg Asp
    370                 375                 380

Val Ala Glu Leu Gly Glu Ala Leu Glu Lys Leu Thr Glu Val Val Gly
385                 390                 395                 400

Thr Thr Val Lys Pro Glu Val Ala Leu Ile Tyr Asp Trp Glu Asn Arg
                405                 410                 415

Trp Ala Val Lys Asp Ser Gln Gly Pro Arg Asn Ser Gly Leu His Tyr
            420                 425                 430

Glu Glu Thr Ala Lys Arg His Tyr Arg Pro Phe Trp Asp Leu Gly Val
        435                 440                 445

Pro Val Asp Ile Ile Asp Ser Glu Cys Ser Phe Asp Ser Tyr Lys Leu
    450                 455                 460

Leu Ile Ala Pro Met Leu Tyr Met Val Arg Pro Gly Val Gly Glu Arg
465                 470                 475                 480

Ile Glu Arg Phe Val Glu Asn Gly Gly Thr Phe Ile Ala Thr Tyr Trp
                485                 490                 495

Thr Gly Ile Val Asp Glu Asn Asp Leu Cys Phe Leu Thr Gly Phe Pro
            500                 505                 510

Gly Pro Leu Arg Lys Thr Leu Gly Ile Trp Ser Glu Glu Ile Asp Ser
        515                 520                 525

Leu His Asp His Asp Ser Asn Gln Val Val Leu Lys Asp Gly Asn Lys
    530                 535                 540

Leu Gly Leu Ser Gly Gln Tyr Thr Ala Arg Glu Leu Cys Asp Leu Ile
545                 550                 555                 560
```

-continued

```
His Leu Glu Gly Ala Glu Ala Leu Ala Val Tyr Gly Glu Asp Phe Tyr
                565                 570                 575

Ala Gly Arg Pro Ala Leu Thr Val Asn His Leu Gly Ala Gly Lys Ala
            580                 585                 590

Tyr Tyr Val Ala Ser Arg Asn Glu Ala Ser Phe Thr Asn Asp Phe Leu
        595                 600                 605

Thr Arg Ile Ile Glu Gln Gly Ile Lys Arg Val Leu Asp Ser Glu
    610                 615                 620

Leu Pro Gln Gly Val Thr Ala Gln Leu Arg Thr Asp Gly Val Asn Asp
625                 630                 635                 640

Tyr Val Phe Val Ser Asn Phe Ser Ala Asn Glu Ala Ser Val Ala Leu
                645                 650                 655

Asp Ala Gln Gln Tyr Thr Asp Leu Leu Thr Gly Ser Ala Leu Asn Asn
            660                 665                 670

Ser Val Glu Leu Lys Pro Tyr Gly Cys Arg Ile Leu Lys Arg Val Ser
        675                 680                 685

Lys
```

<210> SEQ ID NO 69
<211> LENGTH: 698
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(698)

<400> SEQUENCE: 69

```
Met His His His His His Pro Arg Met Ser Met Lys Phe Pro Pro
1               5                   10                  15

Ile Ser Ala Lys Ile Pro Gln Met Leu His Gly Ala Asp Tyr Asn Pro
            20                  25                  30

Asp Gln Trp Gln Lys Tyr Pro Glu Val Leu Glu Asp Ile Arg Leu
        35                  40                  45

Met Lys Leu Ala His Cys Asn Val Met Ser Val Gly Ile Phe Ala Trp
50                  55                  60

Met Ala Ile Glu Pro Glu Gly Val Phe Thr Phe Glu Trp Leu Asp
65                  70                  75                  80

Thr Leu Leu Asp Lys Phe Ala Ala Asn Gly Ile Tyr Ala Leu Leu Ala
                85                  90                  95

Thr Pro Ser Gly Ala Arg Pro Val Trp Met Ser Gln Lys Tyr Pro Glu
            100                 105                 110

Val Leu Arg Val Ala Pro Asn Gly Ile Arg Asn Leu His Gly Ala Arg
        115                 120                 125

His Asn His Cys Phe Ser Ser Pro Val Tyr Arg Glu Lys Val Thr Ile
    130                 135                 140

Met Asn Ser Lys Leu Ala Glu Arg Tyr Ser Asp His Pro Ala Val Ile
145                 150                 155                 160

Gly Trp His Ile Ser Asn Glu Tyr Gly Gly Glu Cys His Cys Ser Tyr
                165                 170                 175

Cys Glu Asp Ala Phe Arg Asp Trp Leu Lys Asn Lys Tyr Gly Thr Leu
            180                 185                 190

Glu Ala Leu Asn Asp Ala Trp Trp Thr Thr Phe Trp Ser His Thr Tyr
        195                 200                 205

Thr Asp Trp Ser Gln Val Glu Ser Pro Thr Glu Arg Gly Glu Lys Ala
```

-continued

```
                210                 215                 220
Val His Gly Gln Asn Val Asp Trp Arg Arg Phe Val Thr Asp Gln Thr
225                 230                 235                 240

Val Asp Phe Cys Arg Asn Glu Ile Ala Pro Leu Arg Ala Ala Asn Ser
                245                 250                 255

Glu Leu Pro Ile Thr Thr Asn Phe Met Leu Asp Phe Glu Pro Leu Asn
                260                 265                 270

Tyr Trp Lys Phe Thr Glu Leu Leu Asp Met Ile Ser Trp Asp Ala Tyr
                275                 280                 285

Pro Thr Trp His Asp Asn Gly Gly Asp Asp Ser Glu Gln Ala Ala Trp
                290                 295                 300

Ile Gly Phe Asn His Asp Val Phe Arg Ser Leu Gly Gly Lys Pro
305                 310                 315                 320

Phe Met Leu Met Glu Ser Thr Pro Ser Met Thr Asn Trp Gln Pro Ile
                325                 330                 335

Ser Lys Val Lys Arg Pro Gly Met His Met Leu Ser Ser Leu Gln Ala
                340                 345                 350

Val Ala His Gly Ser Asp Thr Val Gln Tyr Phe Gln Trp Arg Lys Ser
                355                 360                 365

Arg Gly Ser Ser Glu Lys Leu His Gly Ala Val Val Asp His Val Gly
                370                 375                 380

His Glu His Thr Arg Val Phe Arg Asp Val Ala Glu Leu Gly Glu Ala
385                 390                 395                 400

Leu Glu Lys Leu Thr Glu Val Val Gly Thr Thr Val Lys Pro Glu Val
                405                 410                 415

Ala Leu Ile Tyr Asp Trp Glu Asn Arg Trp Ala Val Lys Asp Ser Gln
                420                 425                 430

Gly Pro Arg Asn Ser Gly Leu His Tyr Glu Thr Ala Lys Arg His
                435                 440                 445

Tyr Arg Pro Phe Trp Asp Leu Gly Val Pro Val Asp Ile Ile Asp Ser
                450                 455                 460

Glu Cys Ser Phe Asp Ser Tyr Lys Leu Leu Ile Ala Pro Met Leu Tyr
465                 470                 475                 480

Met Val Arg Pro Gly Val Gly Glu Arg Ile Glu Arg Phe Val Glu Asn
                485                 490                 495

Gly Gly Thr Phe Ile Ala Thr Tyr Trp Thr Gly Ile Val Asp Glu Asn
                500                 505                 510

Asp Leu Cys Phe Leu Thr Gly Phe Pro Gly Pro Leu Arg Lys Thr Leu
                515                 520                 525

Gly Ile Trp Ser Glu Glu Ile Asp Ser Leu His Asp His Asp Ser Asn
                530                 535                 540

Gln Val Val Leu Lys Asp Gly Asn Lys Leu Leu Ser Gly Gln Tyr
545                 550                 555                 560

Thr Ala Arg Glu Leu Cys Asp Leu Ile His Leu Glu Gly Ala Glu Ala
                565                 570                 575

Leu Ala Val Tyr Gly Glu Asp Phe Tyr Ala Gly Arg Pro Ala Leu Thr
                580                 585                 590

Val Asn His Leu Gly Ala Gly Lys Ala Tyr Tyr Val Ala Ser Arg Asn
                595                 600                 605

Glu Ala Ser Phe Thr Asn Asp Phe Leu Thr Arg Ile Ile Glu Gln Glu
                610                 615                 620

Gly Ile Lys Arg Val Leu Asp Ser Glu Leu Pro Gln Gly Val Thr Ala
625                 630                 635                 640
```

```
Gln Leu Arg Thr Asp Gly Val Asn Asp Tyr Val Phe Val Ser Asn Phe
                645                 650                 655

Ser Ala Asn Glu Ala Ser Val Ala Leu Asp Ala Gln Gln Tyr Thr Asp
            660                 665                 670

Leu Leu Thr Gly Ser Ala Leu Asn Asn Ser Val Glu Leu Lys Pro Tyr
        675                 680                 685

Gly Cys Arg Ile Leu Lys Arg Val Ser Lys
    690                 695

<210> SEQ ID NO 70
<211> LENGTH: 2058
<212> TYPE: DNA
<213> ORGANISM: Paenibacillus woosongensis
<220> FEATURE:
<221> NAME/KEY: CDS
<222> LOCATION: (1)..(2055)
<220> FEATURE:
<221> NAME/KEY: mat_peptide
<222> LOCATION: (1)..(2055)

<400> SEQUENCE: 70 atg acg aag aaa ttt cca ccg atc agc gac agg ctt ccc gtc ttg atg      48
Met Thr Lys Lys Phe Pro Pro Ile Ser Asp Arg Leu Pro Val Leu Met
1               5                   10                  15 cac gga gcg gat tat aac ccg gac caa tgg ctg cat gat cca aag gtg      96
His Gly Ala Asp Tyr Asn Pro Asp Gln Trp Leu His Asp Pro Lys Val
            20                  25                  30 ctg gaa gag gat atc cgc atg atg aag ctc gcc aac tgc aac gta atg     144
Leu Glu Glu Asp Ile Arg Met Met Lys Leu Ala Asn Cys Asn Val Met
        35                  40                  45 gcg ctt ggc atg ttc tcc tgg gct gct ctt gaa cct gaa gaa ggg gta     192
Ala Leu Gly Met Phe Ser Trp Ala Ala Leu Glu Pro Glu Glu Gly Val
    50                  55                  60 ttt acg ttt gaa tgg ctg gac cgg gta ctc gat tcg ttt gcg gcg aac     240
Phe Thr Phe Glu Trp Leu Asp Arg Val Leu Asp Ser Phe Ala Ala Asn
65                  70                  75                  80 ggc att tat gcc tgg ctg tcc acg cca agc ggc gca cgc ccg gcc tgg     288
Gly Ile Tyr Ala Trp Leu Ser Thr Pro Ser Gly Ala Arg Pro Ala Trp
                85                  90                  95 atg tcg gcg aaa tat acc gaa gtg ctg cgg gtg gag aag aac cgc gtc     336
Met Ser Ala Lys Tyr Thr Glu Val Leu Arg Val Glu Lys Asn Arg Val
            100                 105                 110 cgc aat ttg cat ggc atg aga cat aat cac tgc tac aca tcc ccg gtt     384
Arg Asn Leu His Gly Met Arg His Asn His Cys Tyr Thr Ser Pro Val
        115                 120                 125 tac cgg gag aag aca gcg atc att aac ggc aag ctg gcg gag cgc tac     432
Tyr Arg Glu Lys Thr Ala Ile Ile Asn Gly Lys Leu Ala Glu Arg Tyr
    130                 135                 140 gga aac cat cct gcc gtc atc ggc tgg cat att tcg aac gag ctg ggc     480
Gly Asn His Pro Ala Val Ile Gly Trp His Ile Ser Asn Glu Leu Gly
145                 150                 155                 160 gga gac tgc cat tgc gac tat tgt cag gag gcg ttc cgg gca tgg ctg     528
Gly Asp Cys His Cys Asp Tyr Cys Gln Glu Ala Phe Arg Ala Trp Leu
                165                 170                 175 aag gag aaa tat ggc acg ctg gag aag ctt aat ttt gcc tgg tgg aca     576
Lys Glu Lys Tyr Gly Thr Leu Glu Lys Leu Asn Phe Ala Trp Trp Thr
            180                 185                 190 tcc ttc tgg gcc cat acg tac acc gat tgg agt cag atc gag tcg cct     624
Ser Phe Trp Ala His Thr Tyr Thr Asp Trp Ser Gln Ile Glu Ser Pro
        195                 200                 205
```

```
gct cct cac ggg gaa aat atg gtt cac gga cag aac ctg gac tgg cgc    672
Ala Pro His Gly Glu Asn Met Val His Gly Gln Asn Leu Asp Trp Arg
210                 215                 220 cgt ttc gtg acc gat caa atg acg gat ttc tgc aat cat gag atc cag    720
Arg Phe Val Thr Asp Gln Met Thr Asp Phe Cys Asn His Glu Ile Gln
225                 230                 235                 240 tcc gtg aag aag gcg aat cct gcc ttg ccg gcg acg acg aat atg cat    768
Ser Val Lys Lys Ala Asn Pro Ala Leu Pro Ala Thr Thr Asn Met His
        245                 250                 255 atg acg gat ggg ctg gac tac cgg aaa ctg gcc aag att ctt gac gtc    816
Met Thr Asp Gly Leu Asp Tyr Arg Lys Leu Ala Lys Ile Leu Asp Val
            260                 265                 270 att tcc tgg gat gtg tat ccg acc tgg cat gat tat aaa aat gac att    864
Ile Ser Trp Asp Val Tyr Pro Thr Trp His Asp Tyr Lys Asn Asp Ile
                275                 280                 285 gag ctg ggc gct tcg gtc tct ttc tgg cat gat ctg tat cgt tcg ctg    912
Glu Leu Gly Ala Ser Val Ser Phe Trp His Asp Leu Tyr Arg Ser Leu
    290                 295                 300 cag cag aag cca ttc ctg ctg atg gag agt acg ccg agc ctg aca aac    960
Gln Gln Lys Pro Phe Leu Leu Met Glu Ser Thr Pro Ser Leu Thr Asn
305                 310                 315                 320 tgg cag ccg gtc agc aag ctg aag cag ccg ggc atg cat aag ctg tcc   1008
Trp Gln Pro Val Ser Lys Leu Lys Gln Pro Gly Met His Lys Leu Ser
        325                 330                 335 tcc ctg cag gcg gtc gct cac ggc tcg gat tcc gtg caa tat ttc cag   1056
Ser Leu Gln Ala Val Ala His Gly Ser Asp Ser Val Gln Tyr Phe Gln
            340                 345                 350 tgg cgc aag agc aga ggc tcc agc gag aaa ttc cac ggg gcg gtc gtg   1104
Trp Arg Lys Ser Arg Gly Ser Ser Glu Lys Phe His Gly Ala Val Val
                355                 360                 365 gat cac gtt gga cat gag cat aca aga gtg ttc aag gat gtc gcc gat   1152
Asp His Val Gly His Glu His Thr Arg Val Phe Lys Asp Val Ala Asp
    370                 375                 380 ttg gga cgt acg ctt gcc gat att tcc gag att gcg ggc acg ccg act   1200
Leu Gly Arg Thr Leu Ala Asp Ile Ser Glu Ile Ala Gly Thr Pro Thr
385                 390                 395                 400 ccg gcg aag aca gcg att ctc ttc gat tgg gat aat cgc tgg gcc gta   1248
Pro Ala Lys Thr Ala Ile Leu Phe Asp Trp Asp Asn Arg Trp Ala Val
        405                 410                 415 cag gat gcg caa gga ccg cgc aat tca ggc atc cat tat gag gag acg   1296
Gln Asp Ala Gln Gly Pro Arg Asn Ser Gly Ile His Tyr Glu Glu Thr
            420                 425                 430 gta atc gcg cat cac cgg gcg att tgg gag cag ggc gta ccg acg gat   1344
Val Ile Ala His His Arg Ala Ile Trp Glu Gln Gly Val Pro Thr Asp
                435                 440                 445 att atc ggc tcg gag gat gac ttt agc ggt tat aag ctg atc gtt gct   1392
Ile Ile Gly Ser Glu Asp Asp Phe Ser Gly Tyr Lys Leu Ile Val Ala
    450                 455                 460 cca atg ctg tat ctg tgc cgt gag gag acg ggc cgc gag ctg gag aag   1440
Pro Met Leu Tyr Leu Cys Arg Glu Glu Thr Gly Arg Glu Leu Glu Lys
465                 470                 475                 480 ttc gtt gag aat ggc gga act ctg gtt acg acc tac tgg tcc ggc atc   1488
Phe Val Glu Asn Gly Gly Thr Leu Val Thr Thr Tyr Trp Ser Gly Ile
        485                 490                 495 gtc gat gag cat gat ctg tgc cat ctt ggc ggg ttt cca ggg ccg ctg   1536
Val Asp Glu His Asp Leu Cys His Leu Gly Gly Phe Pro Gly Pro Leu
            500                 505                 510 cgc aag acg ctt ggc atc tgg gcg gag gag atc gaa gga ttg tac gat   1584
Arg Lys Thr Leu Gly Ile Trp Ala Glu Glu Ile Glu Gly Leu Tyr Asp
                515                 520                 525
```

```
cat gac cgg aac ggc ata gcg atg gcc gag ggc aat gaa ctg ggc ttc    1632
His Asp Arg Asn Gly Ile Ala Met Ala Glu Gly Asn Glu Leu Gly Phe
        530                 535                 540 acg ggc agc ttc gag tcc cat gaa atc tgc gag ctg att cat acg gaa    1680
Thr Gly Ser Phe Glu Ser His Glu Ile Cys Glu Leu Ile His Thr Glu
545                 550                 555                 560 ggc gcc gag gta ttg gga acc tat acg gac agc ttc tat gcg ggc aaa    1728
Gly Ala Glu Val Leu Gly Thr Tyr Thr Asp Ser Phe Tyr Ala Gly Lys
                565                 570                 575 ccg gca ttg act gtg aac cgc ttc ggg caa ggc cgc gct tac cat atg    1776
Pro Ala Leu Thr Val Asn Arg Phe Gly Gln Gly Arg Ala Tyr His Met
        580                 585                 590 gcg acg cgc ctg aag gac gat ttc ctg ggc gag ttc tac aag cag atc    1824
Ala Thr Arg Leu Lys Asp Asp Phe Leu Gly Glu Phe Tyr Lys Gln Ile
595                 600                 605 gtt aat gtc gca ggc gtt gac cgg gtt att cat act gaa ctg cct gcc    1872
Val Asn Val Ala Gly Val Asp Arg Val Ile His Thr Glu Leu Pro Ala
                610                 615                 620 ggc gtg acc gct cag gtc cgg acg gat ggg gaa ttc gat tat gtg ttc    1920
Gly Val Thr Ala Gln Val Arg Thr Asp Gly Glu Phe Asp Tyr Val Phe
625                 630                 635                 640 gtg atg aac ttc agc gga cag gag cag cat gta caa ctg gat gat cgt    1968
Val Met Asn Phe Ser Gly Gln Glu Gln His Val Gln Leu Asp Asp Arg
                645                 650                 655 caa tat gtg aat atg gaa aca ggc gaa gcg ttg agc gga aaa ctc acc    2016
Gln Tyr Val Asn Met Glu Thr Gly Glu Ala Leu Ser Gly Lys Leu Thr
        660                 665                 670 ttg cct gtt cac gga gta gtt gta ttg aaa cgt ccg gct taa            2058
Leu Pro Val His Gly Val Val Val Leu Lys Arg Pro Ala
                675                 680                 685

<210> SEQ ID NO 71
<211> LENGTH: 685
<212> TYPE: PRT
<213> ORGANISM: Paenibacillus woosongensis

<400> SEQUENCE: 71

Met Thr Lys Lys Phe Pro Pro Ile Ser Asp Arg Leu Pro Val Leu Met
1               5                   10                  15

His Gly Ala Asp Tyr Asn Pro Asp Gln Trp Leu His Asp Pro Lys Val
            20                  25                  30

Leu Glu Glu Asp Ile Arg Met Met Lys Leu Ala Asn Cys Asn Val Met
        35                  40                  45

Ala Leu Gly Met Phe Ser Trp Ala Ala Leu Glu Pro Glu Glu Gly Val
    50                  55                  60

Phe Thr Phe Glu Trp Leu Asp Arg Val Leu Asp Ser Phe Ala Ala Asn
65                  70                  75                  80

Gly Ile Tyr Ala Trp Leu Ser Thr Pro Ser Gly Ala Arg Pro Ala Trp
                85                  90                  95

Met Ser Ala Lys Tyr Thr Glu Val Leu Arg Val Glu Lys Asn Arg Val
            100                 105                 110

Arg Asn Leu His Gly Met Arg His Asn His Cys Tyr Thr Ser Pro Val
        115                 120                 125

Tyr Arg Glu Lys Thr Ala Ile Ile Asn Gly Lys Leu Ala Glu Arg Tyr
    130                 135                 140

Gly Asn His Pro Ala Val Ile Gly Trp His Ile Ser Asn Glu Leu Gly
145                 150                 155                 160
```

```
Gly Asp Cys His Cys Asp Tyr Cys Gln Glu Ala Phe Arg Ala Trp Leu
            165                 170                 175

Lys Glu Lys Tyr Gly Thr Leu Glu Lys Leu Asn Phe Ala Trp Trp Thr
        180                 185                 190

Ser Phe Trp Ala His Thr Tyr Thr Asp Trp Ser Gln Ile Glu Ser Pro
    195                 200                 205

Ala Pro His Gly Glu Asn Met Val His Gly Gln Asn Leu Asp Trp Arg
210                 215                 220

Arg Phe Val Thr Asp Gln Met Thr Asp Phe Cys Asn His Glu Ile Gln
225                 230                 235                 240

Ser Val Lys Lys Ala Asn Pro Ala Leu Pro Ala Thr Thr Asn Met His
                245                 250                 255

Met Thr Asp Gly Leu Asp Tyr Arg Lys Leu Ala Lys Ile Leu Asp Val
            260                 265                 270

Ile Ser Trp Asp Val Tyr Pro Thr Trp His Asp Tyr Lys Asn Asp Ile
        275                 280                 285

Glu Leu Gly Ala Ser Val Ser Phe Trp His Asp Leu Tyr Arg Ser Leu
    290                 295                 300

Gln Gln Lys Pro Phe Leu Leu Met Glu Ser Thr Pro Ser Leu Thr Asn
305                 310                 315                 320

Trp Gln Pro Val Ser Lys Leu Lys Gln Pro Gly Met His Lys Leu Ser
                325                 330                 335

Ser Leu Gln Ala Val Ala His Gly Ser Asp Ser Val Gln Tyr Phe Gln
            340                 345                 350

Trp Arg Lys Ser Arg Gly Ser Ser Glu Lys Phe His Gly Ala Val Val
        355                 360                 365

Asp His Val Gly His Glu His Thr Arg Val Phe Lys Asp Val Ala Asp
370                 375                 380

Leu Gly Arg Thr Leu Ala Asp Ile Ser Glu Ile Ala Gly Thr Pro Thr
385                 390                 395                 400

Pro Ala Lys Thr Ala Ile Leu Phe Asp Trp Asp Asn Arg Trp Ala Val
                405                 410                 415

Gln Asp Ala Gln Gly Pro Arg Asn Ser Gly Ile His Tyr Glu Glu Thr
            420                 425                 430

Val Ile Ala His His Arg Ala Ile Trp Glu Gln Gly Val Pro Thr Asp
        435                 440                 445

Ile Ile Gly Ser Glu Asp Asp Phe Ser Gly Tyr Lys Leu Ile Val Ala
    450                 455                 460

Pro Met Leu Tyr Leu Cys Arg Glu Glu Thr Gly Arg Glu Leu Glu Lys
465                 470                 475                 480

Phe Val Glu Asn Gly Gly Thr Leu Val Thr Thr Tyr Trp Ser Gly Ile
                485                 490                 495

Val Asp Glu His Asp Leu Cys His Leu Gly Phe Pro Gly Pro Leu
            500                 505                 510

Arg Lys Thr Leu Gly Ile Trp Ala Glu Glu Ile Glu Gly Leu Tyr Asp
        515                 520                 525

His Asp Arg Asn Gly Ile Ala Met Ala Glu Gly Asn Glu Leu Gly Phe
530                 535                 540

Thr Gly Ser Phe Glu Ser His Glu Ile Cys Glu Leu Ile His Thr Glu
545                 550                 555                 560

Gly Ala Glu Val Leu Gly Thr Tyr Thr Asp Ser Phe Tyr Ala Gly Lys
                565                 570                 575

Pro Ala Leu Thr Val Asn Arg Phe Gly Gln Gly Arg Ala Tyr His Met
```

```
                580             585             590
Ala Thr Arg Leu Lys Asp Asp Phe Leu Gly Glu Phe Tyr Lys Gln Ile
            595             600             605
Val Asn Val Ala Gly Val Asp Arg Val Ile His Thr Glu Leu Pro Ala
            610             615             620
Gly Val Thr Ala Gln Val Arg Thr Asp Gly Glu Phe Asp Tyr Val Phe
625             630             635             640
Val Met Asn Phe Ser Gly Gln Glu Gln His Val Gln Leu Asp Asp Arg
            645             650             655
Gln Tyr Val Asn Met Glu Thr Gly Glu Ala Leu Ser Gly Lys Leu Thr
            660             665             670
Leu Pro Val His Gly Val Val Leu Lys Arg Pro Ala
            675             680             685

<210> SEQ ID NO 72
<211> LENGTH: 694
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(694)

<400> SEQUENCE: 72

Met His His His His His His Pro Arg Met Thr Lys Lys Phe Pro Pro
1               5               10              15
Ile Ser Asp Arg Leu Pro Val Leu Met His Gly Ala Asp Tyr Asn Pro
            20              25              30
Asp Gln Trp Leu His Asp Pro Lys Val Leu Glu Glu Asp Ile Arg Met
        35              40                  45
Met Lys Leu Ala Asn Cys Asn Val Met Ala Leu Gly Met Phe Ser Trp
    50              55              60
Ala Ala Leu Glu Pro Glu Glu Gly Val Phe Thr Phe Glu Trp Leu Asp
65              70              75                  80
Arg Val Leu Asp Ser Phe Ala Ala Asn Gly Ile Tyr Ala Trp Leu Ser
            85              90              95
Thr Pro Ser Gly Ala Arg Pro Ala Trp Met Ser Ala Lys Tyr Thr Glu
            100             105             110
Val Leu Arg Val Glu Lys Asn Arg Val Arg Asn Leu His Gly Met Arg
            115             120             125
His Asn His Cys Tyr Thr Ser Pro Val Tyr Arg Glu Lys Thr Ala Ile
            130             135             140
Ile Asn Gly Lys Leu Ala Glu Arg Tyr Gly Asn His Pro Ala Val Ile
145             150             155             160
Gly Trp His Ile Ser Asn Glu Leu Gly Gly Asp Cys His Cys Asp Tyr
            165             170             175
Cys Gln Glu Ala Phe Arg Ala Trp Leu Lys Lys Tyr Gly Thr Leu
            180             185             190
Glu Lys Leu Asn Phe Ala Trp Trp Thr Ser Phe Trp Ala His Thr Tyr
            195             200             205
Thr Asp Trp Ser Gln Ile Glu Ser Pro Ala Pro His Gly Glu Asn Met
            210             215             220
Val His Gly Gln Asn Leu Asp Trp Arg Arg Phe Val Thr Asp Gln Met
225             230             235             240
Thr Asp Phe Cys Asn His Glu Ile Gln Ser Val Lys Lys Ala Asn Pro
```

```
            245                 250                 255
Ala Leu Pro Ala Thr Thr Asn Met His Met Thr Asp Gly Leu Asp Tyr
            260                 265                 270

Arg Lys Leu Ala Lys Ile Leu Asp Val Ile Ser Trp Asp Val Tyr Pro
            275                 280                 285

Thr Trp His Asp Tyr Lys Asn Asp Ile Glu Leu Gly Ala Ser Val Ser
            290                 295                 300

Phe Trp His Asp Leu Tyr Arg Ser Leu Gln Gln Lys Pro Phe Leu Leu
305                 310                 315                 320

Met Glu Ser Thr Pro Ser Leu Thr Asn Trp Gln Pro Val Ser Lys Leu
            325                 330                 335

Lys Gln Pro Gly Met His Lys Leu Ser Ser Leu Gln Ala Val Ala His
            340                 345                 350

Gly Ser Asp Ser Val Gln Tyr Phe Gln Trp Arg Lys Ser Arg Gly Ser
            355                 360                 365

Ser Glu Lys Phe His Gly Ala Val Val Asp His Val Gly His Glu His
            370                 375                 380

Thr Arg Val Phe Lys Asp Val Ala Asp Leu Gly Arg Thr Leu Ala Asp
385                 390                 395                 400

Ile Ser Glu Ile Ala Gly Thr Pro Thr Pro Ala Lys Thr Ala Ile Leu
                    405                 410                 415

Phe Asp Trp Asp Asn Arg Trp Ala Val Gln Asp Ala Gln Gly Pro Arg
                    420                 425                 430

Asn Ser Gly Ile His Tyr Glu Glu Thr Val Ile Ala His His Arg Ala
            435                 440                 445

Ile Trp Glu Gln Gly Val Pro Thr Asp Ile Ile Gly Ser Glu Asp Asp
            450                 455                 460

Phe Ser Gly Tyr Lys Leu Ile Val Ala Pro Met Leu Tyr Leu Cys Arg
465                 470                 475                 480

Glu Glu Thr Gly Arg Glu Leu Glu Lys Phe Val Glu Asn Gly Gly Thr
                    485                 490                 495

Leu Val Thr Thr Tyr Trp Ser Gly Ile Val Asp Glu His Asp Leu Cys
                    500                 505                 510

His Leu Gly Gly Phe Pro Gly Pro Leu Arg Lys Thr Leu Gly Ile Trp
            515                 520                 525

Ala Glu Glu Ile Glu Gly Leu Tyr Asp His Asp Arg Asn Gly Ile Ala
            530                 535                 540

Met Ala Glu Gly Asn Glu Leu Gly Phe Thr Gly Ser Phe Glu Ser His
545                 550                 555                 560

Glu Ile Cys Glu Leu Ile His Thr Glu Gly Ala Glu Val Leu Gly Thr
                    565                 570                 575

Tyr Thr Asp Ser Phe Tyr Ala Gly Lys Pro Ala Leu Thr Val Asn Arg
            580                 585                 590

Phe Gly Gln Gly Arg Ala Tyr His Met Ala Thr Arg Leu Lys Asp Asp
            595                 600                 605

Phe Leu Gly Glu Phe Tyr Lys Gln Ile Val Asn Val Ala Gly Val Asp
            610                 615                 620

Arg Val Ile His Thr Glu Leu Pro Ala Gly Val Thr Ala Gln Val Arg
625                 630                 635                 640

Thr Asp Gly Glu Phe Asp Tyr Val Phe Val Met Asn Phe Ser Gly Gln
                    645                 650                 655

Glu Gln His Val Gln Leu Asp Asp Arg Gln Tyr Val Asn Met Glu Thr
            660                 665                 670
```

<210> SEQ ID NO 73
<211> LENGTH: 2058
<212> TYPE: DNA
<213> ORGANISM: Paenibacillus sp- 62253
<220> FEATURE:
<221> NAME/KEY: CDS
<222> LOCATION: (1)..(2055)
<220> FEATURE:
<221> NAME/KEY: mat_peptide
<222> LOCATION: (1)..(2055)

<400> SEQUENCE: 73

| | | | | | | | | | | | | | | | | |
|---|---|---|---|---|---|---|---|---|---|---|---|---|---|---|---|---|
| atg | acg | acc | aaa | ttt | gcc | ccg | ata | agc | gat | aaa | ctg | acc | gtg | ctc | atg | 48 |
| Met | Thr | Thr | Lys | Phe | Ala | Pro | Ile | Ser | Asp | Lys | Leu | Thr | Val | Leu | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cac | ggc | gcc | gac | tat | aat | ccc | gac | caa | tgg | ctg | cac | gat | ccg | aag | gtg | 96 |
| His | Gly | Ala | Asp | Tyr | Asn | Pro | Asp | Gln | Trp | Leu | His | Asp | Pro | Lys | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | gag | gaa | gac | atc | cgg | ctc | atg | aag | ctg | gct | ggc | tgc | aac | gtg | atg | 144 |
| Leu | Glu | Glu | Asp | Ile | Arg | Leu | Met | Lys | Leu | Ala | Gly | Cys | Asn | Val | Met | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | gtc | ggc | att | ttc | tcc | tgg | gcc | gca | ttc | gag | ccg | acc | gaa | ggc | aac | 192 |
| Ala | Val | Gly | Ile | Phe | Ser | Trp | Ala | Ala | Phe | Glu | Pro | Thr | Glu | Gly | Asn | |
| | 50 | | | | | 55 | | | | | 60 | | | | | |

| | | | | | | | | | | | | | | | | |
|---|---|---|---|---|---|---|---|---|---|---|---|---|---|---|---|---|
| ttc | aac | ttc | gaa | tgg | atg | gac | aag | gtg | ctc | gat | tcg | ttc | gcg | gcg | aac | 240 |
| Phe | Asn | Phe | Glu | Trp | Met | Asp | Lys | Val | Leu | Asp | Ser | Phe | Ala | Ala | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggc | atc | tac | gct | tgg | ctg | gcg | acg | ccg | agc | ggc | gcg | cgt | ccg | gca | tgg | 288 |
| Gly | Ile | Tyr | Ala | Trp | Leu | Ala | Thr | Pro | Ser | Gly | Ala | Arg | Pro | Ala | Trp | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | agc | gcc | aag | tat | ccg | gag | gtg | ctc | cgc | acg | gaa | gcg | aat | cgc | gta | 336 |
| Met | Ser | Ala | Lys | Tyr | Pro | Glu | Val | Leu | Arg | Thr | Glu | Ala | Asn | Arg | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| cgc | aac | ctg | cac | ggc | atg | cgg | cat | aac | cac | tgc | aac | acg | tcg | ccg | gtc | 384 |
| Arg | Asn | Leu | His | Gly | Met | Arg | His | Asn | His | Cys | Asn | Thr | Ser | Pro | Val | |
| | | 115 | | | | | 120 | | | | | 125 | | | | |

| | | | | | | | | | | | | | | | | |
|---|---|---|---|---|---|---|---|---|---|---|---|---|---|---|---|---|
| tat | cgc | gag | aag | acg | gcg | atc | atc | aac | ggc | aag | ctc | gcg | gag | cgc | tat | 432 |
| Tyr | Arg | Glu | Lys | Thr | Ala | Ile | Ile | Asn | Gly | Lys | Leu | Ala | Glu | Arg | Tyr | |
| | 130 | | | | | 135 | | | | | 140 | | | | | |

| | | | | | | | | | | | | | | | | |
|---|---|---|---|---|---|---|---|---|---|---|---|---|---|---|---|---|
| ggc | aac | cat | ccg | gct | gtc | ctc | ggc | tgg | cat | att | tcg | aac | gaa | ttc | ggc | 480 |
| Gly | Asn | His | Pro | Ala | Val | Leu | Gly | Trp | His | Ile | Ser | Asn | Glu | Phe | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | gat | tgt | cat | tgc | gac | tac | tgc | caa | gaa | gcg | ttc | cgc | caa | tgg | ctg | 528 |
| Gly | Asp | Cys | His | Cys | Asp | Tyr | Cys | Gln | Glu | Ala | Phe | Arg | Gln | Trp | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | aag | aaa | tac | ggc | tcg | ctc | gat | gcg | ctc | aac | agc | gca | tgg | tgg | acg | 576 |
| Gln | Lys | Lys | Tyr | Gly | Ser | Leu | Asp | Ala | Leu | Asn | Ser | Ala | Trp | Trp | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| acg | ttc | tgg | gcg | cac | acg | tac | acc | gat | tgg | agc | caa | gtg | gaa | tcg | ccg | 624 |
| Thr | Phe | Trp | Ala | His | Thr | Tyr | Thr | Asp | Trp | Ser | Gln | Val | Glu | Ser | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| gct | ccg | cac | ggc | gag | aac | atg | gtg | cac | ggc | cac | aac | ctc | gac | tgg | cgc | 672 |
| Ala | Pro | His | Gly | Glu | Asn | Met | Val | His | Gly | His | Asn | Leu | Asp | Trp | Arg | |
| | 210 | | | | | 215 | | | | | 220 | | | | | |

| | | | | | | | | | | | | | | | | |
|---|---|---|---|---|---|---|---|---|---|---|---|---|---|---|---|---|
| cgc | ttc | gtg | aca | gac | cag | acg | gtg | gac | ttc | tgc | cgc | cac | gag | att | gaa | 720 |
| Arg | Phe | Val | Thr | Asp | Gln | Thr | Val | Asp | Phe | Cys | Arg | His | Glu | Ile | Glu | |

```
                      225                 230                 235                 240
tcg gtg cgc agc gcg aat ccg tcg ctg ccg gcg acg acg aac atg cac        768
Ser Val Arg Ser Ala Asn Pro Ser Leu Pro Ala Thr Thr Asn Met His
                    245                 250                 255 atg atc gaa ggg ctc gac tac cgc aaa ttc gca gag gtg ctc gac gta        816
Met Ile Glu Gly Leu Asp Tyr Arg Lys Phe Ala Glu Val Leu Asp Val
                260                 265                 270 att tcc tgg gat gct tac cca acg tgg cac gag caa gtg gac gac agc        864
Ile Ser Trp Asp Ala Tyr Pro Thr Trp His Glu Gln Val Asp Asp Ser
            275                 280                 285 cag ctg ggc gca tcg gtc gcg ttc tac cat gac ttg tac cgc tcg ctg        912
Gln Leu Gly Ala Ser Val Ala Phe Tyr His Asp Leu Tyr Arg Ser Leu
        290                 295                 300 aag cat aag ccg ttc ctg ctc atg gag agc acg ccg agc ttg acg aac        960
Lys His Lys Pro Phe Leu Leu Met Glu Ser Thr Pro Ser Leu Thr Asn
305                 310                 315                 320 tgg cag ccg gtg agc aag ctg aag cag ccg ggc atg cac cag ctg tcg       1008
Trp Gln Pro Val Ser Lys Leu Lys Gln Pro Gly Met His Gln Leu Ser
                325                 330                 335 tcg ctg cag gcg atc gcg cac ggt tcg gat tcc gtt caa tac ttc caa       1056
Ser Leu Gln Ala Ile Ala His Gly Ser Asp Ser Val Gln Tyr Phe Gln
                340                 345                 350 tgg cgc aaa agc cgg ggc tcg agc gag aaa ttc cac ggc gcg gtc gtc       1104
Trp Arg Lys Ser Arg Gly Ser Ser Glu Lys Phe His Gly Ala Val Val
            355                 360                 365 gac cat gtc ggt cac gag cat acg cgc gtg ttc caa gac gtc gcg aag       1152
Asp His Val Gly His Glu His Thr Arg Val Phe Gln Asp Val Ala Lys
        370                 375                 380 ctc ggc cag acg atg aag gac att tcg gcc gtc gtc ggc acg gta acg       1200
Leu Gly Gln Thr Met Lys Asp Ile Ser Ala Val Val Gly Thr Val Thr
385                 390                 395                 400 ccg tct cag acc gct att ctc ttc gac tgg gac aac cgt tgg gcg atc       1248
Pro Ser Gln Thr Ala Ile Leu Phe Asp Trp Asp Asn Arg Trp Ala Ile
                405                 410                 415 aag gat tcg caa ggt ccg cgc aat atg ggc atc aaa tac gag gag acc       1296
Lys Asp Ser Gln Gly Pro Arg Asn Met Gly Ile Lys Tyr Glu Glu Thr
                420                 425                 430 gtc tac gcc cat cac cgc gcg ctg tgg gag cag ggc gtg ccg acc gat       1344
Val Tyr Ala His His Arg Ala Leu Trp Glu Gln Gly Val Pro Thr Asp
            435                 440                 445 atc atc ggc tcg gaa cag gat ttc gcg ggc tac aag ctc atc gtg gcg       1392
Ile Ile Gly Ser Glu Gln Asp Phe Ala Gly Tyr Lys Leu Ile Val Ala
        450                 455                 460 ccg atg ctg tac ctg tgc cgc gag gag acg ggc cgc aag ctg gag caa       1440
Pro Met Leu Tyr Leu Cys Arg Glu Glu Thr Gly Arg Lys Leu Glu Gln
465                 470                 475                 480 ttc gtg gag cag ggc ggc acg ctc gtg gcc acg tac tgg tcg ggc gtc       1488
Phe Val Glu Gln Gly Gly Thr Leu Val Ala Thr Tyr Trp Ser Gly Val
                485                 490                 495 gtc gac gag cat gac ctg tgc cac ctc ggc ggg ttc ccg ggt ccg ctg       1536
Val Asp Glu His Asp Leu Cys His Leu Gly Gly Phe Pro Gly Pro Leu
                500                 505                 510 cgc aag acg ctc ggc att tgg gcg gag gag atc gag ggc ttg tac gac       1584
Arg Lys Thr Leu Gly Ile Trp Ala Glu Glu Ile Glu Gly Leu Tyr Asp
            515                 520                 525 cat gac cgc aac ggc gtc gcg ctg gcg gaa ggc aat gct ctc ggc ctg       1632
His Asp Arg Asn Gly Val Ala Leu Ala Glu Gly Asn Ala Leu Gly Leu
        530                 535                 540 caa ggc gag ttc gaa gcg ggc gaa atc tgc gag ctg atc cat aca gag       1680
```

| Gln | Gly | Glu | Phe | Glu | Ala | Gly | Glu | Ile | Cys | Glu | Leu | Ile | His | Thr | Glu | |
|---|---|---|---|---|---|---|---|---|---|---|---|---|---|---|---|---|
| 545 | | | | 550 | | | | 555 | | | | 560 | | | | |

```
ggc gcg gag gtg ctc ggc acg tat acg agc agc ttc tac gcg gga cgt       1728
Gly Ala Glu Val Leu Gly Thr Tyr Thr Ser Ser Phe Tyr Ala Gly Arg
            565                 570                 575 ccg gcc ctt acg ctg aac cgg ttc ggt caa gga cgc gcc tac cat atg       1776
Pro Ala Leu Thr Leu Asn Arg Phe Gly Gln Gly Arg Ala Tyr His Met
            580                 585                 590 gcg acg cgg ctg aag gac gac ttc ctg ggc gcg ttc tac aag cgg atc       1824
Ala Thr Arg Leu Lys Asp Asp Phe Leu Gly Ala Phe Tyr Lys Arg Ile
            595                 600                 605 gta gaa gaa gcg ggc gtg gcg cgc gcg atc gac gcg gag ctg ccg gcc       1872
Val Glu Glu Ala Gly Val Ala Arg Ala Ile Asp Ala Glu Leu Pro Ala
    610                 615                 620 ggc gtg acg gca cag gtg cgc acg gac ggc gag acc gac ttc atc ttc       1920
Gly Val Thr Ala Gln Val Arg Thr Asp Gly Glu Thr Asp Phe Ile Phe
    625                 630                 635                 640 ctc atg aac ttc agc ggc tcg gag cag cag gtt gag ctt gat gcg ggc       1968
Leu Met Asn Phe Ser Gly Ser Glu Gln Gln Val Glu Leu Asp Ala Gly
                645                 650                 655 ggc tac cgc gac atg gag agc ggc gag ccg gcc gat acg gcg gtg aag       2016
Gly Tyr Arg Asp Met Glu Ser Gly Glu Pro Ala Asp Thr Ala Val Lys
            660                 665                 670 ctg ccg gtc aac ggt att cga ctg ctg acg cgc caa gcc taa               2058
Leu Pro Val Asn Gly Ile Arg Leu Leu Thr Arg Gln Ala
            675                 680                 685

<210> SEQ ID NO 74
<211> LENGTH: 685
<212> TYPE: PRT
<213> ORGANISM: Paenibacillus sp- 62253

<400> SEQUENCE: 74

Met Thr Thr Lys Phe Ala Pro Ile Ser Asp Lys Leu Thr Val Leu Met
1               5                   10                  15

His Gly Ala Asp Tyr Asn Pro Asp Gln Trp Leu His Asp Pro Lys Val
            20                  25                  30

Leu Glu Glu Asp Ile Arg Leu Met Lys Leu Ala Gly Cys Asn Val Met
        35                  40                  45

Ala Val Gly Ile Phe Ser Trp Ala Ala Phe Glu Pro Thr Glu Gly Asn
    50                  55                  60

Phe Asn Phe Glu Trp Met Asp Lys Val Leu Asp Ser Phe Ala Ala Asn
65                  70                  75                  80

Gly Ile Tyr Ala Trp Leu Ala Thr Pro Ser Gly Ala Arg Pro Ala Trp
                85                  90                  95

Met Ser Ala Lys Tyr Pro Glu Val Leu Arg Thr Glu Ala Asn Arg Val
            100                 105                 110

Arg Asn Leu His Gly Met Arg His Asn His Cys Asn Thr Ser Pro Val
        115                 120                 125

Tyr Arg Glu Lys Thr Ala Ile Ile Asn Gly Lys Leu Ala Glu Arg Tyr
    130                 135                 140

Gly Asn His Pro Ala Val Leu Gly Trp His Ile Ser Asn Glu Phe Gly
145                 150                 155                 160

Gly Asp Cys His Cys Asp Tyr Cys Gln Glu Ala Phe Arg Gln Trp Leu
                165                 170                 175

Gln Lys Lys Tyr Gly Ser Leu Asp Ala Leu Asn Ser Ala Trp Trp Thr
            180                 185                 190
```

-continued

```
Thr Phe Trp Ala His Thr Tyr Thr Asp Trp Ser Gln Val Glu Ser Pro
            195                 200                 205

Ala Pro His Gly Glu Asn Met Val His Gly His Asn Leu Asp Trp Arg
210                 215                 220

Arg Phe Val Thr Asp Gln Thr Val Asp Phe Cys Arg His Glu Ile Glu
225                 230                 235                 240

Ser Val Arg Ser Ala Asn Pro Ser Leu Pro Ala Thr Thr Asn Met His
            245                 250                 255

Met Ile Glu Gly Leu Asp Tyr Arg Lys Phe Ala Glu Val Leu Asp Val
            260                 265                 270

Ile Ser Trp Asp Ala Tyr Pro Thr Trp His Glu Gln Val Asp Asp Ser
            275                 280                 285

Gln Leu Gly Ala Ser Val Ala Phe Tyr His Asp Leu Tyr Arg Ser Leu
            290                 295                 300

Lys His Lys Pro Phe Leu Leu Met Glu Ser Thr Pro Ser Leu Thr Asn
305                 310                 315                 320

Trp Gln Pro Val Ser Lys Leu Lys Gln Pro Gly Met His Gln Leu Ser
                325                 330                 335

Ser Leu Gln Ala Ile Ala His Gly Ser Asp Ser Val Gln Tyr Phe Gln
            340                 345                 350

Trp Arg Lys Ser Arg Gly Ser Ser Glu Lys Phe His Gly Ala Val Val
            355                 360                 365

Asp His Val Gly His Glu His Thr Arg Val Phe Gln Asp Val Ala Lys
            370                 375                 380

Leu Gly Gln Thr Met Lys Asp Ile Ser Ala Val Val Gly Thr Val Thr
385                 390                 395                 400

Pro Ser Gln Thr Ala Ile Leu Phe Asp Trp Asp Asn Arg Trp Ala Ile
                405                 410                 415

Lys Asp Ser Gln Gly Pro Arg Asn Met Gly Ile Lys Tyr Glu Glu Thr
            420                 425                 430

Val Tyr Ala His His Arg Ala Leu Trp Glu Gln Gly Val Pro Thr Asp
            435                 440                 445

Ile Ile Gly Ser Glu Gln Asp Phe Ala Gly Tyr Lys Leu Ile Val Ala
450                 455                 460

Pro Met Leu Tyr Leu Cys Arg Glu Glu Thr Gly Arg Lys Leu Glu Gln
465                 470                 475                 480

Phe Val Glu Gln Gly Gly Thr Leu Val Ala Thr Tyr Trp Ser Gly Val
                485                 490                 495

Val Asp Glu His Asp Leu Cys His Leu Gly Gly Phe Pro Gly Pro Leu
            500                 505                 510

Arg Lys Thr Leu Gly Ile Trp Ala Glu Glu Ile Glu Gly Leu Tyr Asp
            515                 520                 525

His Asp Arg Asn Gly Val Ala Leu Ala Glu Gly Asn Ala Leu Gly Leu
            530                 535                 540

Gln Gly Glu Phe Glu Ala Gly Glu Ile Cys Glu Leu Ile His Thr Glu
545                 550                 555                 560

Gly Ala Glu Val Leu Gly Thr Tyr Thr Ser Ser Phe Tyr Ala Gly Arg
                565                 570                 575

Pro Ala Leu Thr Leu Asn Arg Phe Gly Gln Gly Arg Ala Tyr His Met
            580                 585                 590

Ala Thr Arg Leu Lys Asp Asp Phe Leu Gly Ala Phe Tyr Lys Arg Ile
            595                 600                 605

Val Glu Glu Ala Gly Val Ala Arg Ala Ile Asp Ala Glu Leu Pro Ala
```

```
                610              615              620
Gly Val Thr Ala Gln Val Arg Thr Asp Gly Glu Thr Asp Phe Ile Phe
625              630              635              640

Leu Met Asn Phe Ser Gly Ser Glu Gln Gln Val Glu Leu Asp Ala Gly
                645              650              655

Gly Tyr Arg Asp Met Glu Ser Gly Glu Pro Ala Asp Thr Ala Val Lys
                660              665              670

Leu Pro Val Asn Gly Ile Arg Leu Leu Thr Arg Gln Ala
                675              680              685

<210> SEQ ID NO 75
<211> LENGTH: 694
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(694)

<400> SEQUENCE: 75

Met His His His His His His Pro Arg Met Thr Thr Lys Phe Ala Pro
1               5                10               15

Ile Ser Asp Lys Leu Thr Val Leu Met His Gly Ala Asp Tyr Asn Pro
                20               25               30

Asp Gln Trp Leu His Asp Pro Lys Val Leu Glu Glu Asp Ile Arg Leu
            35               40               45

Met Lys Leu Ala Gly Cys Asn Val Met Ala Val Gly Ile Phe Ser Trp
50              55               60

Ala Ala Phe Glu Pro Thr Glu Gly Asn Phe Asn Phe Glu Trp Met Asp
65              70               75               80

Lys Val Leu Asp Ser Phe Ala Ala Asn Gly Ile Tyr Ala Trp Leu Ala
                85               90               95

Thr Pro Ser Gly Ala Arg Pro Ala Trp Met Ser Ala Lys Tyr Pro Glu
            100              105              110

Val Leu Arg Thr Glu Ala Asn Arg Val Arg Asn Leu His Gly Met Arg
            115              120              125

His Asn His Cys Asn Thr Ser Pro Val Tyr Arg Glu Lys Thr Ala Ile
        130              135              140

Ile Asn Gly Lys Leu Ala Glu Arg Tyr Gly Asn His Pro Ala Val Leu
145              150              155              160

Gly Trp His Ile Ser Asn Glu Phe Gly Gly Asp Cys His Cys Asp Tyr
                165              170              175

Cys Gln Glu Ala Phe Arg Gln Trp Leu Gln Lys Lys Tyr Gly Ser Leu
            180              185              190

Asp Ala Leu Asn Ser Ala Trp Trp Thr Thr Phe Trp Ala His Thr Tyr
            195              200              205

Thr Asp Trp Ser Gln Val Glu Ser Pro Ala Pro His Gly Glu Asn Met
        210              215              220

Val His Gly His Asn Leu Asp Trp Arg Arg Phe Val Thr Asp Gln Thr
225              230              235              240

Val Asp Phe Cys Arg His Glu Ile Glu Ser Val Arg Ser Ala Asn Pro
                245              250              255

Ser Leu Pro Ala Thr Thr Asn Met His Met Ile Glu Gly Leu Asp Tyr
            260              265              270

Arg Lys Phe Ala Glu Val Leu Asp Val Ile Ser Trp Asp Ala Tyr Pro
```

-continued

```
            275                 280                 285
Thr Trp His Glu Gln Val Asp Asp Ser Gln Leu Gly Ala Ser Val Ala
290                 295                 300

Phe Tyr His Asp Leu Tyr Arg Ser Leu Lys His Lys Pro Phe Leu Leu
305                 310                 315                 320

Met Glu Ser Thr Pro Ser Leu Thr Asn Trp Gln Pro Val Ser Lys Leu
            325                 330                 335

Lys Gln Pro Gly Met His Gln Leu Ser Ser Leu Gln Ala Ile Ala His
            340                 345                 350

Gly Ser Asp Ser Val Gln Tyr Phe Gln Trp Arg Lys Ser Arg Gly Ser
            355                 360                 365

Ser Glu Lys Phe His Gly Ala Val Asp His Val Gly His Glu His
370                 375                 380

Thr Arg Val Phe Gln Asp Val Ala Lys Leu Gly Gln Thr Met Lys Asp
385                 390                 395                 400

Ile Ser Ala Val Val Gly Thr Val Thr Pro Ser Gln Thr Ala Ile Leu
                405                 410                 415

Phe Asp Trp Asp Asn Arg Trp Ala Ile Lys Asp Ser Gln Gly Pro Arg
                420                 425                 430

Asn Met Gly Ile Lys Tyr Glu Glu Thr Val Tyr Ala His His Arg Ala
            435                 440                 445

Leu Trp Glu Gln Gly Val Pro Thr Asp Ile Ile Gly Ser Glu Gln Asp
450                 455                 460

Phe Ala Gly Tyr Lys Leu Ile Val Ala Pro Met Leu Tyr Leu Cys Arg
465                 470                 475                 480

Glu Glu Thr Gly Arg Lys Leu Glu Gln Phe Val Gln Gly Gly Thr
                485                 490                 495

Leu Val Ala Thr Tyr Trp Ser Gly Val Val Asp Glu His Asp Leu Cys
            500                 505                 510

His Leu Gly Gly Phe Pro Gly Pro Leu Arg Lys Thr Leu Gly Ile Trp
            515                 520                 525

Ala Glu Glu Ile Glu Gly Leu Tyr Asp His Asp Arg Asn Gly Val Ala
530                 535                 540

Leu Ala Glu Gly Asn Ala Leu Gly Leu Gln Gly Glu Phe Glu Ala Gly
545                 550                 555                 560

Glu Ile Cys Glu Leu Ile His Thr Glu Gly Ala Glu Val Leu Gly Thr
                565                 570                 575

Tyr Thr Ser Ser Phe Tyr Ala Gly Arg Pro Ala Leu Thr Leu Asn Arg
            580                 585                 590

Phe Gly Gln Gly Arg Ala Tyr His Met Ala Thr Arg Leu Lys Asp Asp
            595                 600                 605

Phe Leu Gly Ala Phe Tyr Lys Arg Ile Val Glu Ala Gly Val Ala
610                 615                 620

Arg Ala Ile Asp Ala Glu Leu Pro Ala Gly Val Thr Ala Gln Val Arg
625                 630                 635                 640

Thr Asp Gly Glu Thr Asp Phe Ile Phe Leu Met Asn Phe Ser Gly Ser
                645                 650                 655

Glu Gln Gln Val Glu Leu Asp Ala Gly Gly Tyr Arg Asp Met Glu Ser
            660                 665                 670

Gly Glu Pro Ala Asp Thr Ala Val Lys Leu Pro Val Asn Gly Ile Arg
            675                 680                 685

Leu Leu Thr Arg Gln Ala
            690
```

```
<210> SEQ ID NO 76
<211> LENGTH: 2061
<212> TYPE: DNA
<213> ORGANISM: Paenibacillus sp- 62758
<220> FEATURE:
<221> NAME/KEY: CDS
<222> LOCATION: (1)..(2058)
<220> FEATURE:
<221> NAME/KEY: mat_peptide
<222> LOCATION: (1)..(2058)

<400> SEQUENCE: 76
```

| | | | | | | | | | | | | | | | | |
|---|---|---|---|---|---|---|---|---|---|---|---|---|---|---|---|---|
| atg | tta | aaa | caa | tca | aag | tca | tat | gtc | act | aaa | gca | caa | tcg | atg | ctt | 48 |
| Met | Leu | Lys | Gln | Ser | Lys | Ser | Tyr | Val | Thr | Lys | Ala | Gln | Ser | Met | Leu | |
| 1 | | | | 5 | | | | | 10 | | | | | 15 | | |
| cat | ggt | ggc | gac | tat | aat | cct | gat | caa | tgg | tta | gat | cag | cca | gac | att | 96 |
| His | Gly | Gly | Asp | Tyr | Asn | Pro | Asp | Gln | Trp | Leu | Asp | Gln | Pro | Asp | Ile | |
| | | | 20 | | | | | 25 | | | | | 30 | | | |
| ttg | gca | gat | gat | atc | aaa | tta | atg | aag | ctt | gcg | aat | aca | aat | aca | ttc | 144 |
| Leu | Ala | Asp | Asp | Ile | Lys | Leu | Met | Lys | Leu | Ala | Asn | Thr | Asn | Thr | Phe | |
| | | 35 | | | | | 40 | | | | | 45 | | | | |
| tca | gta | ggt | att | ttt | gct | tgg | agt | gcc | tta | gag | ccg | gag | gaa | gat | gtc | 192 |
| Ser | Val | Gly | Ile | Phe | Ala | Trp | Ser | Ala | Leu | Glu | Pro | Glu | Glu | Asp | Val | |
| 50 | | | | | 55 | | | | | 60 | | | | | | |
| tat | aac | ttt | gag | tgg | cta | gat | gaa | ata | att | aat | aat | att | tat | aac | aat | 240 |
| Tyr | Asn | Phe | Glu | Trp | Leu | Asp | Glu | Ile | Ile | Asn | Asn | Ile | Tyr | Asn | Asn | |
| 65 | | | | | 70 | | | | | 75 | | | | | 80 | |
| ggt | gga | cgt | gtc | atc | ctg | gca | aca | cct | agt | ggt | gca | cgt | cct | gct | tgg | 288 |
| Gly | Gly | Arg | Val | Ile | Leu | Ala | Thr | Pro | Ser | Gly | Ala | Arg | Pro | Ala | Trp | |
| | | | | 85 | | | | | 90 | | | | | 95 | | |
| atg | tct | cag | aaa | tat | cca | gaa | gtg | cta | cgt | gtt | aat | gaa | aga | cgc | gag | 336 |
| Met | Ser | Gln | Lys | Tyr | Pro | Glu | Val | Leu | Arg | Val | Asn | Glu | Arg | Arg | Glu | |
| | | | 100 | | | | | 105 | | | | | 110 | | | |
| aaa | tta | tta | cat | gga | gga | cgt | cat | aac | cac | tgc | ttc | acg | tct | gag | gtt | 384 |
| Lys | Leu | Leu | His | Gly | Gly | Arg | His | Asn | His | Cys | Phe | Thr | Ser | Glu | Val | |
| | | 115 | | | | | 120 | | | | | 125 | | | | |
| tat | cgt | gag | aag | acg | cat | aag | ata | aac | ggt | ttg | tta | gca | gag | cga | tat | 432 |
| Tyr | Arg | Glu | Lys | Thr | His | Lys | Ile | Asn | Gly | Leu | Leu | Ala | Glu | Arg | Tyr | |
| 130 | | | | | 135 | | | | | 140 | | | | | | |
| ggc | gat | cat | cct | gct | tta | ctg | atg | tgg | cat | att | tcg | aat | gag | tat | ggt | 480 |
| Gly | Asp | His | Pro | Ala | Leu | Leu | Met | Trp | His | Ile | Ser | Asn | Glu | Tyr | Gly | |
| 145 | | | | | 150 | | | | | 155 | | | | | 160 | |
| ggt | gaa | tgt | cac | tgt | gat | aaa | tgt | cag | gag | gct | ttc | aga | acc | tgg | ttg | 528 |
| Gly | Glu | Cys | His | Cys | Asp | Lys | Cys | Gln | Glu | Ala | Phe | Arg | Thr | Trp | Leu | |
| | | | | 165 | | | | | 170 | | | | | 175 | | |
| aag | ggc | aaa | tat | aat | aat | gat | cta | aag | gca | ttg | aat | gat | tca | tgg | tgg | 576 |
| Lys | Gly | Lys | Tyr | Asn | Asn | Asp | Leu | Lys | Ala | Leu | Asn | Asp | Ser | Trp | Trp | |
| | | | 180 | | | | | 185 | | | | | 190 | | | |
| gga | ccc | ttc | tgg | agt | cac | acg | atc | ttt | gat | tgg | tca | caa | att | gaa | tct | 624 |
| Gly | Pro | Phe | Trp | Ser | His | Thr | Ile | Phe | Asp | Trp | Ser | Gln | Ile | Glu | Ser | |
| | | 195 | | | | | 200 | | | | | 205 | | | | |
| ccc | tca | cca | att | ggg | gaa | agt | gcc | gtt | cat | ggc | ttg | aac | tta | gat | tgg | 672 |
| Pro | Ser | Pro | Ile | Gly | Glu | Ser | Ala | Val | His | Gly | Leu | Asn | Leu | Asp | Trp | |
| 210 | | | | | 215 | | | | | 220 | | | | | | |
| cgt | cgc | ttt | gtt | acc | gac | caa | aca | att | gat | ttt | tac | gaa | aat | gaa | att | 720 |
| Arg | Arg | Phe | Val | Thr | Asp | Gln | Thr | Ile | Asp | Phe | Tyr | Glu | Asn | Glu | Ile | |
| 225 | | | | | 230 | | | | | 235 | | | | | 240 | |
| gta | cca | ttg | cgg | gaa | atg | acg | cct | gct | gtg | cca | att | aca | acg | aac | ttc | 768 |
| Val | Pro | Leu | Arg | Glu | Met | Thr | Pro | Ala | Val | Pro | Ile | Thr | Thr | Asn | Phe | |
| | | | | 245 | | | | | 250 | | | | | 255 | | |

| | | |
|---|---|---|
| atg gct gat aca ttt gat tta att cca ttt caa tca ctt gat tat agt<br>Met Ala Asp Thr Phe Asp Leu Ile Pro Phe Gln Ser Leu Asp Tyr Ser<br>260             265              270 | | 816 |
| aaa ttt gct aag cat gtc gat gta atc agc tgg gat gct tat cct gca<br>Lys Phe Ala Lys His Val Asp Val Ile Ser Trp Asp Ala Tyr Pro Ala<br>275              280             285 | | 864 |
| tgg cat aat gat tgg gaa aca acc gat aat ctt gcg atg aaa gtg ggc<br>Trp His Asn Asp Trp Glu Thr Thr Asp Asn Leu Ala Met Lys Val Gly<br>290             295              300 | | 912 |
| ttt att aat gac ctt tat cgt agc ttg aaa cag cag ccg ttt cta tta<br>Phe Ile Asn Asp Leu Tyr Arg Ser Leu Lys Gln Gln Pro Phe Leu Leu<br>305              310             315              320 | | 960 |
| atg gag tca acg cca agt ctt gta aac tgg cat aat gtc aac aag gcc<br>Met Glu Ser Thr Pro Ser Leu Val Asn Trp His Asn Val Asn Lys Ala<br>325              330             335 | | 1008 |
| aaa cgt cct gga atg cat ttg ctt tct tcg atg caa atg gtc gct cat<br>Lys Arg Pro Gly Met His Leu Leu Ser Ser Met Gln Met Val Ala His<br>340              345             350 | | 1056 |
| ggc tca gat agt gtg ttg tat ttc cag tgg cgt aaa tct cgc ggt tct<br>Gly Ser Asp Ser Val Leu Tyr Phe Gln Trp Arg Lys Ser Arg Gly Ser<br>355              360             365 | | 1104 |
| tct gag aaa ttc cat ggt gct gcg gta gat cat gac aat agt acg gaa<br>Ser Glu Lys Phe His Gly Ala Ala Val Asp His Asp Asn Ser Thr Glu<br>370              375             380 | | 1152 |
| aat cgt gtg ttt caa gag gtt gcc aaa gta gga gat gta tta ggg aaa<br>Asn Arg Val Phe Gln Glu Val Ala Lys Val Gly Asp Val Leu Gly Lys<br>385              390             395              400 | | 1200 |
| ctg gaa gat gtc gta ggg acc aac cgc ccc gct gat gta gca atc ctt<br>Leu Glu Asp Val Val Gly Thr Asn Arg Pro Ala Asp Val Ala Ile Leu<br>405              410             415 | | 1248 |
| tat gat tgg gag agc aac tgg gct ttg aat gat gca caa ggc ttt gga<br>Tyr Asp Trp Glu Ser Asn Trp Ala Leu Asn Asp Ala Gln Gly Phe Gly<br>420              425             430 | | 1296 |
| cgg aaa aca aaa cag tac cca caa aca tta caa gag cat tat cgt aca<br>Arg Lys Thr Lys Gln Tyr Pro Gln Thr Leu Gln Glu His Tyr Arg Thr<br>435              440             445 | | 1344 |
| ttc tgg gag caa gac att cca gtc gat gtc att aca aaa gat gaa gac<br>Phe Trp Glu Gln Asp Ile Pro Val Asp Val Ile Thr Lys Asp Glu Asp<br>450              455             460 | | 1392 |
| ttt tca aac tac aag cta cta att gtc cca atg ctc tat tta atg agt<br>Phe Ser Asn Tyr Lys Leu Leu Ile Val Pro Met Leu Tyr Leu Met Ser<br>465              470             475              480 | | 1440 |
| gag gag aca att agt cgg ttg aag gca ttt gtt gct aat ggt gga aga<br>Glu Glu Thr Ile Ser Arg Leu Lys Ala Phe Val Ala Asn Gly Gly Arg<br>485              490             495 | | 1488 |
| tta gtc atg acc tat att agt gga ttg gtg aat gag cac gat ctt gct<br>Leu Val Met Thr Tyr Ile Ser Gly Leu Val Asn Glu His Asp Leu Ala<br>500              505             510 | | 1536 |
| tat tta ggt ggc tgg cat agt gat ctt caa gaa atc ttt ggt atg gag<br>Tyr Leu Gly Gly Trp His Ser Asp Leu Gln Glu Ile Phe Gly Met Glu<br>515              520             525 | | 1584 |
| ccg aaa gaa aca gat acc tac tat cct agt gat cgt aac tat gtt cag<br>Pro Lys Glu Thr Asp Thr Tyr Tyr Pro Ser Asp Arg Asn Tyr Val Gln<br>530              535             540 | | 1632 |
| ttc cgt aat aac tcc tat gaa gta aag gat tat gca acc gtc ctt cag<br>Phe Arg Asn Asn Ser Tyr Glu Val Lys Asp Tyr Ala Thr Val Leu Gln<br>545              550             555              560 | | 1680 |
| caa ggt tct gca cgg acg gaa ggt gtg tat caa gaa gat ttc tat aaa<br>Gln Gly Ser Ala Arg Thr Glu Gly Val Tyr Gln Glu Asp Phe Tyr Lys<br>565              570             575 | | 1728 |

```
gat aca ccg gct gtt atg agt cat gaa tat aac aag ggg aaa agc tat     1776
Asp Thr Pro Ala Val Met Ser His Glu Tyr Asn Lys Gly Lys Ser Tyr
            580                 585                 590 tat ata ggg gca cgt ctt aat caa cag ttc cat agg gac ttc tac caa     1824
Tyr Ile Gly Ala Arg Leu Asn Gln Gln Phe His Arg Asp Phe Tyr Gln
        595                 600                 605 gaa att att gac gaa tta gga ctt agt ccg gtt gtt act gtc aaa cat     1872
Glu Ile Ile Asp Glu Leu Gly Leu Ser Pro Val Val Thr Val Lys His
610                 615                 620 ggg aaa ggt gtc tct ata cag aca aga caa ggc gag gat acg gac tat     1920
Gly Lys Gly Val Ser Ile Gln Thr Arg Gln Gly Glu Asp Thr Asp Tyr
625                 630                 635                 640 gtg ttc gtt atg aat ttc act gaa caa acg caa cag gta gaa ttt act     1968
Val Phe Val Met Asn Phe Thr Glu Gln Thr Gln Gln Val Glu Phe Thr
            645                 650                 655 tct gct gta aaa gat ctt gta aca ggg gaa gag cta att ggt gaa gtg     2016
Ser Ala Val Lys Asp Leu Val Thr Gly Glu Glu Leu Ile Gly Glu Val
        660                 665                 670 act tta aat acg tat gaa gta cga att gtt gcg tgt aaa aga taa         2061
Thr Leu Asn Thr Tyr Glu Val Arg Ile Val Ala Cys Lys Arg
    675                 680                 685
```

<210> SEQ ID NO 77
<211> LENGTH: 686
<212> TYPE: PRT
<213> ORGANISM: Paenibacillus sp- 62758

<400> SEQUENCE: 77

```
Met Leu Lys Gln Ser Lys Ser Tyr Val Thr Lys Ala Gln Ser Met Leu
1               5                   10                  15

His Gly Gly Asp Tyr Asn Pro Asp Gln Trp Leu Asp Gln Pro Asp Ile
            20                  25                  30

Leu Ala Asp Asp Ile Lys Leu Met Lys Leu Ala Asn Thr Asn Thr Phe
        35                  40                  45

Ser Val Gly Ile Phe Ala Trp Ser Ala Leu Glu Pro Glu Glu Asp Val
    50                  55                  60

Tyr Asn Phe Glu Trp Leu Asp Glu Ile Ile Asn Ile Tyr Asn Asn
65                  70                  75                  80

Gly Gly Arg Val Ile Leu Ala Thr Pro Ser Gly Ala Arg Pro Ala Trp
                85                  90                  95

Met Ser Gln Lys Tyr Pro Glu Val Leu Arg Val Asn Glu Arg Arg Glu
            100                 105                 110

Lys Leu Leu His Gly Arg His Asn His Cys Phe Thr Ser Glu Val
        115                 120                 125

Tyr Arg Glu Lys Thr His Lys Ile Asn Gly Leu Leu Ala Glu Arg Tyr
    130                 135                 140

Gly Asp His Pro Ala Leu Leu Met Trp His Ile Ser Asn Glu Tyr Gly
145                 150                 155                 160

Gly Glu Cys His Cys Asp Lys Cys Gln Glu Ala Phe Arg Thr Trp Leu
                165                 170                 175

Lys Gly Lys Tyr Asn Asn Asp Leu Lys Ala Leu Asn Asp Ser Trp Trp
            180                 185                 190

Gly Pro Phe Trp Ser His Thr Ile Phe Asp Trp Ser Gln Ile Glu Ser
        195                 200                 205

Pro Ser Pro Ile Gly Glu Ser Ala Val His Gly Leu Asn Leu Asp Trp
    210                 215                 220
```

```
Arg Arg Phe Val Thr Asp Gln Thr Ile Asp Phe Tyr Glu Asn Glu Ile
225                 230                 235                 240

Val Pro Leu Arg Glu Met Thr Pro Ala Val Pro Ile Thr Thr Asn Phe
            245                 250                 255

Met Ala Asp Thr Phe Asp Leu Ile Pro Phe Gln Ser Leu Asp Tyr Ser
        260                 265                 270

Lys Phe Ala Lys His Val Asp Val Ile Ser Trp Asp Ala Tyr Pro Ala
        275                 280                 285

Trp His Asn Asp Trp Glu Thr Thr Asp Asn Leu Ala Met Lys Val Gly
        290                 295                 300

Phe Ile Asn Asp Leu Tyr Arg Ser Leu Lys Gln Gln Pro Phe Leu Leu
305                 310                 315                 320

Met Glu Ser Thr Pro Ser Leu Val Asn Trp His Asn Val Asn Lys Ala
            325                 330                 335

Lys Arg Pro Gly Met His Leu Leu Ser Ser Met Gln Met Val Ala His
            340                 345                 350

Gly Ser Asp Ser Val Leu Tyr Phe Gln Trp Arg Lys Ser Arg Gly Ser
        355                 360                 365

Ser Glu Lys Phe His Gly Ala Ala Val Asp His Asp Asn Ser Thr Glu
    370                 375                 380

Asn Arg Val Phe Gln Glu Val Ala Lys Val Gly Asp Val Leu Gly Lys
385                 390                 395                 400

Leu Glu Asp Val Val Gly Thr Asn Arg Pro Ala Asp Val Ala Ile Leu
                405                 410                 415

Tyr Asp Trp Glu Ser Asn Trp Ala Leu Asn Asp Ala Gln Gly Phe Gly
            420                 425                 430

Arg Lys Thr Lys Gln Tyr Pro Gln Thr Leu Gln Glu His Tyr Arg Thr
        435                 440                 445

Phe Trp Glu Gln Asp Ile Pro Val Asp Val Ile Thr Lys Asp Glu Asp
    450                 455                 460

Phe Ser Asn Tyr Lys Leu Leu Ile Val Pro Met Leu Tyr Leu Met Ser
465                 470                 475                 480

Glu Glu Thr Ile Ser Arg Leu Lys Ala Phe Val Ala Asn Gly Gly Arg
                485                 490                 495

Leu Val Met Thr Tyr Ile Ser Gly Leu Val Asn Glu His Asp Leu Ala
            500                 505                 510

Tyr Leu Gly Gly Trp His Ser Asp Leu Gln Glu Ile Phe Gly Met Glu
        515                 520                 525

Pro Lys Glu Thr Asp Thr Tyr Tyr Pro Ser Asp Arg Asn Tyr Val Gln
        530                 535                 540

Phe Arg Asn Asn Ser Tyr Glu Val Lys Asp Tyr Ala Thr Val Leu Gln
545                 550                 555                 560

Gln Gly Ser Ala Arg Thr Glu Gly Val Tyr Gln Glu Asp Phe Tyr Lys
            565                 570                 575

Asp Thr Pro Ala Val Met Ser His Glu Tyr Asn Lys Gly Lys Ser Tyr
        580                 585                 590

Tyr Ile Gly Ala Arg Leu Asn Gln Gln Phe His Arg Asp Phe Tyr Gln
        595                 600                 605

Glu Ile Ile Asp Glu Leu Gly Leu Ser Pro Val Val Thr Val Lys His
        610                 615                 620

Gly Lys Gly Val Ser Ile Gln Thr Arg Gln Gly Glu Asp Thr Asp Tyr
625                 630                 635                 640

Val Phe Val Met Asn Phe Thr Glu Gln Thr Gln Gln Val Glu Phe Thr
```

```
                   645                 650                 655
Ser Ala Val Lys Asp Leu Val Thr Gly Glu Glu Leu Ile Gly Glu Val
            660                 665                 670

Thr Leu Asn Thr Tyr Glu Val Arg Ile Val Ala Cys Lys Arg
            675                 680                 685

<210> SEQ ID NO 78
<211> LENGTH: 695
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(695)

<400> SEQUENCE: 78

Met His His His His His Pro Arg Met Leu Lys Gln Ser Lys Ser
1               5                   10                  15

Tyr Val Thr Lys Ala Gln Ser Met Leu His Gly Gly Asp Tyr Asn Pro
            20                  25                  30

Asp Gln Trp Leu Asp Gln Pro Asp Ile Leu Ala Asp Ile Lys Leu
        35                  40                  45

Met Lys Leu Ala Asn Thr Asn Thr Phe Ser Val Gly Ile Phe Ala Trp
50                  55                  60

Ser Ala Leu Glu Pro Glu Glu Asp Val Tyr Asn Phe Glu Trp Leu Asp
65                  70                  75                  80

Glu Ile Ile Asn Asn Ile Tyr Asn Asn Gly Gly Arg Val Ile Leu Ala
                85                  90                  95

Thr Pro Ser Gly Ala Arg Pro Ala Trp Met Ser Gln Lys Tyr Pro Glu
            100                 105                 110

Val Leu Arg Val Asn Glu Arg Arg Glu Lys Leu Leu His Gly Gly Arg
        115                 120                 125

His Asn His Cys Phe Thr Ser Glu Val Tyr Arg Glu Lys Thr His Lys
    130                 135                 140

Ile Asn Gly Leu Leu Ala Glu Arg Tyr Gly Asp His Pro Ala Leu Leu
145                 150                 155                 160

Met Trp His Ile Ser Asn Glu Tyr Gly Gly Glu Cys His Cys Asp Lys
                165                 170                 175

Cys Gln Glu Ala Phe Arg Thr Trp Leu Lys Gly Lys Tyr Asn Asn Asp
            180                 185                 190

Leu Lys Ala Leu Asn Asp Ser Trp Trp Gly Pro Phe Trp Ser His Thr
        195                 200                 205

Ile Phe Asp Trp Ser Gln Ile Glu Ser Pro Ser Pro Ile Gly Glu Ser
    210                 215                 220

Ala Val His Gly Leu Asn Leu Asp Trp Arg Arg Phe Val Thr Asp Gln
225                 230                 235                 240

Thr Ile Asp Phe Tyr Glu Asn Glu Ile Val Pro Leu Arg Glu Met Thr
                245                 250                 255

Pro Ala Val Pro Ile Thr Thr Asn Phe Met Ala Asp Thr Phe Asp Leu
            260                 265                 270

Ile Pro Phe Gln Ser Leu Asp Tyr Ser Lys Phe Ala Lys His Val Asp
        275                 280                 285

Val Ile Ser Trp Asp Ala Tyr Pro Ala Trp His Asn Asp Trp Glu Thr
    290                 295                 300

Thr Asp Asn Leu Ala Met Lys Val Gly Phe Ile Asn Asp Leu Tyr Arg
```

```
            305                 310                 315                 320
        Ser Leu Lys Gln Gln Pro Phe Leu Leu Met Glu Ser Thr Pro Ser Leu
                        325                 330                 335

Val Asn Trp His Asn Val Asn Lys Ala Lys Arg Pro Gly Met His Leu
                        340                 345                 350

Leu Ser Ser Met Gln Met Val Ala His Gly Ser Asp Ser Val Leu Tyr
                        355                 360                 365

Phe Gln Trp Arg Lys Ser Arg Gly Ser Ser Glu Lys Phe His Gly Ala
                        370                 375                 380

Ala Val Asp His Asp Asn Ser Thr Glu Asn Arg Val Phe Gln Glu Val
        385                 390                 395                 400

Ala Lys Val Gly Asp Val Leu Gly Lys Leu Glu Asp Val Val Gly Thr
                        405                 410                 415

Asn Arg Pro Ala Asp Val Ala Ile Leu Tyr Asp Trp Glu Ser Asn Trp
                        420                 425                 430

Ala Leu Asn Asp Ala Gln Gly Phe Gly Arg Lys Thr Lys Gln Tyr Pro
                        435                 440                 445

Gln Thr Leu Gln Glu His Tyr Arg Thr Phe Trp Glu Gln Asp Ile Pro
                        450                 455                 460

Val Asp Val Ile Thr Lys Asp Glu Asp Phe Ser Asn Tyr Lys Leu Leu
        465                 470                 475                 480

Ile Val Pro Met Leu Tyr Leu Met Ser Glu Glu Thr Ile Ser Arg Leu
                        485                 490                 495

Lys Ala Phe Val Ala Asn Gly Gly Arg Leu Val Met Thr Tyr Ile Ser
                        500                 505                 510

Gly Leu Val Asn Glu His Asp Leu Ala Tyr Leu Gly Gly Trp His Ser
                        515                 520                 525

Asp Leu Gln Glu Ile Phe Gly Met Glu Pro Lys Glu Thr Asp Thr Tyr
                        530                 535                 540

Tyr Pro Ser Asp Arg Asn Tyr Val Gln Phe Arg Asn Asn Ser Tyr Glu
        545                 550                 555                 560

Val Lys Asp Tyr Ala Thr Val Leu Gln Gln Gly Ser Ala Arg Thr Glu
                        565                 570                 575

Gly Val Tyr Gln Glu Asp Phe Tyr Lys Asp Thr Pro Ala Val Met Ser
                        580                 585                 590

His Glu Tyr Asn Lys Gly Lys Ser Tyr Tyr Ile Gly Ala Arg Leu Asn
                        595                 600                 605

Gln Gln Phe His Arg Asp Phe Tyr Gln Glu Ile Ile Asp Glu Leu Gly
                        610                 615                 620

Leu Ser Pro Val Val Thr Val Lys His Gly Lys Gly Val Ser Ile Gln
        625                 630                 635                 640

Thr Arg Gln Gly Glu Asp Thr Asp Tyr Val Phe Val Met Asn Phe Thr
                        645                 650                 655

Glu Gln Thr Gln Gln Val Glu Phe Thr Ser Ala Val Lys Asp Leu Val
                        660                 665                 670

Thr Gly Glu Glu Leu Ile Gly Glu Val Thr Leu Asn Thr Tyr Glu Val
                        675                 680                 685

Arg Ile Val Ala Cys Lys Arg
                        690                 695

<210> SEQ ID NO 79
<211> LENGTH: 331
<212> TYPE: PRT
<213> ORGANISM: Humicola insolens
```

<220> FEATURE:
<221> NAME/KEY: mat_peptide
<222> LOCATION: (1)..(331)

<400> SEQUENCE: 79

Leu Gln Tyr Lys Gly Val Asp Trp Ser Ser Val Met Val Glu Glu Arg
1               5                   10                  15

Ala Gly Val Arg Tyr Lys Asn Val Asn Gly Gln Glu Lys Pro Leu Glu
            20                  25                  30

Tyr Ile Leu Ala Glu Asn Gly Val Asn Met Val Arg Gln Arg Val Trp
        35                  40                  45

Val Asn Pro Trp Asp Gly Asn Tyr Asn Leu Asp Tyr Asn Ile Gln Leu
    50                  55                  60

Ala Arg Arg Ala Lys Ala Ala Gly Leu Gly Leu Tyr Ile Asn Phe His
65                  70                  75                  80

Tyr Ser Asp Thr Trp Ala Asp Pro Ala His Gln Thr Thr Pro Ala Gly
                85                  90                  95

Trp Pro Ser Asp Ile Asn Asn Leu Ala Trp Lys Leu Tyr Asn Tyr Thr
            100                 105                 110

Leu Asp Ser Met Asn Arg Phe Ala Asp Ala Gly Ile Gln Val Asp Ile
        115                 120                 125

Val Ser Ile Gly Asn Glu Ile Thr Gln Gly Leu Leu Trp Pro Leu Gly
    130                 135                 140

Lys Thr Asn Asn Trp Tyr Asn Ile Ala Arg Leu Leu His Ser Ala Ala
145                 150                 155                 160

Trp Gly Val Lys Asp Ser Arg Leu Asn Pro Lys Pro Lys Ile Met Val
                165                 170                 175

His Leu Asp Asn Gly Trp Asn Trp Asp Thr Gln Asn Trp Trp Tyr Thr
            180                 185                 190

Asn Val Leu Ser Gln Gly Pro Phe Glu Met Ser Asp Phe Asp Met Met
        195                 200                 205

Gly Val Ser Phe Tyr Pro Phe Tyr Ser Ala Ser Ala Thr Leu Asp Ser
    210                 215                 220

Leu Arg Arg Ser Leu Asn Asn Met Val Ser Arg Trp Gly Lys Glu Val
225                 230                 235                 240

Ala Val Val Glu Thr Asn Trp Pro Thr Ser Cys Pro Tyr Pro Arg Tyr
                245                 250                 255

Gln Phe Pro Ala Asp Val Arg Asn Val Pro Phe Ser Ala Ala Gly Gln
            260                 265                 270

Thr Gln Tyr Ile Gln Ser Val Ala Asn Val Ser Ser Val Ser Lys
        275                 280                 285

Gly Val Gly Leu Phe Tyr Trp Glu Pro Ala Trp Ile His Asn Ala Asn
    290                 295                 300

Leu Gly Ser Ser Cys Ala Asp Asn Thr Met Phe Thr Pro Ser Gly Gln
305                 310                 315                 320

Ala Leu Ser Ser Leu Ser Val Phe His Arg Ile
                325                 330

<210> SEQ ID NO 80
<211> LENGTH: 332
<212> TYPE: PRT
<213> ORGANISM: Myceliophthora thermophile
<220> FEATURE:
<221> NAME/KEY: mat_peptide
<222> LOCATION: (1)..(332)

<400> SEQUENCE: 80

```
Ala Leu Thr Tyr Arg Gly Val Asp Trp Ser Val Val Glu Glu
  1               5                  10                  15

Arg Ala Gly Val Ser Tyr Lys Asn Thr Asn Gly Asn Ala Gln Pro Leu
             20                  25                  30

Glu Asn Ile Leu Ala Ala Asn Gly Val Asn Thr Val Arg Gln Arg Val
         35                  40                  45

Trp Val Asn Pro Ala Asp Gly Asn Tyr Asn Leu Asp Tyr Asn Ile Ala
 50                  55                  60

Ile Ala Lys Arg Ala Lys Ala Gly Leu Gly Val Tyr Ile Asp Phe
 65              70                  75                  80

His Tyr Ser Asp Thr Trp Ala Asp Pro Ala His Gln Thr Met Pro Ala
             85                  90                  95

Gly Trp Pro Ser Asp Ile Asp Asn Leu Ser Trp Lys Leu Tyr Asn Tyr
            100                 105                 110

Thr Leu Asp Ala Ala Asn Lys Leu Gln Asn Ala Gly Ile Gln Pro Thr
            115                 120                 125

Ile Val Ser Ile Gly Asn Glu Ile Arg Ala Gly Leu Leu Trp Pro Thr
130                 135                 140

Gly Arg Thr Glu Asn Trp Ala Asn Ile Ala Arg Leu Leu His Ser Ala
145                 150                 155                 160

Ala Trp Gly Ile Lys Asp Ser Ser Leu Ser Pro Lys Pro Lys Ile Met
                165                 170                 175

Ile His Leu Asp Asn Gly Trp Asp Trp Gly Thr Gln Asn Trp Trp Tyr
            180                 185                 190

Thr Asn Val Leu Lys Gln Gly Thr Leu Glu Leu Ser Asp Phe Asp Met
            195                 200                 205

Met Gly Val Ser Phe Tyr Pro Phe Tyr Ser Ser Ala Thr Leu Ser
        210                 215                 220

Ala Leu Lys Ser Ser Leu Asp Asn Met Ala Lys Thr Trp Asn Lys Glu
225                 230                 235                 240

Ile Ala Val Val Glu Thr Asn Trp Pro Ile Ser Cys Pro Asn Pro Arg
                245                 250                 255

Tyr Ser Phe Pro Ser Asp Val Lys Asn Ile Pro Phe Ser Pro Glu Gly
            260                 265                 270

Gln Thr Thr Phe Ile Thr Asn Val Ala Asn Ile Val Ser Ser Val Ser
            275                 280                 285

Arg Gly Val Gly Leu Phe Tyr Trp Glu Pro Ala Trp Ile His Asn Ala
        290                 295                 300

Asn Leu Gly Ser Ser Cys Ala Asp Asn Thr Met Phe Ser Gln Ser Gly
305                 310                 315                 320

Gln Ala Leu Ser Ser Leu Ser Val Phe Gln Arg Ile
                325                 330

<210> SEQ ID NO 81
<211> LENGTH: 12
<212> TYPE: PRT
<213> ORGANISM: Artificial Sequence
<220> FEATURE:
<223> OTHER INFORMATION: SEQ ID NO: 81 is the conserved motif
      GV[T/M]PD[W/M]VQ[I/V]GNE.
<220> FEATURE:
<221> NAME/KEY: misc_feature
<222> LOCATION: (3)..(3)
<223> OTHER INFORMATION: The amino acid in position 3 of the conserved
      motif is either threonine (T) or methionine (M).
<220> FEATURE:
<221> NAME/KEY: misc_feature
```

```
<222> LOCATION: (6)..(6)
<223> OTHER INFORMATION: The amino acid in position 6 of the conserved
      motif is either tryptophan (W) or methionine (M).
<220> FEATURE:
<221> NAME/KEY: misc_feature
<222> LOCATION: (9)..(9)
<223> OTHER INFORMATION: The amino acid in position 9 of the conserved
      motif is either isoleucine (I) or valine (V).

<400> SEQUENCE: 81

Gly Val Xaa Pro Asp Xaa Val Gln Xaa Gly Asn Glu
1               5                   10

<210> SEQ ID NO 82
<211> LENGTH: 13
<212> TYPE: PRT
<213> ORGANISM: Artificial Sequence
<220> FEATURE:
<223> OTHER INFORMATION: SEQ ID NO: 82 is the conserved motif
      WADP[A/G]xQxKPxAW.
<220> FEATURE:
<221> NAME/KEY: misc_feature
<222> LOCATION: (5)..(5)
<223> OTHER INFORMATION: The amino acid in position 5 of the conserved
      motif is either alanine (A) or glycine (G).
<220> FEATURE:
<221> NAME/KEY: misc_feature
<222> LOCATION: (6)..(6)
<223> OTHER INFORMATION: The amino acid in position 6 of the conserved
      motif is any amino acid.
<220> FEATURE:
<221> NAME/KEY: misc_feature
<222> LOCATION: (8)..(8)
<223> OTHER INFORMATION: The amino acid in position 8 of the conserved
      motif is any amino acid.
<220> FEATURE:
<221> NAME/KEY: misc_feature
<222> LOCATION: (11)..(11)
<223> OTHER INFORMATION: The amino acid in position 11 of the conserved
      motif is any amino acid.

<400> SEQUENCE: 82

Trp Ala Asp Pro Xaa Xaa Gln Xaa Lys Pro Xaa Ala Trp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: SEQ ID NO: 83 is the conserved motif
      DW[K/R]RF[V/I]T[A/D]Q[T/M].
<220> FEATURE:
<221> NAME/KEY: misc_feature
<222> LOCATION: (3)..(3)
<223> OTHER INFORMATION: The amino acid in position 3 of the conserved
      motif is either lysine (K) or arginine (R).
<220> FEATURE:
<221> NAME/KEY: misc_feature
<222> LOCATION: (6)..(6)
<223> OTHER INFORMATION: The amino acid in position 6 of the conserved
      motif is either valine (V) or isoleucine (I).
<220> FEATURE:
<221> NAME/KEY: misc_feature
<222> LOCATION: (8)..(8)
<223> OTHER INFORMATION: The amino acid in position 8 of the conserved
      motif is either alanine (A) or aspartic acid (D).
<220> FEATURE:
<221> NAME/KEY: misc_feature
<222> LOCATION: (10)..(10)
<223> OTHER INFORMATION: The amino acid in position 10 of the conserved
      motif is either threonine (T) or methionine (M).

<400> SEQUENCE: 83
```

Asp Trp Xaa Arg Phe Xaa Thr Xaa Gln Xaa
1               5                   10

<210> SEQ ID NO 84
<211> LENGTH: 27
<212> TYPE: PRT
<213> ORGANISM: Bacillus clausii

<400> SEQUENCE: 84

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 85
<211> LENGTH: 687
<212> TYPE: PRT
<213> ORGANISM: Bacillus subtilis

<400> SEQUENCE: 85

Met Met Ser Lys Leu Glu Lys Thr His Val Thr Lys Ala Lys Phe Met
1               5                   10                  15

Leu His Gly Gly Asp Tyr Asn Pro Asp Gln Trp Leu Asp Arg Pro Asp
            20                  25                  30

Ile Leu Ala Asp Asp Ile Lys Leu Met Lys Leu Ser His Thr Asn Thr
        35                  40                  45

Phe Ser Val Gly Ile Phe Ala Trp Ser Ala Leu Glu Pro Glu Glu Gly
    50                  55                  60

Val Tyr Gln Phe Glu Trp Leu Asp Ile Phe Glu Arg Ile His Ser
65                  70                  75                  80

Ile Gly Gly Arg Val Ile Leu Ala Thr Pro Ser Gly Ala Arg Pro Ala
                85                  90                  95

Trp Leu Ser Gln Thr Tyr Pro Glu Val Leu Arg Val Asn Ala Ser Arg
            100                 105                 110

Val Lys Gln Leu His Gly Gly Arg His Asn His Cys Leu Thr Ser Lys
        115                 120                 125

Val Tyr Arg Glu Lys Thr Arg His Ile Asn Arg Leu Leu Ala Glu Arg
    130                 135                 140

Tyr Gly His His Pro Ala Leu Leu Met Trp His Ile Ser Asn Glu Tyr
145                 150                 155                 160

Gly Gly Asp Cys His Cys Asp Leu Cys Gln His Ala Phe Arg Glu Trp
                165                 170                 175

Leu Lys Ser Lys Tyr Asp Asn Ser Leu Lys Thr Leu Asn His Ala Trp
            180                 185                 190

Trp Thr Pro Phe Trp Ser His Thr Phe Asn Asp Trp Ser Gln Ile Glu
        195                 200                 205

Ser Pro Ser Pro Ile Gly Glu Asn Gly Leu His Gly Leu Asn Leu Asp
    210                 215                 220

Trp Arg Arg Phe Val Thr Asp Gln Thr Ile Ser Phe Tyr Glu Asn Glu
225                 230                 235                 240

Ile Ile Pro Leu Lys Glu Leu Thr Pro Asp Ile Pro Ile Thr Thr Asn
                245                 250                 255

Phe Met Ala Asp Thr Pro Asp Leu Ile Pro Tyr Gln Gly Leu Asp Tyr
            260                 265                 270

Ser Lys Phe Ala Lys His Val Asp Ala Ile Ser Trp Asp Ala Tyr Pro
        275                 280                 285

Val Trp His Asn Asp Trp Glu Ser Thr Ala Asp Leu Ala Met Lys Val
290                 295                 300

Gly Phe Ile Asn Asp Leu Tyr Arg Ser Leu Lys Gln Gln Pro Phe Leu
305                 310                 315                 320

Leu Met Glu Cys Thr Pro Ser Ala Val Asn Trp His Asn Val Asn Lys
                325                 330                 335

Ala Lys Arg Pro Gly Met Asn Leu Leu Ser Ser Met Gln Met Ile Ala
            340                 345                 350

His Gly Ser Asp Ser Val Leu Tyr Phe Gln Tyr Arg Lys Ser Arg Gly
        355                 360                 365

Ser Ser Glu Lys Leu His Gly Ala Val Asp His Asp Asn Ser Pro
370                 375                 380

Lys Asn Arg Val Phe Gln Glu Val Ala Lys Val Gly Glu Thr Leu Glu
385                 390                 395                 400

Arg Leu Ser Glu Val Val Gly Thr Lys Arg Pro Ala Gln Thr Ala Ile
                405                 410                 415

Leu Tyr Asp Trp Glu Asn His Trp Ala Leu Glu Asp Ala Gln Gly Phe
            420                 425                 430

Ala Lys Ala Thr Lys Arg Tyr Pro Gln Thr Leu Gln Gln His Tyr Arg
        435                 440                 445

Thr Phe Trp Glu His Asp Ile Pro Val Asp Val Ile Thr Lys Glu Gln
    450                 455                 460

Asp Phe Ser Pro Tyr Lys Leu Leu Ile Val Pro Met Leu Tyr Leu Ile
465                 470                 475                 480

Ser Glu Asp Thr Val Ser Arg Leu Lys Ala Phe Thr Ala Asp Gly Gly
                485                 490                 495

Thr Leu Val Met Thr Tyr Ile Ser Gly Val Val Asn Glu His Asp Leu
            500                 505                 510

Thr Tyr Thr Gly Gly Trp His Pro Asp Leu Gln Ala Ile Phe Gly Val
        515                 520                 525

Glu Pro Leu Glu Thr Asp Thr Leu Tyr Pro Lys Asp Arg Asn Ala Val
    530                 535                 540

Ser Tyr Arg Ser Gln Ile Tyr Glu Met Lys Asp Tyr Ala Thr Val Ile
545                 550                 555                 560

Asp Val Lys Thr Ala Ser Val Glu Ala Val Tyr Gln Glu Asp Phe Tyr
                565                 570                 575

Ala Arg Thr Pro Ala Val Thr Ser His Glu Tyr Gln Gln Gly Lys Ala
            580                 585                 590

Tyr Phe Ile Gly Ala Arg Leu Glu Asp Gln Phe Gln Arg Asp Phe Tyr
        595                 600                 605

Glu Gly Leu Ile Thr Asp Leu Ser Leu Ser Pro Val Phe Pro Val Arg
    610                 615                 620

His Gly Lys Gly Val Ser Val Gln Ala Arg Gln Asp Gln Asp Asn Asp
625                 630                 635                 640

Tyr Ile Phe Val Met Asn Phe Thr Glu Glu Lys Gln Leu Val Thr Phe
                645                 650                 655

Asp Gln Ser Val Lys Asp Ile Met Thr Gly Asp Ile Leu Ser Gly Asp
            660                 665                 670

Leu Thr Met Glu Lys Tyr Glu Val Arg Ile Val Val Asn Thr His
        675                 680                 685

<210> SEQ ID NO 86
<211> LENGTH: 429
<212> TYPE: PRT

<213> ORGANISM: Bacillus subtilis

<400> SEQUENCE: 86

Met Lys Ser Lys Val Lys Met Phe Phe Ala Ala Ile Val Trp Ser
1               5                   10                  15

Ala Cys Ser Ser Thr Gly Tyr Ala Ala Ile Glu Lys Glu Lys His
                20                  25                  30

Val Ser Glu Leu Arg Ala Glu Asp Leu Phe Val Lys Lys Val Glu Gly
        35                  40                  45

Met Asn Lys Asp Phe Ile Lys Gly Ala Asp Val Ser Ser Val Ile Ala
    50                  55                  60

Leu Glu Asn Ser Gly Val Thr Phe Tyr Asn Thr Asn Gly Lys Arg Gln
65                  70                  75                  80

Asp Ile Phe Thr Thr Leu Lys Gln Ala Gly Val Asn Tyr Val Arg Val
                85                  90                  95

Arg Ile Trp Asn His Pro Tyr Asp Ser Asn Gly Asn Gly Tyr Gly Gly
                100                 105                 110

Gly Asn Asn Asp Val Gln Lys Ala Ile Glu Ile Gly Lys Arg Ala Thr
            115                 120                 125

Ala Asn Gly Met Lys Val Leu Ala Asp Phe His Tyr Ser Asp Phe Trp
130                 135                 140

Ala Asp Pro Ala Lys Gln Lys Val Pro Lys Ala Trp Ala Asn Leu Ser
145                 150                 155                 160

Phe Glu Ala Lys Lys Ala Lys Leu Tyr Glu Tyr Thr Lys Gln Ser Leu
                165                 170                 175

Gln Lys Met Ile Lys Glu Gly Val Asp Ile Gly Met Val Gln Val Gly
            180                 185                 190

Asn Glu Thr Thr Gly Gly Phe Ala Gly Glu Thr Asp Trp Thr Lys Met
        195                 200                 205

Cys Gln Leu Phe Asn Glu Gly Ser Arg Ala Val Arg Glu Thr Asn Ser
    210                 215                 220

Asn Ile Leu Val Ala Leu His Phe Thr Asn Pro Glu Thr Ala Gly Arg
225                 230                 235                 240

Tyr Ser Phe Ile Ala Glu Thr Leu Ser Lys Asn Lys Val Asp Tyr Asp
                245                 250                 255

Val Phe Ala Ser Ser Tyr Tyr Pro Phe Trp His Gly Thr Leu Gln Asn
            260                 265                 270

Leu Thr Ser Val Leu Lys Ala Val Ala Asn Thr Tyr Gly Lys Lys Val
        275                 280                 285

Met Val Ala Glu Thr Ser Tyr Thr Tyr Thr Ala Glu Asp Gly Asp Gly
    290                 295                 300

His Gly Asn Thr Ala Pro Lys Ser Gly Gln Thr Leu Pro Tyr Pro Ile
305                 310                 315                 320

Ser Val Gln Gly Gln Ala Thr Ala Val Arg Asp Val Met Glu Ala Val
                325                 330                 335

Ala Asn Thr Gly Lys Ala Gly Leu Gly Val Phe Tyr Trp Glu Pro Ala
            340                 345                 350

Trp Ile Pro Val Gly Pro Lys Thr Gln Ile Glu Lys Asn Lys Val Leu
        355                 360                 365

Trp Glu Thr Tyr Gly Ser Gly Trp Ala Ser Ser Tyr Ala Ala Glu Tyr
    370                 375                 380

Asp Pro Glu Asp Ala Gly Lys Trp Tyr Gly Gly Ser Ala Val Asp Asn
385                 390                 395                 400

Gln Ala Leu Phe Asp Phe Asn Gly His Pro Leu Pro Ser Leu Gln Val
            405                 410                 415

Phe Gln Tyr Ala Glu Ser Gly His Ile Pro Lys Lys Arg
        420                 425

<210> SEQ ID NO 87
<211> LENGTH: 686
<212> TYPE: PRT
<213> ORGANISM: Geobacillus stearothermophilus

<400> SEQUENCE: 87

Met Pro Lys Tyr Glu Arg Thr Tyr Thr Thr Gln Ala Asn Phe Ile Leu
1               5                   10                  15

His Gly Gly Asp Tyr Asn Pro Asp Gln Trp Leu Asp Arg Pro Asp Ile
            20                  25                  30

Leu Gln Ala Asp Leu Glu Leu Met Lys Leu Ser His Thr Asn Thr Phe
        35                  40                  45

Thr Val Gly Val Phe Ala Trp Ser Ala Leu Glu Pro Glu Glu Gly Val
    50                  55                  60

Tyr Arg Phe Glu Trp Leu Asp Lys Val Phe Asp Asp Ile Tyr Arg Ile
65                  70                  75                  80

Gly Gly Arg Val Ile Leu Ala Thr Pro Ser Gly Ala Arg Pro Ala Trp
                85                  90                  95

Leu Ser Gln Lys Tyr Pro Glu Val Leu Arg Val Asn Ala Ala Arg Val
            100                 105                 110

Arg Gln Leu His Gly Gly Arg His Asn His Cys Phe Thr Ser Ser Val
        115                 120                 125

Tyr Arg Glu Lys Thr Gln His Ile Asn Arg Leu Leu Ala Glu Arg Tyr
    130                 135                 140

Gly Asp His Pro Ala Leu Leu Met Trp His Val Ser Asn Glu Tyr Gly
145                 150                 155                 160

Gly Glu Cys His Cys Asn Leu Cys Gln Glu Ala Phe Arg Glu Trp Leu
                165                 170                 175

Lys Lys Lys Tyr Asn His Asp Leu Asp Ala Leu Asn Ala Ala Trp Trp
            180                 185                 190

Thr Ser Phe Trp Ser His Thr Tyr Thr Asp Trp Ser Gln Ile Glu Ser
        195                 200                 205

Pro Ser Pro Ile Gly Glu His Thr Ile His Gly Leu Asn Leu Asp Trp
    210                 215                 220

Lys Arg Phe Val Thr Asp Gln Thr Ile Ser Phe Phe Glu Asn Glu Ile
225                 230                 235                 240

Val Pro Leu Arg Glu Leu Thr Pro His Ile Pro Ile Thr Thr Asn Phe
                245                 250                 255

Met Ala Asp Thr His Asp Leu Ile Pro Phe Gln Gly Leu Asp Tyr Ser
            260                 265                 270

Lys Phe Ala Lys His Leu Asp Val Ile Ser Trp Asp Ala Tyr Pro Ala
        275                 280                 285

Trp His Asn Asp Trp Glu Ser Thr Ala Asp Leu Ala Met Lys Val Gly
    290                 295                 300

Phe Ile Asn Asp Leu Tyr Arg Ser Leu Lys Gln Gln Pro Phe Leu Leu
305                 310                 315                 320

Met Glu Cys Thr Pro Ser Leu Val Asn Trp His Lys Val Asn Lys Ala
                325                 330                 335

Lys Arg Pro Gly Met His Phe Leu Ser Ser Met Gln Met Ile Ala His
            340                 345                 350

Gly Ser Asp Ser Ile Leu Tyr Phe Gln Trp Arg Lys Ser Arg Gly Ser
            355                 360                 365

Phe Glu Lys Phe His Gly Ala Val Val Asp His Asp Asn Arg Thr Asp
        370                 375                 380

Ser Arg Val Phe Gln Glu Val Ala Glu Val Gly Lys Ala Leu Lys Lys
385                 390                 395                 400

Met Ser Gly Ile Val Gly Thr Asn Arg Pro Ala Glu Val Ala Ile Leu
                405                 410                 415

Tyr Asp Trp Glu Asn Asn Trp Ala Leu Asn Asp Ala Gln Gly Phe Ala
            420                 425                 430

Ala Glu Thr Lys Arg Tyr Pro Gln Thr Leu Val Gln His Tyr Arg Pro
        435                 440                 445

Phe Trp Glu Arg Asp Ile Pro Val Asp Val Ile Thr Lys Glu His Asp
    450                 455                 460

Phe Ser Arg Tyr Lys Leu Leu Ile Ala Pro Met Leu Tyr Leu Val Ser
465                 470                 475                 480

Glu Glu Thr Ile Ala Arg Leu Lys Glu Phe Val Ala Asn Gly Gly Thr
                485                 490                 495

Leu Val Met Thr Tyr Ile Ser Gly Ile Val Asp Glu His Asp Leu Ala
            500                 505                 510

Tyr Leu Gly Gly Trp His Gln Asp Leu Arg Glu Met Phe Gly Met Glu
        515                 520                 525

Pro Ile Glu Thr Asp Thr Leu Tyr Pro Arg Asp Arg Asn Ser Val His
    530                 535                 540

Tyr Arg Gly Arg Ser Tyr Glu Leu Lys Asp Tyr Ala Thr Val Ile Lys
545                 550                 555                 560

Ile His Ala Ala Thr Val Glu Gly Val Tyr Glu Asp Asp Phe Tyr Ala
                565                 570                 575

Asp Thr Pro Ala Val Thr Ser Asn Gln Tyr Gly Lys Gly Gln Ala Tyr
            580                 585                 590

Tyr Ile Gly Gly Arg Leu Glu Asp Gln Phe His Arg Asp Phe Tyr Gln
        595                 600                 605

Glu Leu Met Glu Lys Leu Asp Leu Arg Pro Val Leu Phe Val Lys His
    610                 615                 620

Glu Lys Gly Val Ser Val Gln Ala Arg Gln Ala Pro Glu Cys Asp Tyr
625                 630                 635                 640

Val Phe Ile Met Asn Phe Thr Glu Glu Lys Gln Ala Val Val Leu Glu
                645                 650                 655

Glu Lys Val Lys Asp Leu Phe Thr Gly Glu Ile Val Gly Glu Ile
            660                 665                 670

Met Leu Asp Lys Tyr Glu Val Arg Val Val Glu Lys Arg
        675                 680                 685

<210> SEQ ID NO 88
<211> LENGTH: 814
<212> TYPE: PRT
<213> ORGANISM: Geobacillus stearothermophilus

<400> SEQUENCE: 88

Met Gly Lys Gln Phe Leu Phe Val Leu Val Ala Met Met Val Met Ile
1               5                   10                  15

Met Ser Phe Ser Ser Asn His Ile His Lys Ala Ala Ala Asp Ser Tyr
            20                  25                  30

Asn Tyr Leu Ile Asn Gly Gly Phe Glu Ser Asp Phe Trp Ala Asp Gly

```
                35                  40                  45
Ser Trp Thr Val Thr Thr Gln Asp Trp Ser Val Asp Leu Gln Arg
 50                  55                  60
Phe Ser Tyr Ser Asn Asp Ala Trp Ile Val Pro Asn Glu Gly Asp Ser
 65                  70                  75                  80
Ala Phe Lys Tyr Trp Ile Arg Asp Ile Ala Asn Gly Asn Gln Thr Phe
                 85                  90                  95
Thr Leu Lys Gln Thr Ile Gly Gln Leu Pro Pro Gly Ser Tyr Glu Leu
                100                 105                 110
Ser Val Gln Ser Met Gly Gly Ala Gly Asp Glu Ala Gly Tyr Ile Gln
                115                 120                 125
Leu Phe Ala Gly Asp Lys Met Ala Asp Ala Val Val Thr Lys Gly Tyr
130                 135                 140
Asn Ser Trp Glu Thr Val Lys Leu Glu Phe Thr Leu Glu Glu Glu Ala
145                 150                 155                 160
Ser Asn Phe Glu Val Gly Ala Ile Val Thr Gly Glu Pro Asn Ala Trp
                165                 170                 175
Gly Tyr Met Asp His Phe Gln Leu Val Ser Leu Asn Ser Ala Gly Gly
                180                 185                 190
Arg Glu Met Pro Lys Pro Val Pro Ala Asp Ile Phe Val Lys Arg Val
                195                 200                 205
Asp Gly Leu Ser Lys Glu Phe Ile Lys Gly Val Asp Val Ser Ser Ile
                210                 215                 220
Ile Ala Leu Glu Asp Ser Gly Val Lys Phe Tyr Asn Ala Ala Gly Lys
225                 230                 235                 240
Lys Gln Asp Ile Phe Lys Thr Leu Lys Glu Ala Gly Ile Asn Tyr Val
                245                 250                 255
Arg Val Arg Val Trp Asn Asp Pro Tyr Asp Ala Lys Gly His Gly Tyr
                260                 265                 270
Gly Gly Gly Asn Asn Asp Leu Glu Lys Ala Ile Glu Ile Gly Lys Arg
                275                 280                 285
Ala Thr Ala Ser Gly Met Lys Leu Leu Val Asp Phe His Tyr Ser Asp
                290                 295                 300
Phe Trp Ala Asp Pro Ala Lys Gln Arg Pro Pro Lys Ala Trp Ala Lys
305                 310                 315                 320
Leu Asn Phe Glu Ala Lys Lys Ala Leu Tyr Arg Phe Thr Lys Glu
                325                 330                 335
Ser Leu Lys Ala Met Leu Lys Glu Lys Ile Gln Val Gly Met Val Gln
                340                 345                 350
Ile Gly Asn Glu Thr Asn Gly Ala Phe Val Gly Glu Thr Asp Trp Ala
                355                 360                 365
Lys Ile Cys Glu Leu Leu Asn Ala Gly Ser Arg Ala Val Arg Glu Thr
                370                 375                 380
Ser Pro Asn Ile Leu Val Val Leu His Phe Thr Asn Pro Glu Thr Pro
385                 390                 395                 400
Gly Arg Tyr Ala Ser Ile Ala Lys Thr Leu Ala Glu His Lys Val Asp
                405                 410                 415
Tyr Asp Val Phe Ala Ser Ser Tyr Tyr Pro Phe Trp His Gly Thr Leu
                420                 425                 430
```

```
Ala Asn Leu Thr Ser Val Leu Lys Tyr Val Ala Asn Thr Tyr Leu Lys
            435                 440                 445

Lys Val Met Val Ala Glu Thr Ser Tyr Pro Tyr Thr Thr Glu Asp Gly
450                 455                 460

Asp Gly His Glu Asn Thr Ala Pro Lys Ser Ser Gly Gln Thr Leu Asn
465                 470                 475                 480

Tyr Pro Ile Thr Val Gln Gly Gln Ala Asn Ala Ile Arg Asp Val Ile
            485                 490                 495

Gln Ala Val Ala Ala Val Gly Lys Pro Gly Ile Gly Val Phe Tyr Trp
            500                 505                 510

Glu Pro Ala Trp Ile Pro Val Gly Pro Pro Glu Gln Leu Lys Gln Asn
            515                 520                 525

Glu Lys Lys Trp Glu Lys Tyr Gly Ser Gly Trp Ala Ser Ser Phe Ala
            530                 535                 540

Ala Glu Tyr Asp Pro Asp Ala Ala Met Trp His Gly Gly Ser Ala Val
545                 550                 555                 560

Asp Asn Gln Ala Leu Phe Asp Phe Asn Gly Arg Pro Leu Pro Ser Leu
            565                 570                 575

Asn Val Phe Lys Tyr Val Asp Thr Gly Ala Val Ala Pro Leu Lys Ile
            580                 585                 590

Asp Glu Ile Lys Asp Ile Tyr Ile Arg Ala Ala Phe Gly Glu Gln Val
            595                 600                 605

Val Leu Pro Thr Thr Val Thr Ala Thr Tyr Asn Asp Gly Ser Lys His
            610                 615                 620

Leu Val Ser Val Lys Trp Asp Gln Ala Ala Leu Glu Gln Ala Leu Arg
625                 630                 635                 640

Thr Gly Val Gly Thr Tyr Val Ile Gln Gly Val Val Glu Gly Gly Glu
            645                 650                 655

Thr Val Lys Ala His Leu Glu Ile Thr Pro Lys Asn Tyr Val Val Asn
            660                 665                 670

Pro Ser Phe Glu Asp Gln Asp Arg Thr Met Trp Asn Ile Ile Tyr Arg
            675                 680                 685

Asn Gly Thr Ser Pro His Thr Asp Tyr Leu Glu Lys Ala Thr Asp Ala
            690                 695                 700

Lys Ser Gly Asn Tyr Ser Leu His Phe Tyr Ser Asn Glu Ala Val Asp
705                 710                 715                 720

Phe Gln Val Glu Gln Thr Ile Thr Gly Leu Lys Pro Gly Tyr Tyr Asn
            725                 730                 735

Leu Ser Met Phe Leu Gln Ala Gly Asp Ala Pro Asn Ala Glu Ile Tyr
            740                 745                 750

Leu Tyr Ala Lys Thr Gly Asp Lys Glu Tyr Arg Ala Ala Ala Ser Val
            755                 760                 765

Asn Gly Trp Leu Asn Trp Ser Ser Pro Glu Ile His Asp Ile Tyr Ile
            770                 775                 780

Ala Asp Gly Thr Val Thr Ile Gly Ala Ser Ile Lys Ala Asn Gly Gly
785                 790                 795                 800

Ala Trp Gly Thr Leu Asp Asp Phe Gln Leu Tyr Gln Thr Lys
            805                 810
```